(12) United States Patent
Wakita et al.

(10) Patent No.: US 6,555,559 B1
(45) Date of Patent: Apr. 29, 2003

(54) 5,6,7-TRINOR-4,8-INTER-M-PHENYLENE PGI$_2$ DERIVATIVE AND DRUGS CONTAINING THE SAME

(75) Inventors: Hisanori Wakita, Kanagawa (JP); Naohiro Yamada, Kanagawa (JP); Hitoshi Hatakeyama, Kanagawa (JP); Takeshi Ishigaki, Kanagawa (JP); Noriyuki Hirano, Kanagawa (JP); Takeshi Mori, Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/582,071

(22) PCT Filed: Oct. 22, 1999

(86) PCT No.: PCT/JP99/05854

§ 371 (c)(1),
(2), (4) Date: Aug. 1, 2000

(87) PCT Pub. No.: WO00/24727

PCT Pub. Date: May 4, 2000

(30) Foreign Application Priority Data

Oct. 23, 1998 (JP) ............................................ 10-320014

(51) Int. Cl.$^7$ ...................... A61K 31/44; A61K 31/35; A61K 31/395; C07D 405/06; C07D 407/06

(52) U.S. Cl. .................. 514/337; 514/372; 514/378; 514/382; 514/383; 514/444; 514/460; 546/284.1; 548/134; 548/214; 548/247; 548/252; 548/253; 548/266.4; 54/60; 54/214; 54/414

(58) Field of Search .................... 549/60, 414, 214; 514/337, 372, 378, 382, 383, 444, 460; 546/284.1; 548/134, 214, 247, 252, 253, 266.4

(56) References Cited

U.S. PATENT DOCUMENTS 5,401,768 A  *  3/1995 Ohno et al. ................. 549/458

* cited by examiner

Primary Examiner—Bernard Dentz
(74) Attorney, Agent, or Firm—Schnader Harrison Segal & Lewis LLP

(57) ABSTRACT

The present invention provides novel PGI$_2$ derivatives and an anti Helicobacter agent, a platelet function potentiating agent or a cervical ripening agent containing any of the derivatives.

9 Claims, 1 Drawing Sheet

5,6,7-TRINOR-4,8-INTER-M-PHENYLENE PGI$_2$ DERIVATIVE AND DRUGS CONTAINING THE SAME

This application is a 371 of PCT/JP99/05854, with an international filing date of Oct. 22, 1999, and claims priority of JP 10-320014, filed Oct. 23, 1998.

TECHNICAL FIELD

The present invention relates to novel prostaglandin I$_2$ (abbreviated to "PGI$_2$" hereinafter) derivatives and application of the derivatives. Particularly, the present invention relates to novel 5,6,7-trinor-4,8-inter-m-phenylene PGI$_2$ derivatives useful for medicines, and medical application thereof.

BACKGROUND ART

PGI$_2$ (prostacyclin) is a compound found by J. R. Vane et al in 1976, which is a substance biosynthesized in the arterial wall from arachidonic acid through endoperoxide (PGH$_2$ or PGG$_2$) and which has a strong platelet aggregation inhibiting effect, gastric acid secretion inhibiting effect, and dilation of the peripheral vascular system. However, PGI$_2$ which has an unstable exo-enol structure is extremely unstable even in neutral aqueous solution and is subjected to conversion to 6-oxo PGF$_{1\alpha}$ which has little physiological effect. The unstableness of PGI$_2$ causes a great fault in an attempt to use this compound for medicines. PGI$_2$ is also unstable in vivo, and has the fault that the physiological effects are nonpersistent.

On the other hand, the inventors have achieved a series of inventions relating to stable PGI$_2$ derivatives having a skeleton in which the structure of an exo-enol ether moiety which causes the unstableness of PGI$_2$, is changed to inter-m-phenylene (refer to Ohno et at., Japanese Examined Patent Publication Nos. 59-31510, 1-53672, 2-12226, 2-57548, 3-69909, 6-62599, and 7-5582).

Prostaglandin derivatives are used as therapy of ulcers or the like in the digestive area because they are defensive factor potentiators for increasing mucosal blood flow and mucous secretion. However, it is unknown that the PGI$_2$ derivatives have an antibacterial effect on Helicobacter bacteria such as *Helicobacter pylori*, which attract attention as a pathogenic factor of upper gastric diseases such as chronic gastritis, gastroduodenal ulcer, gastric cancer, lymphoma, etc.

Diseases exhibiting a bleeding tendency due to platelet hypofunction in spite of the normal platelet count are generically named platelet functional disorders. The platelet functional disorders are divided into congenital disorders and acquired disorders. The congenital platelet functional disorders are divided into disorders of platelet adhesion, aggregation and releasing dysfunction.

On the other hand, the acquired platelet functional disorders occur with greater frequency than the congenital disorders, and, for example, the acquired disorders are accompanied with various diseases such as chronic renal failure, liver diseases, blood diseases, and the like, and are caused by extracorporeal circulation or medicines. Furthermore, administration of such medicines for diseases exhibiting the bleeding tendency is dangerous because the bleeding tendency is prolonged. Therefore, it is necessary to prevent the bleeding tendency caused by these diseases and the use of medicines.

Although DDAVP (1-deamino-8-arginine vasopressin) or the like is used for the congenital disorders of platelet releasing dysfunction and the acquired platelet functional disorders, in some cases, arterial thrombosis or hyponatremia occurs as a side effect. Although, in case of emergency, platelet transfusion is conducted, a serious side effect occurs due to the production of antibodies against platelets and lymphocytes.

On the other hand, the inventors have reported that PGI$_2$ derivatives have the effect to potentiate the platelet function without through thromboxane A$_2$ (abbreviated to "TXA$_2$" hereinafter) receptors (Miyamdto et al., WO98/11899).

Also the prostaglandin derivatives are known to be useful as medicines for accelerating cervical ripening in the gynecological area.

During pregnancy, the cervical canal is strongly closed for pregnancy continuation up to late pregnancy, for preventing abortion and premature delivery. on the other hand, at the 36th week or later in pregnancy, softening of the cervical canal proceeds for facilitating fetus expulsion, accompanied by dilation of the cervical opening and shortening of the cervical canal length (effacement). This is a phenomenon referred to as "cervical ripening". The cervical ripening is an important factor which controls the process of fatal delivery. Therefore, in order to safely and normally extract a fetus, it is necessary to sufficiently ripen the cervical canal as a preparatory step for delivery before the start of contraction (pains) of the myometrium.

As a medicine for accelerating ripening of the cervical canal, i.e., a cervical ripening agent, prostaglandin E$_2$ (abbreviated to "PGE$_2$" hereinafter) is clinically used. However, PGE$_2$ also has an oxytocic action, and thus has the problem of the possibility of causing excessively contraction of the myometrium. On the other hand, the inventors have reported that PGI$_2$ derivatives are useful as cervical ripening agents without causing the oxytocic action (Ochi et al., WO99/13881).

However, conventional PGI$_2$ derivatives cannot be said to sufficiently remove side effects such as reduction of the blood pressure, etc., and thus the invention of a new PGI$_2$ derivative is in demand.

An object of the present invention is to provide novel PGI$_2$ derivatives having excellent stability in vivo, a strong medical effect, and a little side effect, and medicines each comprising any of the PGI$_2$ derivatives as an active ingredient.

DISCLOSURE OF INVENTION

As a result of intensive research, the inventors succeeded in obtaining novel PGI$_2$ derivatives, and found that these PGI$_2$ derivatives have an excellent anti Helicobacter action, platelet function potentiating effect or cervical ripening effect, and the little action to reduce blood pressure as a side effect, resulting in the achievement of the present invention.

Namely, the present invention provides 5,6,7-trinor-4,8-inter-m-phenylene PGI$_2$ derivatives represented by the following formula (I):

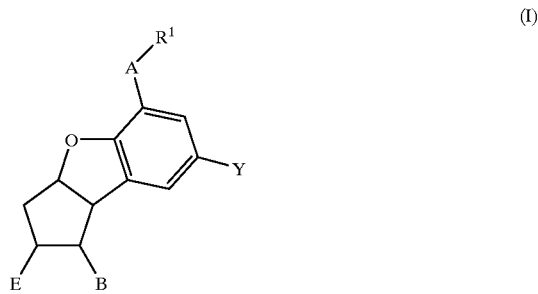

[wherein $R^1$ represents the following:

(A)

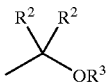

wherein $R^2$ is hydrogen, straight chain alkyl having 1 to 4 carbon atoms, branched alkyl having 3 or 4 carbon atoms, trifluoromethyl, —C(=O)—$R^4$ or —C(=O)—O—$R^4$ wherein $R^4$ is straight chain alkyl having 1 to 12 carbon atoms, branched alkyl having 3 to 14 carbon atoms, cycloalkyl having 3 to 12 carbon atoms, aralkyl having 7 to 12 carbon atoms, phenyl, or substituted phenyl (wherein a substituent is at least one of fluorine, chlorine, bromine, iodine, trifluoromethyl, alkyl having 1 to 4 carbon atoms, nitro, cyano, methoxy, phenyl, phenoxy, p-acetamidebenzamide, —CH=N—NH—C(=O)—$NH_2$, —NH—C(=O)—Ph, —NH—C(=O)—$CH_3$, or —NH—C(=O)—$NH_2$), two $R^2$ groups may be the same or different, and $R^3$ is hydrogen, alkyl having 1 to 4 carbon atoms, acyl having 1 to 4 carbon atoms, aroyl having 7 to 16 carbon atoms, aralkyl having 7 to 16 carbon atoms, tetrahydropyranyl, tetrahydrofuranyl, 1-ethoxyethyl, allyl, tert-butyl, or tert-butyldimethylsilyl;

(B) —$COOR^5$ wherein $R^5$ is:

1) hydrogen or a pharmacologically acceptable cation;
2) straight chain alkyl having 1 to 12 carbon atoms, or branched alkyl having 3 to 14 carbon atoms;
3) —Z—$R^6$
   wherein Z is a valence bond or straight chain or branched alkylene represented by $C_tH_{2t}$ wherein t represents an integer of 1 to 6, and $R^6$ is cycloalkyl having 3 to 12 carbon atoms or substituted cycloalkyl having 3 to 12 carbon atoms substituted by 1 to 3 $R^7$, $R^7$ is hydrogen or alkyl having 1 to 4 carbon atoms;
4) —$(CH_2CH_2O)_nCH_3$
   wherein n is an integer of 1 to 5;
5) —Z—$Ar^1$
   wherein Z is defined as the same as the above, and $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein a substituent is the same as the substituent defined for the substituted phenyl);
6) —$C_tH_{2t}COOR^7$
   wherein t and $R^7$ are defined as the same as the above;
7) —$C_tH_{2t}N(R^7)_2$
   wherein t and $R^7$ are defined as the same as the above, and two $R^7$ groups may be the same or different;
8) —CH($R^8$)—C(=O)—$R^9$
   wherein $R^8$ is hydrogen or benzoyl, and $R^9$ is phenyl, p-bromophenyl, p-chlorophenyl, p-biphenyl, p-nitrophenyl, p-benzamidephenyl, or 2-naphthyl;
9) —$C_nH_{2n}$—W—$R^{10}$
   wherein W is —CH=CH—, —CH=C($R^{10}$)— or —C≡C—, and $R^{10}$ is hydrogen or straight chain or branched alkyl or aralkyl having 1 to 12 carbon atoms, and n is defined as the same as the above; or
10) —CH($CH_2OR^{11}$)$_2$
    wherein $R^{11}$ is alkyl or acyl having 1 to 30 carbon atoms;

(C)

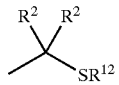

wherein $R^2$ is defined as the same as the above, two $R^2$ groups may be the same or different, $R^{12}$ is hydrogen, straight chain alkyl having 1 to 12 carbon atoms, branched alkyl having 3 to 14 carbon atoms, phenyl, substituted phenyl (wherein a substituent is defined as the same as the substituent defined for the substituted phenyl) or —C(=O)—$R^4$ (wherein $R^4$ is defined as the same as the above);

(D) —$CH_2$—$R^{13}$ wherein $R^{13}$ is the following:

(1)

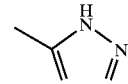

(2)

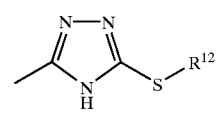

wherein $R^{12}$ is defined as the same as the above;

(3)

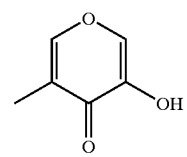

(4)

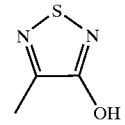

(5)

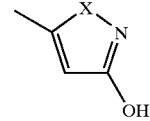

wherein X represents —O— or —S—; or (6) azide;

(E) —C($R^{14}$)$_3$ wherein $R^{14}$ represents hydrogen, fluorine, chlorine, bromine, iodine, cyano or alkyl having 1 to 4 carbon atoms, and all $R^{14}$ groups may be the same or different;

(F)

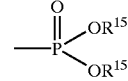

wherein $R^{15}$ represents hydrogen, alkyl having 1 to 4 carbon atoms, phenyl, substituted phenyl (wherein a substituent is the same as the substituent defined for the substituted phenyl), —$CH_2$—$OR^4$ (wherein $R^4$ defined as the same as the above), or a pharmacologically acceptable cation, and two $R^{15}$ may be the same or different;

(G) —N(R$^{16}$)$_2$ wherein R$^{16}$ is hydrogen, straight chain alkyl having 1 to 12 carbon atoms, branched alkyl having 3 to 14 carbon atoms, cycloalkyl having 3 to 12 carbon atoms, cycloalkylalkylene having 4 to 13 carbon atoms, aralkyl having 7 to 12 carbon atoms, —C(=O)—R$^4$, —C(=O)—O—R$^4$, SO$_2$—R$^4$, phenyl or substituted phenyl (wherein a substituent is defined as the same as the substituent defined for the substituted phenyl), R$^4$ is defined as the same as the above, and two R$^{16}$ groups may be the same or different (when one R$^{16}$ represents —SO$_2$—R$^4$, the other R$^{16}$ is not —SO$_2$—R$^4$);

(H) —(C(=O)CH$_2$)$_k$—H wherein k represents an integer of 1 or 2; or (I) —C(=O)—NH—CN Y is hydrogen, alkyl having 1 to 4 carbon atoms, fluorine, chlorine, bromine, formyl, methoxy, or nitro, and B is the following:

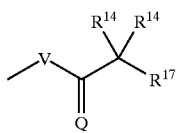
(A)

wherein V represents the following:

(1) —CH$_2$CH$_2$—;

(2) —C≡C—; or (3) —CH=C(R$^7$)—;

wherein R$^7$ is defined as the same as the above, Q is the following:

(1) =O;

(2) —OR$^3$
—R$^2$ (3) —R$^2$
—R$^2$

R$^2$ and R$^3$ are defined as the same as the above, two R$^2$ groups may be the same or different, R$^{14}$ is defined as the same as the above, two R$^{14}$ may be the same or different, and R$^{17}$ is the following:

(1) —Z—R$^{18}$ wherein Z is defined as the same as the above, R$^{18}$ is straight chain alkyl having 1 to 12 carbon atoms, branched alkyl having 3 to 14 carbon atoms, cycloalkyl having 3 to 12 carbon atoms, cycloalkylalkylene having 4 to 13 carbon atoms, cycloalkyl having 3 to 12 carbon atoms substituted by 1 to 3 R$^7$ (wherein R$^7$ is defined as the same as the above), cycloalkylalkylene having 4 to 13 carbon atoms substituted by 1 to 3 R$^7$ (wherein R$^7$ is defined as the same as the above), phenyl, substituted phenyl (wherein a substituent is the same as the substituent defined for the above substituted phenyl), α-naphthyl, 0-naphthyl, 2-pyridyl, 3-pyridyl, 4-pyridyl, α-furyl, β-furyl, α-thienyl, or β-thienyl;

(2) —Z—O—R$^{18}$ wherein Z and R$^{18}$ are defined as the same as the above;

(3) —Z—CH=C(R$^{18}$)$_2$ wherein Z and R$^{18}$ are defined as the same as the above, and two R$^{18}$ may be the same or different; or (4) —Z—C≡C—R$^{18}$ wherein Z and R$^{18}$ are defined as the same as the above;

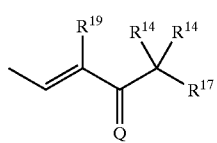
(B)

wherein Q, R$^{14}$ and R$^{17}$ are defined as the same as the above, two R$^{14}$ groups may be the same or different, and R$^{19}$ represents fluorine, chlorine, bromine, or iodine; or

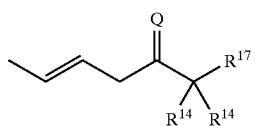
(C)

wherein Q, R$^{14}$ and R$^{17}$ are defined as the same as the above, two R$^{14}$ groups may be the same or different, E represents hydrogen or —OR$^3$ wherein R$^3$ is defined as the same as the above, A is the following:

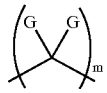

wherein m represents an integer of 0 to 5, G represents hydrogen, fluorine, chlorine, bromine, iodine, trifluoromethyl, straight chain alkyl having 1 to 4 carbon atoms, branched alkyl having 3 to 6 carbon atoms, all G groups may be the same or different, and when B of the formula (I) has the structure shown by the definition (A) (except cases where at least one R$^{14}$ is fluorine, chlorine, bromine, iodine or cyano), and R$^1$ has a structure in which all R$^2$ groups in the definition (A) are hydrogen, or when B of the formula (I) has a structure shown by the definition (A) (except cases where at least one R$^{14}$ is fluorine, chlorine, bromine, iodine or cyano), and R$^1$ has the structure shown by the definition (B), not all G groups are hydrogen; or

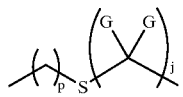

wherein j represents an integer of 1 to 4, p represents an integer of 0 or 1, G represents hydrogen, fluorine, chlorine, bromine, iodine, trifluoromethyl, straight chain alkyl having 1 to 4 carbon atoms, or branched alkyl having 3 to 6 carbon atoms, and all G groups may be the same or different; and the formula (I) represents a d-, l- or dl-isomer].

The present invention also provides an anti Helicobacter agent, a platelet function potentiating agent, or cervical ripening agent, which contains any of the above PGI$_2$ derivatives as an active ingredient.

BEST MODE FOR CARRYING OUT THE INVENTION

Figure 1:
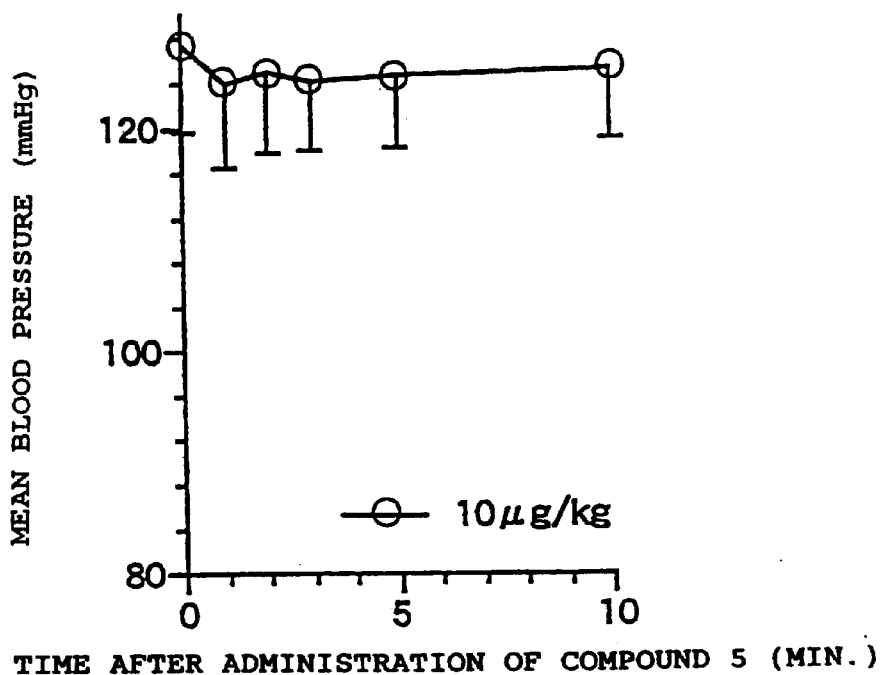
FIG. 1 shows change in mean blood pressure of monkeys after the intravenous administration of compound 5.

In the compounds represented by the above formula (I) obtained in the present invention, examples of straight chain alkyl having 1 to 4 carbon atoms represented by $R^2$ or G include methyl, ethyl, propyl, and butyl.

Examples of branched alkyl having 3 or 4 carbon atoms represented by $R^2$ include isopropyl, isobutyl, tert-butyl, and the like.

Examples of straight chain alkyl having 1 to 12 carbon atoms represented by $R^4$, $R^5$, $R^{12}$, $R^{16}$ or $R^{18}$ include methyl, ethyl, propyl, butyl, pentyl, hexyl, heptyl, octyl, dodecyl, and the like.

Examples of branched alkyl having 3 to 14 carbon atoms represented by $R^4$, $R^5$, $R^{12}$, $R^{16}$ or $R^{18}$ include isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 2-methylnonyl, 1-methyldecanyl, 2-methyldecanyl, 1,1-dimethylbutyl, 2,2-dimethylbutyl, 3,3-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimetylhexyl, 1,1-dimethylheptyl, 2,2-dimethylheptyl, 3,3-dimethylheptyl, 4,4-dimethylheptyl, 5,5-dimethylheptyl, 6,6-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl, and the like.

Examples of cycloalkyl having 3 to 12 carbon atoms represented by $R^4$, $R^6$, $R^{16}$ or $R^{18}$ include cyclopropyl, cyclobutyl, cyclopentyl, cyclohexyl, cycloheptyl, cyclooctyl, cyclononyl, cyclododecyl, and the like.

Examples of aralkyl having 7 to 12 carbon atoms represented by $R^4$ or $R^{16}$ include benzyl, phenethyl, 3-phenylpropyl, 6-phenylhexyl, p-methylbenzyl, p-ethylbenzyl, p-propylbenzyl, p-pentylbenzyl, 3,5-dimethylbenzyl, 3,5-diethylbenzyl, and the like.

Examples of alkyl having 1 to 4 carbon atoms as a substituent of substituted phenyl, or represented by $R^3$, $R^7$, $R^{14}$, $R^{15}$ or Y include methyl, ethyl, propyl, butyl, isopropyl, isobutyl, tert-butyl, and the like.

Examples of acyl having 1 to 4 carbon atoms represented by $R^3$ include formyl, acetyl, propionyl, butyroyl, and the like.

Examples of aroyl having 7 to 16 carbon atoms represented by $R^3$ include benzoyl, phenylacetyl, 3-phenylpropionyl, 10-phenyldecanoyl, p-phenylbenzoyl, α-naphthoyl, β-naphthoyl, and the like.

Examples of aralkyl having 7 to 16 carbon atoms represented by $R^3$ include benzyl, phenethyl, 3-phenylpropyl, 6-phenylhexyl, 10-phenyldecyl, p-methylbenzyl, p-ethylbenzyl, p-propylbenzyl, p-pentylbenzyl, p-nonylbenzyl, 3,5-dimethylbenzyl, 3,5-diethylbenzyl, 3,5-dibutylbenzyl, p-phenylbenzyl, and the like.

Where $R^5$ or $R^{15}$ is a pharmacologically acceptable cation, $R^5$ or $R^{15}$ is a metal cation, an ammonium cation, a amine cation, or a quaternary ammonium cation. $R^5$ or $R^{15}$ is preferably a metal cation or amine cation.

A preferred metal cation is derived from an alkali metal (for example, lithium, sodium, or potassium) or an alkali earth metal (for example, magnesium or calcium). Of course, cations derived from other metals, for example, such as aluminum, zinc, iron, and the like are included in the present invention. However, the cation is not limited.

A pharmacologically acceptable amine cation is derived from a primary, secondary, or tertiary amine. Preferred examples of amines include aliphatic, alicyclic, aromatic or heterocyclic amines having up to 18 carbon atoms, such as methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, 1-methylpiperidine, 4-ethylmorpholine, 1-isopropylpyrrolidine, 2-methylpyrrolidine, 1,4-dimethylpiperadine, 2-methylpiperidine, water-soluble amines and amine containing hydrophilic groups such as mono-, di- and triethanolamine, ethyldiethanolamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl) diethanolamine, galactamine, N-methylglutamine, N-methylglucosamine, ephedrine, phenylephrine, epinephrine, procain, and the like, basic amino acids such as lysine, arginine, and the like. However, amines are not limited.

Examples of cycloalkyl having 1 to 12 carbon atoms, substituted by 1 to 3 $R^7$ groups represented by $R^6$ or $R^{18}$ include 2-methylcyclopropyl, 3-methylcyclobutyl, 3-methylcyclopentyl, 4-methylcyclohexyl, 4-methylcycloheptyl, 5-methylcyclooctyl, 5-methylcyclononyl, and the like.

Examples of straight chain or branched alkyl or aralkyl having 1 to 12 carbon atoms represented by $R^{10}$ include methyl, ethyl, propyl, butyl, pentyl, hexyl, heptyl, octyl, dodecyl, isopropyl, isobutyl, tert-butyl, 4-methylpentyl, 5-methylhexyl, 6-methylheptyl, 7-methyloctyl, benzyl, phenethyl, 3-phenylpropyl, 6-phenylhexyl, p-methylbenzyl, p-ethylbenzyl, p-propylbenzyl, p-pentylbenzyl, 3,5-dimethylbenzyl, 3,5-diethylbenzyl, and the like.

Examples of alkyl or acyl having 1 to 30 carbon atoms represented by $R^{11}$ include methyl, ethyl, propyl, butyl, pentyl, hexyl, octyl, hexadecanyl, octaicosanyl, acetyl, octanoyl, decanoyl, palmitoyl, icosanoyl, hexaicosanoyl, and the like.

Examples of cycloalkylalkylene having 4 to 13 carbon atoms represented by $R^{16}$ or $R^{18}$ include cyclopropylmethyl, cyclobutylmethyl, cyclopentylmethyl, cyclohexylmethyl, cycloheptylmethyl, cyclododecylmethyl, 2-cyclopropylethyl, 2-cyclobutylethyl, 2-cyclopentylethyl, 2-cyclohexylethyl, 2-cycloheptylethyl, 3-cyclopropylpropyl, 3-cyclobutylpropyl, 3-cyclopentylpropyl, 3-cyclohexylpropyl, 3-cycloheptylpropyl, 6-cyclopropylhexyl, 6-cyclobutylhexyl, 6-cyclopentylhexyl, 6-cyclohexylhexyl, 6-cycloheptylhexyl, and the like.

Examples of cycloalkylalkylene having 4 to 13 carbon atoms, substituted by 1 to 3 $R^7$ groups, represented by $R^{18}$ include 2-methylcyclopropylmethyl, 3-methylcyclobutylmethyl, 3-methylcyclopentylmethyl, 4-methylcyclohexylmethyl, 4-methylcycloheptylmethyl, 5-methylcyclooctylmethyl, 5-methylcyclononylmethyl, and the like.

Examples of branched alkyl having 3 to 6 carbon atoms represented by G include isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1,1-dimethylbutyl, 2,2-dimethylbutyl, 3,3-dimethylbutyl, and the like.

Examples of $R^2$ include hydrogen, methyl, ethyl, propyl, butyl, isopropyl, isobutyl, tert-butyl, trifluoromethyl, acetyl, propionyl, benzoyl, phenylacetyl, methoxycarbonyl, ethoxycarbonyl, and the like. $R^2$ is preferably hydrogen, methyl, ethyl, propyl, butyl, isopropyl, isobutyl, tert-butyl, or trifluoromethyl, more preferably hydrogen, methyl, ethyl, propyl, butyl or trifluoromethyl, and most preferably hydrogen or methyl.

Examples of $R^3$ include hydrogen, methyl, ethyl, propyl, butyl, isopropyl, isobutyl, tert-butyl, formyl, acetyl, propionyl, butyloyl, benzoyl, phenylacetyl, 3-phenylpropionyl, 10-phenyldecanoyl, p-phenylbenzoyl, α-naphthoyl, β-naphthoyl, benzyl, phenethyl, 3-phenylpropyl, 6-phenylhexyl, 10-phenyldecyl, p-methylbenzyl, p-ethylbenzyl, p-propylbenzyl, p-pentylbenzyl, p-nonylbenzyl, 3,5-dimethylbenzyl, 3,5-diethylbenzyl, 3,5-dibutylbenzyl, p-phenylbenzyl, tetrahydropyranyl, tetrahydrofuranyl, 1-ethoxyethyl, allyl, tert-butyl, tert-butyldimethylsilyl, and the like. $R^3$ is preferably hydrogen, acetyl, propionyl, butyloyl, benzoyl, phenylacetyl, 3-phenylpropionyl, 10-phenyldecanoyl, p-phenylbenzoyl, α-naphthoyl, β-naphthoyl, tetrahydropyranyl, tetrahydrofuranyl, 1-ethoxyethyl, allyl, or tert-butyldimethylsilyl, more preferably hydrogen, acetyl, tetrahydropyranyl, tetrahydrofuranyl, tert-butyldimethylsilyl, and most preferably hydrogen.

Examples of $R^4$ include methyl, ethyl, propyl, butyl, pentyl, hexyl, heptyl, octyl, dodecyl, isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 2-methylnonyl, 1-methyldecanyl, 2-methyldecanyl, 1,1-dimethylbutyl, 2,2-dimethylbutyl, 3,3-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 1,1-dimethylheptyl, 2,2-dimethylheptyl, 3,3-dimethylheptyl, 4,4-dimethylheptyl, 5,5-dimethylheptyl, 6,6-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl, cyclopropyl, cyclobutyl, cyclopentyl, cyclohexyl, cycloheptyl, cyclooctyl, cyclononyl, cyclododecyl, benzyl, phenethyl, 3-phenylpropyl, 6-phenylhexyl, p-methylbenzyl, p-ethylbenzyl, p-propylbenzyl, p-pentylbenzyl, 3,5-dimethylbenzyl, 3,5-diethylbenzyl, phenyl, p-fluorophenyl, p-nitrophenyl, p-methoxyphenyl, and the like. $R^4$ is preferably methyl, ethyl, propyl, butyl, or phenyl, more preferably methyl, ethyl, or phenyl, and most preferably methyl or phenyl.

Preferred examples of $R^5$ include hydrogen, lithium ion, sodium ion, potassium ion, magnesium ion, calcium ion, cations derived from amines (for example, methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, 1-methylpiperidine, 4-ethylmorpholine, 1-isopropylpyrrolidine, 2-methylpyrrolidine, 1,4-dimethylpiperadine, 2-methylpiperidine, mono-, di- and triethanolamine, ethyldiethanolamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl) diethanolamine, galaclamine, N-methylglutamine, N-methylglucosamine, ephedrine, phenylephrine, epinephrine, procain, lysine, arginine, and the like), methyl, ethyl, propyl, butyl, pentyl, hexyl, heptyl, octyl, dodecyl, and the like. $R^5$ is more preferably hydrogen, lithium ion, sodium ion, potassium ion, magnesium ion, calcium ion, a cation derived from amine (triethylamine, ethylenediamine, diethylenetriamine, or mono-, di- or triethanolamine), methyl, ethyl, propyl, or butyl, and most preferably hydrogen, sodium ion, or methyl.

Examples of $R^6$ include cyclopropyl, cyclobutyl, cyclopentyl, cyclohexyl, cycloheptyl, cyclooctyl, cyclononyl, cyclododecyl, 2-methylcyclopropyl, 3-methylcyclobutyl, 3-methylcyclopentyl, 4-methylcyclohexyl, 4-methylcycloheptyl, 5-methylcyclooctyl, 5-methylcyclononyl, and the like. $R^6$ is preferably cyclopentyl, cyclohexyl, cylheptyl, 3-methylcyclopentyl, 4-methylcyclohexyl, 4-methylcycloheptyl, and more preferably cyclohexyl or 4-methylcyclohexyl, and most preferably cyclohexyl.

Examples of $R^7$ include hydrogen, methyl, ethyl, propyl, butyl, isopropyl, isobutyl, tert-butyl, and the like. $R^7$ is preferably hydrogen, methyl, ethyl, isopropyl, or tert-butyl, more preferably hydrogen, methyl, or ethyl, and most preferably hydrogen or methyl.

$R^8$ represents hydrogen or benzoyl. It is particularly preferably hydrogen.

$R^9$ represents phenyl, p-bromophenyl, p-chlorophenyl, p-biphenyl, p-nitrophenyl, p-benzamidephenyl, or 2-naphthyl. $R^9$ is preferably phenyl, p-bromophenyl, p-chlorophenyl, p-biphenyl, or p-nitrophenyl, more preferably phenyl, p-chlorophenyl, or p-biphenyl, and most preferably phenyl.

Examples of $R^{10}$ include hydrogen, methyl, ethyl, propyl, butyl, pentyl, hexyl, heptyl, octyl, dodecyl, isopropyl, isobutyl, tert-butyl, 4-methylpentyl, 5-methylhexyl, 6-methylheptyl, 7-methyloctyl, benzyl, phenethyl, 3-phenylpropyl, 6-phenylhexyl, p-methylbenzyl, p-ethylbenzyl, p-propylbenzyl, p-pentylbenzyl, 3,5-dimethylbenzyl, 3,5-diethylbenzyl, and the like. $R^{10}$ is preferably hydrogen, methyl, ethyl, propyl, isopropyl, isobutyl, tert-butyl, benzyl, phenethyl, or 3-phenylpropyl, more preferably hydrogen, methyl, ethyl, isopropyl, isobutyl, benzyl, or phenethyl, and most preferably hydrogen, methyl, isopropyl, or benzyl.

Examples of $R^{11}$ include methyl, ethyl, propyl, butyl, pentyl, hexyl, octyl, hexadecanyl, octaicosanyl, acetyl, octanonyl, decanoyl, palmitoyl, icosanoyl, hexaicosanoyl, and the like. $R^{11}$ is preferably methyl, ethyl, propyl, acetyl, octanoyl, or decanoyl, more preferably methyl, ethyl, acetyl, or octanoyl, and most preferably methyl or acetyl.

Examples of $R^{12}$ include hydrogen, methyl, ethyl, propyl, butyl, pentyl, hexyl, heptyl, octyl, dodecyl, isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 2-methylnonyl, 1-methyldecanyl, 2-methyldecanyl, 1,1-dimethylbutyl, 2,2-dimethylbutyl, 3,3-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 1,1-dimethylheptyl, 2,2-dimethylheptyl, 3,3- dimethylheptyl, 4,4-dimethylheptyl, 5,5-dimethylheptyl, 6,6-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl, phenyl, p-fluorophenyl, p-nitrophenyl, p-methoxyphenyl, acetyl, propionyl, and the like. $R^{12}$ is preferably hydrogen, methyl, ethyl, propyl, butyl, phenyl, acetyl, or propionyl, more preferably hydrogen, methyl, ethyl, propyl, phenyl, or acetyl, and most preferably hydrogen, methyl, phenyl or acetyl.

Examples of $R^{14}$ include hydrogen, fluorine, chlorine, bromine, iodine, cyano, methyl, ethyl, propyl, butyl, isopropyl, isobutyl, tert-butyl, and the like. $R^{14}$ is preferably hydrogen, fluorine, cyano, methyl, ethyl, propyl, butyl, isopropyl, isobutyl, or tert-butyl, more preferably hydrogen, fluorine, methyl, ethyl, or isopropyl, and most preferably hydrogen, fluorine, or methyl.

Examples of $R^{15}$ include hydrogen, methyl, ethyl, propyl, butyl, isopropyl, isobutyl, tert-butyl, phenyl, p-fluorophenyl, p-nitrophenyl, p-methoxyphenyl, methoxymethyl, ethoxymethyl, lithium ion, sodium ion, potassium ion, magnesium ion, calcium ion, cations derived from amines (for example, methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, 1-methylpiperidine, 4-ethylmorpholine, 1-isopropylpyrrolidine, 2-methylpyrrolidine, 1,4-dimethylpiperadine, 2-methylpiperidine, mono-, di- and triethanolamine, ethyldiethanolamine, N-butylethanolamine, 2-amino-1-butanol, 2-amino-2-ethyl-1,3-propanediol, tris(hydroxymethyl)aminomethane, N-phenylethanolamine, N-(p-tert-amylphenyl) diethanolamine, galaclamine, N-methylglutamine, N-methylglucosamine, ephedrine, phenylephrine, epinephrine, procain, lysine, arginine, and the like). $R^{15}$ is preferably hydrogen, methyl, ethyl, propyl, butyl, isopropyl, isobutyl, tert-butyl, lithium ion, sodium ion, potassium ion, magnesium ion, calcium ion, a cation derived from amine (triethylamine, ethylenediamine, diethylenetriamine, or mono-, di- or triethanolamine), more preferably hydrogen, methyl, isopropyl, lithium ion, sodium ion, potassium ion, magnesium ion, or calcium ion, and most preferably hydrogen, methyl, or sodium ion.

Examples of $R^{16}$ include hydrogen, methyl, ethyl, propyl, butyl, pentyl, hexyl, heptyl, octyl, dodecyl, isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 2-methylnonyl, 1-methyldecanyl, 2-methyldecanyl, 1,1-dimethylbutyl, 2,2-dimethylbutyl, 3,3-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 1,1-dimethylheptyl, 2,2-dimethylheptyl, 3,3-dimethylheptyl, 4,4-dimethylheptyl, 5,5-dimethylheptyl, 6,6-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl, cyclopropyl, cyclobutyl, cyclopentyl, cyclohexyl, cycloheptyl, cyclooctyl, cyclononyl, cyclododecyl, cyclopropylmethyl, cyclobutylmethyl, cyclopentylmethyl, cyclohexylmethyl, cycloheptylmethyl, cyclododecylmethyl, 2-cyclopropylethyl, 3-cyclobutylethyl, 2-cyclopentylethyl, 2-cyclohexylethyl, 2-cycloheptylethyl, 3-cyclopropylpropyl, 3-cyclobutylpropyl, 3-cyclopentylpropyl, 3-cylcohexylpropyl, 3-cycloheptylpropyl, 6-cyclopropylhexyl, 6-cyclobutylhexyl, 6-cyclopentylhexyl, 6-cyclohexylhexyl, 6-cycloheptylhexyl, benzyl, phenethyl, 3-phenylpropyl, 6-phenylhexyl, p-methylbenzyl, p-ethylbenzyl, p-propylbenzyl, p-pentylbenzyl, 3,5-dimethylbenzyl, 3,5-diethylbenzyl, acetyl, propionyl, benzoyl, phenylacetyl, methoxycarbonyl, ethoxycarbonyl, methylsulfonyl, ethylsulfonyl, phenylsulfonyl, phenyl, p-fluorophenyl, p-nitrophenyl, p-methoxyphenyl, and the like. $R^{16}$ is preferably hydrogen, p-methylbenzyl, p-ethylbenzyl, p-propylbenzyl, p-pentylbenzyl, 3,5-dimethylbenzyl, 3,5-diethylbenzyl, acetyl, propionyl, benzoyl, phenylacetyl, methoxycarbonyl, ethoxycarbonyl, methylsulfonyl, ethylsulfonyl, phenylsulfonyl, phenyl, p-fluorophenyl, p-nitrophenyl, or p-methoxyphenyl, more preferably hydrogen, acetyl, propionyl, benzoyl, phenylacetyl, methylsulfonyl, ethylsulfonyl, phenylsulfonyl, and most preferably hydrogen, acetyl, benzoyl, methylsulfonyl, or phenylsulfonyl.

Examples of $R^{18}$ include methyl, ethyl, propyl, butyl, pentyl, hexyl, heptyl, octyl, dodecyl, isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 2-methylnonyl, 1-methyldecanyl, 2-methyldecanyl, 1,1-dimethylbutyl, 2,2-dimethylbutyl, 3,3-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 1,l-dimethylheptyl, 2,2-dimethylheptyl, 3,3-dimethylheptyl, 4,4-dimethylheptyl, 5,5-dimethylheptyl, 6,6-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl, cyclopropyl, cyclobutyl, cyclopentyl, cyclohexyl, cycloheptyl, cyclooctyl, cyclononyl, cyclododecyl, cyclopropylmethyl, cyclobutylmethyl, cyclopentylmethyl, cyclohexylmethyl, cycloheptylmethyl, cyclododecylmethyl, 2-cyclopropylethyl, 2-cyclobutylethyl, 2-cyclopentylethyl, 2-cyclohexylethyl, 2-cycloheptylethyl, 3-cyclopropylpropyl, 3-cyclobutylpropyl, 3-cyclopentylpropyl, 3-cylcohexylpropyl, 3-cycloheptylpropyl, 6-cyclopropylhexyl, 6-cyclobutylhexyl, 6-cyclopentylhexyl, 6-cyclohexylhexyl, 6-cycloheptylhexyl, 2-methylcyclopropyl, 3-methylcyclobutyl, 3-methylcyclopentyl, 4-methylcyclohexyl, 4-methylcycloheptyl, 5-methylcyclooctyl, 5-methylcyclononyl, 2-methylcyclopropylmethyl, 3-methylcyclobutylmethyl, 3-methylcyclopentylmethyl, 4-methylcyclohexylmethyl, 4-methylcycloheptylmethyl, 5-methylcyclooctylmethyl, 5-methylcyclononylmethyl, phenyl, p-fluorophenyl, p-nitophenyl, p-methoxyphenyl, α-naphthyl, β-naphthyl, 2-pyridyl, 3-pyridyl, 4-pyridyl, α-furyl, β-furyl, α-thienyl, β-thienyl, and the like. $R^{18}$ is preferably methyl, ethyl, propyl, butyl, pentyl, hexyl, isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1,1-dimethylbutyl, 2,2-dimethylbutyl, 3,3-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, cyclopropyl, cyclobutyl, cyclopentyl, cyclohexyl, cycloheptyl, cyclooctyl, cyclononyl, cyclododecyl, cyclopropylmethyl, cyclobutylmethyl, cyclopentylmethyl, cyclohexylmethyl, 2-methylcyclopropyl, 3-methylcyclobutyl, 3-methylcyclopentyl, 4-methylcyclohexyl, 4-methylcycloheptyl, 5-methylcyclooctyl, 5-methylcyclononyl, 2-methylcyclopropylmethyl, 3-methylcyclobutylmethyl, 3-methylcyclopentylmethyl, phenyl, p-fluorophenyl, p-nitrophenyl, and p-methoxyphenyl. $R^{18}$ is more preferably methyl, ethyl, propyl, butyl, isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1,1-dimethylbutyl, 2,2-dimethylbutyl, 3,3-dimethylbutyl, cyclopropyl, cyclobutyl, cyclopentyl, cyclohexyl, cycloheptyl, cyclooctyl, cyclononyl, cyclopropylmethyl, cyclobutylmethyl, cyclopentylmethyl, cyclohexylmethyl, 2-methylcyclopropyl, 3-methylcyclobutyl, 3-methylcyclopentyl, 4-methylcyclohexyl, 4-methylcycloheptyl, 5-methylcyclooctyl, 2-methylcyclopropylmethyl, 3-methylcyclobutylmethyl, 3-methylcyclopentylmethyl, or phenyl. $R^{18}$ is most preferably cyclopentyl, cyclohexyl, cycloheptyl, or phenyl.

$R^{19}$ represents fluorine, chlorine, bromine, or iodine. $R^{19}$ is preferably fluorine, chlorine, or bromine, more preferably fluorine or chlorine, and most preferably fluorine.

Examples of G include hydrogen, fluorine, chlorine, bromine, iodine, trifluoromethyl, methyl, ethyl, propyl, butyl, isopropyl, isobutyl, tert-butyl, 1-methylbutyl, 2-methylbutyl, 3-methylbutyl, 1-methylpentyl, 2-methylpentyl, 3-methylpentyl, 4-methylpentyl, 1,1-dimethylbutyl, 2,2-dimethylbutyl, 3,3-dimethylbutyl, and the like. G is preferably hydrogen, fluorine, chlorine, bromine, iodine, trifluoromethyl, methyl, ethyl, propyl, or butyl, more preferably hydrogen, fluorine, methyl, ethyl, propyl, or butyl, and most preferably hydrogen or fluorine.

Although examples of the compounds represented by the above formula (I) obtained in the present invention are shown in Tables 1 to 9 below, the present invention is not limited to these examples.

TABLE 1

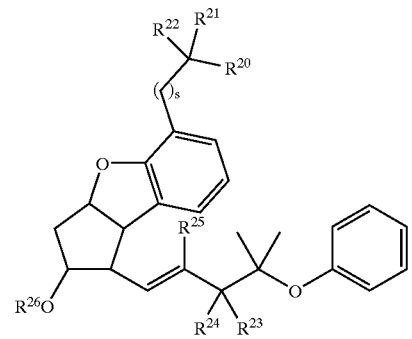

| R20 | R21 | R22 | R23 | R24 | R25 | R26 | S |
|---|---|---|---|---|---|---|---|
| OH | Me | H | OH | H | H | H | 2 |
| OH | Me | Me | OH | H | H | H | 2 |
| OH | CF3 | H | OH | H | H | H | 2 |
| CH2OH | Me | H | OH | H | H | H | 1 |
| CH2OH | Me | Me | OH | H | H | H | 1 |
| CH2OH | Me | Me | OTBS | H | H | TBS | 1 |
| COOH | H | H | OH | H | F | H | 1 |
| COOH | H | H | OH | H | Cl | H | 1 |
| COOMe | H | H | OH | H | F | H | 1 |
| COOMe | H | H | OH | H | Cl | H | 1 |
| COOMe | H | H | O | O | F | Ac | 1 |
| COOMe | H | H | O | O | Cl | Ac | 1 |
| COOH | Me | H | OH | H | H | H | 1 |
| COOMe | Me | H | OH | H | H | H | 1 |
| COOMe | Me | Me | OTBS | H | H | TBS | 1 |
| SH | H | H | OH | H | H | H | 2 |
| SMe | H | H | OH | H | H | H | 2 |
| SMe | H | H | OTBS | H | H | TBS | 2 |
| SAc | H | H | OH | H | H | H | 2 |
| SAc | H | H | OTBS | H | H | TBS | 2 |
| SPh | H | H | OH | H | H | H | 2 |
| SPh | H | H | OTBS | H | H | TBS | 2 |
| CN | H | H | OH | H | H | H | 1 |
| CN | H | H | OTBS | H | H | TBS | 1 |
| CN | CN | H | OH | H | H | H | 2 |

TABLE 1-continued

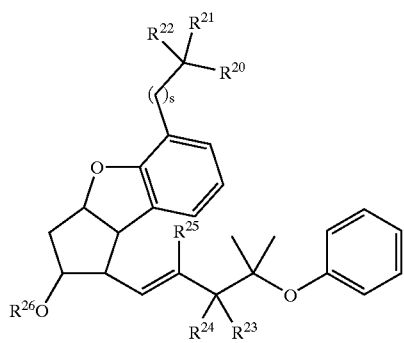

| R20 | R21 | R22 | R23 | R24 | R25 | R26 | S |
|---|---|---|---|---|---|---|---|
| CN | CN | H | OTBS | H | H | TBS | 2 |
| (5-methyl-tetrazolyl) | H | H | OH | H | H | H | 1 |
| N3 | H | H | OH | H | H | H | 2 |
| N3 | H | H | OTBS | H | H | TBS | 2 |
| H | H | H | OH | H | H | H | 2 |
| H | H | H | OTBS | H | H | TBS | 2 |
| F | H | H | OH | H | H | H | 2 |
| P(O)(OH)—OMe | H | H | OH | H | H | H | 1 |
| P(O)(OMe)2 | H | H | OH | H | H | H | 1 |
| P(O)(OMe)2 | H | H | O | O | H | Ac | 1 |
| NH2 | H | H | OH | H | H | H | 2 |
| NH2 | H | H | OTBS | H | H | TBS | 2 |
| N(H)—Ac | H | H | OH | H | H | H | 2 |
| N(H)—Ac | H | H | OTBS | H | H | TBS | 2 |
| N(H)—Bz | H | H | OH | H | H | H | 2 |
| N(H)—Bz | H | H | OTBS | H | H | TBS | 2 |
| N(H)—SO2Me | H | H | OH | H | H | H | 2 |
| N(H)—SO2Me | H | H | OTBS | H | H | TBS | 2 |
| N(H)—SO2Ph | H | H | OH | H | H | H | 2 |
| N(H)—SO2Ph | H | H | OTBS | H | H | TBS | 2 |
| C(O)—Me | H | H | OH | H | H | H | 1 |
| C(O)—CH2—C(O)—Me | H | H | OH | H | H | H | 1 |
| C(O)—CH2—C(O)—Me | H | H | OTBS | H | H | TBS | 1 |
| C(O)—N(H)—CN | H | H | OH | H | H | H | 1 |
| C(O)—N(H)—CN | H | H | OTBS | H | H | TBS | 1 |

TABLE 2

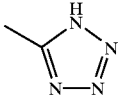

| R20 | R23 | R24 | R25 | R26 | R27 | R28 | R29 | U | r |
|---|---|---|---|---|---|---|---|---|---|
| COOH | OH | H | Br | H | H | H | n-Bu | CH2 | 0 |
| COOMe | OH | H | Br | H | H | H | n-Bu | CH2 | 0 |
| COOMe | O | O | Br | Ac | H | H | n-Bu | CH2 | 0 |
| CH2OH | OH | H | H | H | Me | Me | OPh | S | 0 |
| CH2OH | OTBS | H | H | TBS | Me | Me | OPh | S | 0 |
| COOH | OH | Me | H | H | H | H | n-Pr | CH2 | 1 |
| COOMe | OH | Me | H | Ac | H | H | n-Pr | CH2 | 1 |

TABLE 2-continued
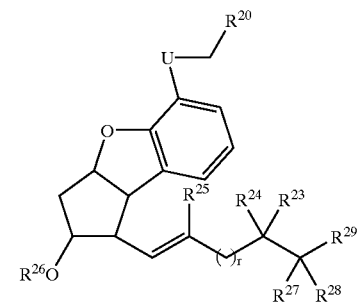
| R20 | R23 | R24 | R25 | R26 | R27 | R28 | R29 | U | r |
|-----|-----|-----|-----|-----|-----|-----|-----|---|---|
| CN | OTBS | H | H | TBS | H | H | 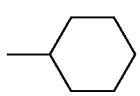 | CH2 | 0 |
| CN | OH | H | H | H | H | H | 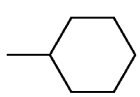 | CH2 | 0 |
| COOMe | O | O | H | Ac | H | H | 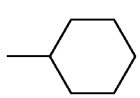 | S | 0 |
| COOMe | OH | H | H | Ac | H | H | 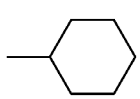 | S | 0 |
| COOMe | OH | H | H | H | H | H | 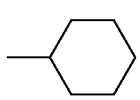 | S | 0 |
| COOMe | O | O | H | TBS | F | F | OPh | CH2 | 0 |
| COOMe | OH | H | H | H | F | F | OPh | CH2 | 0 |
| COOH | OH | H | H | H | F | F | OPh | CH2 | 0 |
TABLE 3
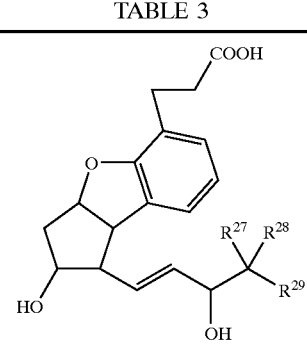
| R27 | R28 | R29 | R27 | R28 | R29 |
|-----|-----|-----|-----|-----|-----|
| F | H |  | F | H |  |
| F | F | 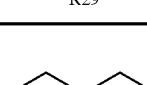 | F | F |  |
TABLE 3-continued
| R27 | R28 | R29 | R27 | R28 | R29 |
|-----|-----|-----|-----|-----|-----|
| F | H | 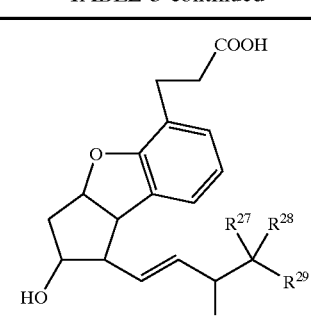 | F | H |  |

TABLE 3-continued

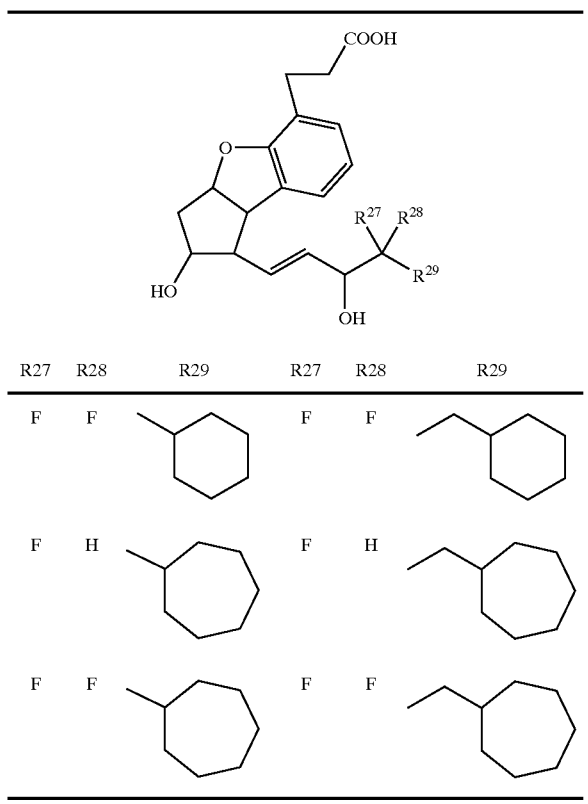

| R27 | R28 | R29 | R27 | R28 | R29 |
|---|---|---|---|---|---|
| F | F | cyclohexyl-CH | F | F | cyclohexyl-CH2 |
| F | H | cycloheptyl-CH | F | H | cycloheptyl-CH2 |
| F | F | cycloheptyl-CH | F | F | cycloheptyl-CH2 |

TABLE 4

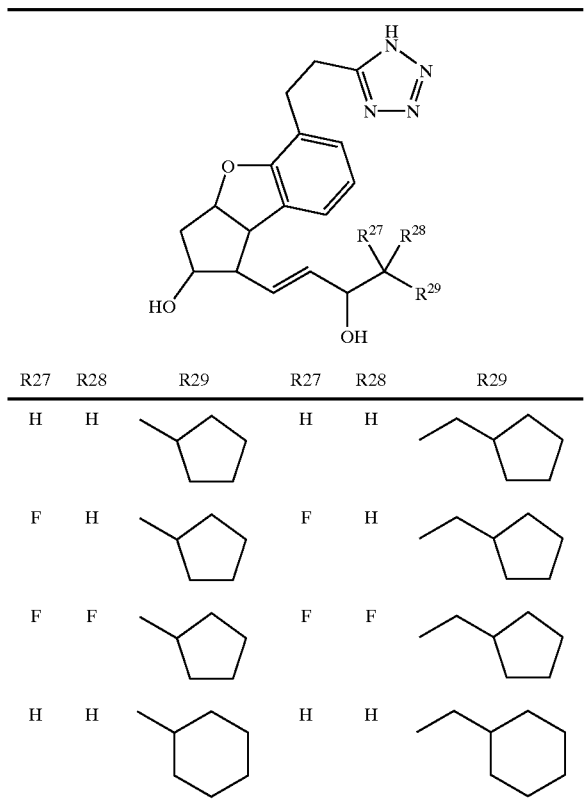

| R27 | R28 | R29 | R27 | R28 | R29 |
|---|---|---|---|---|---|
| H | H | cyclopentyl-CH | H | H | cyclopentyl-CH2 |
| F | H | cyclopentyl-CH | F | H | cyclopentyl-CH2 |
| F | F | cyclopentyl-CH | F | F | cyclopentyl-CH2 |
| H | H | cyclohexyl-CH | H | H | cyclohexyl-CH2 |

TABLE 4-continued

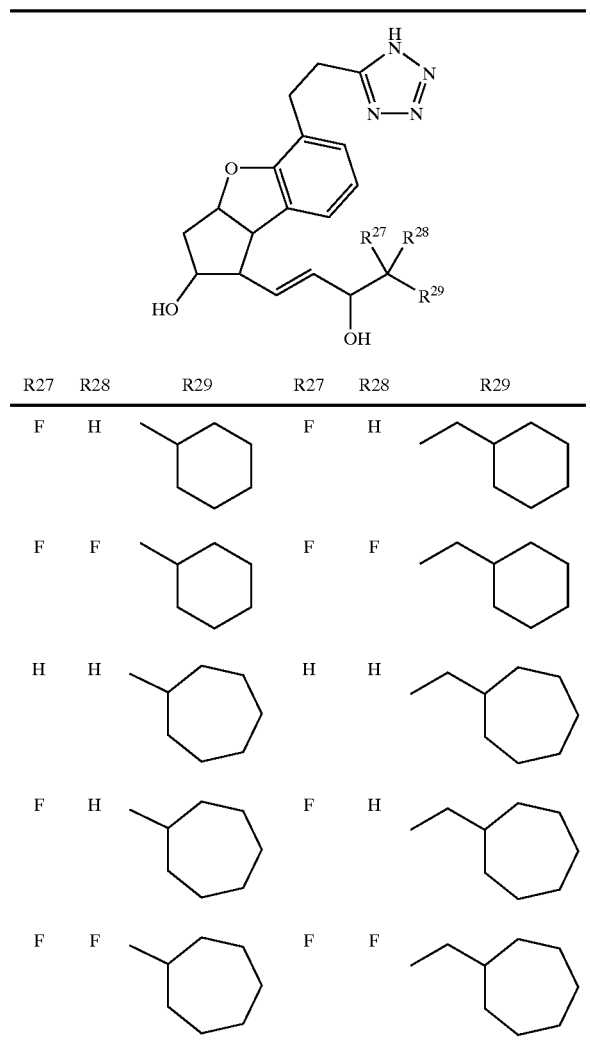

| R27 | R28 | R29 | R27 | R28 | R29 |
|---|---|---|---|---|---|
| F | H | cyclohexyl-CH | F | H | cyclohexyl-CH2 |
| F | F | cyclohexyl-CH | F | F | cyclohexyl-CH2 |
| H | H | cycloheptyl-CH | H | H | cycloheptyl-CH2 |
| F | H | cycloheptyl-CH | F | H | cycloheptyl-CH2 |
| F | F | cycloheptyl-CH | F | F | cycloheptyl-CH2 |

TABLE 5

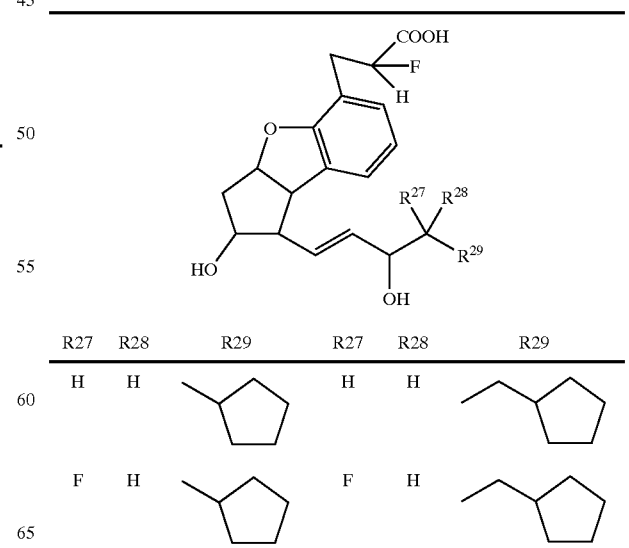

| R27 | R28 | R29 | R27 | R28 | R29 |
|---|---|---|---|---|---|
| H | H | cyclopentyl-CH | H | H | cyclopentyl-CH2 |
| F | H | cyclopentyl-CH | F | H | cyclopentyl-CH2 |

TABLE 5-continued

| R27 | R28 | R29 | R27 | R28 | R29 |
|---|---|---|---|---|---|
| F | F | cyclopentyl | F | F | cyclopentylmethyl |
| H | H | cyclohexyl | H | H | cyclohexylmethyl |
| F | H | cyclohexyl | F | H | cyclohexylmethyl |
| F | F | cyclohexyl | F | F | cyclohexylmethyl |
| H | H | cycloheptyl | H | H | cycloheptylmethyl |
| F | H | cycloheptyl | F | H | cycloheptylmethyl |
| F | F | cycloheptyl | F | F | cycloheptylmethyl |

TABLE 6

| R27 | R28 | R29 | R27 | R28 | R29 |
|---|---|---|---|---|---|
| H | H | cyclopentyl | H | H | cyclopentylmethyl |
| F | H | cyclopentyl | F | H | cyclopentylmethyl |
| F | F | cyclopentyl | F | F | cyclopentylmethyl |
| H | H | cyclohexyl | H | H | cyclohexylmethyl |
| F | H | cyclohexyl | F | H | cyclohexylmethyl |
| F | F | cyclohexyl | F | F | cyclohexylmethyl |
| H | H | cycloheptyl | H | H | cycloheptylmethyl |
| F | H | cycloheptyl | F | H | cycloheptylmethyl |
| F | F | cycloheptyl | F | F | cycloheptylmethyl |

TABLE 7
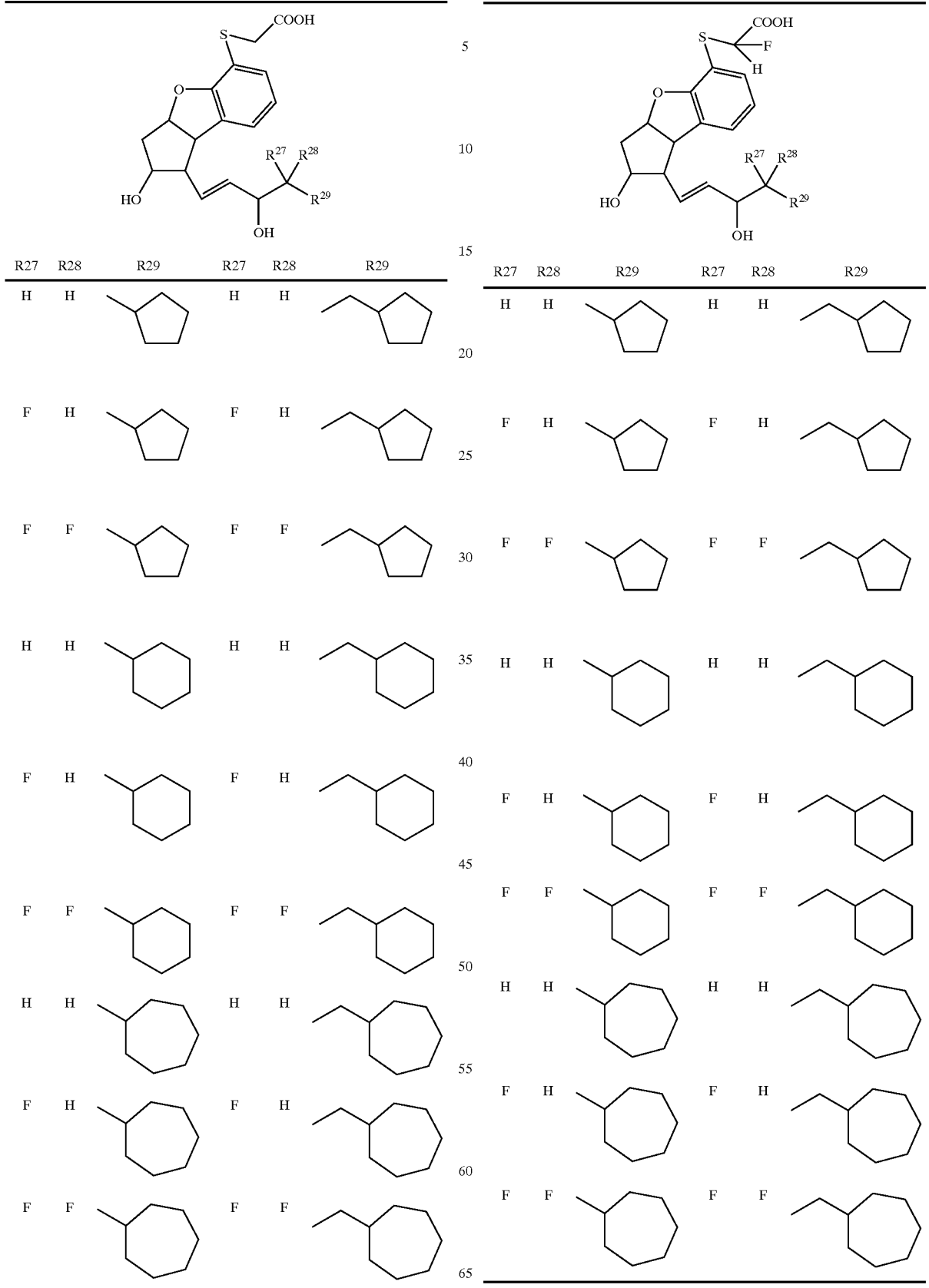
TABLE 8
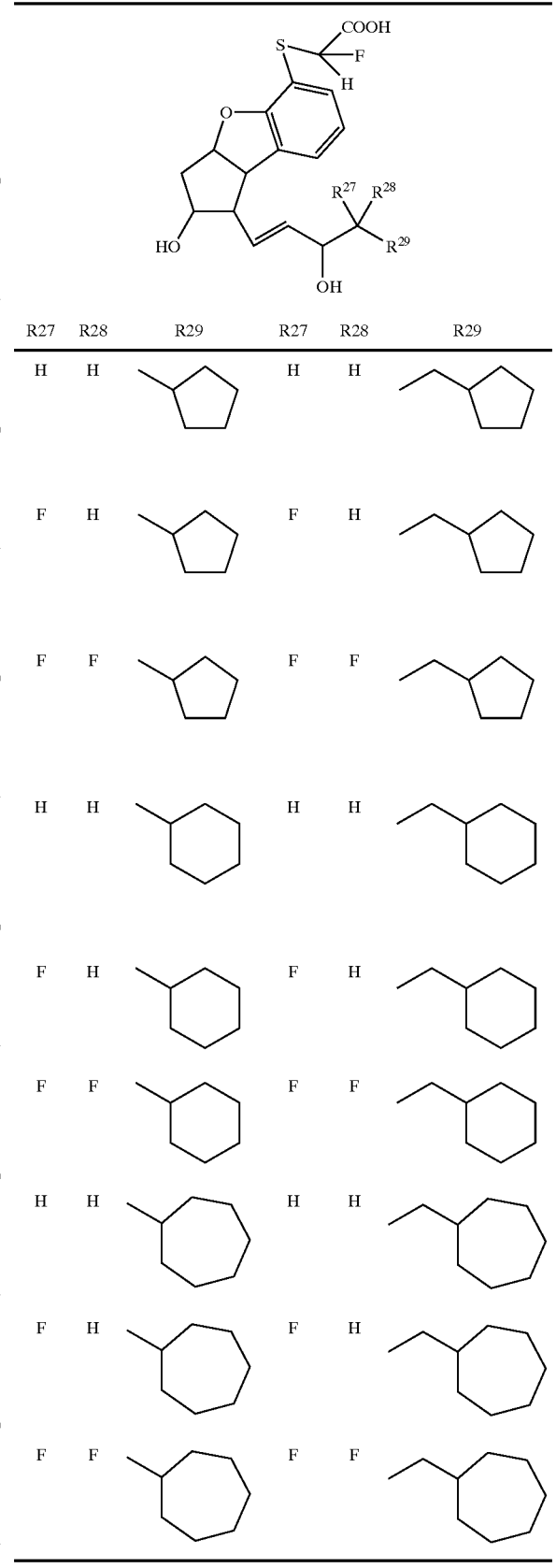

TABLE 9

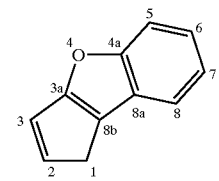

| R27 | R28 | R29 | R27 | R28 | R29 |
|---|---|---|---|---|---|
| H | H | cyclopentyl | H | H | CH2-cyclopentyl |
| F | H | cyclopentyl | F | H | CH2-cyclopentyl |
| F | F | cyclopentyl | F | F | CH2-cyclopentyl |
| H | H | cyclohexyl | H | H | CH2-cyclohexyl |
| F | H | cyclohexyl | F | H | CH2-cyclohexyl |
| F | F | cyclohexyl | F | F | CH2-cyclohexyl |
| H | H | cycloheptyl | H | H | CH2-cycloheptyl |
| F | H | cycloheptyl | F | H | CH2-cycloheptyl |
| F | F | cycloheptyl | F | F | CH2-cycloheptyl |

The compounds represented by the formula (I) obtained in the present invention are named according to the nomenclature of prostaglandin and prostacyclin analogues proposed by N. A. Nelcon et al. (N. A. Nelson, J. Med. Chem., 17. 911 (1974), and R. A. Johnson, D. R. Morton, and N. A. Nelson, Prostaglandins, 15, 737 (1978)). The most fundamental compound among a series of compounds (not included in the present invention) is represented by the following formula and named 5,6,7-trinor-4,8-inter-m-phenylene $PGI_2$ in which numbering is made as shown in the formula.

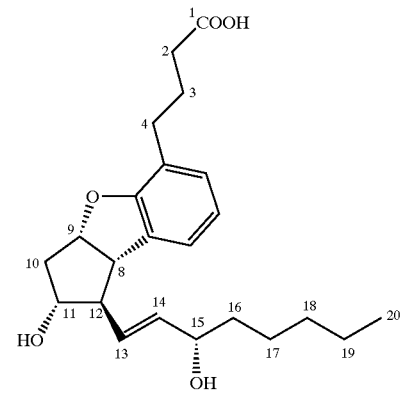

Although this name is not resonably named according to the above references, the nomenclature is applied only to $PGI_2$ derivatives having a unique structure of the present invention, which have a cyclopenta [b] benzofuran skeleton in order to avoid complication. As a rule, the other portions are named according to the rules of the above references. The nomenclature of the above references is also a summary nomenclature. According to IUPAC standard nomenclature, a cyclopenta [b] benzofuran ring is considered as a substituent.

Although the fundamental compound is named 4-{(1R, 2R,3aS,8bS)-2,3,3a,8b-tetrahydro-2-hydroxy-1-[(3S)-(E)-3-hydroxy-1-octene-1-yl]-1H-cyclopenta[b]benzofuran-5-yl} butanoic acid, the compound is named by the summary nomenclature, as described above.

Examples of the names of the compounds of the present invention are -shown below together with the structural formulae thereof.

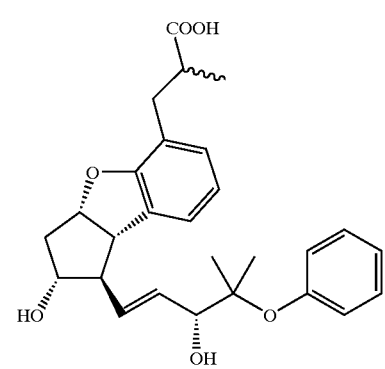

3,16-dimethyl-16-phenoxy-2,5,6,7,18,19,20-heptanor-4, 8-inter-m-phenylene $PGI_2$

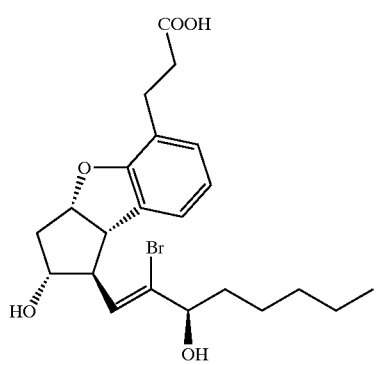
14-bromo-15-epi-2,5,6,7-tetranor-4,8-inter-m-phenylene PGI$_2$
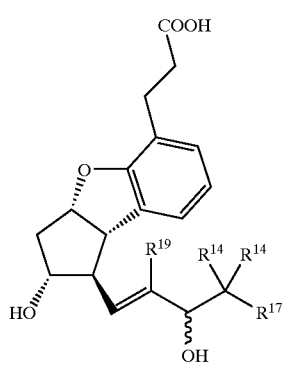
3-(decarboxy-3-(1H-tetrazole-5-yl)-16-phenoxy-2,5,6,7,18,19,20-heptanor-4,8-inter-m-phenylene PGI$_2$
Of the compounds included in the present invention, compounds represented by the following formula can be prepared by the method shown by steps A.
[wherein $R^{14}$, $R^{17}$ and $R^{19}$ are defined as the same as the above]
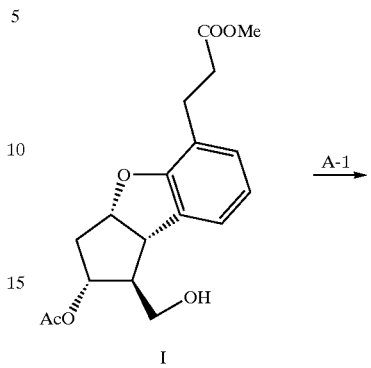
I
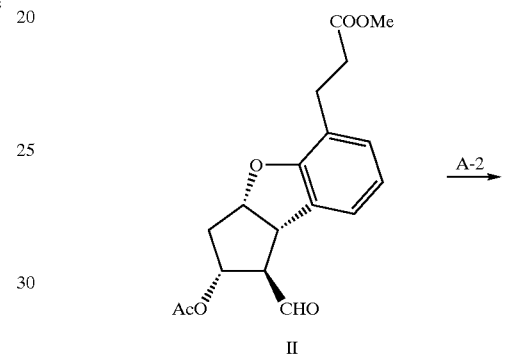
II
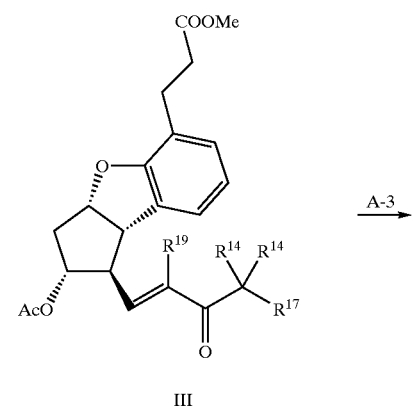
III
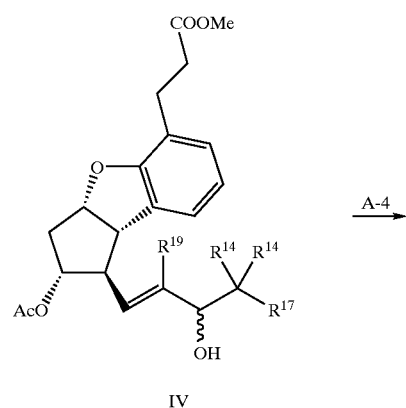
IV

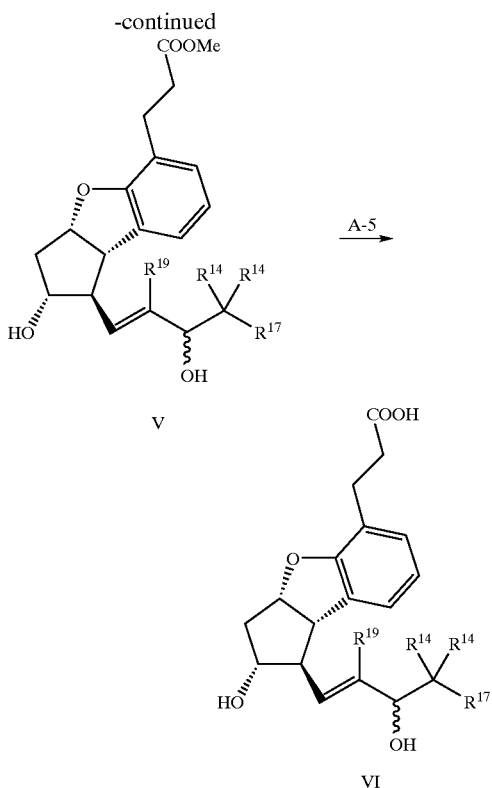

[wherein $R^{14}$, $R^{17}$ and $R^{19}$ are defined as the same as the above]

An example of methods of preparing compound (I) used as a starting material is disclosed in Japanese Examined Patent Publication No. 6-62599. Step A-1 is the step of oxidizing an alcohol to an aldehyde, in which various oxidizing agents can be used. In order to oxidize compound (I), in general, an oxidizing agent, such as a complex (Collin's reagent) of chromic anhydride and pyridine, dimethylsulfoxide-dicyclohexylcarbodiimide, dimethylsulfide-chlorine, N-bromosuccinimide-chlorine, or the like is preferably used. Although the reaction temperature is not limited, the reaction temperature is preferably −78 to 100° C. Although the reaction time is also not limited, and can be appropriately selected according to reaction conditions such as the reaction temperature, etc., the reaction time is preferably about 0.5 to 48 hours. Although the solvent is not limited, for example, dichloromethane, chloroform, benzene, toluene, and the like can preferably be used. Although the concentration of the compound (I) in the reaction mixture is not limited, the concentration is generally about 0.01 to 3 mol/l. Although the concentration of the oxidizing agent is not limited, the concentration is generally about 0.01 to 6 mol/l. Although the compound (I)/oxidizing agent ratio is not limited, the proper molar ratio is generally 1:1 to 1:20.

Step A-2 is carried out by condensing the aldehyde (II) with dimethyl phosphonate represented by the following formula:

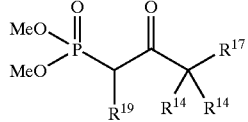

[wherein $R^{14}$, $R^{17}$ and $R^{19}$ are defined as the same as above]

In an ordinary method, the dimethyl phosphonate is reacted with a metal hydride (sodium hydride, potassium hydride, or the like) in an ether solvent such as tetrahydrofuran or dimethoxyethane to form the corresponding salt, followed by the addition of the aldehyde (II). Although the reaction temperature of this reaction is selected in the range of −30 to 100° C., a temperature of 0° C. to room temperature is sufficient for ordinary reaction. Although the reaction time of reaction of dimethylphosphonate and a metal hydride is not limited, and can be appropriately selected according to the reaction condition such as the reaction temperature or the like, the time is generally about 0.1 to 6 hours. Although the concentration of the dimethyl phosphonate in the reaction mixture used for the reaction of dimethyl phosphonate and metal hydride is not limited, the concentration is generally about 0.01 to 3 mol/l. Although the concentration of the metal hydride is not limited, the concentration is generally about 0.01 to 6 mol/l. Although the mixing ratio of dimethyl phosphonate and metal hydride is not limited, the proper molar ratio is generally 2:1 to 1:4. Although the concentration of the aldehyde (II) added to the reaction mixture is not limited, the concentration is generally about 0.01 to 3 mol/l. Although the reaction time is not limited, and can be appropriately selected according to the reaction condition such as the reaction temperature or the like, the time is generally about 0.5 to 48 hours.

The dimethyl phosphonate used in the reaction can be synthesized according to the following procedure:

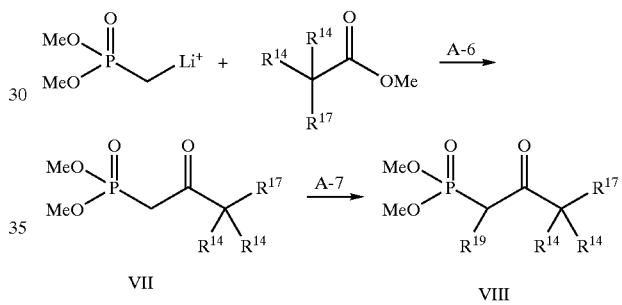

[$R^{14}$, $R^{17}$ and $R^{19}$ are defined as the same as the above]

Step A-6 is the condensation reaction of dimethyl methylphosphonate and an ester. In this reaction, a preferred method comprises reacting dimethyl methylphosphonate with an alkyl metal (butyl lithium or the like) in an ether solvent such as tetrahydrofuran or dimethoxyethane to form a salt, followed by the addition of an ester (refer to E. J. Corey et al., J. Am. Chem. Soc., 88, 5654 (1966)). Although the reaction temperature of this reaction of dimethyl methylphosphonate and alkyl metal is not limited, the temperature is generally −100 to 25° C. Although the reaction time is not limited, and can be appropriately selected according to the reaction condition such as the reaction temperature or the like, the time is generally about 0.1 to 6 hours. Although the concentration of dimethyl methylphosphonate in the reaction mixture is not limited, the concentration is generally about 0.01 to 3 mol/l. Although the concentration of the alkyl metal in the reaction mixture is also not limited, the concentration is generally about 0.01 to 6 mol/l. Although the mixing ratio of dimethyl dimethylphosphonate and alkyl metal is not limited, the proper molar ratio is generally 2:1 to 1:5. Although the reaction temperature of reaction of the ester and the salt formed by reaction of dimethyl methylphosphonate and alkyl metal is not limited, the temperature is generally −100 to 80° C. Although the reaction time is not limited, and can be appropriately selected according to the reaction condition such as the reaction temperature or the like, the time is generally about 0.5 to 48 hours. Although the concentration of the ester added to the reaction solution is also not limited, the concentration is generally about 0.01 to 3 mol/l.

Step A-7 is performed by halogenating the active methylene site of dimethyl phosphonate (VII). This step can be carried out by reacting the dimethyl phosphonate with a metal hydride (sodium hydride, potassium hydride, or the like) in an ether solvent such as tetrahydrofuran or dimethoxyethane to form the corresponding salt, followed by the addition of a halogenating agent. As the halogenating agent, fluorine gas, perchloryl fluoride, $CsSO_4F$, xenon fluoride, N-fluoropyridinium salt, or the like is preferably used for fluorination; chlorine, N-chlorosuccinimide, or the like is preferably used for chlorination; and bromine, N-bromosuccinimide, or the like is preferably used for bromination. However, the halognetaing agent is not limited to these compounds. Although the reaction temperature of this reaction of a dimethyl phosphonate and a metal hydride is not limited, the temperature is generally −100 to 25° C. Although the reaction time is not limited, and can be appropriately selected according to the reaction condition such as the reaction temperature or the like, the time is generally about 0.1 to 6 hours. Although the concentration of the dimethyl phosphonate in the reaction mixture is not limited, the concentration is generally about 0.01 to 3 mol/l. Although the concentration of the metal hydride in the reaction mixture is also not limited, the concentration is generally about 0.01 to 6 mol/l. Although the mixing ratio of a dimethyl phosphonate and a metal hydride is not limited, the proper molar ratio is generally 2:1 to 1:5. Although the reaction temperature of reaction of a halogenating agent and the salt formed by reaction of a dimethyl phosphonate and a metal hydride is not limited, the temperature is generally −100 to 100° C. Although the reaction time is not limited, and can be appropriately selected according to the reaction condition such as the reaction temperature or the like, the time is generally about 0.5 to 48 hours. Although the concentration of the halogenating agent added to the reaction mixture is also not limited, the concentration is generally about 0.01 to 12 mol/l.

Step A-3 represents the preparation of the allyl alcohol (IV) by reducing the α, β-unsaturated ketone (III). For the purpose of the reduction, the reducing agent which can selectively reduce only a ketone group without reduction of an ester group and double bond of α, β-unsaturated ketone is used. For this purpose, metal hydrides, trialkoxyaluminum compounds, or dialkylaluminum compounds are preferably used. Preferred examples of the reducing agent include zinc boron compound $(Zn(BH_4)_2)$, a combined reagent of sodium borohydride and cerium trichloride, diisobutyl(2,6-dimethylphenoxy)aluminum, triisopropoxyaluminum, and the like. However, the reducing agent is not limited to these compounds. In ordinary reaction, the use of the sodium borohydride-cerium trichloride reagent produces preferable results. In this case, methanol is most preferably used as a solvent. In use of a zinc borohydride or organic aluminum reducing agent, an ether solvent such as ether, tetrahydrofuran, or dimethoxyethane is preferably used. Although the reaction temperature is selected in the range of −110 to 80° C., the temperature is generally −78° C. to room temperature. Although the reaction time is not limited, and can be appropriately selected according to the reaction condition such as the reaction temperature or the like, the time is generally about 0.5 to 48 hours. Although the concentration of the α, β-unsaturated ketone (II) in the reaction mixture is not limited, the concentration is generally about 0.01 to 3 mol/l. Although the concentration of the reducing agent is also not limited, the concentration is generally about 0.01 to 6 mol/l. Although the mixing ratio of the α, β-unsaturated ketone (III) and the reducing agent is not limited, the proper molar ratio is generally 4:1 to 1:5. Although the compound IV obtained from step A-3 is a mixture of 15-α and 15-β compounds, the mixture can be used as a starting material for step A-4 without separation.

Step A-4 is the step of transesterification of an acetyl group by methanol. For this purpose, the compound (IV) may be dissolved in methanol, followed by the addition of an appropriate base and allowed to stand or stirring at −30 to 100° C. As the base, anhydrous sodium carbonate, anhydrous potassium carbonate, sodium methoxide, potassium methoxide, or the like is preferably used. Although the concentration of the compound (IV) in the methanol solution before the base is added is not limited, the concentration is generally about 0.01 to 3 mol/l. Although the concentration of the base is also not limited, the concentration is generally about 0.01 to 6 mol/l. Although the time required for allowing to stand or stirring after the base is added is not limited, and can be appropriately selected according to the reaction condition such as the reaction temperature or the like, the time is generally about 0.5 to 48 hours. The compound obtained in step A-4 is a mixture of 15-α and 15-β compounds. The 15-α and 15-β compounds are separated by the technique of column chromatography (normal phase: using an ethyl acetate/cyclohexane solvent mixture to achieve preferable results).

Step A-5 is so-called hydrolysis reaction of an ester. This step is generally achieved by adding a basic aqueous solution of sodium hydroxide, potassium hydroxide, or the like to a methanol solution of the compound (V), and then allowing the resultant mixture to stand or stirring at 0 to 100° C. Although the time required for allowing to stand or stirring is not limited, and can be appropriately selected according to the reaction condition such as the reaction temperature or the like, the time is generally about 0.5 to 48 hours. Although the concentration of the compound (V) in the reaction mixture is not limited, the concentration is generally about 0.01 to 3 mol/l. Although the concentration of the base is also not limited, the concentration is generally about 0.01 to 6 mol/l. Although the mixing ratio of the compound (V) and the base is not limited, the proper molar ratio is generally 1:1 to 1:10.

Of the compounds of the present invention, a compound represented by the following formula can be produced by the method shown by steps B (in the formula of steps B, TBS represents a tert-butyldimethylsilyl group).

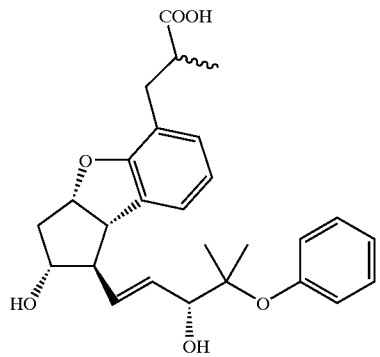

For the compound (IX) shown in the formula of steps B, an example of production methods is disclosed in Japanese Examined Patent Publication No. 6-62599.

Step B-1 is methyl esterification reaction of carboxylic acid, and various methods can be used. A preferred example of the methods uses a methyl esterifying agent such as acid catalyst-methanol, diazomethane, trimethylsilyl diazomethane, dicyclohexylcarbodiimide-methanol, 2-halo-N-methylpyridinium salt-methanol-alkylamine, or the like. However, the esterifying agent is not limited to these agents. Although the acid catalyst is not limited, for example, hydrochloric acid, sulfuric acid, phosphoric acid, and the like can preferably be used. The reaction temperature is selected in the range of −30 to 100° C. Although the reaction time is appropriately set according to the reaction condition such as the reaction temperature or the like, the time is preferably about 0.5 to 48 hours. Although the solvent is not limited, for example, methanol, tetrahydrofuran, 1,4-dioxane, dichloromethane, chloroform, and the like can be used. Although the concentration of the carboxylic acid (IX) in the reaction mixture is not limited, the concentration is generally about 0.01 to 3 mol/l. Although the concentration of the methyl esterifying agent (the total concentration when a mixture is used) is also not limited, the proper concentration is generally about 0.01 to 12 mol/l.

Step B-2 is the step of protecting the hydroxyl groups at the 11 and 15 positions by tert-butyldimethylsilyl groups. For this purpose, the compound (X) may be dissolved in dimethylformamide or a dichloromethane-dimethylformamide solvent mixture, and an appropriate base and silylating agent may be added to the resultant mixture, followed by stirring at 0 to 100° C. As the base, imidazole, triethylamine, ethyldiisopropylamine, pyridine, dimethylaminopyridine or 2,6-lutidine is used. As the silylating agent, tert-butyldimethylsilyl chloride or tert-butyldimethylsilyl trifluoromethanesulfonate is preferably used. In this step, imidazole and tert-butyldimethylsilyl chloride are most preferably used as the base and the silylating agent, respectively, in a dimethylformamide solvent. Although the reaction time is appropriately set according to the reaction condition such as the reaction temperature or the like, the time is preferably about 0.5 to 48 hours. Although the concentration of the compound (X) in the reaction mixture is not limited, the concentration is generally about 0.01 to 3 mol/l. Although the concentration of the base is also not limited, the concentration is generally about 0.01 to 6 mol/l. Although the concentration of the silylating agent is also not limited, the concentration is generally about 0.01 to 12 mol/l. Although the mixing ratio (molar ratio) of the compound (X), the base, and the silylating agent is not limited, the proper ratio is generally about 1:1:1 to 1:16:8.

Step B-3 represents alkylation at X position of a methyl ester. This step can be carried out by reacting methyl ester (XI) with 3 to 10 equivalents of lithium diisopropylamide at low temperature, followed by reaction with methyl iodide. Although tetrahydrofuran is most preferably used as a solvent, the solvent is not limited to this. The reaction temperature of alkylation is generally −80 to 40° C. Although the reaction time is appropriately set according to the reaction condition such as the reaction temperature or the like, the time is preferably about 0.5 to 72 hours. Although the concentration of the methyl ester (XI) in the reaction mixture before methyl iodide is added is not limited, the concentration is generally about 0.01 to 3 mol/l. Although the amount of the methyl iodide added is about 1 to 30 equivalents based on the methyl ester (XI).

Step B-4 is hydrolysis of an ester. This step is conventionally achieved by adding a basic aqueous solution of sodium hydroxide, potassium hydroxide, or the like to a methanol solution of the compound (XII), and then allowing the resultant mixture to stand or stirring at 0 to 100° C. Although the reaction time is appropriately set according to the reaction condition such as the reaction temperature or the like, the time is preferably about 0.5 to 48 hours. Although the concentration of the compound (XII) in the reaction mixture is not limited, the concentration is generally about 0.01 to 3 mol/l. Although the concentration of the base in the reaction mixture is also not limited, the concentration is generally about 0.01 to 6 mol/l.

Step B-5 is deprotection of a tert-butyldimethylsilyl group. In reaction under basic to neutral conditions, tetra-N-butylammonium fluoride or potassium fluoride monohydrate-crown ether is preferably used as a deprotecting agent. In reaction under acidic conditions, acetic acid, diluted sulfuric acid, diluted hydrochloric acid, hydrogen fluoride, p-toluenesulfonic acid, or the like is preferably used. As a solvent, tetrahydrofuran, acetonitrile, cyclohexane, or the like is generally used under basic conditions, and tetrahydrofuran, water, chloroform, acetonitrile, or the like is preferably used under acidic conditions. In this step, tetra-N-butylammonium fluoride-tetrahydrofuran or acetic acid-water-tetrahydrofuran produces most preferable results.

Although the reaction temperature is not limited, the proper reaction temperature is generally 0 to 80° C. Although the reaction time is appropriately set according to the reaction condition such as the reaction temperature or the like, the time is preferably about 0.5 to 48 hours. Although the concentration of the compound (XIII) in the reaction mixture is not limited, the concentration is generally about 0.01 to 3 mol/l. Although the concentration of the deprotecting agent is not limited, the concentration is generally about 0.01 to 6 mol/l. Although the mixing ratio of the compound (XIII) and the deprotecting agent is not limited, the molar ratio is generally about 1:1 to 1:10.

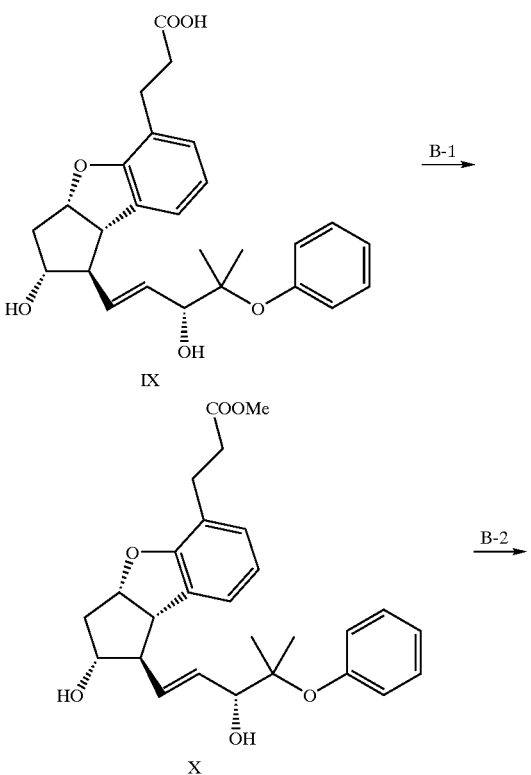

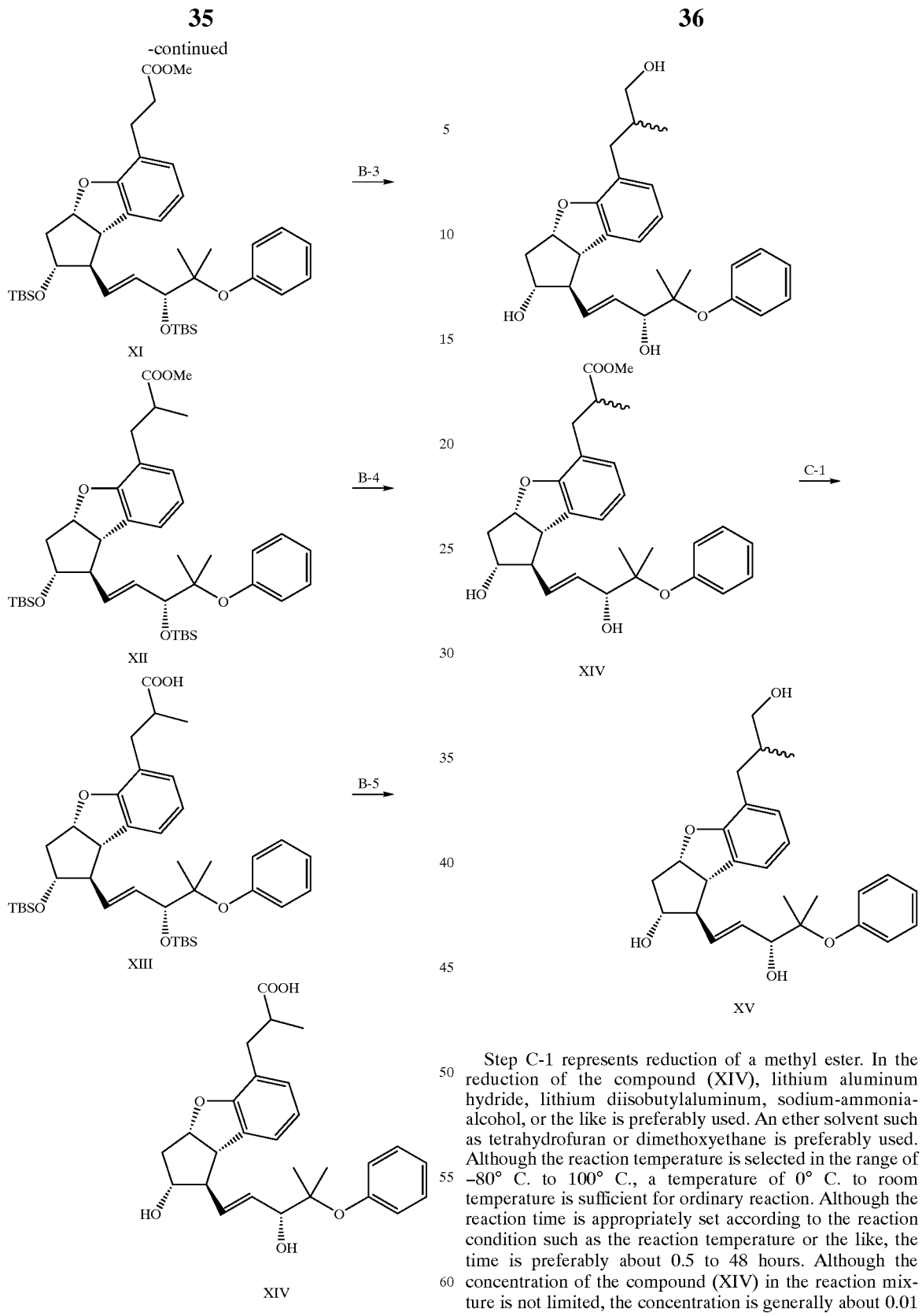

Of the compounds of the present invention, a compound represented by the following formula can be prepared by the method shown by step C.

Step C-1 represents reduction of a methyl ester. In the reduction of the compound (XIV), lithium aluminum hydride, lithium diisobutylaluminum, sodium-ammonia-alcohol, or the like is preferably used. An ether solvent such as tetrahydrofuran or dimethoxyethane is preferably used. Although the reaction temperature is selected in the range of −80° C. to 100° C., a temperature of 0° C. to room temperature is sufficient for ordinary reaction. Although the reaction time is appropriately set according to the reaction condition such as the reaction temperature or the like, the time is preferably about 0.5 to 48 hours. Although the concentration of the compound (XIV) in the reaction mixture is not limited, the concentration is generally about 0.01 to 3 mol/l. Although the concentration of the reducing agent (the total concentration when a mixture is used) is not limited, the concentration is generally about 0.01 to 6 mol/l. Although the mixing ratio of the compound (XIV) and the reducing agent is not limited, the molar ratio is generally about 1:1 to 1:10.

Of the compounds of the present invention, a compound represented by the following formula:

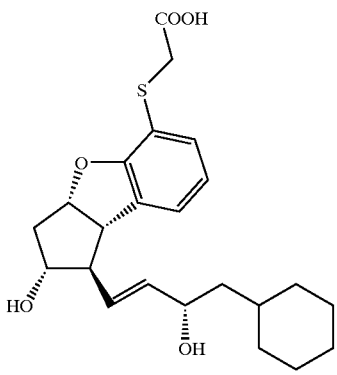

can prepared by the method shown by steps D using a compound represented by the following formula:

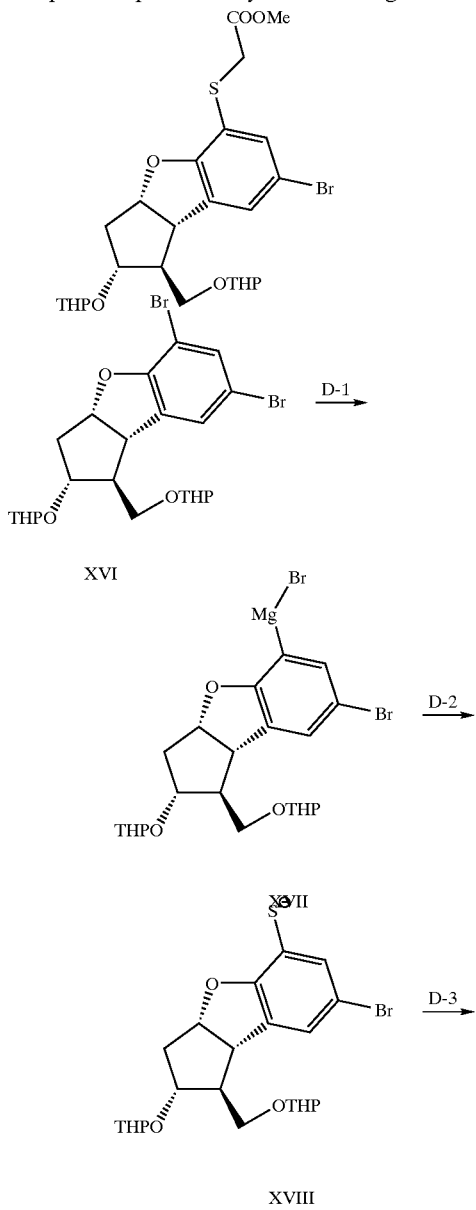

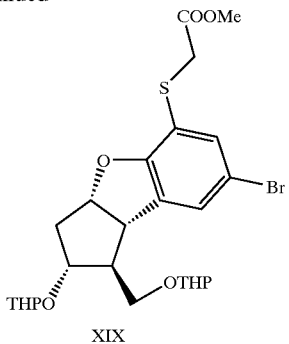

Step D-1 represents halogen-metal transformation. In transformation of the compound (XVI), methylmagnesium bromide, ethylmagnesium bromide, cyclohexylmagnesium bromide, normal butyl lithium, or the like is preferably used, and cyclohexylmagnesium bromide is particularly preferably used. As a solvent, an ether solvent such as tetrahydrofuran or dimethoxyethane is preferably used. Although the reaction temperature is selected in the range of −100° C to 100° C., a temperature of 0° C. to 60° C. is sufficient for ordinary reaction. Although the reaction time is appropriately set according to the reaction condition such as the reaction temperature or the like, the time is preferably about 0.5 to 48 hours. Although the concentration of the compound (XVI) in the reaction mixture is not limited, the concentration is generally about 0.01 to 3 mol/l. Although the concentration of the metal reagent is not limited, the concentration is generally about 0.01 to 6 mol/l. Although the mixing ratio of the compound (XVI) and the metal reagent is not limited, the molar ratio is generally about 1:1 to 1:10.

Step D-2 represents transformation of aryl metal to aryl thiolate. In the transformation step of the compound (XVII), sulfur is preferably used. As a solvent, an ether solvent such as tetrahydrofuran or dimethoxyethane is preferably used. Although the reaction temperature is selected in the range of −100° C. to 100° C., a temperature of 0° C. to 60° C. is sufficient for ordinary reaction. Although the reaction time is appropriately set according to the reaction condition such as the reaction temperature or the like, the time is preferably about 0.5 to 24 hours. Although the concentration of the compound (XVII) in the reaction mixture is not limited, the concentration is generally about 0.01 to 3 mol/l. Although the sulfur concentration is also not limited, the concentration is generally about 0.01 to 6 mol/l. Although the mixing ratio of the compound (XVII) and sulfur is not limited, the molar ratio is generally about 1:1 to 1:10.

Step D-3 is α-carbonylalkylation of the thiolate. In the α-carbonylalkylation of the compound (XVIII), methyl chloroacetate, methyl bromoacetate, or the like is preferably used. As a solvent, an ether solvent such as tetrahydrofuran or dimethoxyethane is preferably used. Although the reaction temperature is selected in the range of −100° C. to 100° C., a temperature of −50° C. to 50° C. is sufficient for ordinary reaction. Although the reaction time is appropriately set according to the reaction condition such as the reaction temperature or the like, the time is preferably about 0.5 to 3 hours. Although the concentration of the compound (XVIII) in the reaction mixture is not limited, the concentration is generally about 0.01 to 3 mol/l. Although the concentration of the alkylating agent is also not limited, the concentration is generally about 0.01 to 6 mol/l. Although the mixing ratio of the compound (XVIII) and the alkylating agent is not limited, the molar ratio is generally about 1:1 to 1:10. The 5,6,7-trinor-4,8-inter-m-phenylene PGI$_2$ derivatives of the present invention can be used for therapy of various diseases. For example, the PGI$_2$ derivatives can be used as anti Helicobacter agent, a platelet function potentiating agent or a cervical ripening agent. More specifically, the derivatives can be used as the anti Helicobacter agent for therapy of gastroduodenal disorder, gastric cancer, lymphoma, etc. which are caused by Helicobacter bacteria such as *Helicobacter pylori* as causative bacteria. The derivatives can be used as the platelet function potentiating agent for therapy of congenital or acquired platelet functional disorder. Examples of congenital platelet functional disorder include storage pool disease, cyclooxygenase deficiency, TXA$_2$ synthase deficiency, TXA$_2$ receptor dysfunction, calcium ionophore refractoriness, and the like. Examples of acquired platelet functional disorders include platelet functional disorders accompanied with diseases such as chronic renal failure, liver diseases, blood diseases, and the like, and caused by extracorporeal circulation or medicines.

A base, an excipient, a solubilizer, a stabilizer, etc., which are conventionally used in preparation of medicines, are added to pharmaceutical compositions containing 5,6,7-trinor-4,8-inter-m-phenylene PGI$_2$ derivatives of the present invention as active ingredient. Examples of such preparation additives include animal oil; plant oil; paraffin; gum arabic; white vaseline; Witepsol; cacao butter; starch; saccharides such as lactose, sucrose, glucose, dextrin, mannitol, and the like; inorganic acid salts such as calcium carbonate, calcium sulfate, and the like; organic acid salts such as sodium citrate, sodium lactate, magnesium stearate, and the like; water-soluble polymers such as methyl cellulose, gelatin, polyethylene glycol, polyvinyl alcohol, polyvinyl pyrrolidone, hydroxyethyl cellulose, hydroxypropyl cellulose, and the like; alcohols such as ethanol, glycerin, propylene glycol, sorbitol, and the like; surfactants such as sorbitan fatty acid esters, polyoxyethylene sorbitan fatty acid esters, polyoxyethylene fatty acid esters, glycerin fatty acid esters, and the like.

The anti Helicobacter agent of the present invention can be orally or parenterally administered for prevention or therapy. Examples of oral administration agents include solid form such as tablets, granules, capsules, powders, and the like, liquid form such as syrups, elixirs, and the like. Examples of parenteral administration agents include injections, rectal administration agents, external applications, inhalations, and the like.

The platelet function potentiating agent of the present invention can be used in various forms. Examples of such forms include semi-solids such as an ointment, a cream, a gel, and the like. The agent can also be used as an intravenous injection. The agent can further be used as an oral agent in a form such as a tablet, a powder, granules, a pill, a capsule, or the like.

The cervical ripening agent of the present invention can be used in various forms. Examples of such forms include vaginal catapasms such as a liquid, a powder, and the like, semi-solids such as a liquid, an ointment, a cream, a gel, and the like, solids such as a vaginal tablet, a vaginal capsule, a pessary, a vaginal suppository, and the like, all of which are conventionally used. The cervical ripening agent can also be used as an injection for hypodermic injection, intravenous injection, local injection or the like. The agent can also be used as an oral administration agent in a form such as a tablet, a powder, granules, a pill, a capsule, or the like.

Specifically, the pharmaceutical compositions of the present invention can be administered as the anti Helicobacter agent, the platelet function potentiating agent, or the cervical ripening agent with one or divided doses of 0.1 μg to 1000 mg/adult per day, depending upon the symptoms, the age, the body weight of the patient, or the form of the agent administered, etc.

The pharmaceutical compositions of the present invention which are the anti Helicobacter agent, the platelet function potentiating agent, or the cervical ripening agent can be used as medicines for animals other than humans.

EXAMPLES

The present invention will be described in further detail below with reference to examples.

In reference examples and examples, the following abbreviations are used.

(1) DME=dimethoxyethane
(2) THF=tetrahydrofuran
(3) TLC=thin layer chromatography
(4) DMF=dimethylformamide
(5) TBSCI=tert-butyldimethylchlorosilane
(6) DCC=dicyclohexylcarbodiimide
(7) DMSO=dimethylsulfoxide
(8) TBAF=tetra-n-butylammonium fluoride

REFERENCE EXAMPLE 1

Dimethyl 1-Fluoro-3-methyl-2-oxo-3-phenoxybutylphosphonate

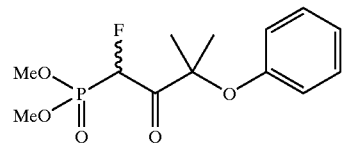

(1)

69% Mineral oil dispersion of sodium hydride 83 mg (2.39 mmol) was added to a solution of dimethyl 3-methyl-2-oxo-3-phenoxybutylphosphoate 625 mg (2.18 mmol) in anhydrous THF 2.2 ml under ice cooling and argon stream, and the resultant mixture was stirred at room temperature for 10 minutes. N-fluoro-2,4,6-trimethypyridinium tetrafluoroborate 520 mg (2.29 mmol) was added to the ice-cold solution, and the mixture was stirred under ice cooling for 1.5 hours and at room temperature for 21.5 hours. The reaction mixture was added to 1N ice-cold hydrochloric acid 10 ml, and then extracted with ethyl acetate (3×10 ml). The combined organic layer was washed in turn with saturated aqueous sodium bicarbonate 10 ml and brine 10 ml, dried, and then concentrated. The thus-obtained oil 739 mg was purified by column chromatography (silica gel; cyclohexane:ethyl acetate=60:40 to 20:80) to obtain the titled compound 125 mg (yield 19%) as a pale yellow oil. The structure of this compound was determined by the following data.

IR (neat): 3482, 1740, 1592, 1491, 1462, 1381, 1273, 1226, 1169, 1045, 954, 851, 794, 754, 701 cm$^{-1}$. $^1$H-NMR (300 MHz, CDCl$_3$): δ 7.30 (2H, t, J=8.2 Hz), 7.12 (1H, t, J=7.4 Hz), 7.05 (2H, d, J=7.7 Hz), 6.17 (1H, dd, J=47.8, 13.8 Hz), 3.88 (3H, d, J=7.4 Hz), 3.85 (3H, d, J=7.4 Hz), 1.54 (3H, s), 1.49 (3H, s). MASS (EI, m/e): 304 (M$^+$).

REFERENCE EXAMPLE 2

Dimethyl 2-Chloro-3-methyl-2-oxo-3-phenoxybutylphosphonate (2)

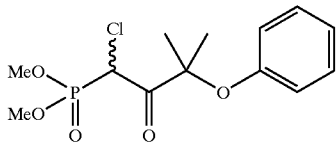

(2)

69% Mineral oil dispersion of sodium hydride 30.3 mg (0.871 mmol) was added to a solution of dimethyl 3-methyl-2-oxo-3-phenoxybutylphosphoate 227 mg (0.793 mmol) in anhydrous DME 2.2 ml under ice cooling and argon stream, and the resultant mixture was stirred at room temperature for 10 minutes. N-chlorosuccinimide 111 mg (0.831 mmol) was added to the ice-cold solution, and the mixture was stirred at room temperature for 1 hour. After acetic acid 0.15 ml was added to the ice-cold reaction mixture, water 5 ml was added to the mixture, and then extracted with ethyl acetate (3×10 ml). The combined organic layer was washed with water 10 ml, dried, and then concentrated. The thus-obtained oil 317 mg was purified by column chromatography (silica gel; cyclohexane:ethyl acetate=50:50) to obtain the titled compound 227 mg (yield 89%) as a colorless oil. The structure of this compound was determined by the following data.

IR (neat): 1735, 1594, 1491, 1459, 1381, 1268, 1226, 1167, 1026, 957, 843, 787, 755 cm$^{-1}$. $^1$H-NMR (300 MHz, CDCl$_3$): δ 7.30 (2H, t, J=7.2 Hz), 7.11 (1H, t, J=7.2 Hz), 7.00 (2H, t, J=7.2 Hz), 5.64 (1H, d, J=14.0 Hz), 3.92 (3H, d, J=6.3 Hz), 3.88 (3H, d, J=6.3 Hz), 1.52 (3H, s), 1.50 (3H, s). MASS (EI, m/e): 322 (M$^+$+2), 320 (M$^+$).

REFERENCE EXAMPLE 3

16-Methyl-16-phenoxy-2,5,6,7,18,19,20-heptanor-4,8-inter-m-phenylene PGI$_2$ Methyl Ester (3)

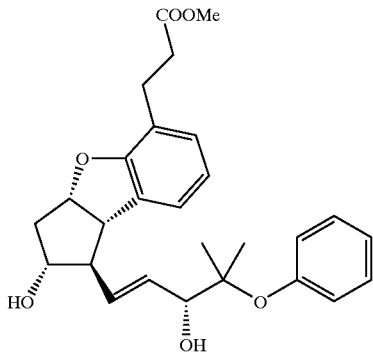

(3)

16-methyl-16-phenoxy-2,5,6,7,18,19,20-heptanor-4,8-inter-m-phenylene PGI$_2$ (3.9 g, 8.5 mmol) was dissolved in methanol (40 mL), and a 1.7M hydrochloric acid/methanol solution (10 mL) was added to the resultant solution, followed by stirring at room temperature overnight. After the disappearance of the starting material was checked by TLC, solid sodium bicarbonate (10 g) was added to the reaction mixture to neutralize it, and the excessive inorganic solid was filtered off. After concentration, the residue was dissolved in ethyl acetate (200 mL), washed with saturated aqueous sodium bicarbonate (200 mL) and brine (150 mL), and then dried over anhydrous sodium sulfate. After concentration, the residue was purified by recrystallization (ethyl acetate/n-hexane=15 mL/35 mL) to obtain the titled compound 3.38 g (yield 88%) as a white crystal. The structure of this compound was determined by the following data.

IR (neat): 3534, 3422, 2980, 1719, 1595, 1491, 1437, 1234, 1131, 1060, 1011, 982, 963, 888, 870, 822, 787, 745, 698 cm$^{-1}$. Melting point: 103.8~104.9° C. $^1$H-NMR (400 MHz, CDCl$_3$): δ 7.30 (2H, t, J=7.8 Hz), 7.13(1H, t, J=7;8 Hz), 7.01–6.95(4H, m), 6.76 (1H, t, J=7.3 Hz), 5.84(1H, dd, J=15.6, 8.3 Hz), 5.72 (1H, dd, J=15.6, 6.4 Hz), 5.18–5.12 (1H, m), 4.21 (1H, d, J=6.4 Hz), 3.99 (1H, dd, J=14.2, 7.8 Hz), 3.66 (3H, s), 3.50 (1H, t, J=8.3 Hz), 3.00 (1H, bs), 2.92–2.87 (2H, m), 2.69–2.62 (3H, m), 2.53 (1H, q, J=7.8 Hz), 2.22 (1H, bs), 2.06–1.98 (1H, m), 1.27 (3H, s), 1.25 (3H, s). MASS (EI, m/e): 452 (M$^+$), 265 (M$^+$–OPh).

| Elemental Analysis | C | H |
|---|---|---|
| Found: | 71.45 | 7.18 |
| Calculated for C$_{24}$H$_{36}$O$_5$ (M$^+$): | 71.66 | 7.13 |

REFERENCE EXAMPLE 4

16-Methyl-16-phenoxy-2,5,6,7,18,19,20-heptanor-4,8-inter-m-phenylene PGI$_2$ Methyl Ester, 11,15-bis (tert-Butyldimethylsilyl Ether) (4)

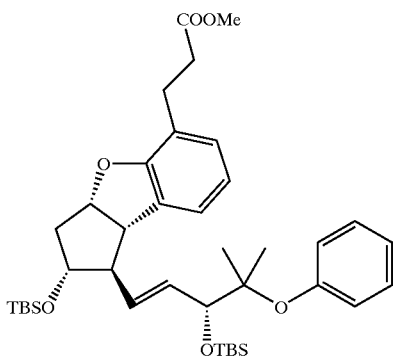

(4)

A solution of TBSCl 2.58 g (0.190 mmol) in anhydrous DMF 20 ml was added to a solution of 16-methyl-16-phenoxy-2,5,6,7,18,19,20-heptanor-4,8-inter-m-phenylene PGI$_2$ methyl ester (3) 1.55 g (3.42 mmol) and imidazole 2.33 g (34.2 mmol) in anhydrous DMF 40 ml under argon stream, and the resultant mixture was stirred at 60° C. overnight. After the reaction mixture was concentrated under reduced pressure, ethyl acetate 100 ml was added to the residue, and the resultant mixture was washed in turn with water (4×20 ml) and brine 20 ml. After drying, the mixture was concentrated under reduced pressure to obtain oil 2.89 g. The thus-obtained oil was purified by column chromatography (109 g of Silica gel FL60D produced by Fuji Silicia Chemical Co., cyclohexane:ethyl acetate=90:10) to obtain the titled compound 2.31 g (yield 99%) as a colorless oil. The structure of this compound was determined by the following data.

IR (neat): 1742, 1595, 1491, 1458, 1363, 1255, 1125, 1006, 978, 837, 775 cm$^{-1}$. $^1$H-NMR (300 MHz, CDCl$_3$): δ 7.29–7.21 (2H, m), 7.08–7.02 (2H, m), 7.00–6.90 (3H, m), 6.72 (1H, dd, J=7.4, 7.4 Hz), 5.82 (1H, dd, J=15.8, 4.9 Hz), 5.71 (1H, dd, J=15.8, 7.1 Hz), 5.14 (1H, ddd, J=9.0, 7.1, 4.9 Hz), 4.21 (1H, d, J=4.9 Hz), 3.98 (1H, ddd, J=7.4, 7.4, 7.1 Hz), 3.67 (3H, s), 3.48 (1H, dd, J=8.2, 7.7 Hz), 2.91–2.82 (2H, m), 2.68–2.59 (3H, m), 2.47 (1H, ddd, J=13.5, 7.4, 6.0 Hz), 1.97 (1H, ddd, J=13.5, 7.4, 4.9 Hz), 1.26 (3H, s), 1.17 (3H, s), 0.94 (9H, s), 0.75 (9H, s), 0.11 (3H, s), 0.09 (3H, s), 0.00 (3H, s), –0.06 (3H, s). MASS (FAB (pos.), m/e): 623 [(M–57)$^+$].

REFERENCE EXAMPLE 5

16-Methyl-16-phenoxy-2,5,6,7,18,19,20-heptanor-4, 8-inter-m-phenylene PGI$_2$, 11,15-bis(tert-Butyldimethylsilyl Ether) (5)

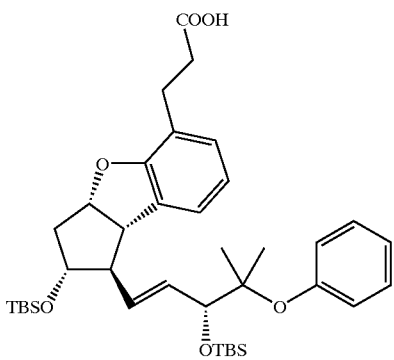

(5)

2N aqueous sodium hydroxide 1.0 ml was added to a solution of 16-methyl-16-phenoxy-2,5,6,7,18,19,20-heptanor-4,8-inter-m-phenylene PGI$_2$ methyl ester, 11,15-bis(tert-butyldimethylsilyl ether) (4) 64.7 mg (0.0950 mmol) in 1.0 ml THF-1.0 ml methanol, and the resultant mixture was stirred at room temperature for 3.5 hours. After 1N hydrochloric acid 2.2 ml was added to the reaction mixture, the resultant mixture was extracted with ethyl acetate (3×10 ml). The combined organic layer was washed with brine 5 ml, dried, and then-concentrated. The thus-obtained oil 65.7 mg was purified by column chromatography (Silica gel FL60D produced by Fuji Silicia Chemical Co., cyclohexane:ethyl acetate=82:18) to obtain the titled compound 62.8 mg (yield 99%) as a colorless oil. The structure of this compound was determined by the following data.

IR (neat): 3400, 1713, 1636, 1597, 1491, 1458, 1253, 1228, 1127, 1007, 909, 837, 775, 737 cm$^{-1}$. $^1$H-NMR (300 MHz, CDCl$_3$): δ 7.29–7.21 (2H, m), 7.09–6.92 (5H, m), 6.73 (1H, dd, J=7.5, 7.5 Hz), 5.82 (1H, dd, J=15.6, 5.3 Hz), 5.71 (1H, dd, J=15.6, 7.9 Hz), 5.14 (1H, ddd, J=9.0, 7.2, 4.4 Hz), 4.21 (1H, d, J=5.3 Hz), 3.98 (1H, ddd, J=6.3, 6.3, 6.3 Hz), 3.49 (1H, dd, J=8.1,–8.1 Hz), 2.92–2.82 (2H, m), 2.72–2.60 (3H, m), 2.47 (1H, ddd, J=13.6, 7.4, 5.8 Hz), 1.98 (1H, ddd, J=13.6, 8.2, 5.5 Hz), 1.26 (3H, s), 1.17 (3H, s), 0.94 (9H, s), 0.75 (9H, s), 0.11 (3H, s), 0.09 (3H, s), 0.00 (3H, s), –0.06 (3H, s). MASS (EI, m/e): m/z 689 [(M+Na)$^+$].

REFERENCE EXAMPLE 6

16-Methyl-16-phenoxy-2,5,6,7,18,19,20-heptanor-4, 8-inter-m-phenylene PGI$_2$ Methyl Ester, 11,15-bis (Tetrahydropyranyl Ether) (6)

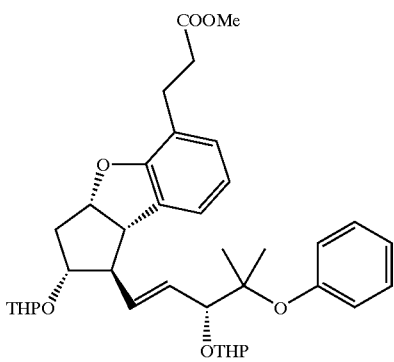

(6)

16-methyl-16-phenoxy-2,5,6,7,18,19,20-heptanor-4,8-inter-m-phenylene PGI$_2$ methyl ester 100 mg (0.22 mmol) was dissolved in THF (3 mL), and dihydropyrane 0.1 mL (1.1 mmol, 5 equivalents) dried with molecular sieve (4A) and p-toluenesulfonic acid monohydrate 2 mg (0.01 mmol, 0.05 equivalent) were added to the resultant mixture, followed by stirring at room temperature for 3 hours. After the disappearance of the starting material was checked by TLC, solid sodium bicabonate was added to the reaction mixture to neutralize it. After the inorganic solid was filtered off, the filtrate was concentrated. The residue was dissolved in ethyl acetate (30 mL), washed with saturated aqueous sodium bicarbonate (30 mL×2), water (30 mL) and brine (30 mL), and then dried over anhydrous sodium sulfate. After concentration, the residue was purified by column chromatography (silica gel; cyclohexane:ethyl acetate=3:1 to 1:1) to obtain the titled compound 112.3 mg (yield 82%) as a colorless oil. The structure of this compound was determined by the following data.

IR (neat): 3480, 2946, 1740, 1595, 1491, 1456, 1352, 1265, 1228, 1201, 1133, 1075, 1023, 977, 907, 868, 739, 700 cm$^{-1}$. $^1$H-NMR (300 MHz, CDCl$_3$): δ 7.26 (2H, t, J=7.4 Hz), 7.11–6.91 (5H, m), 6.76–6.67 (1H, m), 5.91–5.59 (2H, m), 5.19–5.05 (1H, m), 4.98–4.55 (2H, m), 4.24–4.16 (1H, m), 4.11–3.68 (3H, m), 3.67 (3H, s), 3.56–3.38 (3H, m), 2.87 (2H, t, J=7.7 Hz), 2.80–2.55 (4H, m), 2.14–2.00 (1H, m), 2.00–1.20 (18H, m); MASS (EI, m/e):620 (M$^+$).

REFERENCE EXAMPLE 7

2-Decarboxy-2-hydroxy-16-methyl-16-phenoxy-5,6, 7,18,19,20-hexanor-4,8-inter-m-phenylene PGI$_2$, 11, 15-bis(Tetrahydropyranyl Ether) (7)

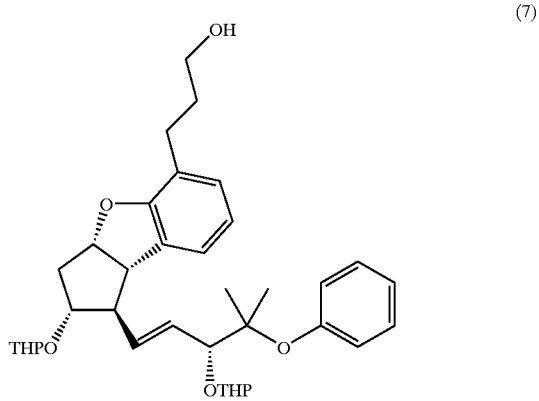

(7)

16-methyl-16-phenoxy-2,5,6,7,18,19,20-heptanor-4,8-inter-m-phenylene PGI$_2$ methyl ester, 11,15-bis (tetrahydropyranyl ether) (6) 112.8 mg (0.18 mmol) was dissolved in anhydrous THF (2 mL). The resultant solution was referred to as solution (A). Lithium aluminum hydride 7.6 mg (2.0 mmol, 1.1 equivalents) was placed in another reactor, and anhydrous THF (1 mL) was added to the reactor, followed by ice cooling. The solution (A) was added to the resultant mixture, and stirred at room temperature for 5 hours. After the disappearance of the starting material was checked by TLC, the reaction was quenched by addition of saturated potassium sodium tartrate. After suction filtration, the filtrate was extracted with ethyl acetate (30 mL×2). The combined organic layer was washed with brine (40 mL×2), and then dried over anhydrous sodium sulfate. After concentration, the residue was purified by column chromatography (silica gel; cyclohexane:ethyl acetate=7:3 to 1:1) to obtain the titled compound 84.7 mg (yield 79%) as a colorless oil. The structure of this compound was determined by the following data.

IR (neat): 3460, 2946, 1595, 1491, 1454, 1354, 1228, 1201, 1133, 1075, 1023, 977, 907, 868, 737, 700 cm$^{-1}$.

$^1$H-NMR (300 MHz, CDCl$_3$): δ 7.26 (2H, t, J=7.4 Hz), 7.11–6.91 (5H, m), 6.80–6.70 (1H, m), 5.93–5.60 (2H, m), 5.20–5.06 (1H, m), 4.95–4.60 (2H, m), 4.25–4.16 (1H, m), 4.10–3.66 (3H, m), 3.65–3.40 (5H, m), 2.82–2.56 (4H, m), 2.18–2.00 (1H, m), 1.98–1.20 (20H, m); MASS (EI, m/e): 592 (M$^+$).

REFERENCE EXAMPLE 8

2-Decarboxy-2-hydroxy-16-methyl-16-phenoxy-5,6,7,18,19,20-hexanor-4,8-inter-m-phenylene PGI$_2$, 11,15-bis(tert-Butyldimethylsilyl Ether) (8)

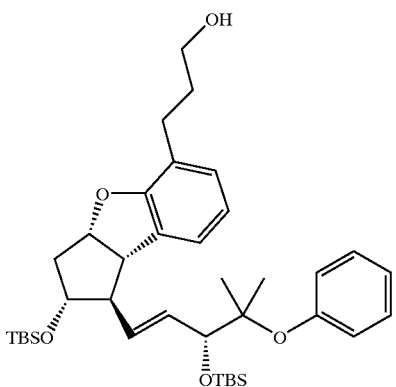

Lithium Aluminum hydride 7.2 mg (0.90 mmol) was added to a solution of 16-methyl-16-phenoxy-2,5,6,7,18,19,20-heptanor-4,8-inter-m-phenylene PGI$_2$ methyl ester, 11,15-bis(tert-butyldimethylsilyl ether) (4) 117 mg (0.172 mmol) in anhydrous THF 3.5 ml under ice cooling and argon stream, and the resultant mixture was stirred at room temperature for 1.5 hours. Saturated aqueous Rochelle salt 8 ml was added to the ice-cold reaction mixture. The mixture was then stirred for a while, and then filtered with a glass filter in which Celite was placed. After the precipitate was washed with ethyl acetate, the resultant filtrate was extracted with ethyl acetate (3×10). The combined organic layer was washed with brine 5 ml, dried, and then concentrated. The thus-obtained oil 117 mg was purified by column chromatography (silica gel; cyclohexane:ethyl acetate=85:15) to obtain the titled compound 103 mg (yield 91%) as a colorless oil. The structure of this compound was determined by the following data.

IR (neat): 3400, 1595, 1491, 1456, 1381, 1363, 1255, 1230, 1193, 1125, 1029, 977, 868, 837, 772 cm$^{-1}$. $^1$H-NMR (300 MHz, CDCl$_3$): δ 7.29–7.21 (2H, m), 7.08–7.02 (2H, m), 7.00–6.90 (3H, m), 6.75 (1H, dd, J=7.4, 7.4 Hz), 5.83 (1H, dd, J=15.7, 5.2 Hz), 5.71 (1H, dd, J=15.8, 7.5 Hz), 5.15 (1H, ddd, J=8.6, 7.3, 4.9 Hz), 4.22 (1H, d, J=5.2 Hz), 3.99 (1H, ddd, J=7.5, 6.6, 6.2 Hz), 3.64–3.56 (2H, m), 3.51 (1H, dd, J=8.6, 7.7 Hz), 2.70–2.61 (3H, m), 2.48 (1H, ddd, J=13.3, 7.5, 4.9 Hz), 2.07 (1H, dd, J=5.5, 5.5 Hz), 1.97 (1H, ddd, J=13.5, 7.5, 4.9 Hz), 1.89–1.73 (2H, m), 1.26 (3H, s), 1.17 (3H, s), 0.94 (9H, s), 0.75 (9H, s), 0.11 (3H, s), 0.09 (3H, s), 0.00 (3H, s), −0.06 (3H, s). MASS (EI, m/e): 652 (M$^+$).

REFERENCE EXAMPLE 9

2-Decarboxy-2-methylsulfonyloxy-16-methyl-16-phenoxy-5,6,7,18,19,20-hexanor-4,8-inter-m-phenylene PGI$_2$, 11,15-bis(tert-Butyldimethylsilyl Ether) (9)

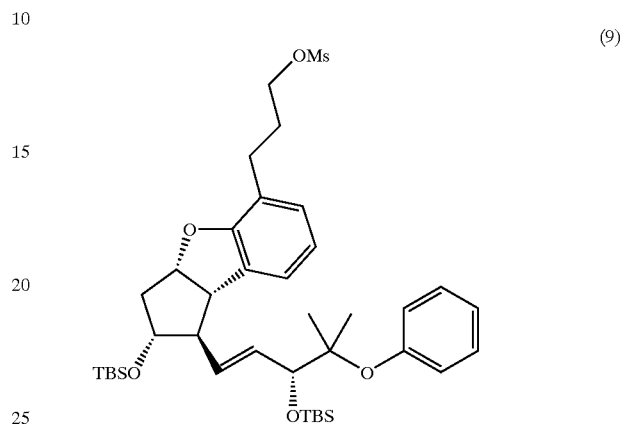

Anhydrous triethylamine 0.13 ml (0.933 mmol) was added to a solution of 2-decarboxy-2-hydroxy-16-methyl-16-phenoxy-5,6,7,18,19,20-hexanor-4,8-inter-m-phenylene PGI$_2$, 11,15-bis(tert-butyldimethylsilyl ether) (8) 60.4 mg (0.0925 mmol) in anhydrous dichloromethane 1.5 ml under argon stream, and the resultant mixture was ice-cooled. Methanesulfonyl chloride 0.035 ml (0.452 mmol) was added to the solution, and the resultant mixture was then stirred at room temperature overnight. After methanol 1 ml was added to the ice-cold reaction mixture, the mixture was concentrated. Then, 0.1N hydrochloric acid 10 ml was added to the residue, and the mixture was extracted with ethyl acetate (3×15 ml). The combined organic layer was washed in turn with saturated aqueous sodium bicarbonate 8 ml, water 8 ml and brine 8 ml, dried, and then concentrated. The thus-obtained oil 76.8 mg was purified by column chromatography (silica gel; cyclohexane:ethyl acetate=85:15) to obtain the titled compound 64.0 mg (yield 95%) as a colorless oil. The structure of this compound was determined by the following data.

IR (neat): 1595, 1491, 1458, 1361, 1255, 1228, 1178, 1125, 1009, 975, 926, 837, 777 cm$^{-1}$. $^1$H-NMR (300 MHz, CDCl$_3$): δ 7.29–7.21 (2H, m), 7.08–7.02 (2H, m), 6.97 (2H, dd, J=8.7, 1.1 Hz), 6.91 (1H, br d, J=6.6 Hz), 6.74 (1H, dd, J=7.4, 7.4 Hz), 5.83 (1H, dd, J=15.7, 4.8 Hz), 5.71 (1H, dd, J=15.7, 7.0 Hz), 5.13 (1H, ddd, J=8.9, 7.4, 4.5 Hz), 4.24 (2H, t, J=6.4 Hz), 4.22 (1H, d, J=4.8 Hz), 3.99 (1H, ddd, J=7.1, 6.4, 6.0 Hz), 3.50 (1H, dd, J=8.9, 7.1 Hz), 3.00 (3H, s), 2.72–2.58 (3H, m), 2.48 (1H, ddd, J=13.5, 7.4, 6.0 Hz), 2.12–1.96 (2H, m), 1.96 (1H, ddd, J=13.5, 6.4, 4.6 Hz), 1.27 (3H, s), 1.17 (3H, s), 0.95 (9H, s), 0.75 (9H, s), 0.11 (3H, s), 0.10 (3H, s), 0.01 (3H, s), −0.06 (3H, s). MASS (EI, m/e): 730 (M$^+$).

REFERENCE EXAMPLE 10

3-Decarboxy-3-aminocarbonyl-16-methyl-16-phenoxy-2,5,6,7,18,19,20-heptanor-4,8-inter-m-phenylene PGI$_2$, 11,15-bis(tert-Butyldimethylsilyl Ether) (10)

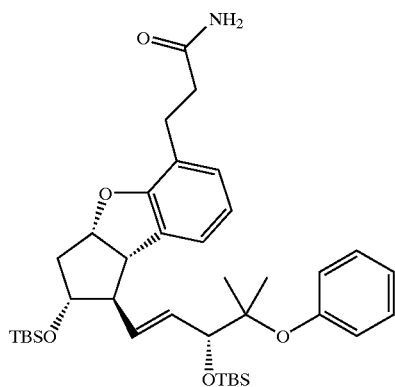

(10)

16-Methyl-16-phenoxy-5,6,7,18,19,20-heptanor-4,8-inter-m-phenylene PGI$_2$, 11,15-bis(tert-butyldimethylsilyl ether) (5) 1.83 g (2.7 mmol) was dissolved in anhydrous dichloromethane (30 mL), oxalyl chloride 0.36 mL (4.1 mmol, 1.5 equivalents) was added to the resultant solution, followed by stirring at room temperature. DMF dried with molecular sieve (4A) 10 drops were added to the mixture by a Pasteur pipet, and the resultant mixture was stirred at room temperature for 10 minutes. A small amount of the reaction solution was poured into a small amount of methanol. At this time, production of a methyl ester compound was checked by TLC, and it was thus decided that an acid chloride was produced. The reaction solution was referred to as "A".

Aqueous ammonia (150 mL) and chloroform (150 mL) were placed in a separating funnel, and the mixture was extracted with chloroform. The reaction solution A was added dropwise to the ammonia-saturated chloroform solution from a dropping funnel over 15 minutes under ice cooling. The resultant mixture was stirred for 30 minutes under ice cooling. After the disappearance of the starting material was checked by TLC, the reaction mixture was concentrated and then extracted with ethyl acetate (100 mL×2). The combined organic layer was washed in turn with 0.1 N hydrochloric acid (150 mL), a saturated aqueous sodium bicarbonate (200 mL), and brine (150 mL), dried over anhydrous sodium sulfate. After concentration, the residue was purified by column chromatography (Silica gel FL60D produced by Fuji Silicia Co.; cyclohexane:ethyl acetate=6:4 to 1:4) to obtain the titled compound 1.17 g (yield 64%) as a colorless oil. The structure of this compound was determined by the following data.

IR (neat): 3196, 2934, 2860, 1669, 1597, 1491, 1458, 1381, 1363, 1255, 1120, 1007, 977, 839, 777, 743 cm$^{-1}$. $^1$H-NMR (300 MHz, CDCl$_3$, d): δ 7.25 (2H, t, J=7.1 Hz), 7.09–6.92 (5H, m), 6.74 (1H, 7.4 Hz), 5.82 (1H, dd, J=15.6, 5.2 Hz), 5.71 (1H, dd, J=15.6, 7.4 Hz), 5.56 (2H, bs), 5.41 (1H, ddd, J=8.8, 7.4, 4.7 Hz), 4.22 (1H, d, J=5.2 Hz), 4.04–3.95 (1H, m), 3.53–3.45 (1H, m), 2.92–2.83 (2H, m), 2.64 (1H, dd, J=14.0, 6.9 Hz), 2.54 (2H, t, J=7.4 Hz), 2.51–2.42 (1H, m), 1.97 (1H, ddd, J=13.7, 7.4, 4.7 Hz), 1.26 (3H, s), 1.17 (3H, s), 0.96 (9H, s), 0.76 (9H, s), 0.11 (3H, s), 0.09 (3H, s), 0.01 (3H, s), −0.06 (3H, s). MASS (EI, m/e): 665 (M$^+$), 650 (M$^+$–CH$_3$).

REFERENCE EXAMPLE 11

2-Decarboxy-2-amino-16-methyl-16-phenoxy-5,6,7,18,19,20-hexanor-4,8-inter-m-phenylene PGI$_2$, 11,15-bis(tert-Butyldimethylsilyl Ether) (11)

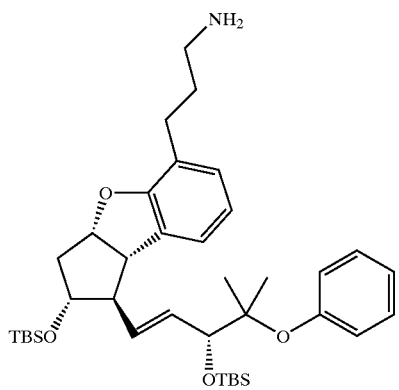

(11)

3-Decarboxy-3-aminocarbonyl-16-methyl-16-phenoxy-2,5,6,7,18,19,20-heptanor-4,8-inter-m-phenylene PGI$_2$, 11,15-bis(tert-butyldimethylsilyl ether) (10) 1.16 g (1.74 mmol) was dissolved in anhydrous THF (30 mL), and lithium aluminum hydride 0.4 g (10.5 mmol, 6 equivalents) was slowly added to the resultant solution under ice cooling, followed by stirring. After the temperature was warmed to room temperature over about 2 hours, the mixture was stirred at room temperature for 19 hours. After the disappearance of the starting material was checked by TLC, the reaction was quenched by the addition of saturated potassium sodium tartrate solution. After suction filtration, the filtrate was extracted with ethyl acetate (100 mL×2). The combined organic layer was washed with brine (100 mL×2), dried over anhydrous sodium sulfate. After concentration, the residue was purified by column chromatography (DM1020, 100 g; ethyl acetate:chloroform=1:1) to obtain the titled compound 531 mg (yield 47%) as a colorless oil. The structure of this compound was determined by the following data.

IR (neat): 3350, 2932, 2860, 1595, 1491, 1456, 1381, 1363, 1255, 1228, 1191, 1125, 837, 777, 696, 669 cm$^{-1}$. $^1$H-NMR (300 MHz, CDCl$_3$): δ 7.25 (2H, t, J=7.7 Hz), 7.09–7.01 (2H, m), 6.97 (2H, d, J=7.4 Hz), 6.92 (1H, d, J=7.7 Hz), 6.73 (1H, t, J=7.4 Hz), 5.82 (1H, dd, J=15.6, 4.9 Hz), 5.72 (1H, dd, J=15.6, 7.4 Hz), 5.17–5.08 (1H, m), 4.22 (1H, d, J=4.9 Hz), 4.02–3.93 (1H, m), 3.52–3.44 (1H, m), 2.73 (2H, t, J=6.9 Hz), 2.68–2.42 (4H, m), 4.83–1.70 (2H, m), 1.26 (3H, s), 1.17 (3H, s), 0.95 (9H, s), 0.76 (9H, s), 0.11 (3H, s), 0.09 (3H, s), 0.01 (3H, s), −0.05 (3H, s). MASS (EI, m/e): 651 (M$^+$).

REFERENCE EXAMPLE 12

Dimethyl 2-{(1S,2R,3aS,8bS)-2,3,3a,8b-tetrahydro-2-hydroxy-1-hydroxymethyl-1H-cyclopenta[b]benzofuran-5-yl}ethylphosphonate (12)

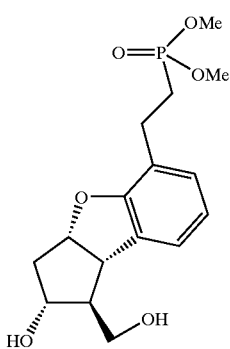

(12)

A solution of dimethyl methylphosphonate 3.76 ml (34.68 mmol) in anhydrous THF (80 ml) was cooled to −78° C. under argon stream, and t-butyl lithium 21.4 ml (1.62 M, 34.68 mmol) was slowly added dropwise to the solution. The resultant mixture was stirred at the same temperature for 45 minutes, and a solution of methyl 1-{(1S,2R,3aS,8bS)-2,3,3a,8b-tetrahydro-2-tetrahydropyranyloxy-1-tetrahydropyranyloxymethyl-1H-cyclopenta[b]benzofuran-5-yl} format 5.00 g (11.56 mmol) in THF (40 ml) was added dropwise, followed by stirring for 30 minutes. After reaction was quenched by the addition of saturated aqueous ammonium chloride, the reaction mixture was extracted with ethyl acetate (200 ml×3). The combined organic layer was washed with brine (50 ml×2), dried, concentrated, and then dried under reduced pressure. The thus-obtained crude product was dissolved in ethanol 60 ml, and the resultant solution was cooled to 0° C. Sodium borohydride 437.3 mg (11.56 mmol) was added to the cold solution, followed by stirring at the same temperature for 3 hours. The reaction mixture was concentrated to about 20 ml, and the residue was cooled to 0° C. After a saturated aqueous ammonium chloride was added to the cold residue little by little until the occurrence of bubbles was stopped, the mixture was extracted with ethyl acetate (100 ml×3). The combined organic layer was washed with brine (50 ml), dried, concentrated, and then dried under reduced pressure. The thus-obtained reduced product was dissolved in ethanol 126 ml, and 3N hydrochloric acid 34 ml and a palladium-carbon (5%) catalyst were added to the resultant solution. After the reaction system was replaced with hydrogen, the resultant mixture was stirred at room temperature overnight. The reaction solution was filtered with Celite, and the filtrate was concentrated to about 60 ml. After a saturated aqueous sodium bicarbonate was added to the residue, the mixture was extracted with chloroform (150 ml×3). The combined organic layer was washed with brine (100 ml), and the combined aqueous layer was extracted with chloroform. The thus-obtained organic layer was mixed with the previous organic layer, and the mixture was dried, and then concentrated. The thus-obtained oil was subjected to column chromatography (silica gel; chloroform:methanol=87:3), and the purified product was recrystallized from a solvent mixture of hexane/ethyl acetate=1/2 150 ml to obtain the titled compound 2.14 g (first crop 2.09 g, second crop 53.1 mg) as white needle (yield 54%). The structure of this compound was determined by the following data.

Melting point: 106~107° C. IR (KBr): 3418, 2946, 2872 1597, 1481, 1460 cm$^{-1}$. $^1$H-NMR (300 MHz, CDCl$_3$): δ 7.04 (d, J=7.4 Hz, 1H), 6.95 (d, J=7.4 Hz, 1H), 6.77 (t, J=7.4 Hz, 1H), 5.16–5.09 (m, 1H), 4.09 (dd, J=7.1 Hz, 14.0 Hz, 1H), 3.95–3.90 (m, 1H), 3.79–3.64 (m, 7H), 3.41 (t, J=8.0 Hz, 1H), 2.95–2.77 (brm, 3H), 2.62–2.53 (brm, 2H), 2.18–1.84 (brm, 4H);

| Elemental Analysis | C | H | P |
|---|---|---|---|
| Found: | 56.04 | 6.75 | 9.19 |
| Calculated for C$_{16}$H$_{23}$O$_6$P (M$^+$): | 56.14 | 6.77 | 9.05 |

REFERENCE EXAMPLE 13

Dimethyl 2-{(1S,2R,3aS,8bS)-2-acetoxy-2,3,3a,8b-tetrahydro-1-hydroxymethyl-1H-cyclopenta[b]benzofuran-5-yl}ethylphosphonate (13)

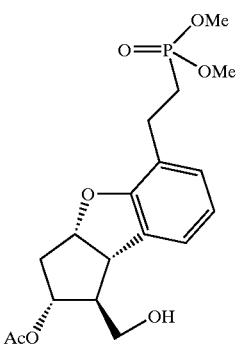

(13)

A solution of dimethyl 2-{(1S,2R,3aS,8bS)-2,3,3a,8b-tetrahydro-2-hydroxy-1-hydroxymethyl-1H-cyclopenta[b]benzofuran-5-yl}ethylphosphonate (12) 1000 mg (2.921 mmol) and triethylamine 3.26 ml (23.368 mol) in anhydrous DMF (20 ml) was cooled to 0° C. under argon atmosphere, and a solution of triphenylmethyl chloride in DMF (5 ml×2) was added to the solution, followed by stirring at room temperature for 2 hours, and then at 60° C. overnight. The reaction mixture was again cooled to 0° C., and triethylamine 1.63 ml (11.684 mmol), N,N-dimethylamindpyridine 713.7 mg (5.842 mmol), and acetic anhydride 0.551 ml (5.842 mmol) were added to the reaction mixture. After the temperature was increased to 60° C., the mixture was stirred for 1 hour. After the mixture was allowed to cool to room temperature, ice-cold ion exchanged water 40 ml was added to the mixture, and the mixture was extracted with ethyl acetate (100 ml×3). The combined organic layer was washed with water (50 ml×2) and brine (50 ml), dried, concentrated, and then dried in vacuo. The thus-obtained yellow oil was dissolved in methanol 30 ml, and hydrogen chloride-methanol (1.387M) 6.32 ml (8.764 mmol) was added to the resultant solution, followed by stirring at room temperature for 2 hours. After sodium bicarbonate was added little by little to neutralize the mixture, the resultant suspension was filtered with Celite, and the filtrate was concentrated. After the precipitate was again filtered off with Celite, the filtrate was concentrated. The residue was subjected to column chromatography (Silica gel FL-60D produced by Fuji Silicia Co.; chloroform:methanol 95:5) to recover dimethyl 2-{(1S, 2R,3aS,8bS)-2,3,3a,8b-tetrahydro-2-hydroxy-1-hydroxymethyl-1H-cyclopenta[b]benzofuran-5-yl}ethylphosphonate (12) used as the starting material (270.6 mg, 27%). The crude product of the titled compound was again purified by column chromatography (DIOL column produced by Yamazen Co.; ethyl acetate) to obtain the titled compound 667.9 mg (1.738 mmol) as a pale yellow oil (yield 60%). The structure of this compound was determined by the following data.

IR (neat): 3352, 2958, 1734, 1460, 1249, 1058, 1033 cm$^{-1}$. $^1$H-NMR (300 MHz, CDCl$_3$): δ 7.05 (d, J=7.4 Hz, 1H), 6.93 (d, J=7.4 Hz, 1H), 6.75 (t, J=7.4 Hz, 1H), 5.23–5.17 (m, 1H), 5.05 (dd, J=5.8, 11.3 Hz, 1H), 3.75–3.64 (m, 9H), 2.81 (q, J=9.1, 16.75 Hz, 2H), 2.59–2.49 (m, 2H), 2.29–2.00 (m., 4H), 1.78 (d, J=1.1 Hz, 3H); MASS (EI, m/e): m/z 384 (M$^+$).

REFERENCE EXAMPLE 14

2-Decarboxy-2-oxo-2-(2,4-pentadione-3-yl)-16-methyl-16-phenoxy-5,6,7,18,19,20-hexanor-4,8-inter-m-phenylene PGI$_2$, 11,15-bis(tert-Butyldimethylsilyl Ether) (14)

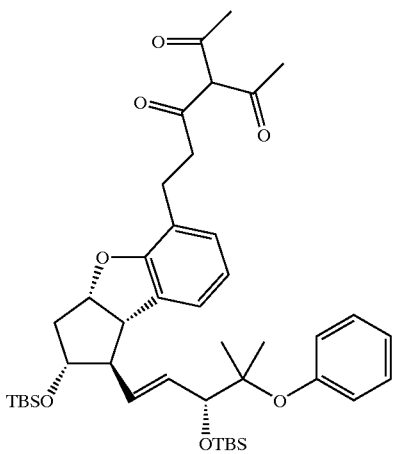

(14)

Oxalyl chloride 16.3 μl and anhydrous DMF (1 droplet) were added to a solution of 16-methyl-16-phenoxy-2,5,6,7,18,19,20-heptanor-4,8-inter-m-phenylene PGI$_2$, 11,15-bis(tert-butyldimethylsilyl ether) (5) 62.3 mg (93.4 μmol) in anhydrous dichloromethane (4 ml) under argon atmosphere, and the resultant mixture was stirred at room temperature for 30 minutes. The reaction mixture was concentrated, and dried under reduced pressure to obtain a crude acid chloride.

A suspension of sodium hydride (69 wt %) 17.5 mg (504.4 μmol) in anhydrous toluene (4 ml) was cooled to 0° C. under argon stream, and acetylacetone 49.9 μl (485.7 μmol) was added to the suspension, followed by stirring at the same temperature. A solution of the previously prepared acid chloride in anhydrous toluene (1 ml×2) was slowly added to the reaction solution, and the resultant mixture was stirred at room temperature,for 2.5 hours. After reaction was quenched by the addition of saturated aqueous ammonium chloride (30 ml), the mixture was extracted with ethyl acetate (50 ml×3). The combined organic layer was washed with water (20 ml) and brine (20 ml), dried, and then concentrated. The residue was purified by column chromatography (Silica gel FL-60D produced by Fuji Silicia Co.; cyclohexane:ethyl acetate=97:3) to obtain the titled compound 43.3 mg (57.8 μmol) as a colorless oil (yield 62%).

IR (neat): 2958, 2932, 2860, 1686, 1595, 1458, 1253, 1125, 83.7, 777 cm$^{-1}$. $^1$H-NMR (300 MHz, CDCl$_3$): δ 7.28–7.22 (m, 2H), 7.08–6.91 (m, 5H), 6.72 (t, J=7.4 Hz, 1H), 5.82 (dd, J=5.2, 15.7 Hz, 1H), 5.71 (dd, J=7.1, 15.1 Hz, 1H), 5.16–5.09 (m, 1H), 4.22 (d, J=4.9 Hz, 1H), 4.02–3.94 (m, 1H), 3.48 (t, J=7.1 Hz, 1H), 3.03–2.43 (m, 6H), 2.36 (s, 1.5H), 2.18 (s, 1.5H), 2.12 (s, 3H), 1.99–1.90 (m, 1H), 1.26 (s, 3H), 1.17 (s, 3H), 0.95 (s, 9H), 0.75 (s, 9H), 0.11 (s, 3H), 0.09 (s, 3H), 0.01 (s, 3H), −0.06 (d, J=1.9 Hz, 3H); MASS (EI, m/e): m/z 748 (M$^+$).

EXAMPLE 1

14-Fluoro-16-methyl-15-oxo-16-phenoxy-2,5,6,7,18,19,20-heptanor-4,8-inter-m-phenylene PGI$_2$ Methyl Ester, 11-Acetate (15)

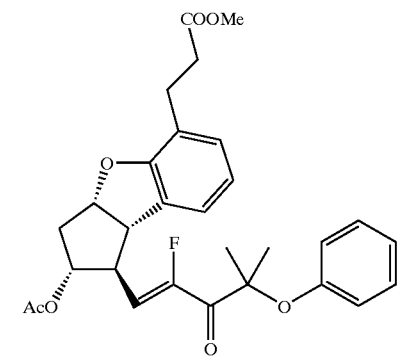

(15)

Anhydrous DMSO 0.25 ml (3.52 mmol), anhydrous pyridine 0.016 ml (0.198 mmol), and trifluoroacetic acid 0.007 ml (0.091 mmol) were added to a solution of methyl 3-{(1S,2R,3aS,8bS)-2-acetoxy-2,3,3a,8b-tetrahydro-1-hydroxymethyl-1H-cyclopenta[b]benzofuran-5-yl}propionate 59.6 mg (0.178 mmol) and DCC 55.2 mg (0.268 mmol) in anhydrous THF 1.0 ml under ice cooling and argon stream, and the resultant mixture was stirred at room temperature for 1 hour (solution A).

Next, 69% mineral oil dispersion of sodium hydride 12.4 mg (0.357 mmol) was added to a solution of dimethyl 1-fluoro-3-methyl-2-oxo-3-phenoxybutylphosphonate (1) 650 mg (2.03 mmol) in anhydrous DME 1.0 ml under ice cooling and argon stream, and the resultant mixture was stirred at room temperature for 19 minutes. The previously prepared solution A was added to the ice-cold resultant solution by using a syringe. The anhydrous DME (2×1 ml) washing solution of the residue of solution A was also added to the ice-cold solution, followed by stirring at room temperature for 1 hour. Then, acetic acid 0.1 ml was added to the ice-cold reaction mixture, and water 5 ml was further added thereto, followed by extraction with ethyl acetate (3×10 ml). The combined organic layer was washed with 5 ml of brine, dried, and then concentrated. The thus-obtained oil was purified by column chromatography [(1) silica gel; cyclohexane:ethyl acetate=90:10→30:70, (2) silica gel; cyclohexane:ethyl acetate=85:15] to obtain the titled compound 45.5 mg (yield 50%) as a colorless oil. The structure of this compound was determined by the following data.

IR (neat): 1741, 1692, 1652, 1597, 1492, 1456, 1370, 1300, 1238, 1196, 1159, 1068, 1009, 990, 958, 869, 754, 695 cm$^{-1}$. $^1$H-NMR (300 MHz, CDCl$_3$): δ 7.28–7.20 (2H, m), 6.98 (1H, t, J=7.4 Hz), 6.93 (1H, d, J=7.4 Hz), 6.77 (2H, d, J=7.7 Hz), 6.66 (1H, t, J=7.7 Hz), 6.49 (1H, dd, J=34.3, 9.9 Hz), 5.09 (1H, ddd, J=8.8, 7.3, 4.3 Hz), 4.92 (1H, ddd, J=12.9, 7.1, 6.9 Hz), 3.66 (3H, s), 3.38 (1H, dd, J=8.8, 6.6 Hz), 3.20 (1H, ddd, J=9.9, 6.9, 6.6 Hz), 2.85 (2H, t, J=7.8

Hz), 2.59 (2H, t, J=7.8 Hz), 2.52 (1H, ddd, J=17.2, 12.9, 7.3 Hz), 2.10 (1H, ddd, J=14.3, 7.1, 4.3 Hz), 1.75 (3H, s), 1.66 (3H, s), 1.64 (3H, s). MASS (EI, m/e): 510 (M$^+$).

An example of methods of producing the starting material, 3-{(1S,2R,3aS,8bS)-2-acetoxy-2,3,3a,8b-tetrahydro-1-hydroxymethyl-1H-cyclopenta[b]benzofuran-5-yl}propionate is disclosed in Japanese Examined Patent Publication No. 5-71592.

EXAMPLE 2

14-Fluoro-16-methyl-16-phenoxy-2,5,6,7,18,19,20-heptanor-4,8-inter-m-phenylene PGI$_2$ Methyl Ester (16) and 15-Epimer (17) Thereof

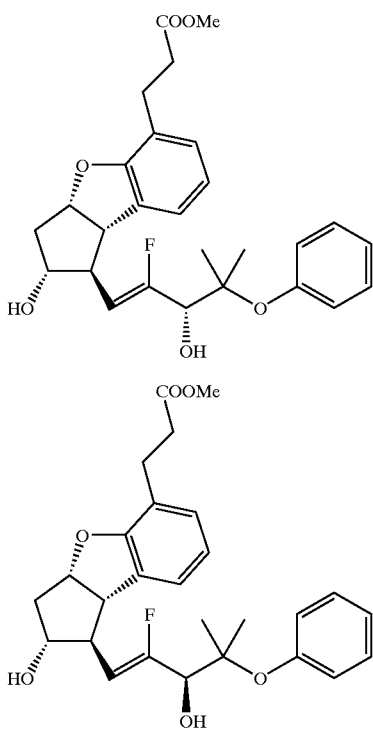

Cerium trichloride heptahydrate 21.7 mg (0.0582 mmol) was added to a solution of 14-fluoro-16-methyl-15-oxo-16-phenoxy-2,5,6,7,18,19,20-heptanor-4,8-inter-m-phenylene PGI$_2$ methyl ester, 11-acetate (15) 13.9 mg (0.0272 mmol) in methanol 1.0 ml and THF 0.5 ml, and the resultant mixture was cooled in ice bath. Sodium borohydride 1.1 mg (0.0291 mmol) was added to the resultant solution, and the resulting mixture was stirred for 1 hour under ice cooling. Saturated aqueous sodium bicarbonate 1 ml was added to the reaction mixture, and the mixture was filtered with a glass filter in which Celite was placed. The precipitate was washed with ethyl acetate 40 ml, and the filtrate was concentrated. The thus-obtained aqueous layer was extracted with ethyl acetate (3×10 ml). The combined organic layer was washed in turn with water 5 ml and brine 5 ml, dried and then concentrated to obtain colorless oil 14.9 mg.

Next, the oil was azeotropically dehydrated with benzene (2×1 ml), and then dissolved in anhydrous methanol 1.0 ml under argon stream. 5.10 mol/L sodium methoxide 0.005 ml (0.0255 mmol) was added to the resultant solution, followed by stirring at room temperature for 4 hours. Acetic acid 0.01 ml was added to the reaction mixture, and the mixture was concentrated. Then, saturated aqueous sodium bicarbonate 5 ml was added to the residue, and the resultant mixture was extracted with ethyl acetate (3×10 ml). The combined organic layer was washed with brine 5 ml, dried, and then concentrated. The thus-obtained oil 14.2 mg was purified by column chromatography (silica gel; cyclohexane:ethyl acetate=50:50) to obtain 14-fluoro-16-methyl-16-phenoxy-15-epi-2,5,6,7,18,19,20-heptanor-4,8-inter-m-phenylene PGI$_2$ methyl ester (17) 6.0 mg (yield 47%) as a colorless oil from the less-polar fractions, and 14-fluoro-16-methyl-16-phenoxy-2,5,6,7,18,19,20-heptanor-4,8-inter-m-phenylene PGI$_2$ methyl ester (16) 6.3 mg (yield 49%) as a colorless oil from the more-polar fractions. The structures of these compounds were determined by the following data.

14-Fluoro-16-methyl-16-phenoxy-2,5,6,7,18,19,20-heptanor-4,8-inter-m-phenylene PGI$_2$ Methyl Ester IR (neat): 3430, 1736, 1594, 1490, 1455, 1370, 1225, 1196, 1140, 1073, 1037, 956, 868, 758, 699 cm$^{-1}$. $^1$H-NMR (300 MHz, CDCl$_3$): δ 7.31 (2H, t, J=7.4 Hz), 7.14 (1H, t, J=7.4 Hz), 7.06–6.95 (4H, m), 6.77 (1H, t, J=7.4 Hz), 5.19 (1H, ddd, J=8.5, 7.0, 4.4 Hz), 5.02 (1H, dd, J=36.5, 9.6 Hz), 4.24 (1H, dd, J=14.5, 4.0 Hz), 4.00 (1H, br dd, J=13.2, 7.4 Hz), 3.65 (3H, s), 3.54 (1H, dd, J=8.5, 6.9 Hz), 3.22 (1H, br d, J=4.1 Hz), 3.05 (1H, ddd, J=9.6, 6.9, 6.9 Hz), 2.94–2.85 (2H, m), 2.69–2.52 (3H, m), 2.10 (1H, ddd, J=14.0, 7.4, 4.4 Hz), 1.95 (1H, br s), 1.33 (3H, s), 1.32 (3H, s). MASS (EI, m/e): 470 (M$^+$).

14-Fluoro-16-methyl-16-phenoxy-15-epi-2,5,6,7,18,19,20-heptanor-4,8-inter-m-phenylene PGI$_2$ Methyl Ester IR (neat): 3454, 1736, 1595, 1490, 1455, 1370, 1259, 1224, 1195, 1137, 1072, 1032, 957, 886, 785, 744, 700 cm$^{-1}$. $^1$H-NMR (300 MHz, CDCl$_3$): δ 7.31 (2H, t, J=7.4 Hz), 7.14 (1H, t, J=7.4 Hz), 7.05–6.95 (4H, m), 6.77 (1H, t, J=7.4 Hz), 5.18 (1H, ddd, J=8.6, 7.1, 4.9 Hz), 5.03 (1H, dd, J=36.5, 9.6 Hz), 4.24 (1H, dd, J=13.7, 3.8 Hz), 4.00 (1H, br dd, J=14.2, 7.0 Hz), 3.65 (3H, s), 3.51 (1H, dd, J=8.6,7.2 Hz), 3.22 (1H, d, J=3.8 Hz), 3.04 (1H, ddd, J=9.6, 7.2, 7.0 Hz), 2.93–2.85 (2H, m), 2.68–2.53 (3H, m), 2.09 (1H, ddd, J=13.7, 7.7, 4.9 Hz), 1.94 (1H, br s), 1.34 (3H, s), 1.31 (3H, s). MASS (EI, m/e): m/z 470 (M$_+$).

EXAMPLE 3

14-Fluoro-16-methyl-16-phenoxy-2,5,6,7,18,19,20-heptanor-4,8-inter-m-phenylene PGI$_2$ (18)

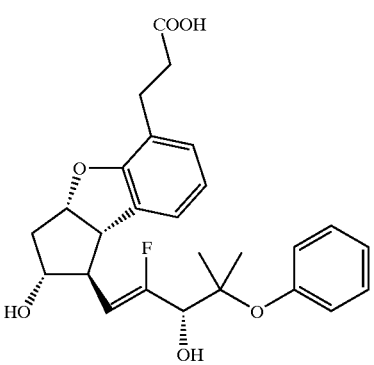

2N aqueous sodium hydroxide 1.0 ml was added to a solution of 14-fluoro-16-methyl-16-phenoxy-2,5,6,7,18,19,20-heptanor-4,8-inter-m-phenylene PGI$_2$ methyl ester (16) 12.7 mg (0.0270 mmol) in methanol 1.0 ml, and the resultant mixture was stirred at room temperature for 1.5 hours. After the reaction mixture was cooled with ice, 1N hydrochloric acid 2.2 ml was added to the mixture, and the mixture was extracted with ethyl acetate (3×10 ml). The combined organic layer was washed with brine 5 ml, dried and then concentrated. The thus-obtained oil 13.8 mg was purified by column chromatography (DIOL; cyclohexane:ethyl acetate= 40:60) to obtain the titled compound 12.5 mg (quantitative) as a colorless oil. The structure of this compound was determined by the following data.

IR (neat): 3426, 1710, 1594, 1490, 1455, 1224, 1193, 1138, 1072, 1039, 955, 884, 785, 745, 699 cm$^{-1}$. $^1$H-NMR (300 MHz, CDCl$_3$): δ 7.31 (2H, t, J=7.4 Hz), 7.14 (1H, t, J=7.4 Hz), 7.06–6.95 (4H, m), 6.77 (1H, t, J=7.4 Hz), 5.18 (1H, ddd, J=8.2, 7.2, 4.5 Hz), 5.00 (1H, dd, J=36.5, 9.6 Hz), 4.23 (1H, d, J=15.1 Hz), 3.99 (1H, ddd, J=7.3, 6.5, 6.3 Hz), 3.52 (1H, dd, J=8.2, 6.9 Hz), 3.03 (1H, ddd, J=9.6, 6.9, 6.5 Hz), 2.96–2.80 (2H, m), 2.72–2.63 (2H, m), 2.54 (1H, ddd, J=14.0, 7.2, 6.5 Hz), 2.08 (1H, ddd, J=14.0, 7.3, 4.5 Hz), 1.32 (3H, s), 1.31 (3H, s). MASS (EI, m/e): 456 (M$^+$). High Resolution Mass Spectrometry (HREIMS): Found: 456.1930 (−1.8 mmu). Calculated for C$_{26}$H$_{29}$FO$_6$ (M$^+$): 456.1948.

EXAMPLE 4

14-Fluoro-16-methyl-16-phenoxy-15-epi-2,5,6,7,18, 19,20-heptanor-4,8-inter-m-phenylene PGI$_2$ (19)

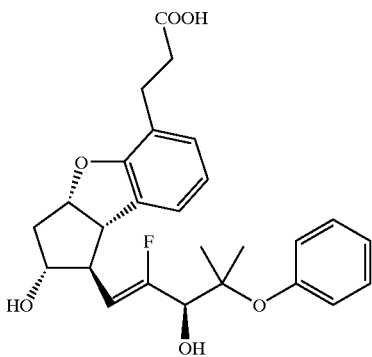

(19)

2N aqueous sodium hydroxide 1.0 ml was added to a solution of 14-fluoro-16-methyl-16-phenoxy-15-epi-2,5,6, 7,18,19,20-heptanor-4,8-inter-m-phenylene PGI$_2$ methyl ester (17) 9.6 mg (0.0204 mmol) in methanol 1.0 ml, and the resultant mixture was stirred at room temperature for 1.5 hours. After the reaction mixture was cooled with ice, 1N hydrochloric acid 2.1 ml was added to the mixture, and the mixture was extracted with ethyl acetate (3×10 ml). The combined organic layer was washed with 5 ml of brine, dried and then concentrated. The thus-obtained oil was purified by column chromatography (DIOL produced by Yamazen Co.; cyclohexane:ethyl acetate=40:60) to obtain the titled compound 9.6 mg (quantitative) as a colorless oil. The structure of this compound was determined by the following data.

IR (neat): 3442, 1710, 1594, 1490, 1454, 1387, 1256, 1223, 1193, 1135, 1071, 1033, 954, 884, 785, 744, 699 cm$^{-1}$. $^1$H-NMR (300 MHz, CDCl3): δ 7.31 (2H, t, J=7.4 Hz), 7.14 (1H, t, J=7.4 Hz), 7.06–6.96 (4H, m), 6.77 (1H, t, J=7.4 Hz), 5.18 (1H, ddd,=8.5, 7.0, 4.5 Hz), 5.03 (1H, dd, J=36.8, 9.6 Hz), 4.23 (1H, d, J=14.0 Hz), 4.00 (1H, ddd, J=7.2, 7.2, 6.9 Hz), 3.51 (1H, dd, J=8.5, 7.2 Hz), 3.03 (1H, ddd, J=9.6, 7.2, 7.2 Hz), 2.96–2.81 (2H, m), 2.74–2.63 (2H, m),.2.56 (1H, ddd, J=13.7, 7.0, 6.9 Hz), 2.08 (1H, m), 1.33 (3H, s), 1.32 (3H, s). MASS (EI, m/e): 456 (M$^+$). High Resolution Mass Spectrometry (HREIMS): Found: 456.1959 (+1.1 mmu). Calculated for C$_{26}$H$_{29}$FO$_6$ (M$^+$): 456.1948.

EXAMPLE 5

14-Chloro-16-methyl-15-oxo-16-phenoxy-2,5,6,7, 18,19,20-heptanor-4,8-inter-m-phenylene PGI$_2$ Methyl Ester, 11-Acetate (20)

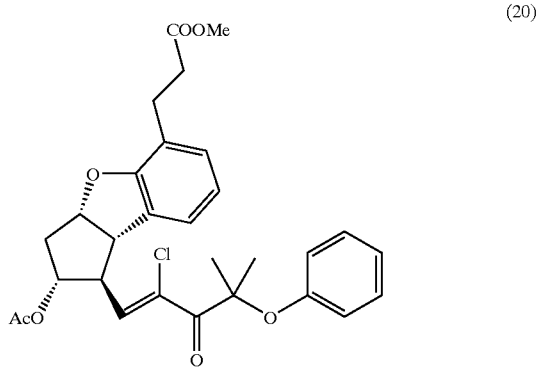

(20)

Anhydrous DMSO 1.40 ml (19.7 mmol), anhydrous pyridine 0.090 ml (1.11 mmol), and trifluoroacetic acid 0.040 ml (0.52 mmol) were added to a solution of methyl 3-{(1S,2R, 3aS,8bS)-2-acetoxy- 2,3,3a,8b-tetrahydro-1-hydroxymethyl-1H-cyclopenta[b]benzofuran-5-yl}propionate 330 mg (0.987 mmol) and DCC 305 mg (1.48 mmol) in anhydrous THF 5.0 ml under ice cooling, and the resultant mixture was stirred at room temperature for 1 hour (solution A).

Next, 69% mineral oil dispersion of sodium hydride 67 mg (1.93 mmol) was added to a solution of dimethyl 1-chloro-3-methyl-2-oxo-3-phenoxybutylphosphonate (2) 650 mg (2.03 mmol) in anhydrous DME 5.0 ml under ice cooling and argon stream, and the resultant mixture was stirred at room temperature for 15 minutes. The previously prepared solution A was added to the ice-cold resultant solution by using a syringe. The anhydrous DME (2×2 ml) washing solution of the residue of solution A was also added to the ice-cold solution, followed by stirring under ice cooling for 1.5 hours, and at room temperature for 1.5 hours. Then, acetic acid 0.3 ml was added to the ice-cold reaction mixture, and water 10 ml was further added thereto, followed by extraction with ethyl acetate (3×20 ml). The combined organic layer was washed with brine 10 ml, dried, and then concentrated. The thus-obtained oil 1.08 g was purified by column chromatography [(1) silica gel; cyclohexane:ethyl acetate=80:20→50:50, (2) silica gel; cyclohexane:ethyl acetate=90:10] to obtain the titled compound 54.4 mg (yield 10%) as a colorless oil. The structure of this, compound was determined by the following data.

IR (neat): 1743, 1690, 1618, 1597, 1492, 1456, 1369, 1299, 1237, 1194, 1160, 1069, 1030, 1008, 964, 891, 863, 810, 752, 695 cm$^{-1}$. $^1$H-NMR (300 MHz, CDCl$_3$): δ 7.51 (1H, d, J=9.0 Hz), 7.28–7.20 (2H, m), 6.99–6.90 (2H, m), 6.68 (1H, d, J=8.4 Hz), 6.66 (1H, t, J=7.4 Hz), 6.52 (1H, d, J=7.1 Hz), 5.03–4.94 (2H, m), 3.66 (3H, s), 3.41–3.26 (2H, m), 2.84 (2H, t, J=7.8 Hz), 2.65–2.52 (2H, m), 2.41 (1H, ddd, J=14.5, 6.7, 6.0 Hz), 2.19 (1H, ddd, J=14.5, 6.0, 3.6 Hz), 1.72 (3H, s), 1.71 (3H, s), 1.70 (3H, s). MASS (EI, m/e): 528 (M$^+$+2), 526 (M$^+$).

EXAMPLE 6

14-Chloro-16-methyl-16-phenoxy-2,5,6,7,18,19,20-heptanor-4,8-inter-m-phenylene PGI$_2$ Methyl Ester (21) and 15-Epimer (22) Thereof

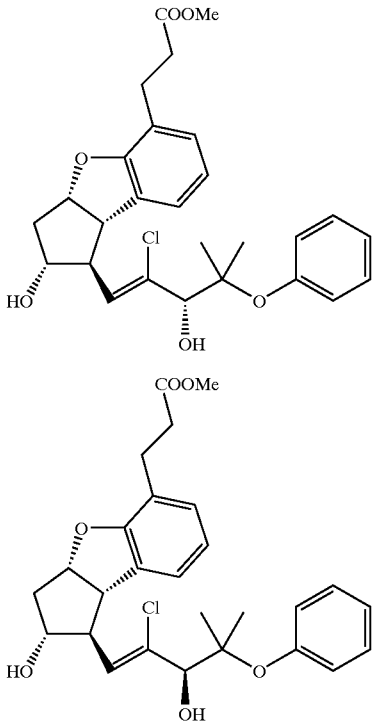

Cerium trichloride heptahydrate 92.6 mg (0.248 mmol) was added to a solution of 14-chloro-16-methyl-15-oxo-16-phenoxy-2,5,6,7,18,19,20-heptanor-4,8-inter-m-phenylene PGI$_2$ methyl ester, 11-acetate (20) 65.4 mg (0.124 mmol) in methanol 1.0 ml and THF 2.0 ml, and the resultant mixture was cooled with ice. Sodium borohydride 4.7 mg (0.124 mmol) was added to the resultant solution, and the resulting mixture was stirred for 2 hours under ice cooling. Saturated aqueous sodium bicarbonate 5 ml was added to the reaction mixture, and the mixture was filtered with a glass filter in which Celite was placed. The precipitate was washed with ethyl acetate 40 ml, and the filtrate was concentrated. The thus-obtained aqueous layer was extracted with ethyl acetate (3×10 ml). The combined organic layer was washed in turn with water 5 ml and brine 5 ml, dried and then concentrated to obtain pale yellow oil 65.2 mg.

Next, the oil was azeotropically dehydrated with benzene (2×1 ml), and then dissolved in anhydrous methanol 2.4 ml under argon stream. 5.10 mol/L sodium methoxide 0.024 ml (0.122 mmol) was added to the resultant solution, followed by stirring at room temperature for 3 hours. Acetic acid 0.03 ml was added to the reaction mixture, and the mixture was concentrated. Then, saturated aqueous sodium bicarbonate 5 ml was added to the residue, and the resultant mixture was extracted with ethyl acetate (3×10 ml). The combined organic layer was washed with brine 5 ml, dried, and then concentrated. The thus-obtained oil 69 mg was purified by preparative thin layer chromatography (silica gel plate; cylcohexane:ethyl acetate=1:1) and column chromatography (silica gel; cyclohexane:ethyl acetate=70:30) to obtain 14-chloro-16-methyl-16-phenoxy-15-epi-2,5,6,7,18,19,20-heptanor-4,8-inter-m-phenylene PGI$_2$ methyl ester (22) 18.0 mg (yield 30%) as a colorless oil from the less-polar fractions, and 14-chloro-16-methyl-16-phenoxy-2,5,6,7,18,19,20-heptanor-4,8-inter-m-phenylene PGI$_2$ methyl ester (21) 19.0 mg (yield 31%) as a colorless oil from the more-polar fractions. The structures of these compounds were determined by the following data.

14-Chloro-16-methyl-16-phenoxy-2,5,6,7,18,19,20-heptanor-4,8-inter-m-phenylene PGI$_2$ Methyl Ester IR (neat): 3444, 1735, 1594, 1490, 1455, 1369, 1259, 1224, 1134, 1072, 1028, 955, 887, 783, 743, 698 cm$^{-1}$. $^1$H-NMR (300 MHz, CDCl$_3$): δ 7.30 (2H, t, J=7.4 Hz), 7.14 (1H, t, J=7.4 Hz), 7.08 (1H, br d, J=7.4 Hz), 7.04–6.95 (3H, m), 6.79 (1H, t, J=7.4 Hz), 5.86 (1H, d, J=9.3 Hz), 5.22 (1H, ddd, J=8.7, 6.9, 3.9 Hz), 4.33 (1H, d, J=5.3 Hz), 4.08 (1H, br ddd, J=6.0, 6.0, 6.0 Hz), 3.65 (3H, s), 3.60 (1H, dd, J=8.7, 5.4 Hz), 3.42 (1H, d, J=5.3 Hz), 3.27 (1H, ddd, J=9.3, 5.4, 5.2 Hz), 2.97–2.82 (2H, m), 2.76–2.56 (2H, m), 2.50 (1H, ddd, J=14.0, 6.9, 6.0 Hz), 2.19 (1H, ddd, J=14.0, 6.0, 3.9 Hz), 2.04 (1H, br s), 1.36 (3H, s), 1.32 (3H, s). MASS (EI, m/e): 488 (M$^+$+2), 486 (M$^+$).

14-Chloro-16-methyl-16-phenoxy-15-epi-2,5,6,7,18,19,20-heptanor-4,8-inter-m-phenylene PGI$_2$ Methyl Ester IR (neat): 3410, 1735, 1593, 1490, 1455, 1369, 1224, 1131, 1074, 1031, 955, 887, 784, 743, 698 cm$^{-1}$. $^1$H-NMR (300 MHz, CDCl$_3$): δ 7.30 (2H, t, J=7.7 Hz), 7.14 (1H, t, J=7.2 Hz), 7.08 (1H, br d, J=7.4 Hz), 7.04–6.95 (3H, m), 6.79 (1H, t, J=7.4 Hz), 5.87 (1H,+d, J=9.3 Hz), 5.22 (1H, ddd, J=8.7, 6.9, 3.8 Hz), 4.32 (1H, d, J=5.2 Hz), 4.08 (1H, br ddd, J=6.0, 5.8, 5.5 Hz), 3.65 (3H, s), 3.60 (1H, dd, J=8.7, 5.5 Hz), 3.43 (1H, d, J=5.2 Hz), 3.27 (1H, ddd, J=9.3, 5.5, 5.5 Hz), 2.95–2.85 (2H, m), 2.73–2.56 (2H, m), 2.50 (1H, ddd, J=14.3, 6.9, 5.8 Hz), 2.18 (1H, ddd, J=14.3, 6.0, 3.8 Hz), 2.04 (1H, br s), 1.35 (3H, s), 1.33 (3H, s). MASS (EI, m/e): 488 (M$^+$+2), 486 (M$^+$).

EXAMPLE 7

14-Chloro-16-methyl-16-phenoxy-2,5,6,7,18,19,2.0-heptanor-4,8-inter-m-phenylene PGI$_2$ (23)

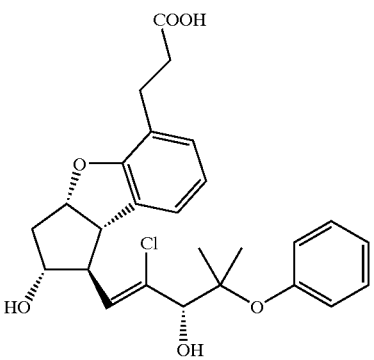

2N aqueous sodium hydroxide 0.5 ml was added to a solution of 14-chloro-16-methyl-16-phenoxy-2,5,6,7,18,19,20-heptanor-4,8-inter-m-phenylene PGI$_2$ methyl ester (21) 8.1 mg (0.017 mmol) in methanol 1.0 ml, and the resultant mixture was stirred at room temperature for 1 hour. After the reaction mixture was cooled with ice, 1N hydrochloric acid 1 ml was added to the mixture, and the mixture was extracted with ethyl acetate (3×10 ml). The combined organic layer was washed with brine 5 ml, dried and then concentrated. The thus-obtained oil was purified by column chromatography (DIOL produced by Yamazen Co.; cyclohexane:ethyl acetate=45:55) to obtain the titled compound 8.8 mg (quantitative) as a colorless oil. The structure of this compound was determined by the following data.

IR (neat): 3406, 1712, 1594, 1490, 1455, 1387, 1262, 1224, 1194, 1132, 1074, 1032, 956, 882, 782, 739, 698 cm$^{-1}$. $^1$H-NMR (300 MHz, CDCl$_3$): δ 7.30 (2H, t, J=7.4 Hz), 7.14 (1H, t, J=7.4 Hz), 7.08 (1H, t, J=7.4 Hz), 7.03–6.96 (3H, m), 6.79 (1H, t, J=7.4 Hz), 5.85 (1H, d, J=9.3 Hz), 5.22 (1H, ddd, J=8.7, 7.0, 3.7 Hz), 4.33 (1H, s), 4.08 (1H, ddd, J=5.6, 5.5, 5.4 Hz), 3.59 (1H, dd, J=8.7, 5.4 Hz), 3.25 (1H, ddd, J=9.9, 5.5, 5.4 Hz), 2.98–2.80 (2H, m), 2.76–2.53 (2H, m), 2.47 (1H, ddd, J=14.3, 7.0, 5.5 Hz), 2.18 (1H, ddd, J=14.3, 5.6, 3.7 Hz), 1.36 (3H, s), 1.32 (3H, s). MASS (EI, m/e): 474 (M$^+$+2), 472 (M$^+$). High Resolution Mass Spectrometry (HREIMS): Found: 472.1671 (+1.9 mmu). Calculated for C$_{26}$H$_{29}$ClO$_6$ (M$^+$): 472.1653.

EXAMPLE 8

14-Chloro-16-methyl-16-phenoxy-15-epi-2,5,6,7,18, 19,20-heptanor-4,8-inter-m-phenylene PGI$_2$ (24)

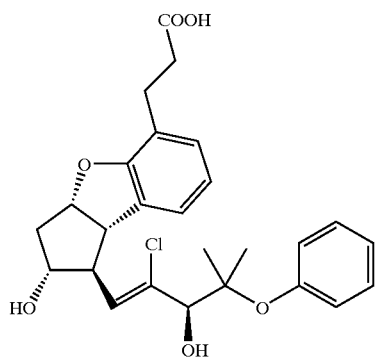

(24)

2N aqueous sodium hydroxide 0.5 ml was added to a solution of 14-chloro-16-methyl-16-phenoxy-15-epi-2,5,6, 7,18,19,20-heptanor-4,8-inter-m-phenylene PGI$_2$ methyl ester (22) 7.8 mg (0.016 mmol) in methanol 1.0 ml, and the resultant mixture was stirred at room temperature for 45 minutes. After the reaction mixture was cooled with ice, 1N hydrochloric acid 1 ml was added to the mixture, and the mixture was extracted with ethyl acetate (3×10 ml). The combined organic layer was washed with brine 5 ml, dried and then concentrated. The thus-obtained oil was purified by column chromatography (DIOL produced by Yamazen Co.; cyclohexane:ethyl acetate=45:55) to obtain the titled compound 8.2 mg (quantitative) as a colorless oil. The structure of this compound was determined by the following data.

IR (neat): 3414, 1711, 1594, 1490, 1455, 1388, 1263, 1224, 1194, 1133, 1072, 1028, 957, 892, 781, 740, 699 cm$^{-1}$. $^1$H-NMR (300 MHz, CDCl$_3$): δ 7.30 (2H, t, J=7.4 Hz), 7.13 (1H, t, J=7.4 Hz), 7.08 (1H, br d, J=7.4 Hz), 7.03–6.96 (3H, m), 6.79 (1H, t, J=7.4 Hz), 5.86 (1H, d, J=9.1 Hz), 5.22 (1H, ddd, J=8.5, 6.9, 3.9 Hz), 4.32 (1H, s), 4.07 (1H, ddd, J=6.0, 5.7, 5.5 Hz), 3.59 (1H, dd, J=8.5, 5.7 Hz), 3.25 (1H, ddd, J=9.1, 5.7, 5.7 Hz), 2.99–2.80 (2H, m), 2.76–2.59 (2H, m), 2.47 (1H, ddd, J=14.3, 6.9, 5.5 Hz), 2.17 (1H, ddd, J=14.3, 6.0, 3.9 Hz), 1.35 (3H, s), 1.33 (3H, s). MASS (EI, m/e): 474 (M$^+$+2), 472 (M$^+$). High Resolution Mass Spectrometry (HREIMS): Found: 472.1637 (−1.6 mmu). Calculated for C$_{26}$H$_{29}$ClO$_6$ (M$^+$): 472.1653.

EXAMPLE 9

14-Bromo-15-oxo-2,5,6,7-tetranor-4,8-inter-m-phenylene PGI$_2$ Methyl Ester, 11-Acetate (25)

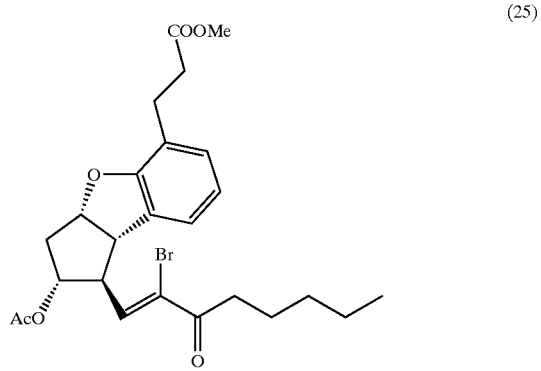

(25)

60% mineral oil dispersion of sodium hydride 96 mg (2.40 mmol) was added to a solution of dimethyl 2-oxoheptyiphosphonate 267 mg (1.20 mmol) in anhydrous DME 4.0 ml under ice cooling and argon stream, and the resultant mixture was stirred at room temperature for 10 minutes. N-bromosuccinimide 214 mg (1.20 mmol) was added to the ice-cold resultant solution, followed by stirring under ice cooling for 2 hours. Then, saturated aqueous ammonium chloride 6 ml was added to the reaction mixture, and the resultant mixture was extracted with ethyl acetate (3×10 ml). The combined organic layer was washed with brine 5 ml, dried, and then concentrated. The thus-obtained oil 408 mg was purified by column chromatography (silica gel, cyclohexane:ethyl acetate 1:1→1:2→1:4) to obtain a fraction containing dimethyl 1-bromo-2-oxoheptylphosphonate 254 mg. This fraction was used for next reaction without further purification.

Next, anhydrous DMSO 0.43 ml (6.06 mmol), anhydrous pyridine 0.027 ml (0.334 mmol), and trifluoroacetic acid 0.012 ml (0.156 mmol) were added to a solution of methyl 3-{(1S,2R,3aS,8bS)-2-acetoxy-2,3,3a,8b-tetrahydro-1-hydroxymethyl-1H-cyclopenta[b]benzofuran-5-yl}propionate 100 mg (0.299 mmol) and DCC 92.5 mg (0.488 mmol) in anhydrous THF 2.0 ml under ice cooling an argon stream, and the resultant mixture was stirred at room temperature 1.5 hours (solution A).

Next, 60% mineral oil dispersion of sodium hydride 24 mg (0.600 mmol) was added to a solution of the fraction containing dimethyl 2-bromo-2-oxoheptylphosphonate 254 mg in anhydrous DME 2.0 ml under ice cooling, and the resultant mixture was stirred for 10 minutes. The previously prepared solution A was added to the resultant solution by using a syringe. The anhydrous DME (2×2 ml) washing solution of the residue of solution A was also added to the ice-cold solution, followed by stirring under ice cooling for 3 hours. Then, saturated aqueous ammonium chloride 6 ml was added to the reaction mixture, and the resultant mixture was extracted with ethyl acetate (3×10 ml). The combined organic layer was washed with brine 5 ml, dried, and then concentrated. The thus-obtained oil 365 mg was purified by column chromatography (silica gel; cyclohexane:ethyl acetate=83:17) to obtain the titled compound 68.6 mg (yield 45%) as a colorless oil. The structure of this compound was-determined by the following data.

IR (neat): 1738, 1460, 1386, 1241, 1067, 795 cm$^{-1}$. $^1$H-NMR (300 MHz, CDCl$_3$): δ 7.10 (1H, dd, J=7.4, 1.0 Hz), 6.99 (1H, dd, t=7.4, 1.0 Hz), 6.93 (1H, d, J=9.3 Hz), 6.78 (1H, dd, J=7.4, 7.4 Hz), 5.29 (1H, ddd, J=8.5, 6.8, 3.8 Hz), 5.08 (1H, ddd, J=5.5, 4.7, 4.7 Hz), 3.75 (1H, dd, J=8.5, 4.7 Hz), 3.67 (3H, s), 3.44 (1H, ddd, J=9.3, 4.7, 4.7 Hz), 2.89 (2H, t, J=7.4 Hz), 2.81 (2H, t, J=7.4 Hz), 2.67–2.59 (2H, m), 2.54 (1H, ddd, J=14.6, 6.8, 5.5 Hz), 2.34 (1H, ddd, J=14.6, 4.7, 3.8 Hz), 1.72 (3H, s), 1.72–1.58 (2H, m), 1.42–1.24 (4H, m), 0.91 (3H, t, J=7.0 Hz). MASS (EI, m/e): 508 (M$^+$+2), 506 (M$^+$).

EXAMPLE 10

14-Bromo-2,5,6,7-tetranor-4,8-inter-m-phenylene PGI$_2$ Methyl Ester (26) and 15-Epimer (27) Thereof

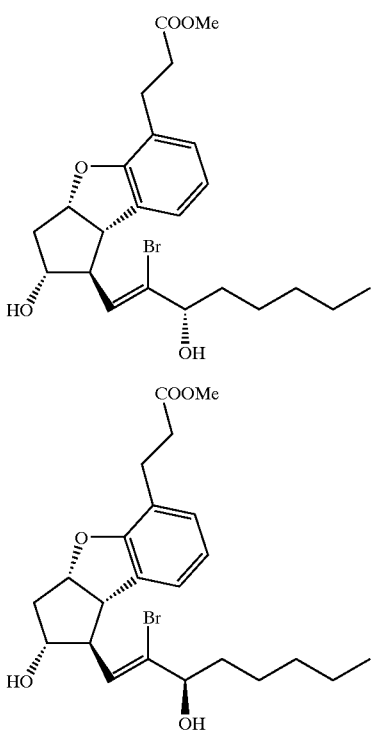

Cerium trichloride heptahydrate 421 mg (1.13 mmol) was added to a solution of 14-bromo-15-oxo-2,5,6,7-tetranor-4,8-inter-m-phenylene PGI$_2$ methyl ester, 11-acetate (25) 573 mg (1.13 mmol) in methanol 24 ml and THF 12 ml, and the resultant mixture was cooled with ice. Sodium borohydride 21.4 mg (0.556 mmol) was added to the resultant solution, and the resulting mixture was stirred for 1 hour under ice cooling. Saturated aqueous sodium bicarbonate 12 ml was added to the reaction mixture, and the mixture was filtered with a glass filter in which Celite was placed. The precipitate was washed with ethyl acetate, and the filtrate was concentrated. The thus-obtained aqueous layer was extracted with ethyl acetate (3×50 ml). The combined organic layer was washed in turn with water 20 ml and brine 20 ml, dried and then concentrated to obtain pale yellow oil 587 mg.

Next, the oil was azeotropically dehydrated with benzene (2×5 ml), and then dissolved in anhydrous methanol 13 ml under argon stream. 5.10 mol/L sodium methoxide 0.075 ml (0.382 mmol) was added to the resultant solution, followed by stirring at room temperature for 2 hours. Acetic acid 0.2 ml was added to the reaction mixture, and the mixture was concentrated. Then, saturated aqueous sodium bicarbonate 20 ml was added to the residue, and the resultant mixture was extracted with ethyl acetate (3×20 ml). The combined organic layer was washed with brine 20 ml, dried, and then concentrated. The thus-obtained oil 487 mg was purified by column chromatography (silica gel; cyclohexane:ethyl acetate=1:1→1:2) to obtain 14-bromo-15-epi-2,5,6,7-tetranor-4,8-inter-m-phenylene PGI$_2$ methyl ester (27) 175 mg (yield 39%) as a colorless oil from the less-polar fractions, and 14-bromo-2,5,6,7-tetranor-4,8-inter-m-phenylene PGI$_2$ methyl ester (26) 45.5 mg (yield 49%) as a colorless oil from the more-polar fractions. The structures of these compounds were determined by the following data.

14-Bromo-2,5,6,7-tetranor-4,8-inter-m-phenylene PGI$_2$ Methyl Ester

IR (neat): 3400, 1736, 1456, 1263, 1160, 1069, 1035, 745 cm$^{-1}$. $^1$H-NMR (300 MHz, CDCl$_3$): δ 7.07 (1H, d, J=7.4 Hz), 6.97 (1H, d, J=7.4 Hz), 6.78 (1H, dd, J=7.4, 7.4 Hz), 5.92 (1H, d, J=9.3 Hz), 5.20 (1H, ddd, J=8.8, 6.9,–4.4 Hz), 4.12 (1H, dd, J=6.6, 6.6 Hz), 4.06 (1H, ddd, J=6.3, 5.8, 5.8 Hz), 3.65 (3H, s), 3.54 (1H, dd, J=8.3, 5.9 Hz), 3.16 (1H, ddd, J=9.3, 5.9, 5.8 Hz), 2.93–2.85 (2H, m), 2.68–2.61 (2H, m), 2.53 (1H, ddd, J=14.0, 6.9, 5.8 Hz), 2.16 (1H, ddd, J=14.0, 6.3, 4.4 Hz), 1.84–1.52 (4H, m), 1.40–1.26 (6H, m), 0.91 (3H, t, J=6.7 Hz). MASS (EI, m/e): 468 (M$^+$+2), 466 (M$^+$).

14-Bromo-15-epi-2,5,6,7-tetranor-4,8-inter-m-phenylene PGI$_2$ Methyl Ester

IR (neat): 3400, 1736, 1710, 1458, 1197, 1069, 746 cm$^{-1}$. $^1$H-NMR (300 MHz, CDCl$_3$): δ 7.14 (1H, d, J=7.4 Hz), 6.97 (1H, d, J=7.4 Hz), 6.80 (1H, dd, J=7.4, 7.4 Hz), 5.90 (1H, d, J=9.4 Hz), 5.24 (1H, ddd, J=8.8, 6.6, 4.0 Hz), 4.13 (1H, dd, J=6.6, 6.6 Hz), 4.07 (1H, ddd, J=5.5, 4.7, 4.7 Hz), 3.65 (3H, s), 3.63 (1H, dd, J=8.8, 4.7 Hz), 3.19 (1H, ddd, J=9.4, 4.7, 4.4 Hz), 2.97–2.80 (2H, m), 2.72–2.55 (2H, m), 2.45 (1H, ddd, J=14.3, 6.6, 5.5 Hz), 2.21 (1H, ddd, J=14.3, 4.7, 4.0 Hz), 1.76–1.54 (4H, m), 1.38–1.26 (6H, m), 0.90 (3H, t, J=6.6 Hz). MASS (EI, m/e): 468 (M$^+$+2), 466 (M$^+$).

EXAMPLE 11

14-Bromo-2,5,6,7-tetranor-4,8-inter-m-phenylene PGI$_2$ (28)

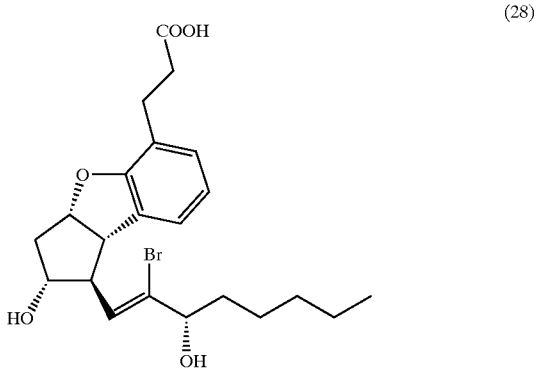

2N aqueous sodium hydroxide 1.0 ml was added to a solution of 14-bromo-2,5,6,7-tetranor-4,8-inter-m-phenylene PGI$_2$ methyl ester (26) 32.4 mg (0.0693 mmol) in methanol 1.0 ml, and the resultant mixture was stirred at room temperature for 1.5 hours. After the reaction mixture was cooled with ice, 1N hydrochloric acid 2.2 ml was added to the mixture, and the mixture was extracted with ethyl acetate (3×10 ml). The combined organic layer was washed with brine 5 ml, dried and then concentrated to obtain oil 33.6 mg. The same process as described above was repeated to obtain oil 2.6 mg from starting material 2.5 mg (0.0053 mmol). The combined oil was together purified by column chromatography (DIOL produced by Yamazen Co.; cyclohexane:ethyl acetate=33:67) to obtain the titled compound 35.2 mg (quantitative) as a colorless oil. The structure of this compound was determined by the following data.

IR (neat): 3380, 1711, 1456, 1267, 1193, 1071, 1035, 953, 866, 741 cm$^{-1}$. $^1$H-NMR (300 MHz, CDCl$_3$): δ 7.06 (1H, d, J=7.1 Hz), 6.98 (1H, d, J=7.1 Hz), 6.78 (1H, dd, J=7.1, 7.1 Hz), 5.90 (1H, d, J=9.3 Hz), 5.18 (1H, m), 4.12 (1H, dd, J=6.6, 6.6 Hz), 4.01 (1H, m), 3.49 (1H, dd, J=8.8, 6.3 Hz), 3.10 (1H, m), 2.99–2.79 (2H, m), 2.77–2.58 (2H, m), 2.50 (1H, ddd, J=13.8, 6.8, 6.3 Hz), 2.20–2.08 (2H, m), 1.78–1.60 (6H, m), 0.91 (3H, t, J=6.7 Hz). MASS (EI, m/e): 454 (M$^+$+2), 452 (M$^+$). High Resolution Mass Spectrometry (HREIMS): Found: 452.1170 (−2.9 mmu). Calculated for C$_{22}$H$_{29}$BrO$_5$ (M$^+$): 452.1199.

EXAMPLE 12

14-Bromo-15-epi-2,5,6,7-tetranor-4,8-inter-m-phenylene PGI$_2$ (29)

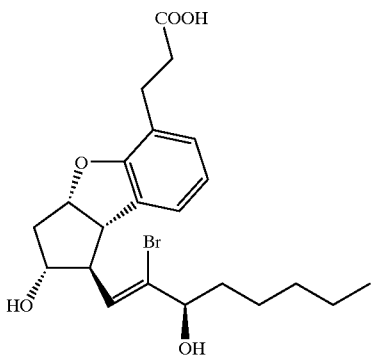

(29)

2N aqueous sodium hydroxide 1.0 ml was added to a solution of 14-bromo-15-epi-2,5,6,7-tetranor-4,8-inter-m-phenylene PGI$_2$ methyl ester (27) 30.0 mg (0.0642 mmol) in methanol 1.0 ml, and the resultant mixture was stirred at room temperature for 3 hours. After the reaction mixture was cooled with ice, 1N hydrochloric acid 2.2 ml was added to the mixture, and the mixture was extracted with ethyl acetate (3×10 ml). The combined organic layer was washed with brine 5 ml, dried and then concentrated. The thus-obtained oil 30.4 mg was purified by column chromatography (DIOL; cyclohexane:ethyl acetate=33:67) to obtain the titled compound 29.3 mg (quantitative) as a colorless oil. The structure of this compound was determined by the following data.

IR (neat): 3400, 1711, 1458, 1071, 745 cm$^{-1}$. $^1$H-NMR (300 MHz, CDCl$_3$) δ 7.14 (1H, d, J=7.4 Hz), 6.98 (1H, d,,J=7.4 Hz), 6.80 (1H, dd, J=7.4, 7.4 Hz), 5.90 (1H, d, J=8.8 Hz), 5.24 (1H, ddd, J=8.6, 6.6, 3.5 Hz), 4.13 (1H, dd, J=6.3, 6.3 Hz), 4.07 (1H, ddd, J=5.0, 5.0, 5.0 Hz, 3.62 (1H, dd, J=8.6, 5.0 Hz), 3.18 (1H, ddd, J=8.8, 5.0, 5.0 Hz, 2.99–2.80 (2H, m), 2.77–2.59 (2H, m), 2.43 (1H, ddd, J=14.4, 6.6, 5.0 Hz), 2.21 (1H, ddd, J=14.4, 5.0, 3.5 Hz), 1.80–1.58 (2H, m), 1.40–1.25 (6H, m), 0.90 (3H, t, J=6.8 Hz). MASS (EI, m/e):454 (M$^+$+2), 452 (M$^+$). High Resolution Mass Spectrometry (HREIMS): Found:452.1196 (−0.3 mmu). Calculated for C$_{22}$H$_{29}$BrO$_5$ (M$^+$):452.1199.

EXAMPLE 13

2-Decarboxy-2-hydroxy-16-phenoxy-2,2,16-trimethyl-5,6,7,18,19,20-hexanor-4,8-inter-m-phenylene PGI$_2$ (30)

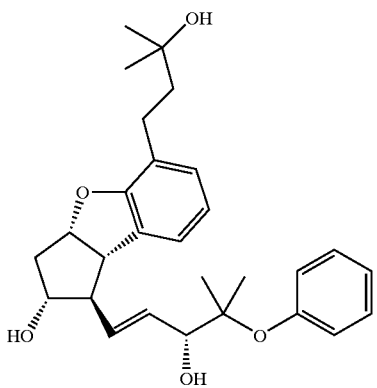

(30)

16-Methyl-16-phenoxy-2,5,6,7,18,19,20-heptanor-4,8-inter-m-phenylene PGI$_2$ methyl ester (3) 100 mg (0.22 mmol) was dissolved in anhydrous THF (1 mL). Methylmagnesium bromide (ether solution, 2.8 M) was added to the resultant solution under ice cooling under argon atmosphere. Since stirring was stopped due to white precipitates, the ice bath was removed so that the mixture was stirred at room temperature. Anhydrous THF 1.5 mL was further added to the mixture to permit stirring. 30 minutes after, the disappearance of the starting material was checked by TLC, and then saturated aqueous ammonium chloride (4 mL) was added to the mixture in the ice bath. The resultant mixture was extracted with ethyl acetate (20 mL×2). The combined organic layer was washed with brine (30 mL×2), and then dried over anhydrous sodium sulfate. After concentration, the residue was purified by column chromatography (silica gel; cyclohexane:ethyl acetate=1:3), and preparative TLC (silica gel; cyclohexane:ethyl acetate=1:3) to obtain the target tertiary alcohol 60 mg (yield 60%) as a colorless amorphousness. The structure of this compound was determined by the following data.

IR (neat): 3400, 2976, 1593, 1543, 1491, 1452, 1226, 1131, 741, 698 cm$^{-1}$. $^1$H-NMR (400 MHz, CDCl$_3$): δ 7.30 (2H, t, J=7.3 Hz), 7.12 (1H, t, J=7.3 Hz), 7.01–6.97 (3H, m), 6.93 (1H, d, J=7.3 Hz), 6.76 (1H, t, J=7.3 Hz), 5.83 (1H, dd, J=15.6, 8.3 Hz), 5.72 (1H, dd, J=15.6, 7.3 Hz), 5.18–5.11 (1H, m), 4.20 (1H, d, J=7.3 Hz), 3.98 (1H, td, J=8.3, 5.9 Hz), 3.50 (1H, dd, J=8.3, 8.3 Hz), 2.70–2.62 (3H, m), 2.52 (1H, dd, J=16.1, 7.8 Hz), 2.06–1.98 (1H, m), 1.81–1.76 (1H, m), 1.277 (3H, s), 1.271 (3H, s), 1.267 (3H, s), 1.25 (3H, s) MASS (EI, m/e): 452 (M$^+$).

EXAMPLE 14

2-Decarboxy-2,16-dimethyl-2-oxo-16-phenoxy-5,6,7,18,19,20-hexanor-4,8-inter-m-phenylene $PGI_2$ (31)

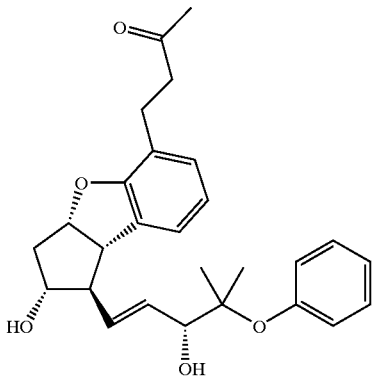

(31)

16-Methyl-16-phenoxy-2,5,6,7,18,19,20-heptanor-4,8-inter-m-phenylene $PGI_2$ (3) 530 mg (1.21 mmol) was dissolved in anhydrous THF (3 mL), followed by two times of azeotropic dehydration under reduced pressure. The residue was then dissolved in anhydrous THF (10 mL), and an ether solution of methyl lithium (1.07M) 5.6 mL (6.0 mmol, 5 equivalents) was added to the resultant solution over 10 minutes under ice cooling, followed by stirring at room temperature for 2.5 hours. Since the disappearance of the starting material was not observed by TLC, methyl lithium 5 mL (4.3 equivalents) was further added to the solution, followed by stirring at room temperature for 1 hour. Since no change was observed by TLC, the reaction mixture was poured into 0.05N hydrochloric acid (100 mL), and then extracted with ethyl acetate (100 mL×2). The combined organic layer was washed with brine (200 mL×2), dried over anhydrous sodium sulfate, and then concentrated. The residue was purified by column chromatography (silica gel; cyclohexane:ethyl acetate=1:3) to obtain the titled compound 324 mg (yield 61%). The thus-obtained compound was further recrystallized from ethyl acetate/n-hexane (3 mL/6 mL) to obtain the titled compound 208 mg (yield 39%) as white crystal. The structure of this compound was determined by the following data.

Melting point: 101.1~102.5° C. IR (KBr): 3386, 2978, 1698, 1593, 1543, 1491, 1458, 1359, 1232, 1152, 1071, 982, 965, 783, 696 $cm^{-1}$. $^1$H-NMR (400 MHz, $CDCl_3$): δ 7.30 (2H, t, J=7.8 Hz), 7.13 (1H, t, J=7.3 Hz), 7.01–6.94 (3H, m), 6.75 (1H, t, J=7.8 Hz), 5.84 (1H, dd, J=15.6, 8.3 Hz), 5.72 (1H, dd, J=15.6, 6.8 Hz), 5.51–5.12 (1H, m), 4.21 (1H, d, J=6.8 Hz), 4.00 (1H, q, J=7.3 Hz), 3.50 (1H, t, J=8.3 Hz), 2.99 (1H, bs), 2.88–2.82 (2H, m), 2.80–2.73 (2H, m), 2.66 (1H, quint, J=6.8 Hz), 2.53 (1H, q, J=7.8 Hz), 2.14 (3H, s), 2.09–1.98 (1H, m), 1.27 (3H, s), 1.25 (3H, s). MASS (EI, m/e): 436 ($M^+$).

| Elemental Analysis: | C | H |
|---|---|---|
| Found: | 74.18 | 7.42 |
| Calculated for $C_{27}H_{32}O_5$: | 74.29 | 7.39 |

EXAMPLE 15

2-Decarboxy-2,16-dimethyl-2-hydroxy-16-phenoxy-5,6,7,18,19,20-hexanor-4,8-inter-m-phenylene $PGI_2$ (32)

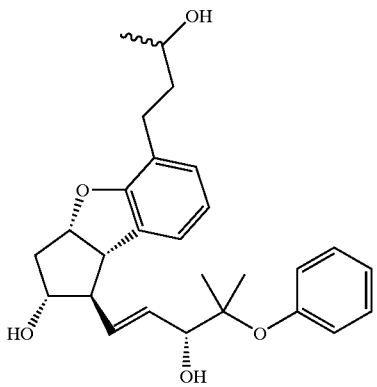

(32)

2-decarboxy-2,16-dimethyl-2-oxo-16-phenoxy-5,6,7,18,19,20-hexanor-4,8-inter-m-phenylene $PGI_2$ (31) (100 mg, 0.23 mmol) was dissolved in ethanol (4 ml), and sodium borohydride (18 mg, 0.48 mmol) was added to the resultant solution, followed by stirring at room temperature for 1 hour. After the disappearance of the starting material was checked by TLC, the reaction was quenched by the addition of several droplets of acetone. After concentration, the residue was extracted with ethyl acetate (40 mL×2). The combined organic layer was washed with water (50 mL×1) and brine (40 mL×2), and then dried over anhydrous sodium sulfate. After concentration, the residue was purified by column chromatography (silica gel; cyclohexane:ethyl acetate=1:4) and three times of preparative TLC (silica gel; cyclohexane:ethyl acetate=1:4) to obtain the titled compound 65.5 mg (yield 65%). The structure of this compound was determined by the following data.

IR (neat): 3400, 3064, 2976, 1595, 1491, 1458, 1369, 1265, 1226, 1133, 1035, 957, 864, 739, 700 $cm^{-1}$. $^1$H-NMR (400 MHz, $CDCl_3$): δ 7.30 (2H, t, J=7.3 Hz), 7.13 (1H, t, J=7.3 Hz), 7.02–6.93 (4H, m), 6.79 (1H, td, J=7.3, 3.4 Hz), 5.84 (1H, dd, J=15.1, 8.3 Hz), 5.72 (1H, dd, J=15.1, 6.8 Hz), 5.21–5.13 (1H, m), 4.21 (1H, d, J=6.8 Hz), 4.06–3.96 (1H, m), 3.76–3.65 (1H, m), 3.54 (1H, dt, J=12.7, 8.3 Hz), 2.79–2.49 (4H, m), 2.09–1.98 (1H, m), 1.27 (3H, s), 1.25 (3H, s), 1.18 (3H, t, J=5.9 Hz). MASS (EI, m/e): 438 ($M^+$).

EXAMPLE 16

3,16-Dimethyl-16-phenoxy-2,5,6,7,18,19,20-heptanor-4,8-inter-m-phenylene PGI$_2$ Methyl Ether (33)

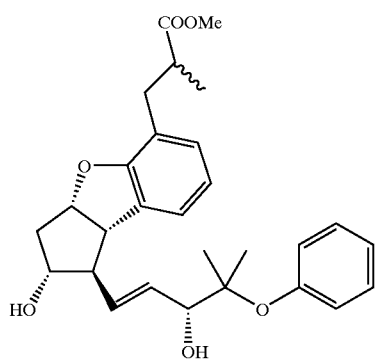

(33)

Diisopropylamine 0.52 mL (3.7 mmol, 3.6 equivalents) was dissolved in anhydrous THF 25 mL, and the resultant solution was cooled to −70° C. n-Butyl lithium n-hexane solution (1.6 M) 2.1 mL (3.4 mmol, 3.3 equivalents) was added to the solution, followed by stirring for 20 minutes. An anhydrous THF solution (5 mL×3) of 16-methyl-16-phenoxy-2,5,6,7,18,19,20-heptanor-4,8-inter-m-phenylene PGI$_2$ methyl ester (3) 465 mg (1.0 mmol) was added to the mixture by a syringe, followed by stirring for 45 minutes. Methyl iodide 96 μL (1.5 mmol, 1.5 equivalents) was added to the reaction solution, and the resultant mixture was stirred at −70° C. for 1 hour. Since no change was observed by TLC, the mixture was stirred at 0° C. in an ice bath for 1 hour. However, no change was observed by TLC, and thus the mixture was further stirred at room temperature for 1 hour. Then, methyl iodide 200 μL (3 mmol, 3 equivalents) was further added to the mixture, followed by stirring at room temperature overnight. However, no change was observed by TLC.

The reaction mixture was poured into ice water, and then extracted with ethyl acetate (150 mL×2). The combined organic layer was washed with brine (200 mL×1), and dried over anhydrous sodium sulfate. After concentration, the residue was purified twice by column chromatography (silica gel; cyclohexane:ethyl acetate=1:1) to obtain the titled compound 257 mg (yield 53%). The structure of this compound was determined by the following data.

IR (neat): 3404, 2980, 1734, 1595, 1491, 1456, 1369, 1226, 1071, 1027, 959, 862, 739, 700 cm$^{-1}$. $^1$H-NMR (400 MHz, CDCl$_3$): δ 7.52 (2H, t, J=7.3 Hz), 7.35 (1H, t, J=7.3 Hz), 7.34–7.14 (4H, m), 6.97 (1H, td, J=7.3, 2.0 Hz), 6.06 (1H, dd, J=15.1, 8.3 Hz), 5.94 (1H, dd, J=15.1, 6.8 Hz), 5.41–5.33 (1H, m), 4.43 (1H, d, J=6.8 Hz), 4.25–4.18 (1H, m), 3.86 (3H, d, J=7.3 Hz), 3.77–3.70 (1H, m), 3.32 (1H, bs), 3.22–3.04 (2H, m), 2.96–2.70 (4H, m), 2.32–2.20 (1H, m), 1.49 (3H, s), 1.48 (3H, s), 1.37 (3H, dd, J=6.8, 2.9 Hz). MASS (EI, m/e: 466 (M$^+$).

EXAMPLE 17

3,16-Dimethyl-16-phenoxy-2,5,6,7,18,19,20-heptanor-4,8-inter-m-phenylene PGI$_2$ (34)

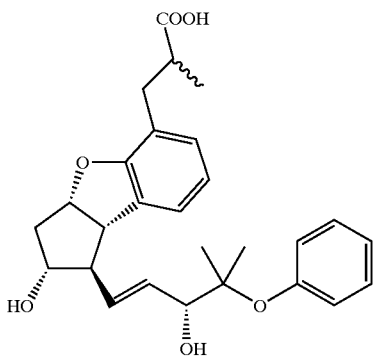

(34)

3,16-Dimethyl-16-phenoxy-2,5,6,7,18,19,20-heptanor-4,8-inter-m-phenylene PGI$_2$ methyl ether (33) 30 mg (0.064 mmol) was suspended in methanol (2 mL), and a 2N aqueous sodium hydroxide (2 mL) was added to the resultant suspension, followed by stirring at room temperature for 3 hours. After the disappearance of the starting material was checked by TLC, 1N hydrochloric acid was added to the reaction mixture to control pH to 1 to 2, and the mixture was concentrated and then extracted with ethyl acetate (30 mL×2). The combined organic layer was washed with brine (30 mL×2), and dried over anhydrous sodium sulfate. After concentration, the residue was sufficiently dried in vacuo to obtain the titled compound 30 mg (yield ~100%). The structure of this compound was determined by the following data.

IR (neat): 3400, 2980, 1711, 1595, 1491, 1456, 1369, 1226, 1133, 1071, 1025, 957, 862, 741, 700 cm$^{-1}$. $^1$H-NMR (400 MHz, CDCl$_3$): δ 7.29 (2H, t, J=7.3 Hz), 7.12 (1H, t, J=7.3 Hz), 7.01–6.93 (4H, m), 6.75 (1H, td, J=7.3, 2.4 Hz), 5.80 (1H, ddd, J=15.1, 8.3, 3.4 Hz), 5.70 (1H, ddd, J=15.1, 7.3, 4.9 Hz), 5.16–5.09 (1H, m), 4.20 (1H, d, J=7.3 Hz), 3.98 (1H, dd, J=14.2, 7.8 Hz), 3.52–3.45 (1H, m), 3.04–2.46 (5H, m), 2.09–1.99 (1H, m), 1.25 (3H, s), 1.24 (3H, s), 1.19 (3H, dd, J=9.3, 6.8 Hz). MASS (EI, m/e): 452 (M$^+$).

EXAMPLE 18

2-Decarboxy-2-hydroxy-3,16-dimethyl-16-phenoxy-5,6,7,18,19,20-hexanor-4,8-inter-m-phenylene PGI$_2$ (35)

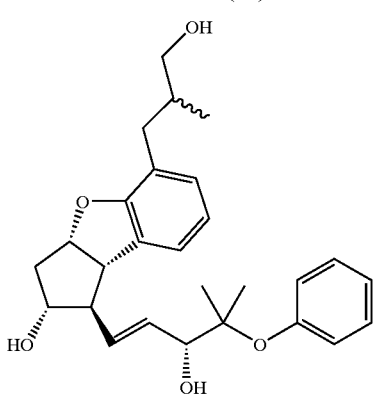

(35)

3,16-Dimethyl-16-phenoxy-2,5,6,7,18,19,20-heptanor-4,8-inter-m-phenylene PGI$_2$ methyl ether (33) 35 mg (0.075 mmol) was dissolved in dichloromethane (2 mL), and 1.02M toluene solution of diisobutylaluminum hydride 0.37 mL (0.38 mmol, 5 equivalents) was added to the resultant solution under ice cooling, followed by stirring 1 hour. After the disappearance of the starting material was checked by TLC, the reaction was quenched by addition of a benzene solution (10%) of methanol, and water was further added. After suction filtration, the filtrate was concentrated, and the residue was extracted with ethyl acetate (30 mL×2). The combined organic layer was washed with brine (30 mL×2), and dried over anhydrous sodium sulfate. After concentration, the residue was purified by preparative TLC (silica gel; cyclohexane:ethyl acetate=1:3) to obtain the titled compound 23 mg (yield 70%). The structure of this compound was determined by the following data.

IR (neat): 3380, 2920, 1593, 1491, 1454, 1369, 1226, 1127, 1073, 1029, 957, 888, 783, 737, 694 cm$^{-1}$. $^1$H-NMR (400 MHz, CDCl$_3$): δ 7.29 (2H, t, J=7.3 Hz), 7.12 (1H, t, J=7.3 Hz), 7.01–6.93 (4H, m), 6.78 (1H, t, J=7.3 Hz), 5.83 (1H, dd, J=15.1, 8.3 Hz), 5.72 (1H, dd, J=15.1, 6.8 Hz), 5.30–5.12 (1H, m), 4.20 (1H, d, J=6.8 Hz), 4.03–3.69 (1H, m), 3.53 (1H, td, J=8.3, 2.9 Hz), 3.41 (1H, dd, J=11.2, 4.9 Hz), 3.37–3.30 (1H, m), 2.68–2.49 (4H, m), 2.07–1.89 (2H, m), 1.26 (3H, s), 1.25 (3H, s), 0.95 (3H, dd, J=13.7, 6.8 Hz). MASS (EI, m/e): 438 (M$^+$).

EXAMPLE 19

3-Decarboxy-3-cyano-16-methyl-16-phenoxy-2,5,6,7,18,19,20-heptanor-4,8-inter-m-phenylene PGI$_2$, 11,15-bis(tert-Butyldimethylsilyl Ether) (36)

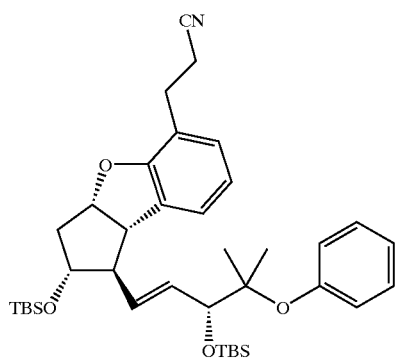

(36)

3-Decarboxy-3-aminocarbonyl-16-methyl-16-phenoxy-2,5,6,7,18,19,20-heptanor-4,8-inter-m-phenylene PGI$_2$, 11,15-bis(tert-butyldimethylsilyl ether) (10) 190.3 mg (0.29 mmol) was dissolved in pyridine (5 mL) treated with potassium hydroxide, and tosyl chloride 81.7 mg (0.43 mmol, 1.5 equivalents) was added to the resultant solution, followed by stirring at room temperature for 3.5 hours. Since the disappearance of the starting material was not observed by TLC, tosyl chloride 81 mg (1.5 equivalents) was further added to the mixture, followed by further stirring at room temperature for 14 hours. After the disappearance of the starting material was checked by TLC, the reaction was quenched by pouring the mixture into ice-cold 1N hydrochloric acid, and the mixture was extracted with ethyl acetate (80 mL×2). The combined organic layer was washed with 1N hydrochloric acid (40 mL), water (50 mL×2), and brine (50 mL), and dried over anhydrous sodium sulfate. After concentration, the residue was purified by column chromatography (silica gel; cyclohexane:ethyl acetate=85:15) to obtain the titled compound 172 mg (yield 92%) as a colorless oil. The structure of this compound was determined by the following data.

IR (neat): 3430, 2932, 2860, 2250, 1597, 1491, 1462, 1381, 1363, 1255, 1230, 1199, 1125, 1007, 978, 837, 777, 741, 698 cm$^{-1}$. $^1$H-NMR (300 MHz, CDCl$_3$): δ 7.26 (2H, t, J=7.4 Hz), 7.13–6.92 (5H, m), 6.76 (1H, t, J=7.4 Hz), 5.82 (1H, dd, J=15.6, 5.5 Hz), 5.71 (1H, dd, J=15.6, 7.7 Hz), 5.18 (1H, ddd, J=8.5, 7.4, 4.1 Hz), 4.21 (1H, d, J=5.2 Hz), 4.00 (1H, dd, J=11.5, 5.8 Hz), 3.52 (1H, dd, J=8.8. 6.6 Hz), 2.98–2.81 (2H, m), 2.73–2.55 (3H, m), 2.46 (1H, ddd, J=13.2, 7.4, 5.8 Hz), 2.03–1.93 (1H, m), 1.27 (3H, s), 1.17 (3H, s), 0.95 (9H, s), 0.75 (9H, s), 0.12 (3H, s), 0.10 (3H, s), 0.00 (3H, s), −0.07 (3H, s). MASS (EI, m/e): 632 ((M−CH$_3$)$^+$), 590 ((M−tBu)$^+$).

EXAMPLE 20

3-Decarboxy-3-cyano-16-methyl-16-phenoxy-2,5,6,7,18,19,20-heptanor-4,8-inter-m-phenylene PGI$_2$ (37)

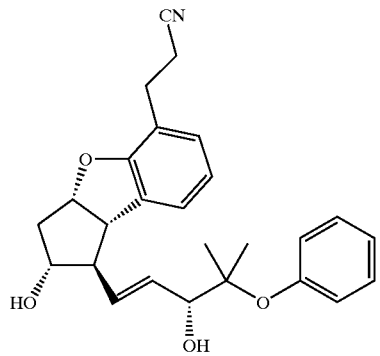

(37)

3-Decarboxy-3-cyano-16-methyl-16-phenoxy-2,5,6,7,18,19,20-heptanor-4,8-inter-m-phenylene PGI$_2$, 11,15-bis(tert-butyldimethylsilyl ether) (36) 90 mg (0.14 mmol) was dissolved in THF (2 mL), and 1.0 M THF solution of TBAF 0.83 mL (0.83 mmol, 6 equivalents) was added to the resultant solution, followed by stirring at room temperature for 18 hours. After the disappearance of the starting material was checked by TLC, the reaction mixture was concentrated. The residue was extracted with ethyl acetate (40 mL×2). The combined organic layer was washed with water (50 mL×2), and brine (40 mL), and dried over anhydrous sodium sulfate. After concentration, the residue was purified by column chromatography (Silica-Gel FL60D produced by Fuji Silicia; cyclohexane:ethyl acetate=1:3) to obtain the titled compound 55.1 mg (yield 94%) as a colorless oil. The structure of this compound was determined by the following data.

IR (neat): 3450, 2938, 2252, 1595, 1491, 1458, 1230, 1140, 1085, 911, 735 cm$^{-1}$. $^1$H-NMR (300 MHz, CDCl$_3$): δ 7.29 (2H, t, J=7.4 Hz), 7.12 (1H, tt, J=7.4, 1.1 Hz), 7.04–6.95 (4H, m), 6.88 (1H, t, J=7.4 Hz), 5.82 (1H, dd, J=15.4, 8.2 Hz), 5.72 (1H, dd, J=15.4, 6.9 Hz), 5.15 (1H, ddd, J=8.8, 7.1, 5.2 Hz), 4.21 (1H, d, J=6.9 Hz), 3.98 (1H, dd, J=14.8, 8.5 Hz), 3.49 (1H, dd, J=8.5, 8.5 Hz), 3.19 (1H, bs), 2.91 (2H, t, J=6.9 Hz), 2.73–2.55 (4H, m), 2.49 (1H, dd, J=16.2, 8.2 Hz), 2.05–1.94 (1H, m), 1.26 (3H, s), 1.25 (3H, s). MASS: M$^+$ was not observed by EI and FAB. Base peak of EI: 135 (C(CH$_3$)$_2$OPh).

EXAMPLE 21

3-Decarboxy-3-(1H-tetrazol-5-yl)-16-methyl-16-phenoxy-2,5,6,7,18,19,20-heptanor-4,8-inter-m-phenylene PGI$_2$ (38)

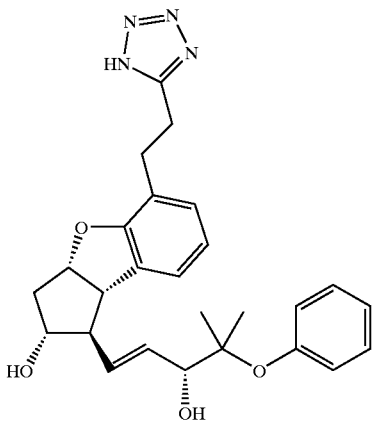

(38)

3-Decarboxy-3-cyano-16-methyl-16-phenoxy-2,5,6,7,18,19,20-heptanor-4,8-inter-m-phenylene PGI$_2$ (37) 55.1 mg (0.13 mmol) was dissolved in N-methyl-2-pyrrolidinone (2 mL), and sodium azide 51.2 mg (0.79 mmol, 6 equivalents) and triethylamine hydrochloride 53.7 mg (0.39 mmol, 3 equivalents) were added to the resultant solution, followed by stirring at 150° C. under argon atmosphere for 49 hours. After the disappearance of the starting material was checked by TLC, the reaction was quenched by pouring the mixture into 1N hydrochloric acid, and then extracted with ethyl acetate (40 mL×2). The combined organic layer was washed with water (80 mL×2), and brine (50 mL), and dried over anhydrous sodium sulfate. After concentration, the residue was purified by column chromatography (DIOL produced by Yamazen Co.; cyclohexane:ethyl acetate=1:3) to obtain the titled compound 51 mg (yield 85%) as a light brown solid. The compound was recrystallized from ethyl acetate/n-hexane=1:2 to obtain the light brown crystal 27 mg. The structure of this compound was determined by the following data.

Melting point: 135.5~136.7° C. IR (neat): 3400, 2862, 1593, 1562, 1491, 1454, 1257, 1226, 1197, 1067, 882, 783, 748, 696 cm$^{-1}$. $^1$H-NMR (300 MHz, CDCl$_3$): δ 7.30 (2H, t, J=7.4 Hz), 7.13 (1H, t, J=7.4 Hz), 7.02–6.95 (3H, m), 6.70–6.62 (2H, m), 5.76 (1H, dd, J=15.4, 7.4 Hz), 5.70 (1H, dd, J=15.4, 6.3 Hz), 5.38–5.28 (1H, m), 4.30–4.23 (1H, m), 4.16 (1H, d, J=5.8 Hz), 3.78–3.70 (1H, m), 3.63–3.50 (1H, m), 3.33–3.13 (2H, m), 2.90–2.74 (2H, m), 2.46–2.32 (1H, m), 2.25–2.15 (1H, m), 1.23 (3H, s), 1.22 (3H, s). MASS (FAB, m/e): 463 ((M+H)$^+$).

| Elemental Analysis: | C | H | N |
|---|---|---|---|
| Calculated for C$_{26}$H$_3$ON$_{42}$O$_4$: | 67.51 | 6.54 | 12.11 |
| Found: | 66.62 | 6.53 | 11.81 |

EXAMPLE 22

2-Decarboxy-2-methoxy-16-methyl-16-phenoxy-5,6,7,18,19,20-hexanor-4,8-inter-m-phenylene PGI$_2$, 11,15-bis(Tetrahydropyranyl Ether) (39)

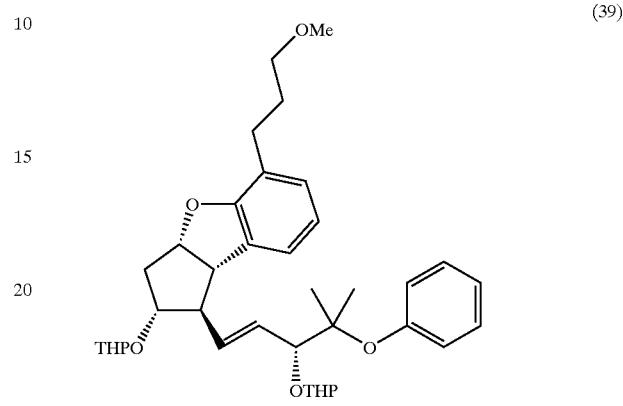

(39)

2-Decarboxy-2-hydroxy-16-methyl-16-phenoxy-5,6,7,18,19,20-hexanor-4,8-inter-m-phenylene PGI$_2$, 11,15-bis(tetrahydropyranyl ether) (7) 35 mg (0.06 mmol) was dissolved in anhydrous THF (2 mL), and sodium hydride (60% dispersion) 3.5 mg (0.09 mmol, 1.5 equivalents) was added to the resultant solution, followed by stirring at room temperature for 5 minutes. Methyl methanesulfonate 7.8 mg (0.07 mmol, 1.2 equivalents) was added to the mixture, followed by stirring at room temperature for 16 hours. Since the unreacted starting material was observed by TLC, sodium hydride 1.5 equivalents and methyl methanesulfonate 0.8 equivalent were further added to the reaction mixture, followed by at room temperature for 6 hours. However, no change was observed by TLC. Therefore, methyl methanesulfonate 0.8 equivalent in another reagent bottle was added to the mixture, followed by at room temperature for 11 hours. As a result, most of the starting material disappeared. Then, the reaction was quenched by addition of saturated aqueous ammonium chloride, and the mixture was extracted with ethyl acetate (30 mL×2). The combined organic layer was washed with brine (40 mL), and dried over anhydrous sodium sulfate. After concentration, the residue was purified by column chromatography (silica gel; cyclohexane:ethyl acetate=4:1) to obtain the titled compound 32.0 mg (yield 89%) as a colorless oil. The structure of this compound was determined by the following data.

IR (neat): 2930, 2868, 1595, 1491, 1456, 1383, 1261, 1230, 1201, 1122, 1075, 1023, 977, 915, 868, 785, 741, 700 cm$^{-1}$. $^1$H-NMR (300 MHz, CDCl$_3$): δ 7.26 (2H, t, J=7.4 Hz), 7.11–6.91 (5H, m), 6.76–6.68 (1H, m), 5.93–5.60 (2H, m), 5.18–5.05 (1H, m), 4.96–4.61 (2H, m), 4.25–4.16 (1H, m), 4.09–3.69 (3H, m), 3.55–3.43 (3H, m), 3.40 (2H, t, J=6.6 Hz), 3.34 (3H, d, J=0.8 Hz), 2.79–2.56 (4H, m), 2.14–2.01 (1H, m), 1.97–1.22 (20H, m). MASS (EI, m/e): 606 (M$^+$).

EXAMPLE 23

2-Decarboxy-2-methoxy-16-methyl-16-phenoxy-5,6,7,18,19,20-hexanor-4,8-inter-m-phenylene PGI₂ (40)

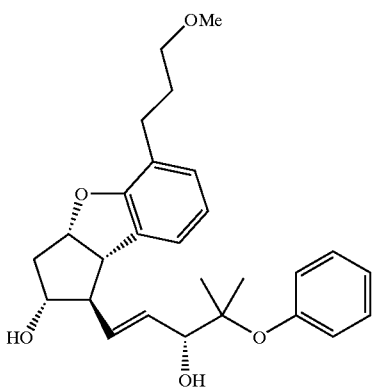

(40)

2-Decarboxy-2-methoxymethyl-16-methyl-16-phenoxy-5,6,7,18,19,20-hexanor-4,8-inter-m-phenylene PGI₂, 11,15-bis(tetrahydropyranyl ether) (39) 30.9 mg (0.05 mmol) was dissolved in ethanol (1 mL), and pyridinium p-toluenesulfonate (PPTS) 2 mg (0.008 mmol, 0.16 equivalent) was added to the resultant solution, followed by stirring at 55° C. for 3 hours. After the disappearance of the starting material was checked by TLC, solid sodium bicarbonate was added to the reaction mixture to neutralize it, and the mixture was then concentrated. The residue was extracted with ethyl acetate (30 mL×2). The combined organic layer was washed with a saturated aqueous sodium bicarbonate (40 mL), water (40 mL) and brine (40 mL), and then dried over anhydrous sodium sulfate. After concentration, the residue was purified by column chromatography (silica gel; cyclohexane:ethyl acetate=2:3~1:3) to obtain the titled compound 21.7 mg (yield 97%) as a colorless oil. The structure of this compound was determined by the following data.

IR (neat): 3400, 2930, 1595, 1491, 1454, 1383, 1226, 1118, 1025, 957, 864, 783, 745, 864 cm⁻¹. ¹H-NMR (300 MHz, CDCl₃): δ 7.29 (2H, t, J=7.4 Hz), 7.12 (1H, tt, J=7.1, 1.1 Hz), 7.02–6.94 (3H, m), 6.91 (1H, d, J=7.1 Hz), 6.75 (1H, t, J=7.4 Hz), 5.83 (1H, dd, J=15.4, 8.2 Hz), 5.71 (1H, dd, J=15.4, 6.9 Hz), 5.11 (1H, ddd, J=9.1, 7.4, 5.5 Hz), 4.20 (1H, d, J=6.9 Hz), 4.00–3.88 (1H, m), 3.50–3.42 (1H, m), 3.40 (2H, t, J=6.6 Hz), 3.34 (3H, s), 2.73–2.58 (3H, m), 2.46 (1H, dd, J=16.8, 8.2 Hz), 2.06–1.82 (3H, m), 1.252 (3H, s), 1.246 (3H, s). MASS (EI, m/e): 438 (M⁺). High Resolution Mass Spectrometry (HREIMS): Found: 438.2435. Calculated for C₂₇H₃₄O₅ (M⁺): 438.24060.

EXAMPLE 24

2-Decarboxy-2-azido-16-methyl-16-phenoxy-5,6,7,18,19,20-hexanor-4,8-inter-m-phenylene PGI₂, 11,15-bis(tert-Butyldimethylsilyl Ether) (41)

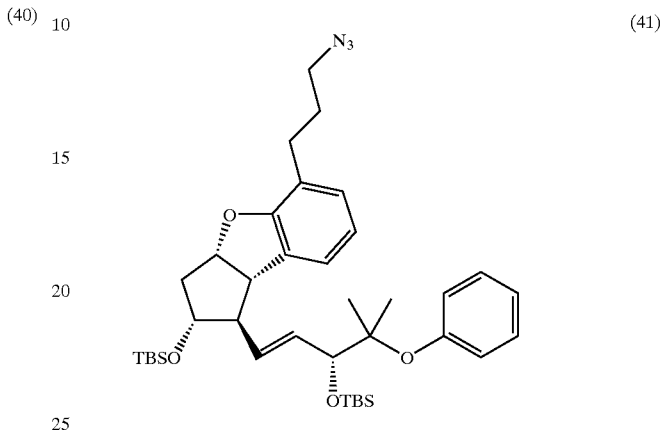

(41)

Sodium azide 28.0 mg (0.431 mmol) was added to a solution of 2-decarboxy-2-methylsulfonyloxy-16-methyl-16-phenoxy-5,6,7,18,19,20-hexanor-4,8-inter-m-phenylene PGI₂, 11,15-bis(tert-butyldimethylsilyl ether) (9) 64.0 mg (0.0875 mmol) in anhydrous DMF 2.0 ml, and the resultant mixture was stirred at 60° C. overnight. After the reaction mixture was cooled with ice, the ice-cold mixture was poured into water 10 ml, and then extracted with ethyl acetate (3×12 ml). The combined organic layer was washed in turn with water 10 ml and brine 10 ml, dried, and then concentrated. The thus-obtained oil 60.6 mg was purified by column chromatography (silica gel; cyclohexane:ethyl acetate=95:5) to obtain the titled compound 55.6 mg (yield 97%) as a colorless oil. The structure of this compound was determined by the following data.

IR (neat): 2100, 1595, 1491, 1473, 1458, 1381, 1363, 1255, 1228, 1197, 1125, 1093, 1025, 1007, 977, 837, 698 cm⁻¹. ¹H-NMR (300 MHz, CDCl₃): δ 7.29–7.21 (2H, m), 7.09–7.02 (2H, m), 6.98 (1H, dd, J=7.5, 1.1 Hz), 6.91 (1H, br d, J=7.1 Hz), 6.74 (1H, dd, J=7.4, 7.4 Hz), 5.83 (1H, dd, J=15.7, 5.2 Hz), 5.72 (1H, dd, J=15.7, 8.0 Hz), 5.13 (1H, ddd, J=8.6, 7.4, 4.7 Hz), 4.22 (1H, d, J=5.2. Hz), 3.98 (1H, ddd, J=7.1, 6.8, 5.9 Hz), 3.49 (1H, dd, J=8.6, 7.4 Hz), 3.30 (2H, t, J=6.9 Hz), 2.70–2.55 (3H, m), 2.48 (1H, ddd, J=13.5, 7.4, 5.9 Hz), 2.02–1.86 (3H, m), 1.27 (3H, s), 1.17 (3H, s), 0.95 (9H, s), 0.76 (9H, s), 0.12 (3H, s), 0.10 (3H, s), 0.01 (3H, s), −0.06 (3H, s). MASS (FAB (pos.), m/e): 649 [(M−28)⁺].

EXAMPLE 25

2-Decarboxy-2-azido-16-methyl-16-phenoxy-5,6,7,18,19,20-hexanor-4,8-inter-m-phenylene $PGI_2$ (42)

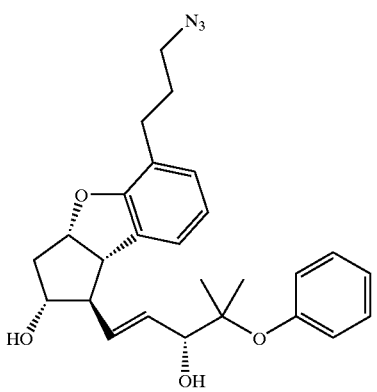

(42)

1.0 M THF solution of tetrabutylammonium fluoride 0.40 ml (0.40 mmol) was added to a solution of 2-decarboxy-2-azido-16-methyl-16-phenoxy-5,6,7,18,19,20-hexanor-4,8-inter-m-phenylene $PGI_2$, 11,15-bis(tert-butyldimethylsilyl ether) (41) 47.0 mg (0.0721 mmol) in anhydrous THF 1.6 ml under argon atmosphere, and the resultant mixture was stirred at room temperature for 5 hours. Saturated aqueous ammonium chloride 6 ml was added to the reaction mixture, and then the resultant mixture was extracted with ethyl acetate (3×12 ml). The combined organic layer was washed with brine 5 ml, dried, and then concentrated. The thus-obtained oil was purified by column chromatography (silica gel; cyclohexane:ethyl acetate=40:60→25:75) to obtain the titled compound 29.0 mg (yield 89%) as a colorless oil. The structure of this compound was determined by the following data.

IR (neat): 3400, 2102, 1595, 1491, 1455, 1369, 1259, 1226, 1195, 1133, 1094, 1071, 1025, 975, 884, 864, 785, 743, 698 cm$^{-1}$. $^1$H-NMR (300 MHz, $CDCl_3$): δ 7.30 (2H, dd, J=7.6, 7.6 Hz), 7.13 (1H, t, J=7.6 Hz), 7.04–6.92 (4H, m), 6.76 (1H, dd, J=7.4, 7.4 Hz), 5.83 (1H; dd, J=15.1, 8.2 Hz), 5.71 (1H, dd, J=15.1, 6.7 Hz), 5.14 (1H, m), 4.21 (1H, br d, J=6.7 Hz), 3.98 (1H, br ddd, J=8.1, 7.4, 5.0 Hz), 3.49 (1H, dd, J=8.3, 8.2 Hz), 3.29 (2H, t, J=6.9 Hz), 3.13 (1H, br s), 2.73–2.60 (3H, m), 2.50 (1H, ddd, J=8.2, 8.2, 8.1 Hz), 2.40 (1H, br s), 2.00 (1H, ddd, J=13.7, 8.5, 5.0 Hz), 1.90 (2H, tt, J=6.9, 6.9 Hz), 1.26 (3H, s), 1.25 (3H, s). MASS (FAB (pos.), m/e): 472 [(M+Na)$^+$], 449 (M$^+$).

EXAMPLE 26

2-Decarboxy-2-amino-16-methyl-16-phenoxy-5,6,7,18,19,20-hexanor-4,8-inter-m-phenylene $PGI_2$ (43)

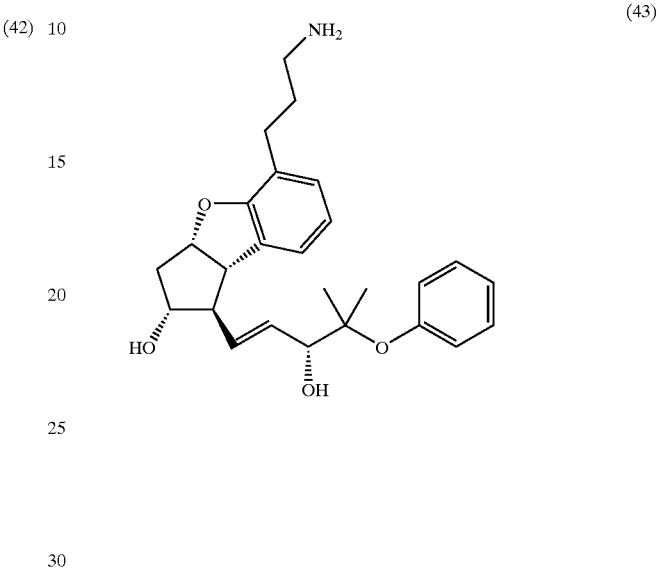

(43)

Lithium aluminum hydride 8.7 mg (0.229 mmol) was added to a solution of 2-decarboxy-2-azido-16-methyl-16-phenoxy-5,6,7,18,19,20-hexanor-4,8-inter-m-phenylene $PGI_2$ (42) 29.0 mg (0.0645 mmol) in anhydrous ether 3.0 ml under ice cooling, and the resultant mixture was refluxed for 3 hours and 20 minutes. After the reaction solution was cooled with ice, saturated aqueous Rochelle salt 8 ml was added to the solution, and then the resultant mixture was stirred for a while and then extracted with ethyl acetate (3×12 ml). The combined organic layer was washed with brine (5 ml), dried, and then concentrated. The thus-obtained oil 25.0 mg was purified by column chromatography (NH-DM1020 produced by Fuji Silicia Co.; chloroform:methanol=50:1) to obtain the titled compound 24.2 mg (yield 88%) as a colorless oil. The structure of this compound was determined by the following data.

IR (neat): 3369, 1593, 1489, 1454, 1367, 1257, 1227, 1191, 1159, 1133, 1099, 1073, 1032, 970, 887, 866, 784, 739, 699 cm$^{-1}$. $^1$H-NMR (300 MHz, $CDCl_3$): δ 7.30 (2H, dd, J=7.6, 7.6 Hz), 7.12 (1H, t, J=7.6 Hz), 7.02–6.90 (4H, m), 6.76 (1H, dd, J=7.4, 7.4 Hz), 5.83 (1H, dd, J=15.4, 8.0 Hz), 5.70 (1H, dd, J=15.4, 6.7 Hz), 5.14 (1H, ddd, J=8.5, 7.3, 5.0 Hz), 4.20 (1H, d, J=6.7 Hz), 3.98 (1H, ddd, J=8.3, 7.7, 6.3 Hz), 3.50 (1H, dd, J=8.5, 8.0 Hz), 2.75–2.56 (4H, m), 2.52 (1H, ddd, J=8.0, 8.0, 8.0 Hz), 2.20–1.70 (6H, m), 1.74 (2H, tt, J=7.4, 7.4 Hz), 1.25 (3H, s), 1.24 (3H, s). MASS (FAB (pos.), m/e): 424 [(M+H)$^+$]. High Resolution Mass Spectrometry (HRMS, FAB (pos.)): Found: 424.2520 (−3.2 mmu). Calculated for $C_{26}H_{34}NO_4$ [(M+H)$^+$]: 424.2552.

EXAMPLE 27

2-Decarboxy-2-amino-16-methyl-16-phenoxy-5,6,7,18,19,20-hexanor-4,8-inter-m-phenylene PGI$_2$ Hydrochloride (44)

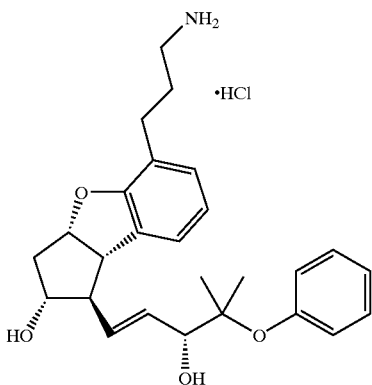

(44)

1.387M hydrogen chloride-methanol solution 0.07 ml (0.0971 mmol) was added to a solution of 2-decarboxy-2-amino-16-methyl-16-phenoxy-5,6,7,18,19,20-hexanor-4,8-inter-m-phenylene PGI$_2$ (43) 28.0 mg (0.0661 mmol) in anhydrous methanol 1.0 ml under ice cooling, and the resultant mixture was stirred for a while. After the reaction mixture was concentrated, the residue was purified by column chromatography (Sephadex LH-20 2.5 g; methanol) to obtain amine hydrochloride 29.0 mg as a colorless oil. The thus-obtained amine hydrochloride 29.0 mg was crystallized from ether to obtain the titled compound 12.6 mg (yield 41%) as a colorless powder. The structure of this compound was determined by the following data.

Melting point: 75.0–76.0° C. IR (neat): 3358, 1595, 1491, 1455, 1385, 1368, 1261, 1226, 1189, 1134, 1098, 1073, 1030, 972, 886, 864, 783, 764, 743, 699 cm$^{-1}$. $^1$H-NMR (300 MHz, CDCl$_3$): δ 7.82 (1H, br), 7.29 (2H, dd, J=7.4, 7.4 Hz), 7.11 (1H, t, J=7.4 Hz), 7.04–6.96 (4H, m), 6.89 (1H, br d, J=7.4 Hz), 6.76 (.1H, dd, J=7.4, 7.4 Hz), 5.77 (1H, dd, J=15.3, 7.5 Hz), 5.68 (1H, dd, J=15.3, 6.8 Hz), 5.21 (1H, m), 4.15 (1H, d, J=6.8 Hz), 4.08 (1H, m), 3.58 (1H, m), 3.48 (1H, m), 3.38 (1H, br s), 2.92 (1H, m), 2.83–2.62 (3H, m), 2.55 (1H, m), 2.36 (1H, m), 2.27 (1H, m), 2.18 (1H, m), 1.87 (1H, m), 1.72 (1H, m), 1.23 (3H, s), 1.22 (3H, s).

EXAMPLE 28

2-Decarboxy-2-methylsulfonylamino-16-methyl-16-phenoxy-5,6,7,18,19,20-hexanor-4,8-inter-m-phenylene PGI$_2$, 11,15-bis(tert-Butyldimethylsilyl Ether) (45)

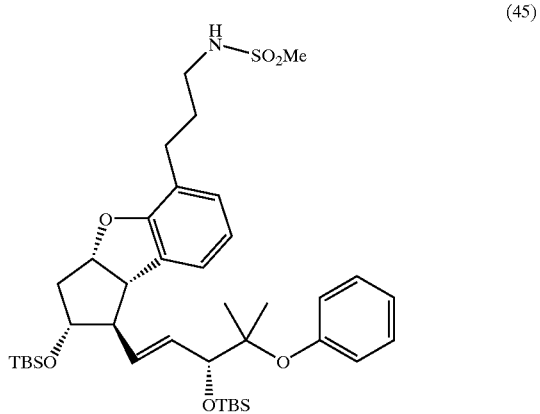

(45)

2-Decarboxy-2-amino-16-methyl-16-phenoxy-5,6,7,18,19,20-hexanor-4,8-inter-m-phenylene PGI$_2$, 11,15-bis(tert-butyldimethylsilyl ether) (11) 20.8 mg (0.032 mmol) was dissolved in anhydrous dichloromethane (2 mL), and triethylamine (8.9 μL, 2.0 equivalents) and methanesulfonyl chloride (3.7 μL, 1.5 equivalents) were added the resultant solution, followed by stirring at room temperature for 1 hour. After the disappearance of the starting material was checked by TLC, the reaction was quenched by the addition of methanol (1 mL). After concentration, the residue was extracted with ethyl acetate (30 mL×2). The combined organic layer was washed with water (50 mL×2) and brine (50 mL), and then dried over anhydrous sodium sulfate. After concentration, the residue was purified by column chromatography (silica gel; cyclohexane:ethyl acetate= 7:3~6:4) to obtain the titled compound 17.8 mg (yield 76%) as a colorless oil. The structure of this compound was determined by the following data.

IR (neat): 3300, 2930, 2860, 1742, 1595, 1491, 1456, 1363, 1325, 1257, 1079, 1027, 975, 837, 777, 733, 698 cm$^{-1}$. $^1$H-NMR (300 MHz, CDC$_3$): δ 7.25 (2H, t, J=7.7 Hz), 7.10–7.00 (2H, m), 6.97 (2H, d, J=7.4 Hz), 6.90 (1H, d, J=6.3 Hz), 6.75 (1H, t, J=7.7 Hz), 5.81 (1H, dd, J=15.4, 4.9 Hz), 5.71 (1H, dd, J=15.4, 7.7 Hz), 5.20–5.08 (1H, m), 4.21 (1H, d, J=4.9 Hz), 4.03–3.94 (1H, m), 3.54–3.45 (1H, m), 3.18–3.05 (2H, m), 2.93 (3H, s), 2.70–2.40 (4H, m), 2.07–1.90 (3H, m), 1.26 (3H, s), 1.25 (3H, s), 0.95 (9H, s), 0.75 (9H, s), 0.11 (3H, s), 0.09 (3H, s), 0.01 (3H, s), −0.06 (3H, s). MASS (EI, m/e): 672 ((M−tBu)$^+$), 636 ((M−OPh)$^+$).

EXAMPLE 29

2-Decarboxy-2-methylsulfonylamino-16-methyl-16-phenoxy-5,6,7,18,19,20-hexanor-4,8-inter-m-phenylene PGI$_2$ (46)

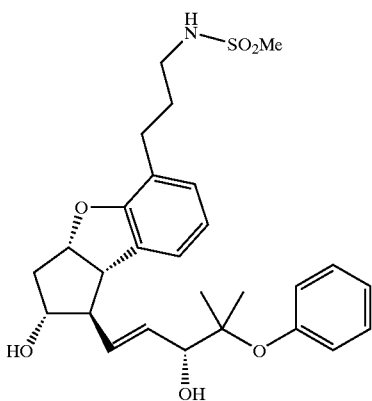

(46)

2-Decarboxy-2-methylsulfonylamino-16-methyl-16-phenoxy-5,6,7,18,19,20-hexanor-4,8-inter-m-phenylene PGI$_2$, 11,15-bis(tert-butyldimethylsilyl ether) (45) 16 mg (0.02 mmol) was dissolved in anhydrous THF (1 mL), and 1.0 M THF solution of TBAF 0.13 mL (0.13 mmol, 6 equivalents) was added to the resultant solution, followed by stirring at room temperature for 5 hours. Although the disappearance of the starting material was checked by TLC, a mono-TBS compound remained, and thus stirring was continued at room temperature for 19 hours. After the completion of reaction was checked by TLC, the reaction mixture was concentrated, and the residue was extracted with ethyl acetate (20 mL×2). The combined organic layer was washed with water (30 mL×2) and brine (20 mL), and then dried over anhydrous sodium sulfate. After concentration, the residue was purified by column chromatography (Silica Gel FL60D produced by Fuji Silicia Co.; cyclohexane:ethyl acetate=1:3~1:9) to obtain the titled compound 10 mg (yield 100%) as a colorless oil. The structure of this compound was determined by the following data.

IR (neat): 3420, 2936, 1595, 1491, 1454, 1319, 1228, 1149, 1075, 1025, 977, 864, 739, 700 cm$^{-1}$. $^1$H-NMR (300 MHz, CDCl$_3$): δ 7.29 (2H, t, J=7.4 Hz), 7.12 (1H, t, J=7.4 Hz), 7.02–6.91 (4H, m), 6.78 (1H, t, J=7.4 Hz), 5.80 (1H, dd, J=15.4, 8.0 Hz), 5.71 (1H, dd, J=15.4, 6.9 Hz), 5.17 (1H, ddd, J=8.8, 7.1, 4.4 Hz), 4.79 (1H, t, J=6.3 Hz), 4.19 (1H, d, J=6.9 Hz), 4.02 (1H, q, J=7.1 Hz), 3.59–3.50 (1H, m), 3.22–3.00 (3H, m), 2.90 (3H, s), 2.77–2.51 (5H, m), 2.11–1.99 (1H, m), 1.98–1.77 (2H, m), 1.25 (3H, s), 1.24 (3H, s). MASS (EI, m/e): 501 (M$^+$).

EXAMPLE 30

2-Decarboxy-2-phenylsulfonylamino-16-methyl-16-phenoxy-5,6,7,18,19,20-hexanor-4,8-inter-m-phenylene PGI$_2$, 11,15-bis(tert-Butyldimethylsilyl Ether) (47)

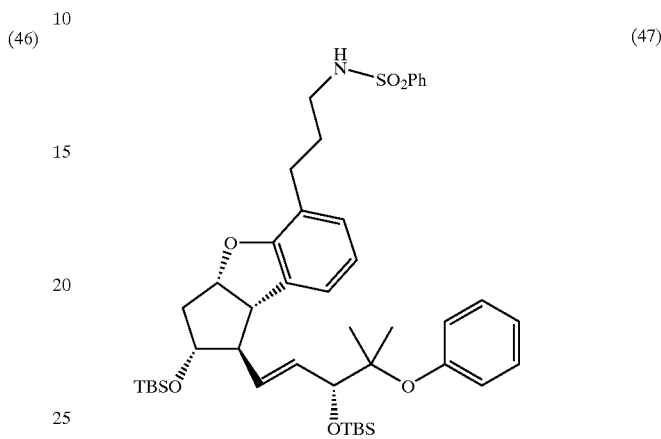

(47)

2-Decarboxy-2-amino-16-methyl-16-phenoxy-5,6,7,18,19,20-hexanor-4,8-inter-m-phenylene PGI$_2$, 11,15-bis(tert-butyldimethylsilyl ether) (11) 28.8 mg (0.044 mmol) was dissolved in anhydrous dichloromethane (2 mL), and triethylamine (12.3 µL, 0.088 mmol, 2.0 equivalents) and benzenesulfonyl chloride (8.4 µL, 0.066 mmol, 1.5 equivalents) were added to the resultant solution, followed by stirring at room temperature for 3 hours. After the disappearance of the starting material was checked by TLC, the reaction was quenched by the addition of methanol (1 mL). Then, the reaction mixture was concentrated, and the residue was extracted with ethyl acetate (30 mL×2). The combined organic layer was washed with water (30 mL×2) and brine (30 mL), and then dried over anhydrous sodium sulfate. After concentration, the residue was purified by column chromatography (Silica Gel FL60D produced by Fuji Silicia Co.; cyclohexane:ethyl acetate=9:1) to obtain the titled compound 25 mg (yield 72%) as a colorless oil. The structure of this compound was determined by the following data.

IR (neat): 3430, 2934, 2860, 1595, 1491, 1450, 1330, 1255, 1228, 1162, 1125, 1094, 837, 777, 690 cm$^{-1}$. $^1$H-NMR (300 MHz, CDCl$_3$): δ 7.89–7.78 (2H, m), 7.60–7.45 (3H, m), 7.25 (2H, t,.J=7.7 Hz), 7.06 (1H, d, J=7.1 Hz), 7.02 (1H, d, J=6.9 Hz), 6.97 (2H, d, J=7.4 Hz), 6.80 (1H, d, J=6.9 Hz), 6.71 (1H, t, J=7.4 Hz), 5.80 (1H, dd, J=15.4, 5.2 Hz), 5.71 (1H, dd, J=15.4, 7.4 Hz), 5.14–5.04 (1H, m), 4.21 (1H, d, J=5.2 Hz), 3.98 (1H, q, J=6.0 Hz), 3.46 (1H dd, J=8.5, 7.1 Hz), 3.04–2.86 (2H, m), 2.67–2.40 (4H, m), 2.00–1.87 (1H, m), 1.79–1.67 (2H, m), 1.26 (3H, s), 1.17 (3H, s), 0.95 (9H, s), 0.74 (9H, s), 0.11 (3H, s), 0.09 (3H, s), −0.00 (3H, s), −0.07 (3H, s) MASS (FAB (pos.), m/e): 778 ((M+H−CH$_3$)$^+$), 734 ((M+H−tBu)$^+$).

EXAMPLE 31

2-Decarboxy-2-phenylsulfonylamino-16-methyl-16-phenoxy-5,6,7,18,19,20-hexanor-4,8-inter-m-phenylene $PGI_2$ (48)

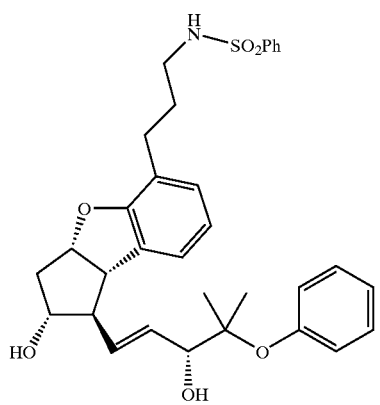

(48)

2-Decarboxy-2-phenylsulfonylamino-16-methyl-16-phenoxy-5,6,7,18,19,20-hexanor-4,8-inter-m-phenylene $PGI_2$, 11,15-bis(tert-butyldimethylsilyl ether) (47) 25 mg (0.032 mmol) was dissolved in anhydrous THF (2 mL), 1.0M THF solution of TBAF 0.19 mL (0.19 mmol, 6 equivalents) was added to the resultant solution, followed by stirring at room temperature for 24 hours. After the disappearance of the starting material was checked by TLC, the reaction mixture was concentrated, and the residue was extracted with ethyl acetate (30 mL×2). The combined organic layer was washed with water (30 mL×2) and brine (30 mL), and then dried over anhydrous sodium sulfate. After concentration, the residue was purified by column chromatography (Silica Gel FL60D produced by Fuji Silicia Co.; cyclohexane:ethyl acetate=1:3) to obtain the target benzenesulfonylamine 15.4 mg (yield 85%) as a colorless oil. The structure of this compound was determined by the following data.

IR (neat): 3420, 2936, 1595, 1491, 1452, 1369, 1325, 1228, 1160, 1094, 1025, 739, 692 cm$^{-1}$. $^1$H-NMR (300 MHz, CDCl$_3$): δ 7.83 (2H, dt, J=6.9, 1.6 Hz), 7.59–7.45 (3H, m), 7.29 (2H, t, J=7.4 Hz), 7.12 (1H, tt, J=7.4, 1.1 Hz), 6.98 (2H, dt, J=7.4, 1.1 Hz), 6.93 (1H, d, J=7.1 Hz), 6.85 (1H, d, J=6.6 Hz), 6.74 (1H, d, J=7.4 Hz), 5.80 (1H, dd, J=15.4, 8.2 Hz), 5.70 (1H, dd, J=15.4, 6.6 Hz), 5.17–5.07 (1H, m), 4.99–4.92 (1H, m), 4.19 (1H, d, J=6.6 Hz), 4.00 (1H, q, J=6.6 Hz), 3.50 (1H, t, J=8.2 Hz), 3.21 (1H, bs), 3.01–2.87 (2H, m), 2.76 (1H, bs), 2.65–2.46 (4H, m), 2.08–1.97 (1H, m), 1.83–1.62 (2H, m), 1.25 (3H, s), 1.24 (3H, s). MASS (FAB (pos.), m/e): 564 ((M+H)$^+$). High Resolution Mass Spectrometry (HRMS, FAB (pos.)): Found: 564.2407000. Calculated for C$_{32}$H$_{37}$NO$_6$S$^+$H [(M+H)$^+$]: 564.241955.

EXAMPLE 32

2-Decarboxy-2-acetylamino-16-methyl-16-phenoxy-5,6,7,18,19,20-hexanor-4,8-inter-m-phenylene $PGI_2$, 11,15-bis(tert-Butyldimethylsilyl Ether) (49)

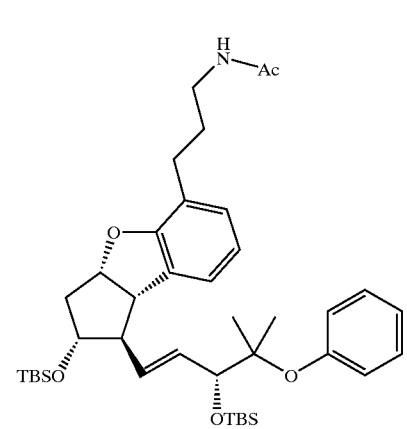

(49)

2-Decarboxy-2-amino-16-methyl-16-phenoxy-5,6,7,18,19,20-hexanor-4,8-inter-m-phenylene $PGI_2$, 11,15-bis(tert-butyldimethylsilyl ether) (11) 30.1 mg (0.046 mmol) was dissolved in anhydrous dichloromethane (1 mL), and triethylamine (32 μL, 0.23 mmol, 5 equivalents) and acetic anhydride (5 μL, 0.055 mmol, 1.2 equivalents) were added to the resultant solution, followed by stirring for 30 minutes. After the disappearance of the starting material was checked by TLC, the reaction was quenched by the addition of methanol 1 mL, and the mixture was extracted with ethyl acetate (40 mL×2). The combined organic layer was washed with aqueous sodium bicarbonate (50 mL) and brine (50 mL×2), and then dried over anhydrous sodium sulfate. After concentration, the residue was purified by column chromatography (silica gel; cyclohexane:ethyl acetate=6:4~3:7) to obtain the titled compound 18.9 mg (yield 59%). The structure of this compound was determined by the following data.

IR (neat): 3286, 2932, 2890, 2860, 1653, 1595, 1557, 1491, 1473, 1456, 1381, 1363, 1255, 1228, 1125, 1006, 909, 837, 777, 735, 696 cm$^{-1}$. $^1$H-NMR (300 MHz, CDCl$_3$): δ 7.29–7.20 (2H, m), 7.05 (2H, t, J=7.1 Hz), 7.00–6.94 (2H, m), 6.91 (1H, d, J=6.6 Hz), 6.75 (1H, t, J=7.4 Hz), 5.87–5.77 (2H, m), 5.72 (1H, dd, J=15.9, 7.7 Hz), 5.19–5.09 (1H, m), 4.22 (1H, d, J=4.9 Hz), 4.04–3.95 (1H, m), 3.54–3.46 (1H, m), 3.23 (2H, q, J=6.6 Hz), 2.69–2.43 (4H, m), 2.02–1.91 (1H, m), 1.97 (3H, s), 1.85–1.73 (2H, m), 1.26 (3H, s), 1.17 (3H, s), 0.95 (9H, s), 0.76 (9H, s), 0.11 (3H, s), 0.09 (3H, s), 0.01 (3H, s), −0.06 (3H, s). MASS (FAB (pos.), m/e): 678 ((M−Me)$^+$), 636 ((M−tBu)$^+$), 600 ((M−OPh)$^+$).

EXAMPLE 33

2-Decarboxy-2-acetylamino-16-methyl-16-phenoxy-5,6,7,18,19,20-hexanor-4,8-inter-m-phenylene PGI$_2$ (50)

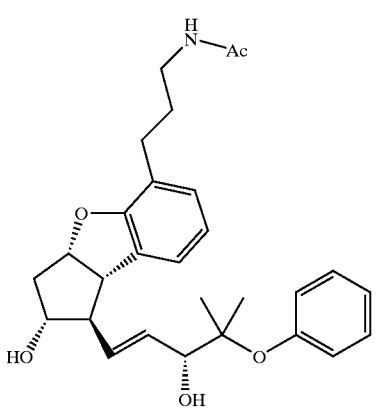

2-Decarboxy-2-acetylamino-16-methyl-16-phenoxy-5,6,7,18,19,20-hexanor-4,8-inter-m-phenylene PGI$_2$, 11,15-bis(tert-butyldimethylsilyl ether) (49) 18.9 mg (0.027 mmol) was dissolved in anhydrous THF (1 mL), and THF solution of TBAF (1M) 0.16 mL (0.16 mmol, 6 equivalents) was added to the resultant solution, followed by stirring at room temperature overnight. After the disappearance of the starting material was checked by TLC, the mixture was concentrated, and the residue was extracted with ethyl acetate (30 mL×2). The combined organic layer was washed with water (50 mL×2) and brine (50 mL), and then dried over anhydrous sodium sulfate. After concentration, the residue was purified by column chromatography (Silica Gel FL60D produced by Fuji Silicia Co.; cyclohexane:ethyl acetate=1:4~ethyl acetate~ethyl acetate:methanol=9:1) to obtain the titled compound 11.1 mg (yield 88%). The structure of this compound was determined by the following data.

IR (neat): 3330, 2934, 1634, 1595, 1491, 1454, 1369, 1226, 1133, 1071, 1027, 975, 911, 864, 729 cm$^{-1}$. $^1$H-NMR (300 MHz, CDCl$_3$): δ 7.32–7.25 (2H, m), 7.12 (1H, tt, J=7.4, 1.1 Hz), 7.01–6.96 (2H, m), 6.94 (2H, d, J=7.4 Hz), 6.76 (1H, t, J=7.4 Hz), 5.80 (1H, dd, J=15.4, 8.2 Hz), 5.76 (1H, bs), 5.70 (1H, dd, J=15.4, 6.9 Hz), 5.15 (1H, ddd, J=8.8, 7.1, 4.7 Hz), 4.19 (1H, d, J=6.9 Hz), 4.06–3.97 (1H, m), 3.53 (1H, t, J=8.2 Hz), 3.28–3.10 (3H, m), 2.72–2.50 (4H, m), 2.10–1.68 (3H, m), 1.94 (3H, s), 1.25 (3H, s), 1.24 (3H, s). MASS (FAB (pos.), m/e): 466 ((M+H)$^+$). High Resolution Mass Spectrometry (HRMS, FAB (pos.)): Found: 466.2586. Calculated for C$_{28}$H$_{35}$NO$_5$+H [(M+H)$^+$]: 466.2515.

EXAMPLE 34

2-Decarboxy-2-benzoylamino-16-methyl-16-phenoxy-5,6,7,18,19,20-hexanor-4,8-inter-m-phenylene PGI$_2$, 11,15-bis(tert-Butyldimethylsilyl Ether) (51)

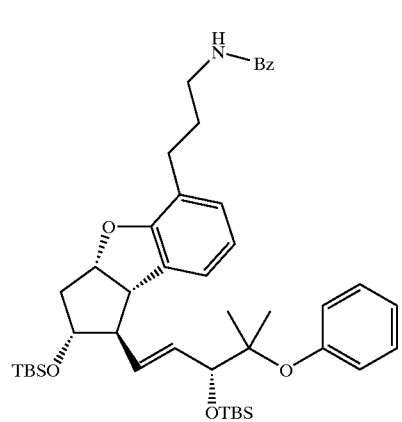

2-Decarboxy-2-amino-16-methyl-16-phenoxy-5,6,7,18,19,20-hexanor-4,8-inter-m-phenylene PGI$_2$, 11,15-bis(tert-butyldimethylsilyl ether) (11) 34.2 mg (0.052 mmol) was dissolved in anhydrous dichloromethane (1 mL), and triethylamine (36.6 μL, 0.26 mmol, 5 equivalents) and benzoyl chloride (7.2 μL, 0.062 mmol, 1.2 equivalents) were added to the resultant solution under ice cooling, followed by stirring for 30 minutes. After the disappearance of the starting material was checked by TLC, the reaction was quenched by the addition of methanol (1 mL), and the mixture was extracted with ethyl acetate (40 mL×2). The combined organic layer was washed with water (50 mL×2), saturated sodium bicarbonate (50 mL) and brine. (50 mL), and then dried over anhydrous sodium sulfate. After concentration, the residue was purified twice by column chromatography (silica gel; cyclohexane:ethyl acetate= 3:1~1:3) to obtain the titled compound 21.4 mg (yield 54%). The structure of this compound was determined by the following data.

IR (neat): 3320, 2932, 2860, 1640, 1580, 1543, 1491, 1454, 1363, 1253, 1122, 837, 777, 696 cm$^{-1}$. $^1$H-NMR (300 MHz, CDCl$_3$): δ 7.75 (2H, dt, J=6.6, 1.6 Hz), 7.52–7.38 (3H, m), 7.25 (2H, t, J=7.4 Hz), 7.09–7.02 (2H, m), 7.01–6.93 (3H, m), 6.78 (1H, t, J=7.4 Hz), 6.72 (1H, m), 5.81 (1H, dd, J=15.6, 5.5 Hz), 5.71 (1H, dd, J=15.6, 8.2 Hz), 5.13 (1H, ddd, J=8.8, 7.4, 4.7 Hz), 4.22 (1H, d, J=5.5 Hz), 3.98 (1H, dd, J=12.6, 7.1 Hz), 3.53–3.36 (3H, m), 2.69–2.54 (3H, m), 2.44 (1H, ddd, J=13.7, 7.4, 6.0 Hz), 2.00–1.86 (3H, m), 1.26 (3H, s), 1.17 (3H, s), 0.95 (9H, s), 0.74 (9H, s), 0.12 (3H, s), 0.10 (3H, s), −0.01 (3H, s), −0.07 (3H, s). MASS (FAB (pos.), m/e): 740 ((M−Me)$^+$), 698 ((M−tBu)$^+$).

EXAMPLE 35

2-Decarboxy-2-benzoylamino-16-methyl-16-phenoxy-5,6,7,18,19,20-hexanor-4,8-inter-m-phenylene $PGI_2$ (52)

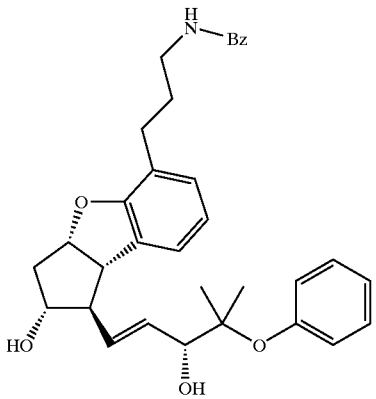

(52)

2-Decarboxy-2-benzoylamino-16-methyl-16-phenoxy-5,6,7,18,19,20-hexanor-4,8-inter-m-phenylene $PGI_2$, 11,15-bis(tert-butyldimethylsilyl ether) (51) 21.4 mg (0.028 mmol) was dissolved in anhydrous THF (1 mL), and THF solution of TBAF (1M) 0.17 mL (0.17 mmol, 6 equivalents) was added to the resultant solution, followed by stirring at room temperature overnight. After the disappearance of the starting material was checked by TLC, the reaction mixture was concentrated, and the residue was extracted with ethyl acetate (30 mL×2). The combined organic layer was washed with water (50 mL×2) and brine (50 mL), and then dried over anhydrous sodium sulfate. After concentration, the residue was purified by column chromatography (Silica Gel FL60D produced by Fuji Silicia Co.; cyclohexane:ethyl acetate=3:7~ethyl acetate) to obtain the titled compound 13.9 mg (yield 94%). The structure of this compound was determined by the following data.

IR (neat): 3350, 2978, 2934, 1642, 1595, 1578, 1543, 1491, 1454, 1369, 1299, 1226, 1133, 1027, 911, 731, 698 $cm^{-1}$. $^1$H-NMR (300 MHz, $CDCl_3$): δ 7.35 (2H, td, J=6.6, 1.6 Hz), 7.51–7.38 (3H, m), 7.29 (2H, t, J=7.4 Hz), 7.12 (1H, tt, J=7.4, 1.1 Hz), 7.20–6.93 (4H, m), 6.79 (1H, t, J=7.4 Hz), 6.61 (1H, m), 5.80 (1H, dd, J=15.6, 8.2 Hz), 5.70 (1H, dd, J=15.6, 6.9 Hz), 5.14 (1H, ddd, J=8.8, 7.4, 4.7 Hz), 4.19 (1H, d, J=6.9 Hz), 3.99 (1H, td, J=7.7, 6.0 Hz), 3.51 (1H, dd, J=16.5, 8.5 Hz), 3.40 (2H, dd, J=12.6, 6.6 Hz), 3.20 (1H, bs), 2.75–2.46 (4H, m), 2.06–1.84 (3H, m), 1.25 (3H, s), 1.24 (3H, s). MASS (FAB (pos.), m/e): 528 ((M+H)$^+$). High Resolution Mass Spectrometry (HRMS, FAB (pos.)): Found: 528.2747. Calculated for $C_{33}H_{37}NO_5$+H [(M+H)$^+$]: 528.2750.

EXAMPLE 36

2-Decarboxy-2-fluoro-16-methyl-16-phenoxy-5,6,7,18,19,20-hexanor-4,8-inter-m-phenylene $PGI_2$ (53)

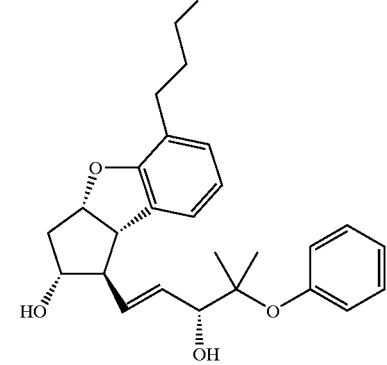

(53)

2-Decarboxy-2-methylsulfonyloxy-16-methyl-16-phenoxy-5,6,7,18,19,20-hexanor-4,8-inter-m-phenylene $PGI_2$, 11,15-bis(tert-butyldimethylsilyl ether) (9) 28 mg (0.038 mmol) was dissolved in dry THF (2 mL), and 1M THF solution of TBAF 0.23 mL (0.23 mmol, 6 equivalents) was added to the resultant solution, followed by stirring at room temperature for 40 hours. The reaction mixture was concentrated, and the residue was extracted with ethyl acetate (30 mL×2). The combined organic layer was washed with water (50 mL×2) and brine (30 mL), and then dried over anhydrous sodium sulfate. After concentration, the residue was purified by column chromatography (Silica Gel FL60D produced by Fuji Silicia Co.; cyclohexane:ethyl acetate=4:6) to obtain the titled compound 9.7 mg (yield 58%) as a colorless oil. The structure of this compound was determined by the following data.

IR (neat): 3420, 2936, 1595, 1491, 1456, 1226, 1133, 1071, 1021, 743, 698 $cm^{-1}$. $^1$H-NMR, (300 MHz, $CDCl_3$): δ 7.29 (2H, t, J=7.4 Hz), 7.12 (1H, t, J=7.4 Hz), 7.02–6.96 (3H, m), 6.93 (1H, d, J=7.4 Hz), 6.76 (1H, t, J=7.4 Hz), 5.81 (1H, dd, J=15.4, 8.2 Hz), 5.71 (1H, dd, J=15.4, 6.9 Hz), 5.12 (1H, ddd, J=8.5, 7.1, 5.8 Hz), 4.46 (2H, dt, J=47.2, 6.0 Hz), 4.20 (1H, d, J=6.9 Hz), 3.96 (1H, q, J=6.3 Hz), 3.47 (1H, t, J=8.8 Hz), 3.25 (1H, bs), 2.78 (1H, bs), 2.74–2.62 (3H, m), 2.47 (1H, q, J=8.2 Hz), 2.13–1.86 (3H, m), 1.26 (3H, s), 1.25 (3H, s). MASS (EI, m/e): 426 (M$^+$). High Resolution Mass Spectrometry (HREIMS): Found: 426.2201. Calculated for $C_{26}H_{31}FO_4$ (M$^+$): 426.2207.

EXAMPLE 37

2-Decarboxy-2-hydroxy-2-trifluoromethyl-16-methyl-16-phenoxy-5,6,7,18,19,20-hexanor-4,8-inter-m-phenylene PGI$_2$ (54)

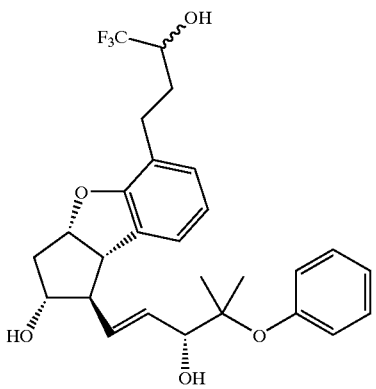

(54)

2-Decarboxy-2-hydroxy-16-methyl-16-phenoxy-5,6,7,18,19,20-hexanor-4,8-inter-m-phenylene PGI$_2$, 11,15-bis(tert-butyldimethylsilyl ether) (8) 360 mg (0.55 mmol) was dissolved in anhydrous dichloromethane (5 mL), and oxalyl chloride (0.11 mL, 2.2 equivalents) and triethylamine (0.38 mL, 5 equivalents) were added to the resultant solution, followed by stirring under ice cooling for 30 minutes. After the disappearance of the starting material was checked by TLC, saturated aqueous ammonium chloride (20 mL) was added to the reaction mixture, and the resultant mixture was extracted with ethyl acetate (30 mL×2). The combined organic layer was washed with water (50 mL), saturated aqueous ammonium chloride (50 mL) and brine (50 mL), and then dried over anhydrous sodium sulfate. After evaporation of the solvent, the residue was purified by column chromatography (silica gel; cyclohexane:ethyl acetate=5:1) to obtain aldehyde 340 mg (yield 95%).

The thus-obtained aldehyde 36.8 mg (0.056 mmol) was dissolved in anhydrous THF (1 mL), and trifluoromethyl trimethylsilane (CF3TMS) 12.5 μL (0.085 mol. 1.5 equivalents) and 1M THF solution of TBAF 0.28 mL (0.28 mmol, 5 equivalents) were added to the resultant solution, followed by stirring at room temperature for 9 hours. Since TLC showed the behavior that the TBS group was not easily deprotected, TBAF 5 equivalents was further added to the reaction mixture, followed by stirring overnight. Then, TBAF (5 equivalents) and CF3TMS (2 equivalents) were further added, and the resultant mixture was stirred overnight. The reaction was quenched by the addition of acetone (2 mL), and the mixture was concentrated. The residue was extracted with ethyl acetate (30 mL×2). The combined organic layer was washed with water (50 mL×2) and brine (40 mL), and then dried over anhydrous sodium sulfate. After the concentration, the residue was purified by column chromatography (Silica Gel FL60D produced by Fuji Silicia Co.; cyclohexane:ethyl acetate=1:1) to obtain the titled compound 21.5 mg (yield 78%). The structure of this compound was determined by the following data.

IR (neat): 3420, 2922, 1593, 1491, 1452, 1383, 1278, 1226, 1160, 1129, 1020, 870 cm$^{-1}$. $^1$H-NMR (300 MHz, CDCl$_3$): δ 7.29 (2H, t, J=7.7 Hz), 7.12 (1H, t, J=7.4 Hz), 7.05–6.90 (4H, m), 6.79 (1H, td, J=7.4, 3.0 Hz), 5.80 (1H, ddd, J=15.4, 8.2, 3.6 Hz), 5.70 (1H, dd, J=15.4, 6.9 Hz), 5.24–5.12 (1H, m), 4.19 (1H, dd, J=6.9, 2.0 Hz), 4.08–3.93 (1H, m), 3.92–3.71 (1H, m), 3.61–3.47 (1H, m), 3.31–3.03 (2H, m), 2.89–2.44 (5H, m), 2.10–1.85 (3H, m), 1.25 (3H, s), 1.24 (3H, s). MASS (EI, m/e): 492 (M$^+$). High Resolution Mass Spectrometry (HREIMS): Found: 492.2090. Calculated for C$_{27}$H$_{31}$F$_3$O$_5$ (M$^+$): 492.2124.

EXAMPLE 38

15-Dehydroxy-16-hydroxy-16-methyl-2,5,6,7-tetranor-4,8-inter-m-phenylene PGI$_2$ Methyl Ester, 11-Acetate (55)

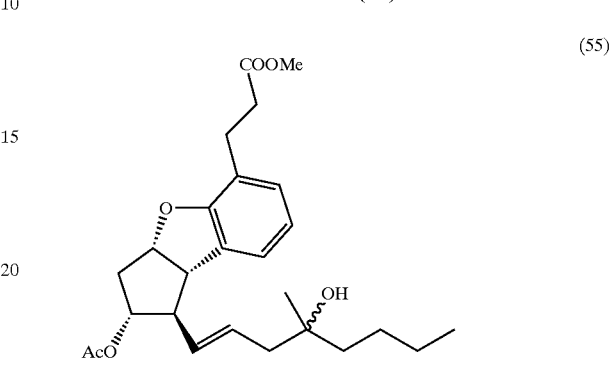

(55)

Anhydrous DMSO 0.423 ml (6.000 mmol), anhydrous pyridine 0.027 ml (0.330 mmol), and trifluoroacetic acid 0.012 ml (0.150 mmol) were added to a solution of methyl 3-{(1S,2R,3aS,8bS)-2-acetoxy-2,3,3a,8b-tetrahydro-1-hydroxymethyl-1H-cyclopenta[b]benzofuran-5-yl}propionate 100.3 mg (0.300 mmol) and DCC 92.8 mg (0.450 mmol) in 0.6 ml of anhydrous THF under ice cooling and argon stream, followed by stirring at room temperature for 1 hour. The reaction mixture was concentrated, and the residue was filtered. The precipitate was washed with ethyl acetate (50 ml), the filtrate was washed with (water (10 ml×3) and saturated brine (10 ml). The organic layer was dried over anhydrous sodium sulfate, filtered, concentrated, and then dried under reduced pressure to obtain crude aldehyde.

Next, methyl triphenylphosphonium iodide 242.5 mg was dried at 100° C. under reduced pressure for 2 hours. After the air in a reactor was replaced with argon, anhydrous THF (2 ml) was added to the reactor, and cooled to 0° C. t-Butyl lithium (1.62 N) 0.741 ml was slowly added, and the resultant mixture was stirred at the same temperature for 1 hour. Then, a solution of 2-methylhexaneoxide 68.5 mg in THF (1 ml) was added to the mixture, followed by stirring at 0° C. for 1 hour, and then at room temperature for 3 hours. A solution of the previously prepared aldehyde in diethyl ether (2 ml) was then added to the reaction mixture, and the resultant mixture was stirred at room temperature overnight. After the reaction mixture was filtered, the precipitate was washed with ether (50 ml), and the filtrate was washed with water (10 ml) and brine (10 ml). The organic layer was concentrated, and the residue was purified by column chromatography (silica gel; cyclohexane:ethyl acetate=4:1) to obtain the titled compound 27.1 mg (yield 20%). The structure of this compound was determined by the following data.

IR (neat): 2930, 1736, 1458, 1241, 1195 cm$^{-1}$. $^1$H-NMR (300 MHz, CDCl$_3$): δ 6.98 (t, J=7.4 Hz, 2H), 6.75 (t, J=7.4 Hz, 1H), 5.66–5.46 (m, 2H), 5.24–5.17 (m, 1H), 4.930 (dd, J=6.6, 13.2 Hz,.1H), 3.67 (s, 3H), 3.58 (t, J=7.1 Hz, 1H), 2.76–2.66 (m, 1H), 2.65–2.56 (m, 3H), 2.21 (d, J=6.6 Hz, 2H), 2.11–2.02 (m, 1H), 1.79 (s, 3H), 1.57–1.15 (m, 9H), 0.94–0.85 (m, 3H).

EXAMPLE 39

15-Dehydroxy-16-hydroxy-16-methyl-2,5,6,7-tetranor-4,8-inter-m-phenylene $PGI_2$ (56)

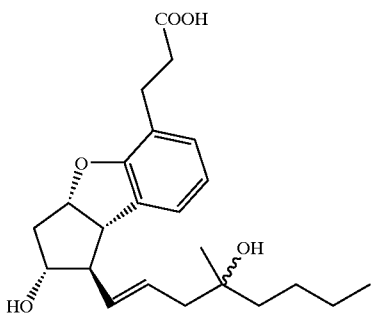

(56)

Sodium methoxide (5.10N) 0.012 ml was added to a solution of 15-dehydroxy-16-hydroxy-16-methyl-2,5,6,7-tetranor-4,8-inter-m-phenylene $PGI_2$ methyl ester, 11-acetate (55) 27.1 mg (0.061 mmol) in methanol (2 ml), followed by stirring at room temperature overnight. After the pH of the reaction solution was adjusted to 7 by 0.1N hydrochloric acid, the solution was concentrated, and the residue was dissolved in ethyl acetate 20 ml. The resultant solution was washed with water (10 ml) and brine (10 ml), concentrated and then dried to obtain a colorless oil. The thus-obtained oil was dissolved in methanol (1 ml), and aqueous sodium hydroxide (2N) 0.5 ml was added to the resultant solution, followed by stirring at room temperature for 2 hours. After the reaction. mixture was acidified with 1N hydrochloric acid, methanol was distilled off under reduced pressure, and the residue was extracted with ethyl acetate (20 ml×3). The combined organic layer was washed with water (10 ml) three times, and it was checked that the pH of the aqueous phase was 7. The organic layer was further washed with brine (10 ml), dried over sodium sulfate, and then filtered. After the filtrate was concentrated, the residue was purified by column chromatography (DIOL produced by Yamazen Co.; cyclohexane:ethyl acetate=1:1) to the titled compound 9.8 mg (yield 60%) as a colorless oil. The structure of this compound was determined by the following data.

IR (neat): 2934, 2866, 1711, 1456, 1263, 1193, 1067, 739 cm$^{-1}$. $^1$H-NMR (300 MHz, CDCl$_3$): δ 7.00–6.97 (m, 2H), 6.76 (t, J=7.4 Hz, 1H), 5.63 (td, J=7.1, 14.3 Hz, 1H), 5.50 (dd, J=8.2, 15.4 Hz, 1H), 5.15–5.08 (m, 1H), 3.92 (dd, J=8.0, 14.3 Hz), 3.44 (t, J=8.2 Hz), 2.97–2.81 (m, 2H), 2.75–2.56 (m, 3H), 2.45 (dd, J=8.2, 16.2 Hz, 1H), 2.24 (s, 1H), 2.22 (s, 1H), 2.04–1.93 (m, 1H), 1.46–1.25 (m, 6H), 1.18 (d, J=2.5 Hz, 3H), 0.94–0.89 (m, 3H).

EXAMPLE 40

2-Decarboxy-2-dicyanomethyl-16-methyl-16-phenoxy-5,6,7,18,19,20-hexanor-4,8-inter-m-phenylene $PGI_2$, 11,15-bis(tert-Butyldimethylsilyl Ether) (57)

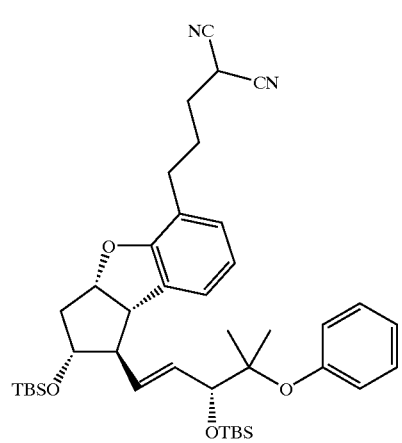

(57)

Potassium t-butoxide 84.0 mg (0.748 mmol) was added to a solution of malononitrile 52.0 mg (0.787 mmol) in THF 1.5 ml under ice cooling and argon stream, and the resultant mixture was stirred at room temperature for 30 minutes. A solution of 2-decarboxy-2-methylsulfonyloxy-16-methyl-16-phenoxy-5,6,7,18,19,20-hexanor-4,8-inter-m-phenylene $PGI_2$, 11,15-bis(tert-butyldimethylsilyl ether) (9) 17.0 mg (0.0233 mmol) in anhydrous THF 1.5 ml was added to the above ice-cold solution, followed by stirring at 70° C. for 27 hours. After the reaction mixture was cooled with ice, saturated aqueous ammonium chloride 8 ml was added, and the resultant mixture was extracted with ethyl acetate (3×12 ml). The combined organic layer was washed with brine 5 ml, dried, and then concentrated. The thus-obtained oil 60.1 mg was purified by column chromatography (silica gel; cyclohexane:ethyl acetate=95:5~80:20) to obtain the titled compound 13.1 mg (yield 80%) as a colorless oil. The structure of this compound was determined by the following data.

IR (neat): 1595, 1490, 1458, 1384, 1254, 1225, 838, 776 cm$^{-1}$. $^1$H-NMR (300 MHz, CDCl$_3$): δ 7.28–7.21 (2H, m), 7.10–7.02 (2H, m), 6.97 (2H, dd, J=8.7, 1.2 Hz), 6.89 (1H, br d, J=6.6 Hz), 6.76 (1H, dd, J=7.4, 7.4 Hz), 5.83 (1H, dd, J=16.0, 5.8 Hz), 5.71 (1H, dd, J=16.0, 7.6 Hz), 5.16 (1H, ddd, J=8.8, 7.4, 4.4 Hz), 4.22 (1H, d, J=4.7 Hz), 3.99 (1H, ddd, J=6.6, 6.6, 5.7 Hz), 3.89 (1H, t, J 6.9 Hz), 3.52 (1H, dd, J=8.8, 6.7 Hz), 2.73–2.53 (3H, m), 2.47 (1H, ddd, J=13.7, 7.4, 5.7 Hz), 2.12–1.87 (5H, m), 1.27 (3H, s), 1.17 (3H, s), 0.95 (9H, s), 0.74 (9H, s), 0.11 (3H, s), 0.09 (3H, S), 0.00 (3H, s), −0.07 (3H, s). MASS (EI, m/e): 700 (M$^+$).

EXAMPLE 41

2-Decarboxy-2-dicyanomethyl-16-methyl-16-phenoxy-5,6,7,18,19,20-hexanor-4,8-inter-m-phenylene PGI₂ (58)

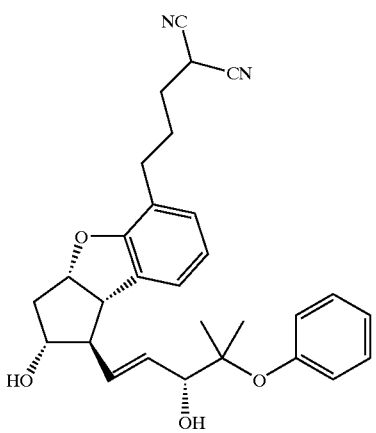

(58)

Acetic acid 0.60 ml and water 0.20 ml were added to a solution of 2-decarboxy-2-dicyanomethyl-16-methyl-16-phenoxy-5,6,7,18,19,20-hexanor-4,8-inter-m-phenylene PGI₂, 11,15-bis(tert-butyldimethylsilyl ether) (57) 20.7 mg (0.0295 mmol) in anhydrous THF 0.20 ml under argon atmosphere, followed by stirring at 70° C. for 43.5 hours. The reaction mixture was added to ice-cold saturated aqueous sodium bicarbonate 10 ml, and the resultant mixture was stirred for a while, and then extracted with ethyl acetate (3×15 ml). The combined organic layer was washed with brine 6 ml, dried, and then concentrated. The thus-obtained oil 16.2 mg was purified by column chromatography (silica gel; cyclohexane:ethyl acetate=95:5→15:85) to obtain the titled compound 7.8 mg (yield 55%) as a colorless oil. The structure of this compound was determined by the following data.

IR (neat): 3390, 1632, 1595, 1490, 1454, 1385, 1259, 1226, 1194, 1132, 1072, 1026, 974, 866, 786, 743 cm⁻¹.
¹H-NMR (300 MHz, CDCl₃): δ 7.29 (2H, dd, J=7.8, 7.8 Hz), 7.12 (1H, t, J=7.4 Hz), 7.02–6.90 (4H, m), 6.78 (1H, dd, J=7.4, 7.4 Hz), 5.83 (1H, dd, J=15.4, 8.0 Hz), 5.71 (1H, dd, J=15.4, 6.9 Hz), 5.15 (1H, ddd, J=8.8, 7.2, 5.1 Hz), 4.20 (1H, d, J=6.9 Hz), 3.99 (1H, ddd, J=8.0, 8.0, 6.3 Hz), 3.89 (1H, t, J=6.7 Hz), 3.51 (1H, dd, J=8.5, 8.2 Hz), 3.19 (1H, br s), 2.71–2.59 (3H, m), 2.50 (1H, ddd, J 8.0, 8.0, 7.7 Hz), 2.08–1.88 (5H, m), 1.67 (1H, br s), 1.25 (3H, s), 1.25 (3H, s). MASS (FAB (neg.), m/e): 471 [(M–H)⁻]. High Resolution Mass Spectrometry ((FAB (neg.)): Found: 471.2313 (−2.9 mmu). Calculated for C₂₉H₃₁N₂O₄ [(M–H)⁻]: 471.2342.

EXAMPLE 42

3-Decarboxy-3-dimethoxyphosphonyl-16-methyl-15-oxo-16-phenoxy-2,5,6,7,18,19,20-heptanor-4,8-inter-m-phenylene PGI₂, 11-acetate (59)

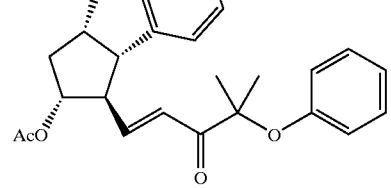

(59)

A solution of dimethyl 2-((1S,2R,3aS,8bS)-2-acetoxy-2,3,3a,8b-tetrahydro-1-hydroxymethyl-1H-cyclopenta[b]benzofuran-5-yl) ethylphosphonate (13) 667.9 mg (1.738 mmol), DMSO 2.45 ml (34.76 mmol), and pyridine 0.155 ml (1.912 mmol) in anhydrous THF (6 ml) was cooled to 0° C. under argon atomsphere, and trifluoroacetic acid 67 μl (0.869 mmol) was added to the cold solution. Then, a solution of dicyclohexylcarbodiimide 717.2 mg (3.476 mmol) in anhydrous THF (4 ml×2) was slowly added dropwise to the reaction mixture, followed by stirring at the same temperature for 5 minutes. The reaction mixture was warmed to room temperature, and stirred for 3 hours, and then the solvent was distilled off under reduced pressure. After ethyl acetate 30 ml was added to the residue, the resultant mixture was filtered under suction, and the filter paper was washed with ethyl acetate. The filtrate was washed with water (5 ml) and brine (5 ml), and the aqueous phase was extracted with ethyl acetate (15 ml×3). The combined organic layer was dried, and then concentrated. The residue was dried under reduced pressure to obtain aldehyde as oil (containing white solid derived from a urea derivative).

A suspension of sodium hydride (69 wt %) 90.7 mg (2.607 mmol) in anhydrous THF was cooled to 0° C. under argon atmosphere, and a solution of dimethyl 3,3-dimethyl-2-oxo-3-phenoxybutylphosphonate (746.3 mg, 2.607 mmol) in anhydrous THF (2 ml×2) was slowly added dropwise to the cold suspension. After the resultant mixture was stirred at the same temperature for 2 hours, a solution of the previously obtain crude aldehyde in anhydrous THF (2 ml×2) was slowly added to the mixture, followed by further stirring at the same temperature overnight. The reaction was quenched by the addition of saturated aqueous ammonium chloride, and the mixture was extracted with ethyl acetate (15 ml×3). The combined organic layer was washed with water (10 ml) and brine (10 ml), dried, and then concentrated. The thus-obtained oil was purified by column chromatography (silica gel; cyclohexane:ethyl acetate=1:4→ethyl acetate→chloroform:methanol=97:3) to obtain the titled compound 776.9 mg (1.432 mmol) as a pale yellow oil (yield 82%). The structure of this compound was determined by the following data.

IR (neat): 1740, 1630, 1456, 1238, 1060, 1035 cm⁻¹.
¹H-NMR (300 MHz, CDCl₃): δ 7.26–7.19 (m, 2H), 6.93

(d=7.4, 1H), 6.75 (t, J=7.42, 1H), 5.23–5.17 (m, 1H), 5.05 (dd, J=5.8, 11.26 Hz, 1H), 3.75–3.64 (m, 9H), 2.81 (q, J=9.1, 16.8 Hz, 2H), 2.59–2.49 (m, 2H), 2.29–2.00 (m, 4H), 1.78 (d, J=1.1 Hz, 3H). MASS (EI, m/e): 542 (M)$^+$.

EXAMPLE 43

3-Decarboxy-3-dimethoxyphosphonyl-16-methyl-16-phenoxy-2,5,6,7,18,19,20-heptanor-4,8-inter-m-phenylene PGI$_2$ (60) and 15-Epimer (61) Thereof

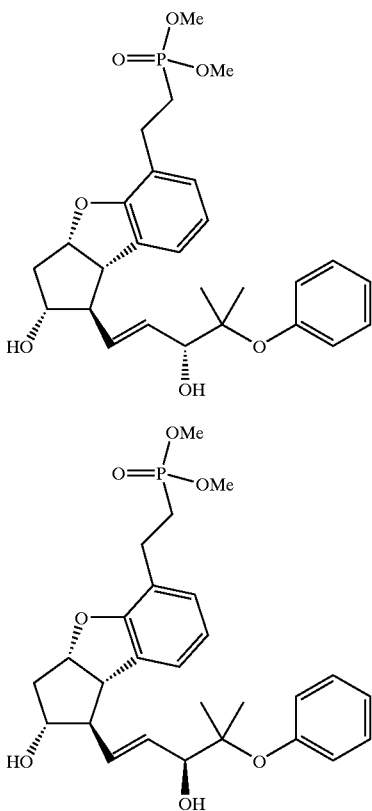

A solution of 3-decarboxy-3-dimethoxyphosphonyl-16-methyl-15-oxo-16-phenoxy-2,5,6,7,18,19,20-heptanor-4,8-inter-m-phenylene PGI$_2$, 11-acetate (59) 776.9 mg (1.432 mmol) and cerium trichloride heptahydrate 533.5 mg (1.432 mmol) in methanol (14 ml) was cooled to 0° C., and sodium borohydride 54.2 mg (1.432 mmol) was added to the cold solution portionwise, followed by stirring at the same temperature for 4 hours. After a hydrogen chloride-methanol solution (1.387M) was added dropwise to the mixture to adjust pH to 7, the reaction solution was concentrated, and the residue was dissolved in ethyl acetate (20 ml), followed by suction filtration. The filtrate was washed with water (5 ml) and brine (5 ml), dried, and then concentrated. The residue was dried under reduced pressure to obtain a crude product of 11-acetoxy-15-hydroxyphosphonate as a pale yellow oil. The thus-obtained oil was dissolved in methanol 14 ml, and methanol solution of sodium methoxide (5.10M) 0.281 ml (1.432 mmol) was added to the resultant solution, followed by stirring at room temperature for 3 hours. After a hydrogen chloride-methanol solution (1.387M) was added dropwise to the mixture to adjust pH to 7, the reaction solution was concentrated, and the residue was dissolved in dichloromethane (20 ml). After suction filtration, the filtrate was concentrated, and the residue was subjected to column chromatography (silica gel; chloroform:acetone=1:1) to isolate an epimer of the 15-position hydroxyl group. The crude product was recrystallized from cyclohexane/ethyl acetate= 1/1 to obtain 3-decarboxy-3-dimethoxyphosphonyl-16-methyl-16-phenoxy-2,5,6,7,18,19,20-heptanor-4,8-inter-m-phenylene PGI$_2$ (more-polar product) 265.5 mg (0.528 mmol) as while crystal (yield 37%). The product was purified again by column chromatography (silica gel; chloroform:methanol=40:1) to obtain 3-decarboxy-3-dimethoxyphosphonyl-16-methyl-16-phenoxy-15-epi-5,6,7,18,19,20-heptanor-4,8-inter-m-phenylene PGI$_2$ (less-polar product) 328.0 mg (0.653 mmol) as a colorless oil (yield 46%). The structures of these compounds were determined by the following data.

3-Decarboxy-3-dimethoxyphosphonyl-16-methyl-16-phenoxy-2,5,6,7,18,19,20-heptanor-4,8-inter-m-phenylene PGI$_2$ IR (neat): 3448, 3366, 2976, 2936, 1595, 1491, 1456, 1243, 1038, 1023 cm$^{-1}$. $^1$H-NMR (300 MHz, CDCl$_3$): δ 7.31–7.25 (m, 2H), 7.14–7.09 (m, 1H), 7.00–6.93 (m, 4H), 6.75 (t, J=7.4 Hz, 1H), 5.81 (dd, J=8.2, 15.4 Hz, 1H), 5.70 (dd, J=6.9, 15.4 Hz, 1H), 5.16–5.09 (m, 1H), 4.19 (dd, J=3.3, 6.9 Hz, 1H), 3.99–3.90 (m, 1H), 3.74 (d, J=0.8 Hz, 3H), 3.70 (d, J=0.6 Hz, 3H), 3.46 (t, J=8.5 Hz, 1H), 3.08–3.20 (br, 1H), 3.08–3.02 (br, 1H), 2.88–2.79 (m, 1H), 2.70–2.61 (m, 1H), 2.46 (dd, J=8.2, 16.2 Hz, 1H), 2.16–1.85 (m, 4H), 1.27 (s, 3H), 1.24 (s, 3H). MASS (FAB (pos.), m/e): 503 (M+H)$^+$. Elemental Analysis: Calculated: C, 64.53%, H, 7.02%, P, 6.16%. Found: C, 64.38%, H, 7.11%, P, 5.95%.

3-Decarboxy-3-dimethoxyphosphonyl-16-methyl-16-phenoxy-15-epi-2,5,6,7,18,19,20-heptanor-4,8-inter-m-phenylene PGI$_2$ IR (neat): 3338, 2980, 1595, 1491, 1456, 1230, 1035 cm$^{-1}$. $^1$H-NMR (300 MHz, CDCl$_3$): δ 7.33–7.26 (m, 2H), 7.15–7.09 (m, 1H), 7.03–6.95 (m, 4H), 6.76 (t, J=7.4 Hz, 1H), 5.90–5.69 (m, 2H), 5.19–5.12 (m, 1H), 4.23–4.20 (m, 1H), 4.00–3.94 (brm, 1H), 3.73 (d, J=1.9 Hz, 3H), 3.70 (d, J=1.6 Hz, 3H), 3.54 (t, J=8.2 Hz, 1H), 2.98 (d, J=3.3 Hz, 1H), 2.89–2.79 (m, 2H), 2.67–2.51 (m, 2H), 2.16–1.97 (m, 4H), 1.25 (s, 3H), 1.23 (s, 3H). MASS (FAB (pos.), m/e): 503 (M+H)$^+$. High Resolution Mass Spectrometry (FAB (pos.)): Calculated for C$_{27}$H$_{36}$O$_7$P (M+H)$^+$: 503.2199 (M+H)$^+$. Found: 503.2219 (M+H)$^+$.

EXAMPLE 44

3-Decarboxy-3-hydroxymethoxyphosphonyl-16-methyl-16-phenoxy-2,5,6,7,18,19,20-heptanor-4,8-inter-m-phenylene PGI$_2$ (62)

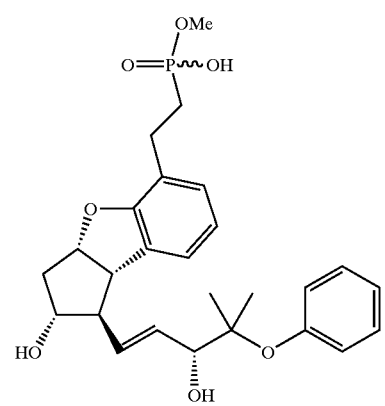

Sodium hydroxide 54.6 mg (1.365 mmol) was added to a solution of 3-decarboxy-3-dimethoxyphosphonyl-16- methyl-16-phenoxy-2,5,6,7,18,19,20-heptanor-4,8-inter-m-phenylene PGI$_2$ (60) 13.7 mg (27.3 μmol) in a mixture of methanol (1.5 ml) and water (0.5 ml), followed by stirring at 80° C. for 4 hours. The reaction mixture was allowed to cool to room temperature, and the pH was adjusted to about 3 with 1N hydrochloric acid. Then, the mixture was concentrated to remove methanol, and the residual aqueous solution was extracted with a chloroform/methanol (7/1) mixture (20 ml×3). The combined organic layer was dried, and then concentrated. The residue was purified by reverse phase column chromatography (YMC-pack, ODS-AM, water/acetonitrile=82/18→50/50) to obtain a colorless oil. The thus-obtained oil was further subjected to gel filtration column (Sephadex, LH-20, methanol) to obtain the titled compound 11.2 mg (22.9 μmol) as a colorless oil (yield 84%). The structure of this compound was determined by the following data.

IR (neat): 3376, 1491, 1457, 1226, 1196, 1047 cm$^{-1}$. $^1$H-NMR (300 MHz, CD$_3$OD): δ 7.30–7.25 (m, 2H), 7.10–6.95 (m, 5H), 6.70 (t, J=7.4 Hz, 1H), 5.89–5.75 (m, 2H), 5.08 (dd, J=7.4, 14.8 Hz, 1H), 4.15 (d, J=6.0 Hz, 1H), 3.94–3.87 (m, 1H), 3.63 (d, J=10.2 Hz, 1H), 3.45 (t, J=8.8 Hz, 1H), 2.78 (brm, 2H), 2.70–2.61 (m, 1H), 2.36–2.31 (m, 1H), 1.98–1.80 (m, 3H), 1.29 (s, 3H), 1.25 (s, 3H). MASS (FAB (neg.), m/e): 487 (M–H)$^-$, 975 (2M–H)$^-$. High Resolution Mass Spectrometry ((FAB (neg.)): Calculated for C$_{26}$H$_{32}$O$_7$P (M–H)$^-$: 487.5096 (M–H)$^-$. Found: 487.1917.

EXAMPLE 45

3-Decarboxy-3-hydroxymethoxyphosphonyl-16-methyl-16-phenoxy-15-epi-2,5,6,7,18,19,20-heptanor-4,8-inter-m-phenylene PGI$_2$ (63)

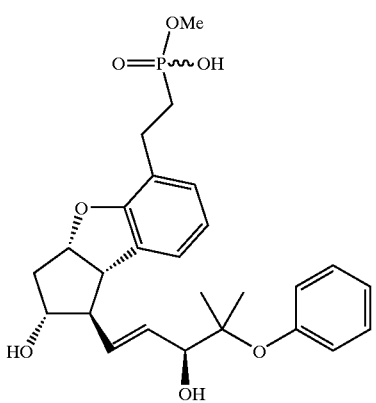

3-Decarboxy-3-dimethoxyphosphonyl-16-methyl-16-phenoxy-15-epi-2,5,6,7,18,19,20-heptanor-4,8-inter-m-phenylene PGI$_2$ (61) 11.2 mg (22.3 μmol) was hydrolyzed with sodium hydroxide 44.6 mg (1.115 mmol) by the same method as Example 44. After worked up, the product was purified by reverse phase column chromatography and gel filtration column to obtain the titled compound 8.9 mg (18.2 μmol) as a colorless oil (yield 82%). The structure of this compound was determined by the following data.

IR (neat): 3472, 1491, 1458, 1228, 1195, 1044 cm$^{-1}$. $^1$H-NMR (300 MHz, CD$_3$OD): δ 7.29–7.23 (m, 2H), 7.09–7.02 (m, 4H), 6.95 (d, J=7.4 Hz, 1H), 6.71 (t, J=7.4 Hz, 1H), 5.85–5.83 (m, 2H), 5.11–5.04 (m, 1H), 4.16–4.14 (m, 1H), 3.94–3.86 (m, 1H), 3.64 (d, J=10.4 Hz, 1H), 3.47 (t, J=8.8 Hz, 1H), 2.84–2.76 (brm, 2H), 2.67–2.60 (m, 1H), 2.36–2.34 (brm, 1H), 2.04–1.93 (brm, 2H), 1.90–1.80 (m, 1H), 1.28 (s, 3H), 1.23 (s, 3H). MASS (FAB (neg.), m/e): 487 (M–H)$^-$. High Resolution Mass Spectrometry (FAB (neg.)): Calculated for C26H32O7P (M–H)$^-$: 487.5096 (M–H)$^-$. Found: 487.1912.

EXAMPLE 46

3-Decarboxy-3-cyanaminocarbonyl-16-methyl-16-phenoxy-2,5,6,7,18,19,20-heptanor-4,8-inter-m-phenylene PGI$_2$, 11,15-bis(tert-Butyldimethylsilyl Ether) (64)

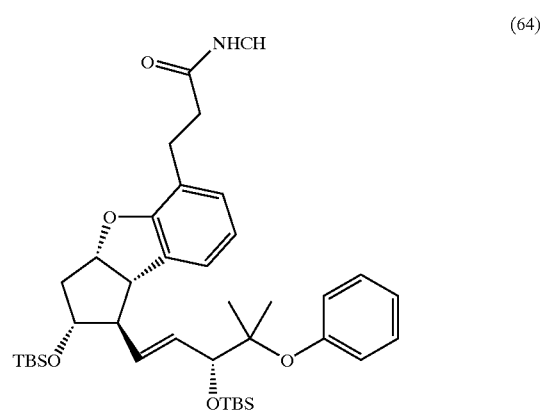

Oxalyl chloride 24 μl (0.278 mmol) was added to a solution of 16-methyl-16-phenoxy-2,5,6,7,18,19,20-heptanor-4,8-inter-m-phenylene PGI$_2$, 11,15-bis(tert-butyldimethylsilyl ether) (5) 92.8 mg (0.139 mmol) in anhydrous dichloromethane (3 ml) under argon atmosphere, and then anhydrous DMF 1 drop was added to the resultant mixture. After stirring at room temperature for 2 hours, the mixture was concentrated, and the residue was dried under reduced pressure to obtain acid chloride.

A suspension of sodium hydride (69 wt %) 24.2 mg (0.696 mmol) in anhydrous DMF (2 ml) was cooled to 0° C. under argon atmosphere, and a solution of cyanoamide 29.2 mg (0.696 mmol) in anhydrous DMF (0.5 ml×2) was added dropwise to the suspension, followed by stirring at room temperature for 2 hours. Then, the above acid chloride in anhydrous DMF (1 ml×2) was added to the reaction mixture, followed by stirring at room temperature for 1.5 hours. The reaction was quenched by the addition of saturated aqueous ammonium chloride, and the mixture was extracted with ethyl acetate (20 ml×3). The combined organic layer was washed with water (15 ml×5) and brine (15 ml), dried, and then concentrated. The thus-obtained oil was subjected to TLC (silica gel plate) separation, and the purified product was further subjected to gel filtration (Sephadex LH-20, methanol) to obtain the titled compound 42.9 mg (0.062 mmol) as a colorless oil (yield 45%). The structure of this compound was determined by the following data.

IR (neat): 2958, 2932, 2892, 2860, 2264, 1734, 1597, 1491, 1460, 1255, 1125, 839, 777, 735 cm$^{-1}$. $^1$H-NMR (300 MHz, CDCl$_3$): δ 7.29–7.22 (m, 2H), 7.09–6.91 (m, 5H), 6.75 (t, J=7.4 Hz, 1H), 6.77–5.79 (m, 2H), 5.21–5.15 (brs, 1H), 4.22 (d, J=4.67, 1H), 4.00 (dd, J=6.6, 12.4 Hz, 1H), 3.54–3.49 (m, 1H), 2.97–2.63 (br, dd, J=6.6, 13.8 Hz, 5H), 2.52–2.43 (m, 1H), 2.03–1.94 (m, 1H), 1.27 (s, 3H), 1.17 (s, 3H), 0.95 (s, 9H), 0.74 (s, 9H), 0.12–0.07 (m, 12H). MASS (FAB (pos.), m/e) 713 (M+Na)$^+$, 735 (M+2Na)$^+$.

EXAMPLE 47

3-Decarboxy-3-cyanaminocarbonyl-16-methyl-16-phenoxy-2,5,6,7,18,19,20-heptanor-4,8-inter-m-phenylene PGI$_2$ (65)

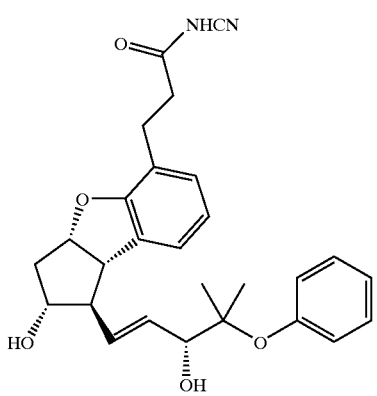

(65)

EXAMPLE 48

2-Decarboxy-16-methyl-16-phenoxy-5,6,7,18,19,20-hexanor-4,8-inter-m-phenylene PGI$_2$, 11,15-bis(tert-Butyldimethylsilyl Ether) (66)

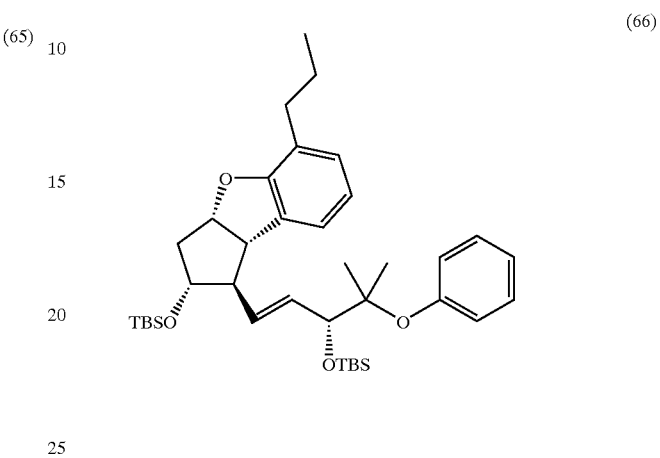

(66)

Tetrabutylammonium fluoride (1M in THF) 0.20 ml (0.200 mmol) was added to a solution of 3-decarboxy-3-cyanaminocarbonyl-16-methyl-16-phenoxy-2,5,6,7,18,19,20-heptanor-4,8-inter-m-phenylene PGI$_2$, 11,15-bis(tert-butyldimethylsilyl ether) (64) 34.9 mg (50.5 µmol) in anhydrous THF (2 ml) under argon atmosphere, and the resultant mixture was stirred at room temperature overnight. Tetrabutylammonium fluoride (1N THF solution) 0.20 ml (0.200 mmol) was further added to the reaction solution, and the mixture was stirred at room temperature for 2 hours. Then, the reaction solution was concentrated, and the residue was dissolved in ethyl acetate (40 ml). The resultant solution was washed with water (10 ml) and brine (10 ml), and the organic layer was dried, and filtered. The filtrate was concentrated, and the thus-obtained oil was purified by column chromatography (DIOL produced by Yamazen Co.; cyclohexane:ethyl acetate=1:2) to obtain the titled compound 18.7 mg (40.4 µmol) as a colorless oil (yield 80%). The structure of this compound was determined by the following data.

IR (neat): 2984, 2934, 2260, 1734, 1595, 1491, 1456, 1224, 733 cm$^{-1}$. $^1$H-NMR (300 MHz, CDCl$_3$): δ 7.30–7.25 (m, 2H), 7.10–6.95 (m, 5H), 6.70 (t, J=7.4 Hz, 1H), 5.89–5.75 (m, 2H), 5.08 (dd, J=7.4, 14.8 Hz, 1H), 4.15 (d, J=6.0 Hz, 1H), 3.94–3.87 (m, 1H), 3.63 (d, J=10.2 Hz, 1H), 3.45 (t, J=8.8 Hz, 1H), 2.78 (brm, 2H), 2.70–2.61 (m, 1H), 2.36–2.31 (m, 1H), 1.98–1.80 (m, 3H), 1.29 (s, 3H), 1.25 (s, 3H).

A solution of 2-decarboxy-2-methylsulfonyloxy-16-methyl-16-phenoxy-5,6,7,18,19,20-hexanor-4,8-inter-m-phenylene PGI$_2$, 11,15-bis(tert-butyldimethylsilyl ether) (9) 29.0 mg (39.7 µmol) in anhydrous THF (3 ml) was cooled to 0° C. under argon atmosphere, and lithium aluminum hydride 3.0 mg (79.4 mmol) was added to the cold solution, followed by stirring at 0° C. for 1 hour and at room temperature for 4 hours. Lithium aluminum hydride 3.0 mg (79.4 µmol) was further added to the mixture, and then the reaction solution was warmed to 60° C., and the stirred for 3 hours. After the reaction mixture was allowed to cool to room temperature, and quenched by the addition of aqueous Rochelle salt (20 ml), and the mixture was extracted with ethyl acetate (20 ml×3). The combined organic layer was washed with water (15 ml) and brine (15 ml), dried, and then concentrated. The thus-obtained oil was purified by thin layer chromatography (silica gel; cyclohexane:ethyl acetate=100:1) to obtain the titled compound 21.0 mg (33.0 µmol) as a colorless oil (yield 83%). The structure of this compound was determined by the following data.

IR (neat): 2960, 2932, 2860, 1454, 1257, 1125, 837, 777 cm$^{-1}$. $^1$H-NMR (300 MHz, CDCl$_3$): δ 7.29–7.22 (m, 2H), 7.09–6.92 (m, 5H), 6.74 (t, J=7.4 Hz, 1H), 5.84 (dd, J=5.2, 15.7 Hz, 1H), 5.74 (dd, J=7.42, 15.7 Hz. 1H) 5.16–5.09 (m, 1H), 4.24 (d, J=5.2, 1H), 3.98 (dd, J=7.4, 13.2 Hz, 1H), 3.48 (t, J=8.24, 1H), 2.64 (dd, J=7.4, 14.6 Hz, 1H), 2.57–2.46 (m, 3H), 2.02–1.93 (m, 1H), 1.69–1.56 (m, 2H), 1.27 (s, 3H), 1.18 (s, 3H), 0.98–0.93 (m, 12H), 0.77 (s, 9H), 0.12 (s, 3H), 0.11 (s, 3H), 0.02 (s, 3H), –0.04 (s, 3H). MASS (EI, m/e): 636 (M)$^+$.

EXAMPLE 49

2-Decarboxy-16-methyl-16-phenoxy-5,6,7,18,19,20-hexanor-4,8-inter-m-phenylene PGI$_2$ (67)

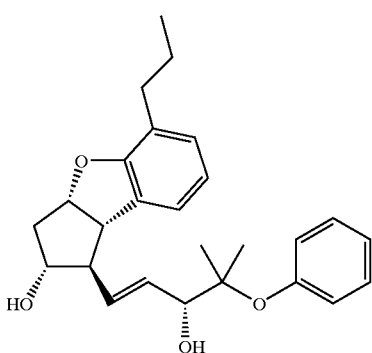

Tetra-n-butylammonium fluoride (1M in THF) 0.143 ml (0.143 μmol) was added to a solution of 2-decarboxy-16-methyl-16-phenoxy-5,6,7,18,19,20-hexanor-4,8-inter-m-phenylene PGI$_2$, 11,15-bis(tert-butyldimethylsilyl ether) (66) 18.2 mg (28.6 μmol) in anhydrous THF (2 ml) under argon atmosphere, followed by stirring at room temperature overnight. The reaction solution was concentrated, and the residue was dissolved in ethyl acetate 20 ml. The resultant solution was washed with water (5 ml) and brine (5 ml) once each, dried, and then concentrated. The thus-obtained oil was purified by column chromatography (silica gel; cyclohexane:ethyl acetate=50:50→25:75) to obtain the titled compound 11.4 mg (27.99 μmol) as a colorless oil (yield 98%). The structure of this compound was determined by the following data.

IR (neat): 2966, 2936, 1491, 1452, 1226, 735, 698 cm$^{-1}$. $^1$H-NMR (300 MHz, CDCl$_3$): δ 7.32–7.26 (m, 2H), 7.15–7.10 (m, 1H), 7.00–6.90 (m, 4H), 6.75 (t, J=7.4 Hz, 1H), 5.82 (dd, J=8.5, 15.1 Hz, 1H), 5.70 (dd, J=7.1, 15.4 Hz, 1H), 5.15–5.08 (m, 1H), 4.20, (d, J=7.1 Hz, 1H), 3.95 (dd, J=8.5, 14.8 Hz, 1H), 3.47 (t, J=8.8 Hz, 1H), 3.28 (brs, 1H), 2.82 (brs, 1H), 2.72–2.64 (m, 1H), 2.56–2.44 (m, 3H), 2.13–1.95 (m, 1H), 1.62 (q, J=7.4, 15.1 Hz, 2H), 1.26 (s, 3H), 1.25 (s, 3H). MASS (EI, m/e): 408 (M)$^+$. High Resolution Mass Spectrometry (HREIMS): Calculated for C$_{26}$H$_{32}$O$_4$ (M$^+$): 408.2301. Found: 408.2268.

EXAMPLE 50

2-Decarboxy-2-phenylthio-16-methyl-16-phenoxy-5,6,7,18,19,20-hexanor-4,8-inter-m-phenylene PGI$_2$, 11,15-bis(tert-Butyldimethylsilyl Ether) (68)

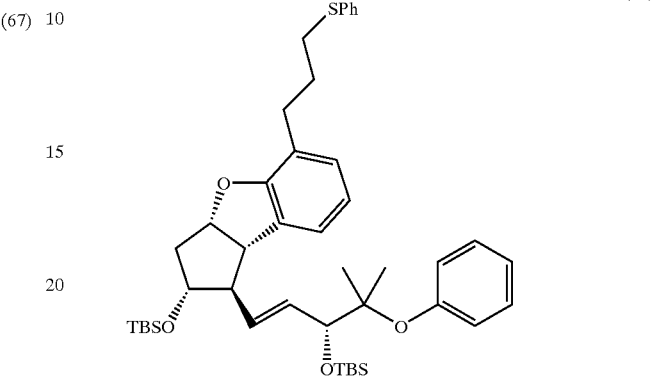

Phenyl mercaptan 0.024 ml (233 μmol) was added to a suspension of sodium hydride (69 wt %) 8.1 mg (233 μmol) in anhydrous THF (1 ml) under argon atmosphere, and the resultant mixture was stirred at room temperature for 20 minutes. Anhydrous DMF 0.5 ml was added to the suspension, and the mixture was then cooled to 0° C., and 2-decarboxy-2-methylsulfonyloxy-16-methyl-16-phenoxy-5,6,7,18,19,20-hexanor-4,8-inter-m-phenylene PGI$_2$, 11,15-bis(tert-butyldimethylsilyl ether) (9) 34.0 mg (46.5 μmol) in anhydrous THF (0.5 ml×2) was added to the mixture, followed by stirring at room temperature for 2 hours. Low-boiling-point substances were distilled off under reduced pressure, and the residue was dissolved in ethyl acetate 20 ml. The resultant solution was washed with water (5 ml) and brine (5 ml) once each, dried, and then concentrated. The residue was purified by thin layer chromatography (silica gel; cyclohexane:ethyl acetate=40:1) to obtain the titled compound 37.0 mg as a pale yellow oil (quantitative). The structure of this compound was determined by the following data.

IR (neat): 2956, 2932, 2860, 1456, 1253, 1125, 837, 777, 739 cm$^{-1}$. $^1$H-NMR (300 MHz, CDCl$_3$): δ 7.33–6.91 (m, 12H), 6.73 (t, J=7.4 Hz, 1H), 5.84 (dd, J=5.2, 15.7 Hz, 1H), 5.74 (dd, J=7.4, 15.9 Hz, 1H), 5.15–5.08 (m, 1H), 4.24 (d, J=4.9 Hz, 1H), 3.99 (dd, J=7.4, 12.9 Hz, 1H), 3.48 (t, J=8.2 Hz, 1H), 2.95 (t, J=7.1 Hz, 2H), 2.72–2.61 (m, 3H), 2.54–2.45 (m, 1H), 2.01–1.92 (m, 3H), 1.28 (s, 3H), 1.19 (s, 3H), 0.96 (s, 9H), 0.78 (s, 9H), 0.13 (s, 3H), 0.11 (s, 3H), 0.02 (s, 3H), −0.03 (s, 3H). MASS (EI, m/e): 744 (M)$^+$.

EXAMPLE 51

2-Decarboxy-2-phenylthio-16-methyl-16-phenoxy-5,6,7,18,19,20-hexanor-4,8-inter-m-phenylene PGI$_2$ (69)

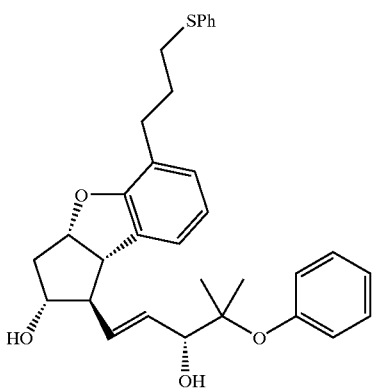
(69)

Tetra-n-butylammonium fluoride (1M in THF) 0.226 ml (226 μmol) was added to a solution of 2-decarboxy-2-phenylthio-16-methyl-16-phenoxy-5,6,7,18,19,20-hexanor-4,8-inter-m-phenylene PGI$_2$, 11,15-bis(tert-butyldimethylsilyl ether) (68) 33.6 mg (45.1 μmol) in anhydrous THF (2 ml) under argon atmosphere, followed by stirring at room temperature overnight. The reaction solution was concentrated, and the residue was dissolved in ethyl acetate 20 ml. The resultant solution was washed with water (5 ml) and brine (5 ml) once each, dried, and then concentrated. The thus-obtained oil was subjected to column chromatography (silica gel; cyclohexane:ethyl acetate=1:2) to obtain the titled compound 16.4 mg (31.7 μmol) as a colorless oil (yield 70%). The structure of this compound was determined by the following data.

IR (neat): 1491, 1454, 1226, 737, 696 cm$^{-1}$. $^1$H-NMR (300 MHz, CDCl$_3$): δ 7.33–7.10 (m, 8H), 7.00–6.90 (m, 4H), 6.74 (t, J=7.4 Hz, 1H), 5.82 (dd, J=8.2, 15.4 Hz, 1H), 5.70 (dd, J=7.1, 15.4 Hz, 1H), 5.09 (dd, J=7.1, 14.6 Hz, 1H), 4.20 (d, J=6.9 Hz, 1H), 3.94 (dd, J=9.1, 15.4 Hz, 1H), 3.45 (t, J=9.1 Hz, 1H), 3.35 (br, 1H), 2.93 (t, J=7.1 Hz, 1H), 2.73–2.63 (m, 3H), 2.45 (dd, J=8.5, 16.8 Hz, 1H), 2.00–1.90 (m, 3H), 1.25 (s, 3H), 1.25 (s, 3H). MASS (EI, m/e): 516 (M)$^+$. High Resolution Mass Spectrometry (HREIMS): Calculated for C$_{32}$H$_{36}$O$_4$S (M$^+$): 516.2335 (M$^+$). Found: 516.2336.

EXAMPLE 52

2-Decarboxy-2-methylthio-16-methyl-16-phenoxy-5,6,7,18,19,20-hexanor-4,8-inter-m-phenylene PGI$_2$, 11,15-bis(tert-Butyldimethylsilyl Ether) (70)

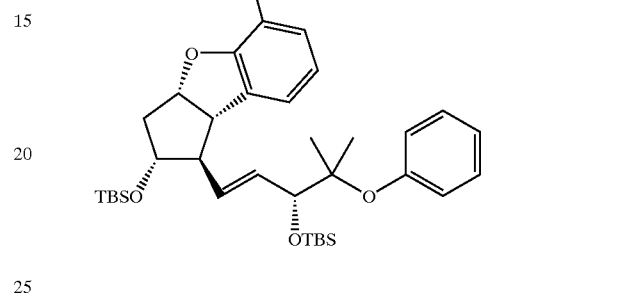
(70)

33 μmol) was added to a solution of sodium thiomethoxide 15.9 mg (227 μmol) in anhydrous DMF under argon atmosphere, and the resultant mixture was stirred at room temperature for 20 minutes. Anhydrous DMF 0.5 ml was then added to the resultant suspension, and the mixture was cooled to 0° C. A solution of 2-decarboxy-2-methylsulfonyloxy-16-methyl-16-phenoxy-5,6,7,18,19,20-hexanor-4,8-inter-m-phenylene PGI$_2$, 11,15-bis(tert-butyldimethylsilyl ether) (9) 33.2 mg (45.4 μmol) in anhydrous DMF (0.5 ml×2) was added to the mixture, followed by stirring at room temperature for 2 hours. After the pH was adjusted to about 4 with 1N hydrochloric acid, the reaction solution was concentrated, and the residue was dissolved in ethyl acetate 20 ml. The resultant solution was washed with water (5 ml) and brine (5 ml) once each, dried, and then concentrated. The residue was subjected to thin layer chromatography (silica gel; cyclohexane:ethyl acetate=40:1) to obtain the titled compound 21.6 mg (31.6 μmol) as a colorless oil (yield 70%). The structure of this compound was determined by the following data.

IR (neat): 2956, 2932, 2860, 1491, 1458, 1255, 1125, 837, 777 cm$^{-1}$. $^1$H-NMR (300 MHz, CDCl$_3$): δ 7.29–7.22 (m, 2H), 7.08–6.92 (m, 5H), 6.73 (t, J=7.4 Hz, 1H), 5.84 (dd, J=5.2, 15.7 Hz, 1H), 5.72 (dd, J=7.1, 15.7 Hz, 1H), 5.16–5.09 (m, 1H), 4.23 (d, J=4.9 Hz, 1H), 3.98 (dd, J=7.4, 12.9 Hz, 1H), 3.48 (t, J=7.4 Hz, 1H), 2.67–2.45 (m, 6H), 2.10 (s, 3H), 2.01–1.85 (m, 3H), 1.27 (s, 3H), 1.17 (s, 3H), 0.95 (s, 9H), 0.77 (s, 9H), 0.12 (s, 3H), 0.10 (s, 3H), 0.01 (s, 3H), −0.05 (s, 3H). MASS, (EI, m/e): 682 (M)$^+$.

EXAMPLE 53

2-Decarboxy-2-methylthio-16-methyl-16-phenoxy-5,6,7,18,19,20-hexanor-4,8-inter-m-phenylene PGI$_2$ (71)

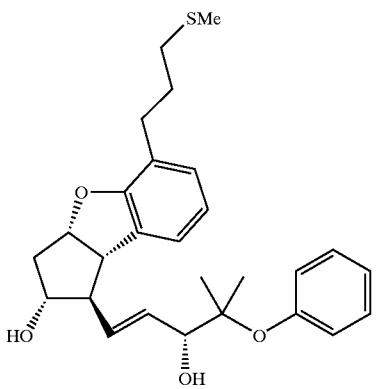

(71)

Tetra-n-butylamminium fluoride (1M in THF) 0.139 ml (139 μmol) was added to a solution of 2-decarboxy-2-methylthio-16-methyl-16-phenoxy-5,6,7,18,19,20-hexanor-4,8-inter-m-phenylene PGI$_2$, 11,15-bis(tert-butyldimethylsilyl ether) (70) 18.9 mg (27.7 μmol) in anhydrous THF (2 ml) under argon atmosphere, followed by stirring at room temperature overnight. The reaction solution was concentrated, and the residue was dissolved in ethyl acetate 20 ml. The resultant solution was washed with water (5 ml) and brine (5 ml) once each, dried, and then concentrated. The thus-obtained oil was subjected to column chromatography (silica gel; cyclohexane:ethyl acetate=2:3) to obtain the titled compound 11.5 mg (25.3 μmol) as colorless oil (yield 91%). The structure of this compound was determined by the following data.

IR (neat): 2976, 2922, 1595, 1491, 1454, 1226, 698 cm$^{-1}$. $^1$H-NMR (300 MHz, CDCl$_3$): δ 7.32–7.26 (m, 2H), 7.15–7.10 (m, 1H), 7.00–6.91 (m, 4H), 6.75 (t, J=7.4 Hz, 1H), 5.82 (dd, J=8.2, 15.4 Hz, 1H), 5.70 (dd, J=6.9, 15.4 Hz, 1H), 5.15–5.08 (m, 1H), 4.20 (d, J=6.9 Hz, 1H), 3.95 (dd, J=8.5, 14.8 Hz, 1H), 3.47 (t, J=8.5, 1H), 3.27 (br, 1H), 2.79–2.63 (m, 4H), 2.54–2.43 (m, 3H), 2.09 (s, 3H), 2.03–1.85 (m, 3H), 1.25 (s, 3H), 1.24 (s, 3H). MASS (EI, m/e): 454 (M)$^+$. High Resolution Mass Spectrometry (HREIMS): Calculated for C$_{27}$H$_{34}$O$_4$S (M$^+$): 454.6306 (M$^+$). Found: 454.2200.

EXAMPLE 54

2-Decarboxy-2-acetylthio-16-methyl-16-phenoxy-5,6,7,18,19,20-hexanor-4,8-inter-m-phenylene PGI$_2$, 11,15-bis(tert-Butyldimethylsilyl Ether) (72)

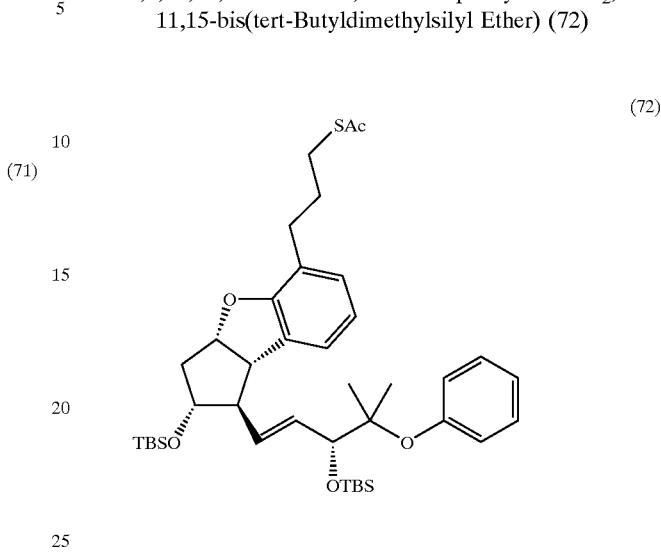

(72)

A solution of 2-decarboxy-2-hydroxy-16-methyl-16-phenoxy-5,6,7,18,19,20-hexanor-4,8-inter-m-phenylene PGI$_2$, 11,15-bis(tert-butyldimethylsilyl ether) (8) 383.1 mg, 2-fluoro-N-methylpyridinium-p-toluenesulfonate 249.5 mg (0.881 mmol), and triethylamine 0.123 ml (0.881 mmol) in a mixture of anhydrous benzene-acetone (1:1) (5 ml) was stirred at room temperature for 1 hour. And then a solution of thioacetic acid 0.126 ml (1.761 mmol) and triethylamine 0.245 ml (1.761 mmol) in a mixture of anhydrous benzene-acetone (1:1) (5 ml) was added to the above solution, followed by stirring under reflux overnight. The resultant mixture was cooled to room temperature, and the solvents were distilled off under reduced pressure. Then, ethyl acetate 20 ml was added to the residue, and the mixture was washed with water (5 ml×3) and brine (5 ml) once each, dried, and then concentrated. The residue was subjected to column chromatography (silica gel; cyclohexane:toluene=1:1) remove impurities on the less-polar fractions. The solvent was changed to cyclohexane/ethyl acetate=1/1 to obtain the titled compound 346.7 mg (0.488 mmol) as a pale yellow oil (yield 83%). The structure of this compound was determined by the following data.

IR (neat): 2956, 2932, 2860, 1694, 1253, 1125, 837, 777 cm$^{-1}$. $^1$H-NMR (300 MHz, CDCl$_3$): δ 7.26 (t, J=8.0 Hz, 1H), 7.08–6.90 (m, 5H), 6.74 (t, J=7.4 Hz, 1H), 5.84 (dd, J=5.5, 15.7 Hz, 1H), 5.73 (dd, J=7.4, 15.7 Hz, 1H), 5.17–5.10 (m, 1H), 4.24 (d, J=5.2 Hz, 1H), 3.99 (dd, J=7.1, 12.9 Hz, 1H), 3.49 (t, J=8.2 Hz, 1H), 2.91 (t, J=7.4 Hz, 2H), 2.68–2.60 (m, 3H), 2.58–2.45 (m, 1H), 2.33 (s, 1H), 2.05–1.84 (m, 3H), 1.28 (s, 3H), 1.18 (s, 3H), 0.96 (s, 9H), 0.77 (s, 9H), 0.13 (s, 3H), 0.11 (s, 3H), 0.02 (s, 3H), −0.04 (s, 3H). MASS (EI, m/e): 710 (M)$^+$.

EXAMPLE 55

2-Decarboxy-2-acetylthio-16-methyl-16-phenoxy-5,6,7,18,19,20-hexanor-4,8-inter-m-phenylene PGI$_2$ (73)

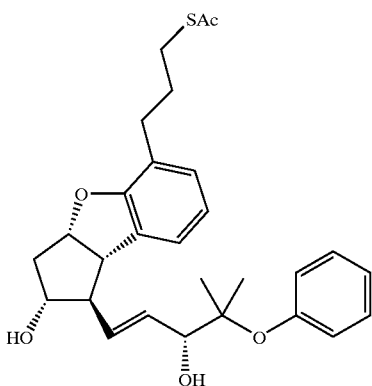
(73)

Acetic acid-THF-water (3:1:1) 1 ml was added to 2-decarboxy-2-acetylthio-16-methyl-16-phenoxy-5,6,7,18,19,20-hexanor-4,8-inter-m-phenylene PGI$_2$, 11,15-bis(tert-butyldimethylsilyl ether) (72) 32.6 mg (45.8 μmol), and the mixture was heated to 75° C. and stirred overnight. After the mixture was allowed to cool to room temperature, the reaction was quenched by the portionwise addition of sodium bicarbonate, and the reaction mixture was extracted with ethyl acetate (15 ml×3). The combined organic layer was washed with brine (10 ml), dried, and then concentrated. The residue was subjected to column chromatography (silica gel; cyclohexane:ethyl acetate=4:6) to obtain the titled compound 16.3 mg (33.8 μmol) as a colorless oil (yield 74%). The structure of this compound was determined by the following data.

IR (neat): 2976, 2932, 1690, 1595, 1491, 1454, 1226, 1133, 733 cm$^{-1}$. $^1$H-NMR (300 MHz, CDCl$_3$): δ 7.32–7.26 (m, 2H), 7.15–7.10 (m, 1H), 7.01–6.93 (m, 4H), 6.75 (t, J=7.4 Hz, 1H), 5.83 (dd, J=8.2, 15.4 Hz, 1H), 5.71 (dd, J=6.6, 15.4 Hz, 1H), 5.17–5.10 (m, 1H), 4.21 (d, J=6.6 Hz, 1H), 4.02–3.96 (m, 1H), 3.50 (t, J=8.5 Hz, 1H), 3.09 (br, 1H), 2.87 (t, J=7.4 Hz, 1H), 2.70–2.60 (m, 3H), 2.52 (dd, J=7.7, 15.7 Hz, 1H), 2.41 (br, 1H), 2.32 (s, 3H), 2.06–1.83 (m, 3H), 1.26 (s, 3H), 1.24 (s, 3H). MASS (EI, m/e): 482 (M)$^+$.

EXAMPLE 56

2-Decarboxy-2-mercapto-16-methyl-16-phenoxy-5,6,7,18,19,20-hexanor-4,8-inter-m-phenylene PGI$_2$ (74)

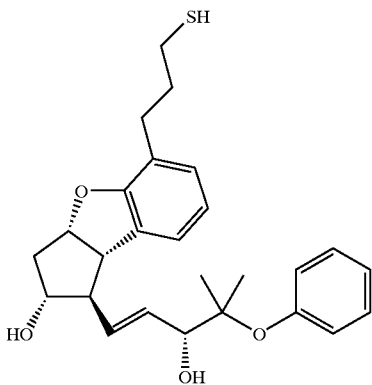
(74)

2N aqueous sodium hydroxide 0.5 ml was added to a solution of 2-decarboxy-2-acetylthio-16-methyl-16-phenoxy-5,6,7,18,19,20-hexanor-4,8-inter-m-phenylene PGI$_2$ (73) 16.3 mg (33.8 μmol) in methanol (2 ml), and the mixture was stirred at 45° C. for 4 hours and at 65° C. overnight. After the pH was adjusted to 7 with 1N hydrochloric acid, the mixture was concentrated to remove methanol. The precipitated solid was dissolved in water 5 ml, and the resultant solution was extracted with ethyl acetate (10 ml×3). The combined organic layer was washed with brine (10 ml), dried, and then concentrated. The thus-obtained oil was purified by thin layer chromatography (silica gel; ethyl acetate) to obtain the titled compound 7.2 mg (16.3 μmol) as a colorless oil (yield 48%). The structure of this compound was determined by the following data.

IR (neat): 2936, 1491, 1454, 1226, 909, 733 cm$^{-1}$. $^1$H-NMR (300 MHz, CDCl$_3$): δ 7.31–7.25 (m, 2H), 7.14–7.09 (m, 1H), 7.00–6.90 (m, 1H), 6.74 (t, J=7.4 Hz, 1H), 5.81 (dd, J=8.2, 15.4 Hz, 1H), 5.70 (dd, J=7.1, 15.4 Hz, 1H), 5.12–5.02 (m, 1H), 4.19 (d, J=6.9 Hz, 1H), 3.93 (dd, J=9.1, 14.8 Hz, 1H), 3.44 (t, J=8.5 Hz, 1H), 3.32 (br, 1H), 3.01 (br, 1H), 2.72–2.61 (m, 6H), 2.45 (dd, J=8.5, 16.8 Hz, 1H), 2.02–1.92 (m, 3H), 1.25 (s, 3H), 1.24 (s, 3H). MASS (EI, m/e): 440 (M)$^+$.

EXAMPLE 57

16-Phenoxy-3,3,16-trimethyl-2,5,6,7,18,19,20-heptanor-4,8-inter-m-phenylene PGI$_2$ Methyl Ester, 11,15-bis(tert-Butyldimethylsilyl Ether) (75)

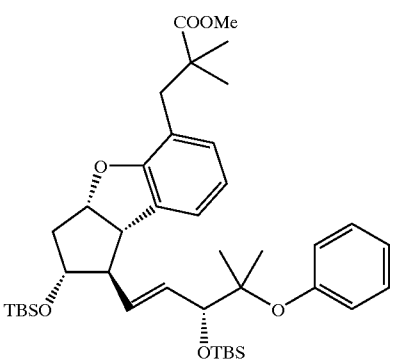
(75)

A solution of diisopropylamine 0.036 ml (0.257 mmol) in anhydrous THF (2 ml) was cooled to −78° C. under argon atmosphere, and n-butyl lithium 0.149 ml (0.257 mmol) was added to the cold solution, followed by stirring at the same temperature for 20 minutes. 16-Methyl-16-phenoxy-2,5,6,7,18,19,20-heptanor-4,8-inter-m-phenylene PGI$_2$ methyl ester, 11,15-bis(tert-butyldimethylsilyl ether) (4) 70 mg (0.103 mmol) in anhydrous THF (1 ml×2) was slowly added dropwise to the reaction solution, followed by further stirring at the same temperature for 30 minutes. Then, methyl iodide 0.019 ml (0.309 mmol) was added to the solution, followed by stirring at room temperature overnight. After the reaction was quenched by the addition of saturated aqueous ammonium chloride (20 ml), the mixture was extracted with ethyl acetate (20 ml×3). The combined organic layer was washed with water (15 ml×2) and brine (15 ml), dried, and then concentrated. The residue was dried under reduced pressure to obtain a monomethyl and dimethyl compound mixture as a colorless oil.

Similarly, a solution of diisopropylamine 0.144 ml (1.030 mmol) in anhydrous THF (2 ml) was cooled to −78° C. under argon atmosphere, and n-butyl lithium 0.599 ml (1.030 mmol) was added to the solution, followed by stirring at the same temperature for 20 minutes. A solution of the previously prepared methyl adduct mixture in anhydrous THF (1 ml×2) was slowly added dropwise to the reaction mixture, followed by stirring at the same temperature for 30 minutes. Then, methyl iodide 0.096 ml (1.545 mmol) was added to the reaction mixture, followed by stirring at room temperature for 10 hours. After the reaction was quenched by the addition of saturated aqueous ammonium chloride (20 ml), the mixture was extracted with ethyl acetate (20 ml×3). The combined organic layer was washed with water (15 ml×2) and brine (15 ml), dried, and then concentrated. The residue was purified by thin layer chromatography (silica gel; cyclohexane:ethyl acetate=20:1) to obtain the titled compound 34.5 mg (48.7 μmol) as a colorless oil (yield 47%). The structure of this compound was determined by the following data.

IR (neat): 2958, 2932, 2860, 1734, 1255, 1127, 837, 777 cm$^{-1}$. $^1$H-NMR (300 MHz, CDCl$_3$): δ 7.29–7.22 (m, 2H), 7.08–6.95 (m, 4H), 6.85–6.82 (m, 1H), 6.70 (t, J=7.4 Hz, 1H), 5.84 (dd, J=5.2, 15.7 Hz, 1H), 5.73 (dd, J=7.4, 15.7 Hz, 1H), 5.10–5.03 (m, 1H), 4.23 (d, J=4.9 Hz, 1H), 4.00–3.93 (m, 1H), 3.67 (s, 3H), 3.46 (t, J=8.0 Hz, 1H), 2.86 (d, J=13.2 Hz, 1H), 2.79 (d, J=13.2 Hz, 1H), 2.61 (dd, J=7.4, 14.8 Hz, 1H), 2.54–2.45 (m, 1H), 1.97–1.88 (m, 1H), 1.27 (s, 3H), 1.19 (s, 3H), 1.18 (s, 3H), 1.17 (s, 3H), 0.95 (s, 9H), 0.78 (s, 9H), 0.12 (s, 3H), 0.10 (s, 3H), 0.02 (s, 3H), −0.04 (s, 3H). MASS (EI, m/e): 708 (M)$^+$.

EXAMPLE 58

2-Decarboxy-2-hydroxy-16-phenoxy-3,3,16-trimethyl-5,6,7,18,19,20-hexanor-4,8-inter-m-phenylene PGI$_2$, 11,15-bis(tert-Butyldimethylsilyl Ether) (76)

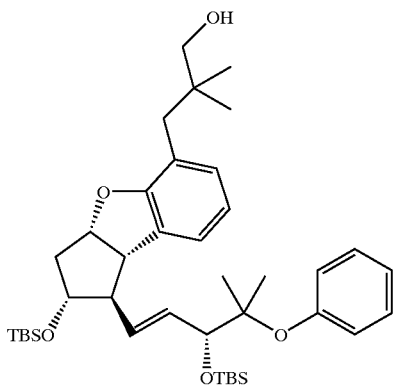

(76)

Lithium aluminum hydride 3.0 mg (78.6 μmol) was added to a solution of 16-phenoxy-3,3,16-trimethyl-2,5,6,7,18,19,20-heptanor-4,8-inter-m-phenylene PGI$_2$ methyl ester, 11,15-bis(tert-butyldimethylsilyl ether) (75) in anhydrous THF (2 ml) under argon atmosphere, and the mixture was stirred at room temperature for 6.5 hours. Saturated aqueous Rochelle salt (15 ml) was added to the reaction mixture, and the mixture was extracted with ethyl acetate (20 ml×3). The combined organic layer was washed with water (20 ml) and brine (20 ml) once each, dried, and then concentrated. The residue was purified by thin layer chromatography (silica gel; cyclohexane:ethyl acetate=7:1) to obtain the titled compound 18.9 mg (27.7 μmol) as a colorless oil (yield 71%). The structure of this compound was determined by the following data.

IR (neat): 2958, 2932, 2860, 1127, 837, 775 cm$^{-1}$. $^1$H-NMR (300 MHz, CDCl$_3$): δ 7.28–7.22 (m, 2H), 7.08–6.95 (m, 4H), 6.88 (d, J=6.6 Hz, 1H), 6.76 (t, J=7.4 Hz, 1H), 5.84 (dd, J=5.2, 15.4 Hz, 1H), 5.71 (dd, J=7.7, 15.4 Hz, 1H), 5.21–5.14 (m, 1H), 4.22 (d, J=5.2 Hz, 1H), 4.00 (dd, J=6.6, 12.6 Hz, 1H), 3.55 (dd, J=6.59, 9.1 Hz, 1H), 3.39 (t, J=7.1 Hz, 1H), 3.09 (d, J=2.7 Hz, 1H), 3.06 (d, J=2.7 Hz, 1H), 2.68 (dd, J=6.6, 13.7 Hz, 1H), 2.55–2.43 (m, 3H), 2.05–1.94 (m, 1H), 1.27 (s, 3H), 1.17 (s, 3H), 0.95 (s, 9H), 0.93 (s, 3H), 0.91 (s, 3H), 0.76 (s, 9H), 0.12 (s, 3H), 0.10 (s, 3H), 0.01 (s, 3H), −0.08 (s, 3H). MASS (EI, m/e): 680 (M)$^+$.

EXAMPLE 59

2-Decarboxy-2-hydroxy-16-phenoxy-3,3,16-trimethyl-5,6,7,18,19,20-hexanor-4,8-inter-m-phenylene PGI$_2$ (77)

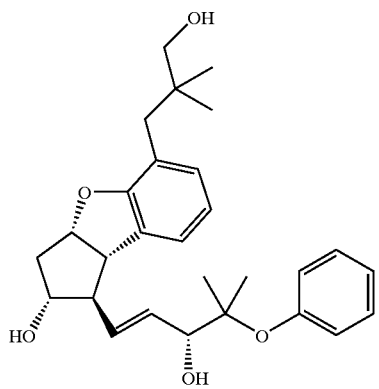

(77)

Tetra-n-butylammonium fluoride (1M in THF) 0.132 ml (132 μmol) was added to a solution of 2-decarboxy-2-hydroxy-16-phenoxy-3,3,16-trimethyl-5,6,7,18,19,20-hexanor-4,8-inter-m-phenylene PGI$_2$, 11,15-bis(tert-butyldimethylsilyl ether) (76) 18.0 mg (26.4 μmol) in anhydrous THF (2 ml) under argon atmosphere, and the mixture was stirred at room temperature overnight. After the reaction solution was concentrated, water 5 ml was added to the residue, and the resultant mixture was extracted with ethyl acetate (10 ml×3). The combined organic layer was washed with brine (10 ml), dried, and then concentrated. The thus-obtained oil was purified by column chromatography (silica gel; cyclohexane:ethyl acetate=15:85→0:100) to obtain the titled compound 11.1 mg (24.5 μmol) as a white solid (yield 93%). The structure of this compound was determined by the following data.

IR (neat): 2924, 1491, 1452, 1228, 10138, 733 cm$^{-1}$. $^1$H-NMR (300 MHz, CDCl$_3$): δ 7.32–7.26 (m, 2H), 7.15–7.09 (m, 1H), 7.01–6.91 (m, 4H), 6.78 (t, J=7.4 Hz, 1H), 5.82 (dd, J=8.0, 15.4 Hz, 1H), 5.71 (dd, J=6.9, 15.4 Hz, 1H), 5.19–5.12 (m, 1H), 4.20 (d, J=6.6 Hz, 1H), 3.99 (dd, J=7.7, 13.7 Hz, 1H), 3.53 (t, J=8.2 Hz, 1H), 3.25 (br, 2H), 3.07 (s, 2H), 2.67–2.44 (m, 4H), 2.06–1.97 (m, 1H), 1.25 (s, 3H), 1.24 (s, 3H), 0.93 (s, 3H), 0.90 (s, 3H). MASS (EI, m/e): 452 (M)$^+$. High Resolution Mass Spectrometry (HREIMS): Calculated for C$_{28}$H$_{36}$O$_5$ (M$^+$): 452.5908. Found: 452.2553 (M)$^+$.

EXAMPLE 60

2-Decarboxy-2-acetonyl-2-oxo-16-methyl-16-phenoxy-5,6,7,18,19,20-hexanor-4,8-inter-m-phenylene PGI₂, 11,15-bis(tert-Butyldimethylsilyl Ether) (78)

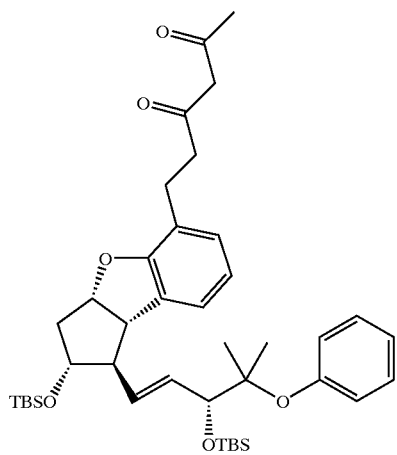

Barium hydroxide octahydrate 18.2 mg (57.8 μmol) was added to a solution of 2-decarboxy-2-oxo-2-(2,4-pentadione-3-yl)-16-methyl-16-phenoxy-5,6,7,18,19,20-hexanor-4,8-inter-m-phenylene PGI₂, 11,15-bis(tert-butyldimethylsilyl ether) (14) 43.3 mg (57.8 μmol) in a mixture of ethanol (10 ml) and water 4 ml, and the mixture was stirred at 60° C. for 5 hours. After the reaction solution (white suspension) was concentrated to remove ethanol, the residue was dissolved in ethyl acetate 20 ml, and the resultant mixture was washed with 0.1N hydrochloric acid (10 ml). The aqueous layer was extracted with ethyl acetate (10 ml×2), and the combined organic layer was washed with water (10 ml) and brine (10 ml) once each, dried, and then concentrated. The residue was purified by thin layer chromatography (silica gel; cyclohexane:ethyl acetate=7:1) to obtain the titled compound 23.4 mg (33.1 μmol) as a colorless oil (yield 57%). The structure of this compound was determined by the following data.

IR (neat): 2958, 2932, 2860, 1597, 1491, 1458, 1253, 1127, 837, 777 cm⁻¹. ¹H-NMR (300 MHz, CDCl₃): δ 7.28–7.22 (m, 2H), 7.08–6.90 (m, 5H), 6.73 (t, J=7.4 Hz, 1H), 5.83 (dd, J=4.9, 15.7 Hz, 1H), 5.71 (dd, J=8.2, 15.9 Hz, 1H), 5.51 (s, 0.8H), 5.17–5.10 (m, 1H), 4.22 (d, J=4.7 Hz, 1H), 3.98 (dd, J=7.1, 12.6 Hz, 1H), 3.57 (s, 0.4H), 3.49 (t, J=7.1 Hz, 1H), 2.87–2.82 (m, 2H), 2.67–2.44 (m, 4H), 2.21 (s, 0.6H), 2.04 (s, 2.4H), 2.01–1.93 (m, 1H), 1.27 (s, 3H), 1.17 (s, 3H), 0.95 (s, 9H), 0.76 (s, 9H), 0.11 (s, 3H), 0.10 (s, 3H), 0.01 (s, 3H), −0.05 (s, 3H). MASS (EI, m/e): 706 (M)⁺.

EXAMPLE 61

2-Decarboxy-2-acetonyl-2-oxo-16-methyl-16-phenoxy-5,6,7,18,19,20-hexanor-4,8-inter-m-phenylene PGI₂ (79)

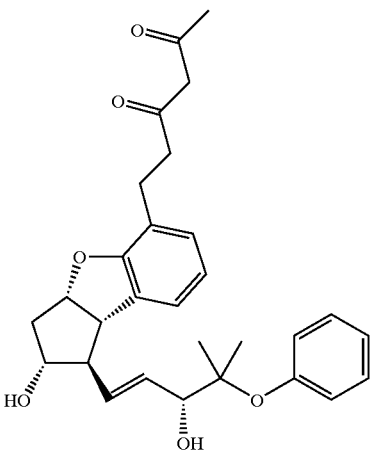

Tetra-n-butylammonium fluoride (1M in THF) 0.160 ml (160 μmol) was added to a solution of 2-decarboxy-2-acetonyl-2-oxo-16-methyl-16-phenoxy-5,6,7,18,19,20-hexanor-4,8-inter-m-phenylene PGI₂, 11,15-bis(tert-butyldimethylsilyl ether) (78) 22.6 mg (32.0 μmol) in anhydrous THF (2 ml) under argon atmosphere, and the mixture was stirred at room temperature overnight. After the reaction mixture was concentrated, the residue was dissolved in ethyl acetate 20 ml, and the resultant mixture was washed with water (5 ml) and brine (5 ml) once each, dried, and then concentrated. The thus-obtained oil was purified by column chromatography (Silica Gel FL-60D produced by Fuji Silicia Co.; cyclohexane:ethyl acetate=50:50→30:70), and thin layer chromatography (silica gel; ethyl acetate) to obtain the titled compound 12.0 mg (25.1 μmol) as a colorless oil (yield 78%). The structure of this compound was determined by the following data.

IR (neat): 3368, 2980, 2936, 1595, 1491, 1456, 1228, 735 cm⁻¹. ¹H-NMR (300 MHz, CDCl₃): δ 15.45 (br, 0.8H), 7.31–7.26 (m, 2H), 7.12 (t, J=7.3 Hz, 1H), 7.00–6.92 (m, 3H), 6.77–6.71 (m, 1H), 5.82 (dd, J=8.2, 15.2 Hz, 1H), 5.70 (dd, J=6.9, 15.2 Hz, 1H), 5.50 (s, 0.8H), 5.15–5.08 (m, 1H), 4.20 (d, J=6.9 Hz, 1H), 3.95 (dd, J=7.9, 14.5 Hz, 1H), 3.56 (s, 0.4H), 3.46 (t, J=8.6 Hz, 1H), 3.32 (br, 1H), 2.89–2.24 (m, 6H), 2.19 (s, 0.6H), 2.03–1.93 (m, 3.4H), 1.25 (s, 3H), 1.24 (s, 3H). MASS (EI, m/e): 478 (M)⁺. High Resolution Mass Spectrometry (HREIMS): Calculated for $C_{29}H_{34}O_6$ (M⁺): 478.5854. Found: 478.2326 (M)⁺.

EXAMPLE 62

2-Decarboxy-2-hydroxy-5,6,7-trinor-4-thia-4,8-inter-m-phenylene PGI$_2$ (80)

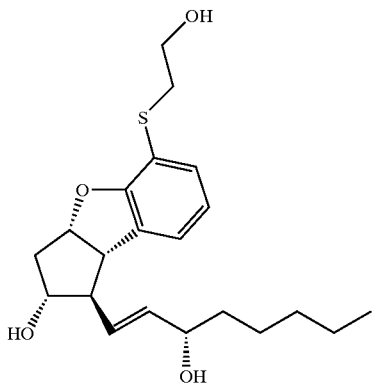

(80)

2,5,6,7-Tetranor-4-thia-4,8-inter-m-phenylene PGI$_2$ methyl ester 100 mg (0.24 mmol) was dissolved in anhydrous tetrahydrofuran 5 mL, and lithium aluminum hydride 15 mg (0.40 mmol, 1.66 equivalents) was added to the resultant solution under ice cooling, followed by stirring. After the completion of reaction was checked by TLC, ethyl acetate (2 mL) was added to the reaction mixture, and water was added to the solution. The resultant mixture was extracted with ethyl acetate (30 mL×2), and the combined organic layer was washed with saturated aqueous sodium bicarbonate (30 mL) and brine (30 mL), and dried over anhydrous sodium sulfate. After concentration (crude amount 97 mg, crude yield 100%), purification was attempted by column chromatography (silica gel; ethyl acetate). However, the residue could not sufficiently be purified. Therefore, purification was further attempted by column chromatography (silica gel; chloroform:acetonitrile=1:1~1:2), preparative TLC (silica gel; ethyl acetate), column chromatography (alumina; ethyl acetate:isopropanol=9:1~4:1), preparative TLC (silica gel; ethyl acetate), and gel filtration column (Sephadex, methanol). However, the product could not sufficiently be purified. Although fractionation was attempted by HPLC fractionation (YMC SH-043, S-15 SIL, ethyl acetate), the product could not sufficiently be purified. Finally, the product was purified by preparative TLC (silica gel; ethyl acetate:isopropanol=9:1) to obtain colorless oil 22 mg (yield 24%). The structure of this compound was determined by the following data.

IR (neat): 3400, 2932, 1439, 1265, 1210, 1023, 739, 551 cm$^{-1}$. $^1$H-NMR (400 MHz, CD$_3$OD): δ 7.08 (1H, dd, J=7.8, 1.0 Hz), 7.02 (1H, d, J=7.8 Hz), 6.75 (1H, t, J=7.8 Hz), 5.79 (1H, dd, J=15.6, 8.3 Hz), 5.55 (1H, dd, J=15.6, 6.8 Hz), 5.16–5.10 (1H, m), 4.59 (1H, s), 4.06 (1H, dd, J=13.2, 6.4 Hz), 3.90 (1H, dt, J=6.8, 8.8 Hz), 3.60 (2H, t, J=6.8 Hz), 3.47 (1H, t, J=8.8 Hz), 2.98 (2H, dt, J=6.8, 2.4 Hz), 2.68–2.60 (1H, m), 2.29 (1H, dd, J=16.6, 8.3 Hz), 1.91–1.84 (1H, m), 1.63–1.26 (8H, m), 0.92 (3H, t, J=6.8 Hz). MASS (EI, m/e): 378 (M$^+$). High Resolution Mass Spectrometry (HREIMS): Found: 378.1852. Calculated for C$_{21}$H$_{30}$O$_4$S : 378.1865.

REFERENCE EXAMPLE 15

16-Cyclohexyl-2,5,6,7,17,18,19,20-octanor-4,8-inter-m-phenylene PGI$_2$ Methyl Ester, 11,15-bis(tert-Butyldimethylsilyl Ether) (81)

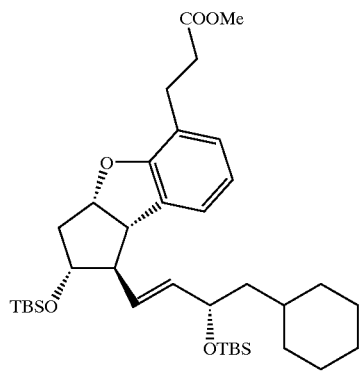

(81)

A solution of TBSCl 0.91 g (6.0 mmol) in anhydrous DMF 4 ml was added to a solution of 16-cyclohexyl-2,5,6,7,17,18,19,20-octanor-4,8-inter-m-phenylene PGI$_2$ methyl ester 0.50 g (12 mmol) and imidazole 0.82 g (12 mmol) in anhydrous DMF 10 ml under argon stream, and the mixture was stirred at room temperature overnight. After the reaction mixture was concentrated under reduced pressure, ethyl acetate 100 ml was added to the residue, and the resultant mixture was washed in turn with water (4×20 ml) and brine 20 ml, dried, and then concentrated. The thus-obtained oil 0.93 g was purified by column chromatography (silica gel 15 g; cyclohexane:ethyl acetate=90:10) to obtain the titled compound 0.75 g (yield 97%) as a colorless oil. The structure of this compound was determined by the following data.

IR (neat): 2952, 2926, 2855, 1742, 1596, 1471, 1455, 1361, 1300, 1253, 1194, 1092, 1069, 1003, 970, 939, 836, 771 cm$^{-1}$. $^1$H-NMR (300 MHz, CDCl$_3$): δ 6.97 (1H, d, J=7.4 Hz), 6.91 (1H, d, 7.4 Hz), 6.70 (1H, t, 7.4 Hz), 5.54–5.52 (2H, m), 5.12–5.05 (1H, m), 3.92–3.85 (1H, m), 3.64 (3H, s), 3.41 (1H, J=8.2 Hz), 2.87–2.82 (2H, m), 2.63–2.58 (2H, m), 2.52–2.40 (2H, m), 1.96–1.87 (1H, m), 1.68–1.16 (12H, m), 0.88 (9H, s), 0.74 (9H, s), 0.04–0.06 (12H, m). MASS (EI, m/e): 585 [(M−tBu)$^+$].

REFERENCE EXAMPLE 16

3-Decarboxy-3-aminocarbonyl-16-cyclohexyl-2,5,6,7,17,18,19,20-octanor-4,8-inter-m-phenylene PGI$_2$ Methyl Ester, 11,15-bis(tert-Butyldimethylsilyl Ether) (82)

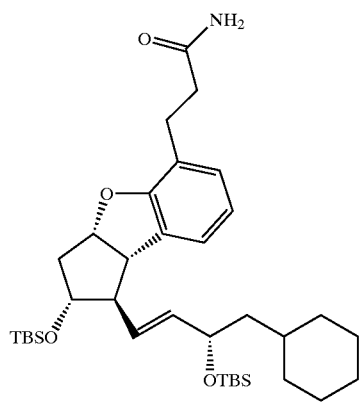

(82)

3N aqueous sodium hydroxide 0.50 ml was added to a solution of 16-cyclohexyl-2,5,6,7,17,18,19,20-octanor-4,8- inter-m-phenylene PGI$_2$ methyl ester, 11,15-bis(tert-butyldimethylsilyl ether) (81) 710 mg (1.1 mmol) in THF 2.2 ml and methanol 2.2 ml, and the mixture was stirred at room temperature for 1 hour. Since the disappearance of the starting material was not observed by TLC, aqueous sodium hydroxide 0.50 ml was further added to the reaction mixture, followed by further stirring at room temperature for 3 hours. After the disappearance of the starting material was checked by TLC, 1N hydrochloric acid 3.5 ml was added to the reaction mixture, and the resultant mixture was extracted with ethyl acetate (3×20 ml). The combined organic layer was washed with water (2×10 ml) and brine 10 ml, dried, and then concentrated to crude carboxylic acid 0.66 g (crude yield 95%) as a colorless oil.

The thus-obtained crude carboxylic acid 600 mg (1.0 mmol) was dissolved in anhydrous dichloromethane 30 ml, and oxalyl chloride 0.26 ml (3.0 mmol) was added to the resultant solution, followed by stirring at room temperature for 1 hour. After concentration, anhydrous cyclomethane 10 ml was added to the residue to form reaction solution A.

Aqueous ammonia 100 ml and chloroform 100 ml were placed in a separating funnel, followed by extraction with chloroform. The reaction solution A was added dropwise to the ammonia-saturated chloroform solution under ice cooling, followed by stirring under ice cooling for 3 hours. After the disappearance of the starting material was checked by TLC, the reaction solution was concentrated, and the residue was extracted with ethyl acetate (100 ml×2). The combined organic layer was washed with 0.1N hydrochloric acid 150 ml, water 200 ml and brine 150 ml, and dried over anhydrous sodium sulfate. After concentration, the residue was purified by column chromatography (silica gel 20 g; benzene:ethyl acetate=3:1~1:1) to obtain the titled compound 380 mg (yield 63%) as a white amorphousness. The structure of this compound was determined by the following data.

IR (neat): 3344, 3194, 2926, 2854, 1667, 1615, 1471, 1451, 1405, 1388, 1361, 1254, 1192, 1121, 1004, 966 cm$^{-1}$. $^1$H-NMR (300 MHz, CDCl$_3$): δ 7.00–6.94 (2H, m), 6.80–6.71 (1H, m), 5.62–5.54 (2H, m), 5.58–5.41 (1H, brs), 5.40–5.20 (1H, brs), 5.15–5.07 (1H, m), 4.26–4.18 (1H, m), 3.95–3.88 (1H, m), 3.47–3.41 (1H, m), 2.90–2.85 (2H, m), 2.57–2.43 (4H, m), 2.04–1.89 (1H, m), 1.71–1.11 (12H, m), 0.90 (9H, s), 0.71 (9H, s), 0.06–0.05 (12H, m). MASS (EI, m/e): 627 (M$^{30}$), 570 [(M–tBu)$^+$].

EXAMPLE 63

3-Decarboxy-3-cyano-16-cyclohexyl-2,5,6,7,17,18, 19,20-octanor-4,8-inter-m-phenylene PGI$_2$, 11,15-bis(tert-Butyldimethylsilyl Ether) (83)

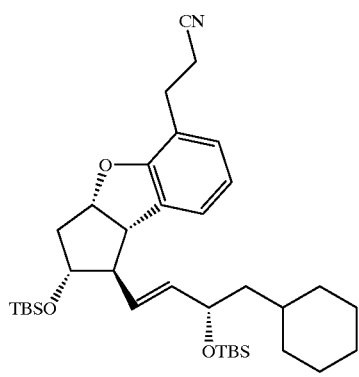

(83)

3-Decarboxy-3-aminocarbonyl-16-cyclohexyl-2,5,6,7, 17,18,19,20-octanor-4,8-inter-m-phenylene PGI$_2$, 11,15-bis(tert-butyldimethylsilyl ether) (82) 380 mg (0.60 mmol) was dissolved in pyridine 10 ml, and tosyl chloride 340 mg (1.8 mmol) was added to the resultant solution, followed by stirring room temperature for 17 hours. After the disappearance of the starting material was checked by TLC, the reaction was quenched by the pouring the mixture into ice-cold 1N hydrochloric acid, and the mixture was extracted with ethyl acetate (2×200 ml). The combined organic layer was washed with 1N hydrochloric acid 100 ml, water (2×20 ml) and brine 100 ml, and dried over anhydrous sodium sulfate. After concentration, the residue was purified by column chromatography (silica gel 20 g; cyclohexane-:ethyl acetate=20:1) to obtain the titled compound 200 mg (yield 53%) as a colorless oil. The structure of this compound was determined by the following data.

IR (neat): 2926, 2854, 2708, 2659, 2246, 1666, 1597, 1471, 1457, 1406, 1386, 1360, 1253, 1197, 1089, 1002, 938 cm$^{-1}$. $^1$H-NMR (300 MHz, CDCl$_3$): δ 7.04 (1H, d, J=7.1 Hz), 6.95 (1H, d, J=7.1 Hz), 6.76 (1H, t, J=7.1 Hz), 5.61–5.48 (2H, m), 5.17–5.10 (1H, m), 4.23–4.17 (1H, m), 3.93 (1H, q, J=6.9 Hz), 3.49–3.44 (1H, m), 2.94–2.81 (2H, m), 2.66–2.40 (4H, m), 1.99–1.90 (1H, m), 1.75–1.67 (5H, m), 1.55–1.11 (7H, m), 0.90 (9H, s), 0.75 (9H, s), 0.07–0.06 (12H, m). MASS (EI, m/e): 594 [(M–CH$_3$)$^+$], 552 [(M–tBu)$^+$].

EXAMPLE 64

3-Decarboxy-3-cyano-16-cyclohexyl-2,5,6,7,17,18, 19,20-octanor-4,8-inter-m-phenylene PGI$_2$ (84)

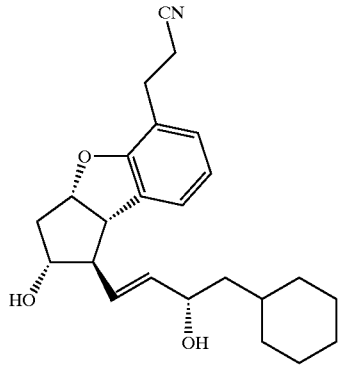

(84)

3-Decarboxy-3-cyano-16-cyclohexyl-2,5,6,7,17,18,19, 20-octanor-4,8-inter-m-phenylene PGI$_2$, 11,15-bis(tert-butyldimethylsilyl ether) (83) 200 mg (0.32 mmol) was dissolved in THF 10 ml, and 1.0M THF solution of TBAF 1.0 ml (1.0 mmol) was added to the resultant solution, followed by stirring at room temperature for 5.5 hours. Since the disappearance of the starting material was not observed by TLC, 1.0M THF solution of TBAF 1.0 ml (1.0 mmol) was further added to the reaction mixture, followed by further stirring at room temperature for 12 hours. After the disappearance of the starting material was checked by TLC, water 40 ml was added to the reaction mixture, and the mixture was extracted with ethyl acetate (2×40 ml). The combined organic layer was washed with brine 200 ml, and dried over anhydrous sodium sulfate. After concentration, the residue was purified by column chromatography (silica gel 10 g; cyclohexane:ethyl acetate=1:2) to obtain the titled compound 85 mg (yield 70%) as a colorless oil. The structure of this compound was determined by the following data.

IR (neat): 3388, 2922, 2850, 2247, 1647, 1579, 1455, 1345, 1257, 1196 cm$^{-1}$. $^1$H-NMR (309 MHz, CDCl$_3$): δ 6.99 (2H, d, J=7.7 Hz), 6.79 (1H, t, 7.7 Hz), 5.61–5.52 (2H, m), 5.15–5.08 (1H, m), 4.23 (1H, q, J=6.6 Hz), 3.90 (1H, q, J=8.2 Hz), 3.42 (1H, t, J=8.8 Hz), 2.96–2.83 (2H, m), 2.71–2.59 (3H, m), 2.38 (1H, q, J=8.8 Hz), 2.00–1.91 (1H, m), 1.79–1.70 (6H, m), 1.53–1.14 (6H, m), 1.01–0.91 (2H, m). MASS (EI, m/e): 381 (M+).

EXAMPLE 65

3-Decarboxy-3-(1H-tetrazol-5-yl)-16-cyclohexyl-2, 5,6,7,17,18,19,20-octanor-4,8-inter-m-phenylene PGI₂ (85)

(85)

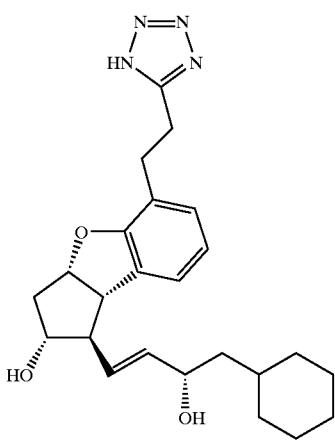

3-Decarboxy-3-cyano-16-cyclohexyl-2,5,6,7,17,18,19, 20-octanor-4,8-inter-m-phenylene PGI₂ (84) 74 mg (0.20 mmol) was dissolved in N-methyl-2-pyrrolidinone 3.5 ml, and Sodium azide 87 mg (1.2 mmol) and triethylamine hydrochloride 92 mg (0.60 mmol) were added to the resultant solution, followed by stirring under argon atmosphere at 150° C. for 56 hours. Since the disappearance of the starting material was not observed by TLC, sodium azide 87 mg (1.2 mmol) and triethylamine hydrochloride 92 mg (0.60 mmol) were further added to the reaction mixture, followed by further stirring at 150° C. for 24 hours. After the disappearance of the starting material was checked by TLC, the reaction was quenched by the pouring the mixture into 1N hydrochloric acid, and the mixture was extracted with ethyl acetate (2×100 ml). The combined organic layer was washed with water (2×100 ml) and brine 100 ml, and dried over anhydrous sodium sulfate. After concentration, the residue was purified by column chromatography (DIOL produced by Yamazen Co.; cyclohexane:ethyl acetate=1:3) to obtain the titled compound 47 mg (yield 57%) as a light brown amorphousness. The structure of this compound was determined by the following data.

IR (KBr): 3386, 2922, 2850, 1655, 1560, 1509, 1450, 1257, 1194, 1064, 973, 863, 744 cm⁻¹. ¹H-NMR (300 MHz, CDCl₃): δ 6.98 (1H, d, J=6.9 Hz), 6.72–6.64 (2H, m), 5.59–5.57 (1H, m), 5.34–5.24 (1H, brs), 4.26–4.20 (2H, m), 4.08–3.42 (2H, m), 3.29–3.16 (2H, m), 2.80–2.72 (1H, m), 2.15–1.99 (3H, m), 1.79–1.68 (6H, m), 1.51–1.11 (6H, m), 0.97–0.90 (2H, m). High Resolution Mass Spectrometry (HREIMS): Found: 424.2456 (+2.9 mmu). Calculated for C₂₄H₃₂N₄O₃ (M+): 424.2427.

REFERENCE EXAMPLE 17

Methyl 3-{(1S*,2R*,3aS*,8bS*)-7-Bromo-2,3,3a, 8b-tetrahydro-2-tetrahydropyranyloxy-1-tetrahydropyranyloxymethyl-1H-cyclopenta[b] benzofuran-5-yl}thioacetate (86)

(86)

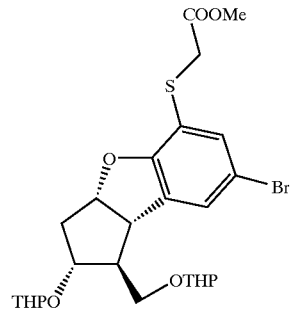

0.415N cyclohexylmagnesium bromide 6.8 ml (2.82 mmol) was added to a solution of {(1S*,2R*,3aS*,8bS*)-5,7-dibromo-2,3,3a,8b-tetrahydro-2-tetrahydropyranyloxy-1-tetrahydropyranyloxymethyl-1H-cyclopenta[b] benzofuran 1.22 g (2.3 mmol) in THF 6 ml, followed by stirring at 45° C. overnight. The reaction mixture was cooled to room temperature, and sulfur 88 mg (2.75 mmol) was added to the mixture, followed by stirring at 45° C. for 30 minutes. The reaction mixture was cooled to room temperature, and methyl bromoacetate (387 mg, 2.53 mmol) was added to the mixture, followed by stirring at room temperature for 5 minutes. Saturated aqueous ammonium chloride was added to the reaction mixture, and the mixture was extracted with ethyl acetate (3×30 ml). The combined organic layer was washed with water 20 ml and brine 20 ml, and then dried. After concentration under reduced pressure, the residue was purified by column chromatography (silica gel; cyclohexane:ethyl acetate=3:1 ethyl acetate) to obtain the titled compound 0.651 g (yield 51%). The structure of this compound was determined by the following data.

IR (neat): 2943, 2868, 1739, 1443, 1275, 1200, 1161, 1134, 1075, 1034, 869 cm⁻¹. ¹H-NMR (300 MHz, CDCl₃): δ 7.34–7.27 (2H, m), 5.30–5.23 (1H, m), 4.64–4.53 (2H, m), 4.13–3.21 (12H, m), 2.58–2.34 (2H, m), 2.20–2.02 (1H, m), 1.85–1.24 (12H, m). MASS (EI, m/e): 556 (M+).

REFERENCE EXAMPLE 18

Methyl 3-{(1S*,2R*,3aS*,8bS*)-2,3,3a,8b-Tetrahydro-2-hydroxy-1-hydroxymethyl-1H-cyclopenta[b]benzofuran-5-yl}thioacetate (87)

(87)

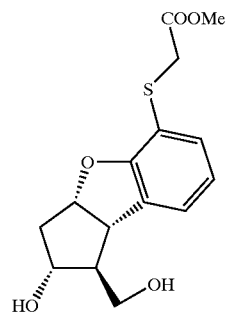

10% palladium carbon 2.8 g was added to a solution of 3-{(1S*,2R*,3aS*,8bS*)-7-bromo-2,3,3a,8b-tetrahydro-2-tetrahydropyranyloxy-1-tetrahydropyranyloxymethyl-1H- cyclopenta[b]benzofuran-5-yl}thioacetate (86) 1.02 g (1.83 mmol) in THF 5 ml and methanol 20 ml, argon replacement and then hydrogen replacement were carried out, followed by stirring at room temperature overnight. After argon replacement, the reaction mixture was filtered with Kiriyama funnel, and the precipitate was washed with methanol 200 ml. The filtrate was concentrated under reduced pressure, and the residue was purified by column chromatography (silica gel; ethyl acetate) to obtain the titled compound 0.266 g (yield 47%). The structure of this compound was determined by the following data.

IR (neat): 3389, 2950, 1731, 1635, 1587, 1439, 1296, 1209, 1141, 1073, 1027, 937, 899, 845, 777, 736 cm$^{-1}$. $^1$H-NMR (300 MHz, CDCl$_3$): δ 7.22–7.19 (1H, m), 7.14–7.10 (1H, ddd, J=7.4; 5.2, 1.1 Hz), 6.83–6.78 (1H, t, J=7.4 Hz), 5.28–5.22 (1H, m), 4.17–4.10 (1H, m), 3.89–3.84 (1H, dd, J=10.4, 5.8 Hz), 3.78–3.66 (2H, m), 3.66 (3H, s), 3.58–3.48 (2H, m), 2.60–2.51 (1H. m), 2.21–2.09 (2H, m). MASS (EI, m/e): 310 (M$^+$).

REFERENCE EXAMPLE 19

Methyl 3-{(1S,2R*,3aS*,8bS*)-2-Acetoxy-2,3,3a,8b-tetrahydro-1-hydroxymethyl-1H-cyclopenta[b]benzofuran-5-yl}thioacetate (88)

(88)

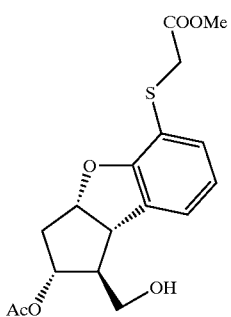

Anhydrous triethylamine 0.65 ml (4.66 mmol) and trityl chloride 629 mg (2.26 mmol) were in turn added to a solution of methyl 3-{(1S-,2R*,3aS*,8bS*)-2,3,3a,8b-tetrahydro-2-hydroxy-1-hydroxymethyl-1H-cyclopenta[b]benzofuran-5-yl}thioacetate (87) 350 mg (1.13 mmol) in THF 3.2 ml under argon stream, followed by reflux for 3 hours. After the disappearance of the starting material was checked by TLC, pyridine 1.4 ml (17.3 mmol) and acetic anhydride 1.1 ml (11.7 mmol) were in turn added to the reaction mixture, followed by stirring at room temperature overnight. After the disappearance of the starting material was checked by TLC, hydrogen chrolide-methanol 1.1 ml (2.9 mmol) was added to the reaction mixture, followed by stirring at room temperature for 1 hour. Sodium bicarbonate 2.1 g was added to the reaction mixture, and the mixture was stirred for 10 minutes. The mixture was filtered with a Kiriyama funnel, and the filtrate was concentrated under reduced pressure. 1N Hydrochloric acid 10 ml was added to the resulting residue, and the mixture was extracted with ethyl acetate (3×30 ml). The combined organic layer was washed with brine, dried and then concentrated under reduced pressure. The residue was purified by column chromatography (silica gel; normal hexane:ethyl acetate=1:1) to obtain the titled compound 278 mg (yield 70%). The structure of this compound was determined by the following data.

IR (neat): 3447, 2923, 2850, 1737, 1655, 1441, 1375, 1241, 1212, 1137, 1053, 1028, 973 cm$^{-1}$. $^1$H-NMR (300 MHz, CDCl$_3$): δ 7.26–7.20 (1H, m), 7.14–7.11 (1H, ddd, J=7.4, 5.2, 1.1 Hz), 6.83–6.78 (1H, t, J=7.4 Hz), 5.33–5.27 (1H, m), 5.10–5.04 (1H, q, J=5.8 Hz), 3.75–3.69 (3H, m), 3.68 (3H, s), 3.63 (2H, s), 2.62–2.52 (1H, m), 2.31–2.23 (2H, m), 2.13 (1H, m), 1.84 (3H, s). MASS (EI, m/e): 352 (M$^+$).

EXAMPLE 66 dl-16-Cyclohexyl-15-oxo-2,5,6,7,17,18,19,20-octanor-4-thia-4,8-inter-m-phenylene PGI$_2$ Methyl Ester, 11-Acetate (89)

(89)

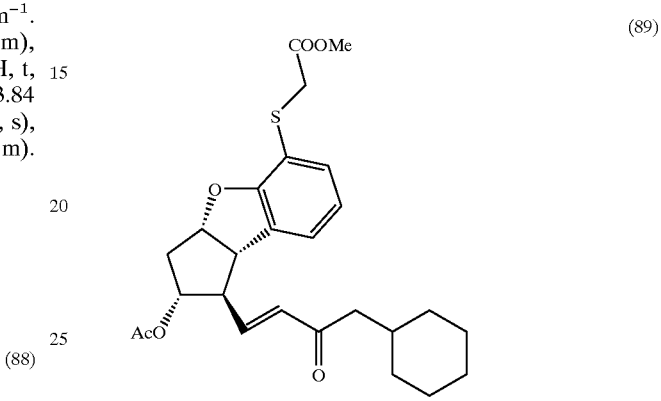

Anhydrous pyridine 0.058 ml (0.719 mmol), anhydrous DMSO 1.26 ml, trifluoroacetic acid 0.028 ml (0.361 mmol), and DCC 222 mg (1.076 mmol) were in turn added to a solution of methyl 3-{(1S*,2R*,3aS*,8bS*)-2-acetoxy-2,3,3a,8b-tetrahydro-1-hydroxymethyl-1H-cyclopenta[b]benzofuran-5-yl}thioacetate (88) 253 mg (0.718 mmol) in THF 3.8 ml under argon atmosphere, followed by stirring at room temperature for 1.5 hours. The reaction mixture was filtered with a Pasteur pipet with a cotton plug, and the residue was washed with anhydrous THF (2×1 ml) to form solution A.

A suspension of sodium hydride (60 wt %) 43.2 mg (1.08 mmol) in anhydrous THF 5 ml was cooled to 0° C. under argon atmosphere, and a solution of dimethyl 3-cyclohexyl-2-oxopropylphosphonate 268.1 mg (1.08 mmol) in anhydrous THF 3 ml was added to the suspension, followed by stirring at the same temperature for 30 minutes. The previously obtained solution A was added to the resulting mixture, and the mixture was stirred at room temperature for 15 minutes. After the reaction was quenched by the addition of saturated aqueous ammonium chloride 15 ml, the mixture was extracted with ethyl acetate (2×30 ml). The combined organic layer was washed with brine, dried and then concentrated. The resulting residue was purified by column chromatography (silica gel; normal hexane:ethyl acetate=2:1) to obtain the titled compound 273 mg (yield 81%). The structure of this compound was determined by the following data.

IR (neat): 2925, 2850, 1739, 1696, 1671, 1627, 1441, 1374, 1238, 1137, 1057, 1027, 735 cm$^{-1}$. $^1$H-NMR (300 MHz, CDCl$_3$): δ 7.26–7.22 (1H, m), 7.04–7.02 (1H, d, J=7.1 Hz), 6.83–6.78 (1H, t, J=7.7 Hz), 6.77–6.69 (1H, dd, J=15.8, 8.1 Hz), 6.22–6.16 (1H, dd, J=15.8, 1.1 Hz), 5.38–5.32 (1H, m), 5.04–4.98 (1H, q, J=5.8 Hz), 3.76–3.64 (1H, m). 3.69 (3H, s), 3.64 (2H, s), 2.97–2.94 (1H, m), 2.65–2.58 (1H, m), 2.44–2.42 (2H, d, 6.9 Hz), 2.27–2.24 (1H, m), 1.85 (1H, m), 1.77 (3H, s), 1.75–1.65 (6H, m), 1.31–1.16 (4H, m), 0.98–0.94 (2H, m). MASS (EI, m/e): 472 (M$^+$).

EXAMPLE 67 dl-16-Cyclohexyl-2,5,6,7,17,18,19,20-octanor-4-thia-4,8-inter-m-phenylene PGI₂ Methyl Ester, 11-Acetate (90)

(90)

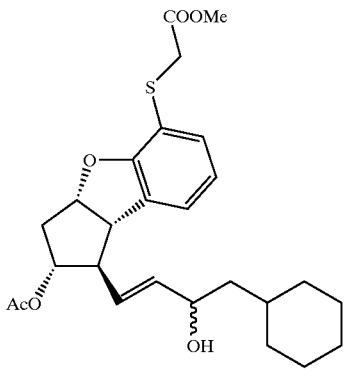

Cerium trichloride heptahydrate 430.4 mg (1.16 mmol) was added to a solution of dl-16-cyclohexyl-15-oxo-2,5,6,7,17,18,19,20-octanor-4-thia-4,8-inter-m-phenylene PGI₂ methyl ester, 11-acetate (89) 273 mg (0.578 mmol) in methanol 5 ml and THF 5 ml, and sodium borohydride 24 mg (0.63 mmol) was added to the resultant solution at 0° C., followed by stirring for 5 minutes. Water 10 ml was added to the reaction mixture, and the mixture was stirred at room temperature for 10 minutes, and then extracted with ethyl acetate (2×30 ml). The combined organic layer was washed with brine, dried and then filtered. After the filtrate was concentrated under reduced pressure, the residue was purified by column chromatography (silica gel; normal hexane-:ethyl acetate=2:1~1:1) to obtain the titled compound 243 mg (yield 81%). The structure of this compound was determined by the following data.

IR (neat): 2923, 2850, 1737, 1656, 1441, 1374, 1241, 1212, 1137, 1053, 1028, 973 cm⁻¹. ¹H-NMR (300 MHz, CDCl₃): δ 7.23–7.20 (1H, d, J=7.7 Hz), 7.08–7.04 (1H, m), 6.81–6.76 (1H, t, J=7.7 Hz), 5.35–5.29 (2H, m), 4.94–4.91 (1H, m), 4.22 (1H, m), 3.68–3.58 (6H, m), 2.82–2.80 (1H, m), 2.59–2.54 (1H, m), 2.19–2.15 (1H, m), 1.78–0.89 (16H, m). MASS (EI, m/e) 474 (M⁺).

EXAMPLE 68 dl-16-Cyclohexyl-2,5,6,7,17,18,19,20-octanor-4-thia-4,8-inter-m-phenylene PGI₂ Methyl Ester (91)

(91)

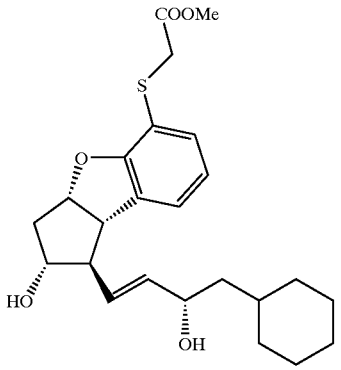

1M methanol solution of sodium methoxide 0.160 ml (0.16 mmol) was added to a solution of dl-16-cyclohexyl-2,5,6,7,17,18,19,.20-octanor-4-thia-4,8-inter-m-phenylene PGI₂ methyl ester, 11-acetate (90) 243 mg (0.512 mmol) in anhydrous methanol 4 ml, followed by stirring at room temperature for 1.5 hours. After the disappearance of the starting material was checked by TLC, acetic acid 0.027 ml (0.473 mmol) was added to the reaction mixture, and the mixture was concentrated under reduced pressure. Then, the residue was extracted with ethyl acetate 30 ml and water 10 ml, and the aqueous layer was again extracted with ethyl acetate. The combined organic layer was washed with brine, dried and then concentrated under reduced pressure. The residue was purified by column chromatography (silica gel; ethyl acetate→ethyl acetate:methanol=10:1) to obtain the titled compound 100 mg (yield 45%). The structure of this compound was determined by the following data.

IR (neat): 3377, 2922, 2849, 1738, 1586, 1439, 1273, 1210, 1139, 1021, 974 cm⁻¹. ¹H-NMR (300 MHz, CDCl₃): δ 7.28–7.22 (1H, m), 7.06–7.03 (1H, ddd, J=7.4, 5.2, 1.1 Hz), 6.81–6.76 (1H, t, J=7.7 Hz), 5.62–5.58 (2H, m), 5.26–5.19 (1H, m), 4.24–4.22 (1H, m), 3.96–3.93 (1H, m), 3.67 (3H, s), 3.57–3.48 (2H, m), 2.67–2.58 (1H, m), 2.52–2.47 (1H, m), 2.11–2.04 (1H, m), 1.79–1.63 (6H, m), 1.51–1.20 (5H, m), 0.98–0.94 (2H, m). MASS (EI, m/e): 432 (M⁺).

EXAMPLE 69 dl-16-Cyclohexyl-2,5,6,7,17,18,19,20-octanor-4-thia-4,8-inter-m-phenylene PGI₂ (92)

(92)

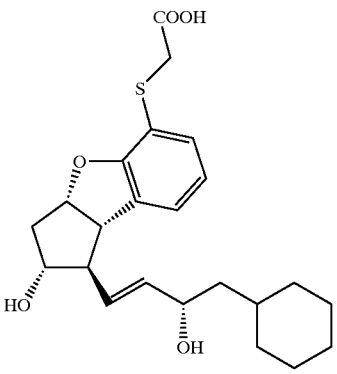

1N aqueous sodium hydroxide 0.700 ml (0.7 mmol) was added to a solution of dl-16-cyclohexyl-2,5,6,7,17,18,19,20-octanor-4-thia-4,8-inter-m-phenylene PGI₂, methyl ester (91) 100 mg (0.231 mmol) in methanol 5 ml, followed by stirring at room temperature for 1 hour. After the disappearance of the starting material was checked by TLC, water 5 ml and 1N acetic acid was in turn added to the reaction mixture, and the pH of the solution was adjusted to about 2. Then, the mixture was extracted with ethyl acetate (2×20 ml), and the combined organic layers was washed with brine, dried and then concentrated under reduced pressure. The residue was recrystallized from a normal hexane-ethyl acetate system to obtain the titled compound 71 mg (yield 74%). The structure of this compound was determined by the following data.

IR (KBr): 3279, 2922, 2848, 1718, 1440, 1413, 1303, 1175, 1023, 986, 728 cm⁻¹. ¹H-NMR (300 MHz, CDCl₃): δ 7.26–7.23 (1H, m), 7.04–7.01 (1H, d, J=7.7 Hz), 6.81–6.76 (1H, t, J=7.7 Hz), 5.62–5.46 (2H, m), 5.23–5.16 (1H, m), 4.25–4.18 (1H, m), 3.94–3.89 (1H, m), 3.71–3.66 (1H, d, J=14.6 Hz), 3.48–3.43 (2H, m), 2.64–2.55 (1H, m), 2.42–2.35 (1H, m), 2.10–2.01 (1H, m), 1.78–1.69 (6H, m), 1.51–1.13 (5H, m), 0.94 (1H, m). MASS (EI, m/e): 418 (M⁺). Elemental Analysis: Calculated for (as monohydrate): C, 63.28%, H, 7.39%. Found: C, 62.99%, H, 7.29%.

EXAMPLE 70

16,16-Difluoro-15-oxo-16-phenoxy-2,5,6,7,17,18,
19,20-octanor-4,8-inter-m-phenylene PGI$_2$ Methyl
Ester, 11-tert-Butyldimethylsilyl Ether (93)

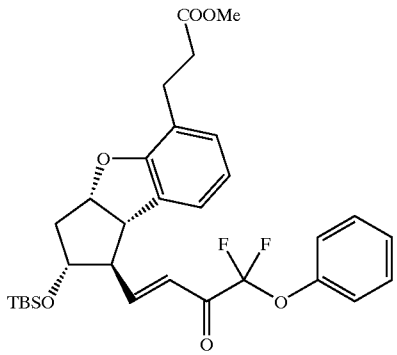

(93)

Anhydrous DMSO 0.33 ml (4.65 mmol), anhydrous pyridine 0.021 ml (0.260 mmol), and trifluoroacetic acid 0.009 ml (0.117 mmol) were added to a solution of methyl 3-{(1S,2R,3aS,8bS)-2,3,3a,8b-tetrahydro-2-tert-butyldimethylsiloxy-hydroxymethyl-1H-cyclopenta[b]benzofuran-5-yl}propionate 115 mg (0.234 mmol) and DCC 73 mg (0.353 mmol) in anhydrous THF 2.0 ml under ice cooling under argon atmosphere, followed by stirring at room temperature for 1 hour to form reaction solution A.

Tallium ethoxide 0.065 ml (0.918 mmol) was added to an ice-cold solution of dimethyl 3,3-difluoro-2-oxo-3-phenoxypropylphosphonate 275 mg (0.935 mmol) in anhydrous THF 1.8 ml, followed by stirring at room temperature for 25 minutes. The previously prepared solution A was added to the ice-cold solution. Anhydrous THF (2×1 ml) washing solution of the residual solution A was also added to the resultant mixture, followed by stirring at room temperature for 25 hours. Acetic acid 0.08 ml, celite, and saturated aqueous potassium iodide solution 10 ml were added to the ice-cold reaction mixture, and the resultant mixture was filtered with a glass filter in which celite was placed. Then, the precipitate was washed with ethyl acetate 50 ml, and the filtrate was washed with water (3×15 ml), saturated aqueous sodium bicarbonate 15 ml, and brine 15 ml, dried and then concentrated under reduced pressure. The resulting residue was purified by two times of column chromatography [((1) Silica Gel FL-60D produced by Fuji Silisia Chemical Co. 30 g; cyclohexane:ethyl acetate=95:5, (2) silica gel; toluene:ethyl acetate=97:3] to obtain the titled compound 106 mg (yield 79%) as a colorless oil. The structure of this compound was determined by the following data.

IR (neat): 3336, 2954, 2934, 2862, 1734, 1628, 1597, 1493, 1456, 1363, 1303, 1257, 1193, 1160, 1036, 957, 861, 837, 777, 743 cm$^{-1}$. $^1$H-NMR (300 MHz, CDCl$_3$): δ 7.43–7.38 (2H, m), 7.34–7.17 (4H, m), 6.98 (1H, d, J=6.6 Hz), 6.91 (1H, d, J=7.4 Hz), 6.76 (1H, dd, J=7.4, 7.4 Hz), 6.65 (1H, dd, J=15.7, 1.2 Hz), 5.13 (1H, ddd, J=9.1, 7.4, 6.0 Hz), 4.04 (1H, m), 3.67 (3H, s), 3.57 (1H, dd, J=9.0, 9.0 Hz), 2.94–2.88 (2H, m), 2.84 (1H, ddd, J=8.8, 8.8, 8.8 Hz), 2.78–2.57 (3H, m), 2.00 (1H, m), 0.79 (9H, s), 0.03 (3H, s), 0.02 (3H, s). MASS (EI, m/e): 572 (M$^+$).

EXAMPLE 71

16,16-Difluoro-16-phenoxy-2,5,6,7,17,18,19,20-
octanor-4,8-inter-m-phenylene PGI$_2$ Methyl Ester
(94) and 15-Epimer (95) Thereof

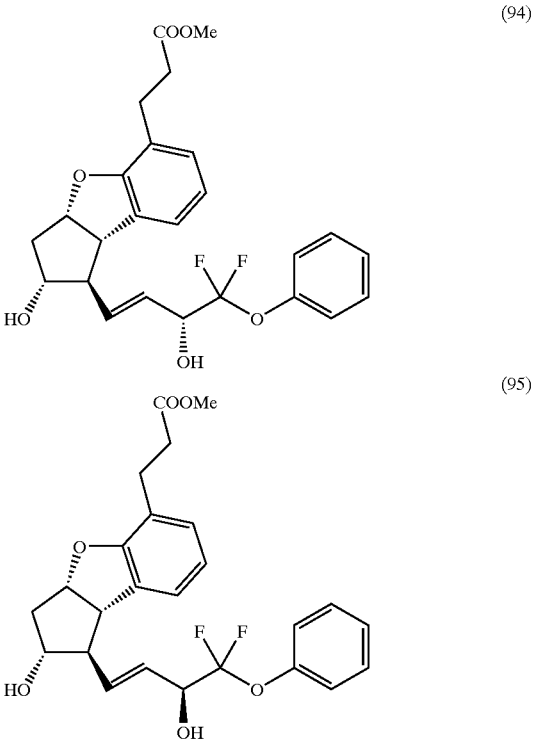

Cerium trichloride heptahydrate 56 mg (0.150 mmol) was added to a solution of 16,16-difluoro-15-oxo-16-phenoxy-2,5,6,7,17,18,19,20-octanor-4,8-inter-m-phenylene PGI$_2$ methyl ester, 11-tert-butyldimethylsily ether (93) 40.7 mg (0.0711 mmol) in anhydrous methanol 1.5 ml and anhydrous THF 3.0 ml under argon atmosphere, and the resultant mixture was cooled with ice. Sodium borohydride 23 mg (0.061 mmol) was added to the resultant solution, and the resulting mixture was stirred for 2 hours under ice cooling. Saturated aqueous sodium bicarbonate 7 ml was added to the reaction mixture, and the mixture was filtered with a glass filter in which celite was placed. The precipitate was washed with ethyl acetate 25 ml, and then the filtrate was separated into an organic layer and an aqueous layer. The aqueous layer was extracted with ethyl acetate (2×10 ml), and the combined organic layer was washed with brine 5 ml, dried and then concentrated under reduced pressure. The resulting residue was purified by column chromatography (silica gel; cyclohexane:ethyl acetate=85:15) to obtain allyl alcohol derivatives 32.5 mg (yield 79%) as a colorless oil.

Next, 1.0M THF solution of TBAF 0.10 ml (0.10 mmol) was added to a solution of the above oil 32.5 mg (0.0565 mmol) in anhydrous THF 2.4 ml, followed by stirring at room temperature for 3.5 hours. Saturated aqueous ammonium chloride 6 ml was added to the reaction mixture, and the mixture was extracted with ethyl acetate (3×10 ml). The combined organic layer was washed with brine 6 ml, dried, and then concentrated under reduced pressure. The residue was purified by column chromatography (silica gel; cylcohexane:ethyl acetate=40:60→25:75) to obtain 16,16-difluoro-16-phenoxy-15-epi-2,5,6,7,17,18,19,20-octanor-4, 8-inter-m-phenylene PGI$_2$ methyl ester (95) 5.8 mg (yield 22%) as a colorless oil from the less-polar fractions, and 16,16-difluoro-16-phenoxy-2,5,6,7,17,18,19,20-octanor-4,8-inter-m-phenylene PGI$_2$ methyl ester (94) 15.6 mg (yield 60%) as a colorless oil from the more-polar fractions. The structures of these compounds were determined by the following data.

16,16-Difluoro-16-phenoxy-2,5,6,7,17,18,19,20-octanor-4,8-inter-m-phenylene PGI$_2$ Methyl Ester IR (neat): 3378, 2944, 1735, 1595, 1492, 1454, 1259, 1198, 1159, 1066, 975, 862, 746 cm$^{-1}$. $^1$H-NMR (300 MHz, CDCl$_3$): δ 7.40–7.31 (2H, m), 7.28–7.16 (3H, m), 6.97 (2H, d, J=7.4 Hz), 6.73 (1H, dd, J=7.4, 7.4 Hz), 5.97 (1H, dd, J=15.4, 8.8 Hz), 5.80 (1H, dd, J=15.4, 6.9 Hz), 5.11 (1H, ddd, J=9.1, 7.4, 5.5 Hz), 4.56 (1H, br dd, J=13.0, 6.9 Hz), 3.97 (1H, br ddd, J=8.7, 8.7, 6.3 Hz), 3.66 (3H, s), 3.46 (1H, dd, J=8.8, 8.8 Hz), 3.35 (1H, br s), 2.93–2.84 (2H, m), 2.74–2.57 (3H, m), 2.51 (1H, ddd, J=8.5, 8.5, 8.5 Hz), 1.98 (1H, ddd, J=13.8, 9.2, 5.4 Hz), 1.79 (1H, br s). MASS (EI, m/e): 460 (M$^+$).

16,16-Difluoro-16-phenoxy-15-epi-2,5,6,7,17,18,19,20-octanor-4,8-inter-m-phenylene PGI$_2$ Methyl Ester IR (neat): 3376, 2936, 1721, 1595, 1492, 1259, 1199, 1157, 1065, 978, 862, 749 cm$^{-1}$. $^1$H-NMR (300 MHz, CDCl$_3$): δ 7.41–7.33 (2H, m), 7.28–7.16 (3H, m), 7.03 (1H, d, J=7.4 Hz), 6.97 (1H, d, 6.9 Hz), 6.75 (1H, dd, J=7.4, 7.4 Hz), 6.05 (1H, ddd, J=15.4, 8.5, 1.1 Hz), 5.84 (1H, dd, J=15.4, 5.2 Hz), 5.16 (1H, ddd, J=8.8, 7.1, 4.9 Hz), 4.59 (1H, m), 4.04 (1H, br dd, J=14.7, 7.8 Hz), 3.66 (3H, s), 3.54 (1H, dd, J=8.3, 8.3 Hz), 2.95–2.85 (2H, m), 2.75–2.54 (5H, m), 2.04 (1H, ddd, J=13.7, 8.8, 5.0 Hz), 1.86 (1H, br s). MASS (EI, m/e): 460 (M$^+$).

EXAMPLE 72
16,16-Difluoro-16-phenoxy-2,5,6,7,17,18,19,20-octanor-4,8-inter-m-phenylene PGI$_2$ (96)

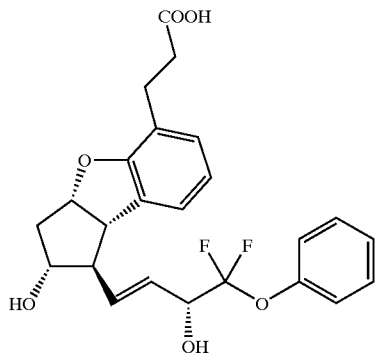

(96)

2N aqueous sodium hydroxide 0.6 ml was added to a solution of 16,16-difluoro-16-phenoxy-2,5,6,7,17,18,19,20-octanor-4,8-inter-m-phenylene PGI$_2$ methyl ester (94) 15.6 mg (0.0339 mmol) in methanol 1.2 ml, followed by stirring at room temperature for 1 hour. 1N hydrochloric acid 1.5 ml was added to the ice-cooled reaction mixture, and the mixture was extracted with ethyl acetate (3×12 ml). The combined organic layer was washed in turn with water 5 ml and brine 5 ml, dried and then concentrated under reduced pressure. The resulting residue was recrystallized from a cyclohexane-ethyl acetate to obtain titled compound 16.0 mg (yield 90%) as a colorless powder. The structure of this compound was determined by the following data.

Melting point: 145.0~146.0° C. IR (KBr): 3428, 3282, 3050, 2896, 1703, 1594, 1493, 1455, 1411, 1316, 1271, 1245, 1175, 1100, 1045, 957, 859, 772, 746, 723, 690 cm$^{-1}$. $^1$H-NMR (300 MHz, CDCl$_3$): δ 7.42–7.33 (2H, m), 7.27–7.18 (3H, m), 6.99 (1H, d, J=7.4 Hz), 6.95 (1H, d, J=7.4 Hz), 6.67 (1H, dd, J=7.4, 7.4 Hz), 6.03 (1H, dd, J=15.6, 8.2 Hz), 5.76 (1H, dd, J=15.6, 7.2 Hz), 5.09 (1H, m), 4.50 (1H, dd, J=13.9, 6.8 Hz), 3.96 (1H, ddd, J=9.6, 9.6, 6.6 Hz), 3.45 (1H, dd, J=9.3, 9.3 Hz), 2.83 (2H, t, J=7.8 Hz), 2.68 (1H, ddd, J=13.5, 6.9, 6.6 Hz), 2.57 (2H, t, J=7.8 Hz), 2.36 (1H, ddd, J=9.3, 9.0, 8.5 Hz), 1.88 (1H, ddd, J=13.5, 10.2, 5.8 Hz). MASS (EI, m/e): 446 (M$^+$). High Resolution Mass Spectrometry (HREIMS): Found: 446.1537 (−0.4 mmu). Calculated for C$_{24}$H$_{24}$F$_2$O$_6$ (M$^+$): 446.1541.

Table 10 shows the compounds used in various bioassays in the present invention.

TABLE 10

Examples of PGI$_2$ derivatives

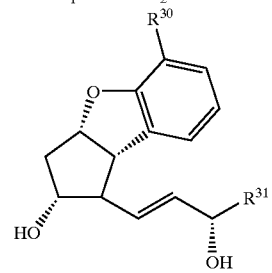

| Compound Nos. | R$^{30}$ | R$^{31}$ |
|---|---|---|
| 1 | —S—CH$_2$—CH$_2$—OH | —C$_5$H$_{11}$ |
| 2 | —CH$_2$—C(CH$_3$)$_2$—CH$_2$—OH | —C(CH$_3$)$_2$—O—C$_6$H$_5$ |
| 3 | —CH$_2$—CH(CH$_3$)—CO$_2$H | —C(CH$_3$)$_2$—O—C$_6$H$_5$ |
| 4 | —CH$_2$—CH$_2$—CH$_2$—NH—C(=O)—C$_6$H$_5$ | —C(CH$_3$)$_2$—O—C$_6$H$_5$ |
| 5 | —CH$_2$—CH$_2$—(5-tetrazole) | —CH$_2$—(cyclohexyl) |
| 6 | —CH$_2$—CH$_2$—COOH | —C(F)$_2$—O—C$_6$H$_5$ |

EXAMPLE 73

Measurement of Antibacterial Activity of $PGI_2$ Derivatives on *Helicobacter pylori*

A blank disk (produced by Beckton Deckinson Co.,) was placed in a brain heart infusion agar medium containing 7% horse blood and coated with *Helicobacter pylori* (three strains of ATCC43504, ATCC43526, and TK1402). The disk was soaked with 10 μl of a solution of a test compound in dimethylsulfoxide, and then cultured under microaerophilic conditions including 5% of $O_2$, 10% of $CO_2$ and 85% of $N_2$ at 37° C. for 4 days. After the completion of culture, the diameter of a growth inhibition circle formed around the disk was measured, and the lethal concentration (LC) of each test compound was computed according to the computation expression of Hultmark et al. (The EMBO Journal, 2, 571–576, 1983). The results are shown in Table 11.

TABLE 11

Antibacterial activity (lethal concentration LC) of $PGI_2$ derivatives on *Helicobacter pylori*

| Compound No. | Unit | ATCC43504 | ATCC43526 | TK1402 |
|---|---|---|---|---|
| Dimethylsulfoxide | | ND | ND | ND |
| 1 | μM | 141 ± 27 | 169 ± 6 | 151 ± 4 |
| 2 | μM | 75 ± 8 | 119 ± 22 | 124 ± 20 |

ND = not detected

It was recognized from the results that compounds 1 and 2 have the antibacterial activity on *Helicobacter pylori*.

EXAMPLE 74

Measurement of Antibacterial Activity of $PGI_2$ Derivatives on *Helicobacter pylori*

As test strains, 2 commercial ATCC strains (ATCC4350 strain and TACC43526 strain) of *Helicobacter pylori*, and 25 clinical isolates were used. Each of the strains was inoculated into a brain heart infusion agar medium containing 7% horse blood, and cultured under microaerophilic conditions including 5% of $O_2$, 10% of $CO_2$ and 85% of $N_2$ at 37° C. After culture for 3 to 4 days, colonies of each strain formed on the medium were collected, and suspended in a brain heart infusion medium containing 10% of fetal calf serum so that turbidity was McFarland No. 1 (the number of bacteria was about 3×108/ml) to form a test bacterial suspension. On the other hand, a test compound (compound 4) was dissolved in dimethylsulfoxide, and a diluent in a double dilution series was prepared with dimethylsulfoxide so that the final concentration of the solvent was 0.5%, to form a test drug solution. 100 μl of the test drug solution was mixed with 20 ml of a brain heart infusion agar medium containing 7% horse blood and about 45° C., and the resultant mixture was solidified by allowing to cool to form a test medium. Next, about 5 μl of test bacterial suspension was inoculated into the medium by using a micro planter, and then cultured under microaerophilic conditions including 5% of $O_2$, 10% of $CO_2$ and 85% of $N_2$ at 37° C. for 4 days. For each of the strains, the minimum growth inhibition concentration (MIC) of the test compound was determined, at which no visible growth (formation of colonies) was observed with the naked eyes. The minimum concentration at which growth of 50% of the total 27 stains used in the test was inhibited was $MIC_{50}$, and the minimum concentration at which growth of 90% the strains used was inhibited was $MIC_{90}$. The results are shown in Table 12.

TABLE 12

Antibacterial activity of $PGI_2$ derivatives on *Helicobacter pylori*

| Compound No. | $MIC_{50}$ (μM) | $MIC_{90}$ (μM) |
|---|---|---|
| 4 | 12.5 | 50 |

| Concentration of Compound 4 (μM) | Number of strains inhibited/total strains | Growth inhibition rate (%) |
|---|---|---|
| 50 | 26/27 | 96.3 |
| 25 | 20/27 | 74.1 |
| 12.5 | 11/27 | 40.7 |

It was recognized from the results that compound 4 has the antibacterial activity on *Helicobacter pylori*.

EXAMPLE 75

Measurement of Antibacterial Activity of $PGI_2$ Derivatives on Helicobacter Bacteria A blank disk (produced by Beckton Deckinson Co.,) was placed in a brain heart infusion agar medium containing 7% horse blood and coated with *Helicobacter mustelae* (ATCC43772) and *Helicobacter muridarum* (ATCC49282). The disk was soaked with 10 μl of a solution of test compound in dimethylsulfoxide, and then cultured under microaerophilic conditions including 5% of $O_2$, 10% of $CO_2$ and 85% of $N_2$ at 37° C. for 4 days. After the completion of culture, the diameter of a growth inhibition circle formed around the disk was measured, and the lethal concentration (LC) of each test compound was computed according to the computation expression of Hultmark et al. (The EMBO Journal, 2, 571–576, 1983). The results are shown in Table 13.

TABLE 13

Antibacterial activity (lethal concentration LC) of $PGI_2$ derivatives on Helicobacter bacteria

| Compound No. | Unit | Helicobacter mustelae ATCC43772 | Helicobacter muridarum ATCC49282 |
|---|---|---|---|
| Dimethylsulfoxide | | ND | ND |
| 2 | μM | 156 | 83.6 |

ND = not detected

It was recognized from the results that compound 2 has the antibacterial activity on Helicobacter bacteria.

EXAMPLE 76

Measurement of Antibacterial Activity of $PGI_2$ Derivatives on Bacteria Other Than Helicobacter Bacteria Antibacterial activities on *Escherichia coli* (ATCC43827), *Staphylococcus aureus* (two clinical isolates of 081119-016 and 081120-073), and *Lactobacillus lactis* (three species of ATCC4356, ATCC12315 and ATCC35020) were tested. As a medium, a drug sensitive disk medium (produced by Nikken Biochemical laboratory Co., Ltd.), a tryptosoy agar medium, and a lactobacilli MRS agar medium were used for *Escherichia coli, Staphylococcus* aureus, and *Lactobacillus lactis*, respectively. A disk was placed on each of the media coated with bacteria, and soaked with 10 μl of a solution of a test compound in dimethylsulfoxide. Then the disk was cultured in 100% air at 37° C. for 1 to 2 days. After the completion of culture, the diameter of a growth inhibition circle formed around the disk was measured, and the lethal concentration (LC) of each test compound was computed according to the computation expression of Hultmark et al. (The EMBO Journal, 2, 571–576, 1983). The results are shown in Table 14.

TABLE 14

Antibacterial activity (lethal concentration LC) of $PGI_2$ derivatives on Helicobacter bacteria

| Compound No. | Unit | Helicobacter mustelae ATCC43772 | Helicobacter muridarum ATCC49282 |
|---|---|---|---|
| Dimethylsulfoxide | | ND | ND |
| 2 | μM | 156 | 83.6 |

ND = not detected

It was recognized from the results that compounds 1 and 2 have no action on other bacteria except for Helicobacter bacteria, and the antibacterial activity are selectively expressed for Helicobacter bacteria.

EXAMPLE 77

Effect of $PGI_2$ Derivatives on Human Platelet Aggregation

The blood collected from healthy persons was centrifuged to separate platelet-rich plasma (PRP) and platelet-poor plasma (PPP). A $TXA_2$ antagonist SQ-29548 was added to PRP. and 1 minute after, platelet aggregation was induced with ADP. Immediately after the induction of platelet aggregation, compound 3 (10 μM) was added. Experiment was carried out for 3 examples per group. The results are shown in Table 15.
(P<0.05, Paired t-Test)

TABLE 15

Platelet aggregation potentiating effect of $PGI_2$ derivatives

| Compound No. | Platelet aggregation (%) |
|---|---|
| Control | 38 ± 4.9 |
| 3 | 54 ± 1.7 |

The results indicate that compound 3 potentiated platelet aggregation.

EXAMPLE 78

Cervical Ripening Action of $PGI_2$ Derivatives

The cervical ripening effect of compounds 5 and 6 (10 μg/body) were tested in female mature Hartley guinea pigs. Test drugs were compound 5 and 6 which were formulated in 3% hydroxypropyl cellulose each.

Experiment was carried out for 4 to 12 animals per group. 100 μl of the test drug or a base thereof was administered into the vaginae at 9 o'clock, 17 o'clock and 9 o'clock of the next day, and 4 hours after the final administration, the cervical canals were isolated by dissection. Then, each of the cervical canals was pulled at a rate of 3×2 mm/min to measure the tension produced in the tissue at the indicated times. As an index of cervical ripening, the maximum tension produced until the tissue was broken, and the gradient value which is the value of the maximum tension divided by the distance of pulling until the tissue was broken were tested. It is thought that decreases in these values show cervical ripening.

The results are shown in Table 16 (*: P<0.05, **: P<0.01, comparison with a base administration group, Dunnett's method).

TABLE 16

| | Number of examples | Maximum tension (g) average ± standard error | Gradient value (g/mm) average ± standard error |
|---|---|---|---|
| Base administration group (control group) | 12 | 299.1 ± 31.5 | 25.5 ± 2.4 |
| Compound 5 administration group | 17 | 134.2 ± 23.1** | 14.8 ± 1.0** |
| Compound 6 administration group | 4 | 167.6 ± 38.2* | 15.9 ± 1.9* |

*P < 0.05, **P < 0.01, comparison with a base administration group (Dunnett's method)

The results indicate that compounds 5 and 6 have the excellent cervical ripening effect.

EXAMPLE 79

Effect of $PGI_2$ Derivative on Blood Pressure (Recognition That a Blood Pressure Reducing Effect is Removed)

In order to recognize that the compounds of the present invention have the little effect to reduce blood pressure as a side effect, the effect on blood pressure was examined. In experiment, male cynomolgus monkeys (body weight, 4 to 6 kg) were anaesthetized with pentobarbital (25 to 30 mg/kg, intravenous administration), retained at a supine position and the mean blood pressure was measured by a cannula inserted into the femoral artery under artificial respiration. A test compound was administered from a cannula inserted into a cutaneous vein of the forearm, and changes in blood pressure due to the administration were measured at the indicated times (3 examples per group).

The control compound A used for control was a conventional $PGI_2$ derivative disclosed in the following specification.

Control compound A: 6-16-cyclohexyl-2,5,6,7,17,18,19, 20-octanor-4,8-inter-m-phenylene $PGI_2$, Japanese Examined Patent Publication No. 6-62599.

Figure 2:
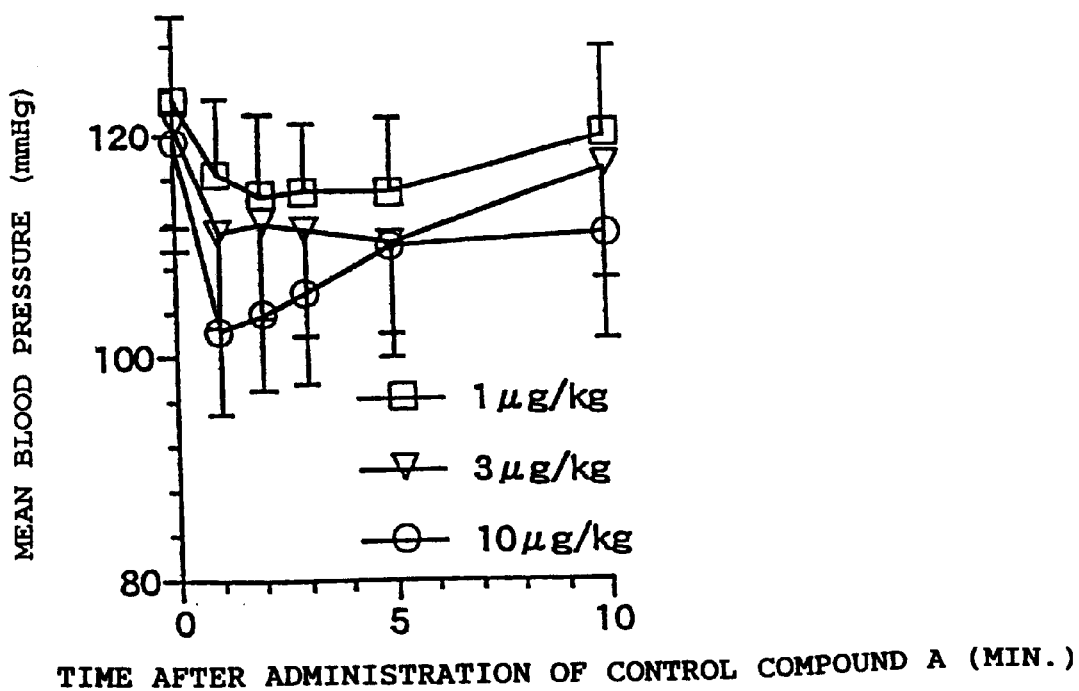
FIG. 2 shows change in mean blood pressure of monkeys after the intravenous administration of control compound A.

The results are shown in FIGS. 1 and 2. The intravenous administration of 10 μg of comound 5 of the present invention showed no change in mean blood pressure (FIG. 1). On the other hand, the intravenous administration of 1 to 10 μg of control compound A showed the significant effect to reduce blood pressure in a dose-dependent manner (FIG. 2).

These results indicate that the $PGI_2$ derivatives of the present invention have the less effect to reduce blood pressure as a side effect, and are significant usefulness as medicines, in comparison with conventional $PGI_2$ derivatives.

Industrial Applicability

The present invention provides novel $PGI_2$ derivatives which have excellent stability in vivo, strong medical effects and little side effect, and which are useful as an anti helicobacter agent, a platelet function potentiating agent or a cervical ripening agent.

What is claimed is:

1. A 5,6,7-trinor-4,8-inter-m-phenylene PGI$_2$ derivative represented by the following formula (1):

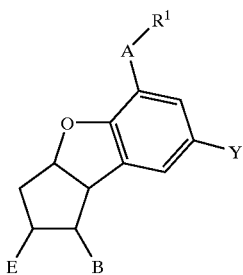
(I)

wherein R$^1$ represents the following:
(D) —CH$_2$—R$^{13}$
wherein R$^{13}$ is the following:

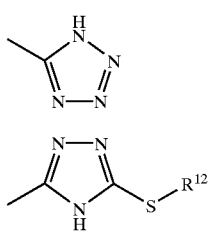
(1)

(2)

wherein R$^{12}$ is hydrogen, straight chain alkyl having 1 to 12 carbon atoms, branched alkyl having 3 to 14 carbon atoms, phenyl, substituted phenyl (wherein a substituent is defined as the same as the substituent defined for the substituted phenyl) or —C(=O)—R$^4$ (wherein R$^4$ is straight chain alkyl having 1 to 12 carbon atoms, branched alkyl having 3 to 14 carbon atoms, cycloalkyl having 3 to 12 carbon atoms, aralkyl having 7 to 12 carbon atoms, phenyl, or substituted phenyl (wherein a substituent is at least one of fluorine, chlorine, bromine, iodine, trifluoromethyl, alkyl having 1 to 4 carbon atoms, nitro, cyano, methoxy, phenyl, phenoxy, p-acetamidebenzamide, —CH=N—NH—C(=O)—NH$_2$, —NH—C(=O)—Ph, —NH—C(=O)—CH$_3$, or —NH—C(=O)—NH$_2$);

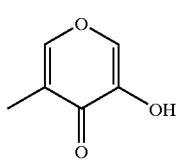
(3)

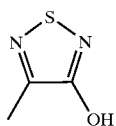
(4)

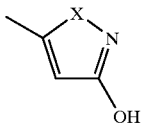
(5)

wherein X represents —O— or —S—; or
(6) azide;

Y is hydrogen, alkyl having 1 to 4 carbon atoms, fluorine, chlorine, bromine, formyl, methoxy, or nitro, B is the following:

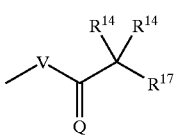
(A)

wherein V represents the following:
(1) —CH$_2$CH$_2$—;
(2) —C≡C—; or
(3) —CH=C(R$^7$)—;
wherein R$^7$ is hydrogen or alkyl having 1 to 4 carbon atoms, Q is the following:
(1) =O;
(2) —OR$^3$
—R$^2$
(3) —R$^2$
—R$^2$ R$^2$ is hydrogen, straight chain alkyl having 1 to 4 carbon atoms, branched alkyl having 3 or 4 carbon atoms, trifluoromethyl, —C(=O)—R$^4$ or —C(=O)—O—R$^4$ and R$^3$ is hydrogen, alkyl having 1 to 4 carbon atoms, acyl having 1 to 4 carbon atoms, aroyl having 7 to 16 carbon atoms, aralkyl having 7 to 16 carbon atoms, tetrahydropyranyl, tetrahydrofuranyl, 1-ethoxyethyl, allyl, tert-butyl, or tert-butyldimethylsilyl, two R$^2$ groups may be the same or different, R$^{14}$ is hydrogen, fluorine, chlorine, bromine, iodine, cyano or alkyl having 1 to 4 carbon atoms, two R$^{14}$ may be the same or different, and R$^{17}$ is the following:
(1) —Z—R$^{18}$
wherein Z is a valence bond or straight chain or branched alkylene represented by C$_t$H$_{2t}$, wherein t represents an integer of 1 to 6, R$^{18}$ is straight chain alkyl having 1 to 12 carbon atoms, branched alkyl having 3 to 14 carbon atoms, cycloalkyl having 3 to 12 carbon atoms, cycloalkylalkylene having 4 to 13 carbon atoms, cycloalkyl having 3 to 12 carbon atoms substituted by 1 to 3 R$^7$ (wherein R$^7$ is defined as the same as the above), cycloalkylalkylene having 4 to 13 carbon atoms substituted by 1 to 3 R$^7$ (wherein R$^7$ is defined as the same as the above), phenyl, substituted phenyl (wherein a substituent is the same as the substituient defined for the above substituted phenyl), α-naphthyl, β-naphthyl, 2-pyridyl, 3-pyridyl, 4-pyridyl, α-furyl, β-furyl, α-thienyl, or β-thienyl;
(2) —Z—O—R$^{18}$
wherein Z and R$^{18}$ are defined as the same as the above;
(3) —Z—CH=C(R$^{18}$)$_2$
wherein Z and R$^{18}$ are defined as the same as the above, and two R$^{18}$ may be the same or different; or (4) —Z—C≡C—R$^{18}$
wherein Z and R$^{18}$ are defined as the same as the above;

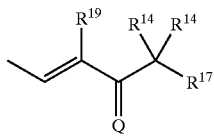

(B)

wherein Q, R$^{14}$ and R$^{17}$ are defined as the same as the above, two R$^{14}$ groups may be the same or different, and R$^{19}$ represents fluorine, chlorine, bromine, or iodine; or

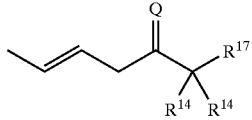

(C)

wherein Q, R$^{14}$ and R$^{17}$ are defined as the same as the above, and two R$^{14}$ groups may be the same or different, E represents hydrogen or —OR$^3$ wherein R$^3$ is defined as the same as the above, and A is the following:

wherein m represents an integer of 0 to 5, G represents hydrogen, fluorine, chlorine, bromine, iodine, trifluoromethyl, straight chain alkyl having 1 to 4 carbon atoms, branched alkyl having 3 to 6 carbon atoms, all G groups may be the same or different; or

wherein j represents an integer of 1 to 4, p represents an integer of 0 or 1, G represents hydrogen, fluorine, chlorine, bromine, iodine, trifluoromethyl, straight chain alkyl having 1 to 4 carbon atoms, or branched alkyl having 3 to 6 carbon atoms, and all G groups may be the same or different; and the formula (I) represents a d-, l- or dl-isomer.

2. A 5,6,7-trinor-4,8-inter-m-phenylene PGI$_2$ derivative represented by the following formula (I):

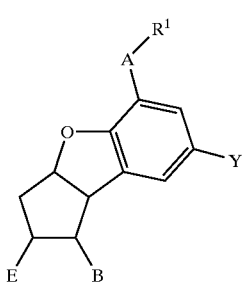

(I)

wherein R$^1$ represents:

(D) —CH$_2$—R$^{13}$ wherein R$^{13}$ is:

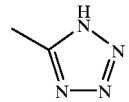

(1)

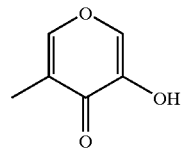

(3)

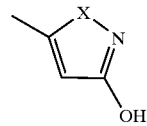

(5)

wherein X is —O— or —S—;
Y is hydrogen, fluorine, chlorine, or bromine, and B is:

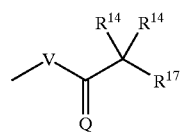

(A)

wherein V is:
 (1) —CH$_2$CH$_2$—;
 (2) —C≡C—; or
 (3) —CH=CH—;
Q is:
 (1) =O;
 (2) —OR$^3$
    —R$^2$
 (3) —R$^2$
    —R$^2$ R$^2$ is hydrogen, straight chain alkyl having 1 to 4 carbon atoms, branched alkyl having 3 or 4 carbon atoms, or trifluoromethyl, R$^3$ is hydrogen; alkyl having 1 to 4 carbon atoms, acyl having 1 to 4 carbon atoms, aroyl having 7 to 16 carbon atoms, aralkyl having 7 to 16 carbon atoms, tetrahydropyranyl, tetrahydrofuranyl, 1-ethoxyethyl, allyl, tert-butyl, or tert-butyldimethylsilyl, two R$^2$ groups may be the same or different, R$^{14}$ is hydrogen, fluorine, chlorine, bromine, iodine, cyano or alkyl having 1 to 4 carbon atoms, two R$^{14}$ may be the same or different, and R$^{17}$ is:
 (1) —Z—R$^{18}$
 (2) —Z—O—R$^{18}$ wherein Z is a valance bond or straight chain or branched alkylene represented by C$_t$H$_{2t}$, wherein t represents an integer of 1 to 6, R$^{18}$ is straight chain alkyl having 1 to 6 carbon atoms, branched alkyl having 3 to 8 carbon atoms; cycloalkyl having 3 to 12 carbon atoms, cycloalkylalkylene having 4 to 7 carbon atoms, cycloalkyl having 3 to 12 carbon atoms substituted by 1 to 3 R$^7$ (wherein R$^7$ is hydrogen or alkyl having 1 to 4 carbon atoms), cycloalkylalkylene having 4 to 7 carbon atoms substituted by 1 to 3 R$^7$ (wherein R$^7$ is defined as the same as above), phenyl, or substituted phenyl (wherein a substituent is at least one of fluorine, chlorine, bromine, iodine, trifluoromethyl, alkyl having 1 to 4 carbon atoms, nitro, cyano, methoxy, phenyl, phenoxy, p-acetamidebenzamide, —CH=N—NH—C(=O)—NH$_2$, —NH—C(=O)—Ph, —NH—C(=O)—CH$_3$, or —NH—C(=O)—NH$_2$);

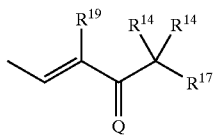

(B)

wherein Q is the following in the definition of claim 1:
(1) =O;
(2) —OR$^3$
    —R$^2$
(3) —R$^2$
    —R$^2$ R$^2$ is hydrogen, straight chain alkyl having 1 to 4 carbon atoms, branched alkyl having 3 or 4 carbon atoms, or trifluoromethyl in the definition of claim 1, R$^3$ is defined as the same as claim 1, two R$^2$ groups may be the same or different, R$^{14}$ is defined as the same as claim 1, two R$^{14}$ may be the same or different, R$^{17}$ is:
(1) —Z—R$^{18}$
(2) —Z—O—R$^{18}$ wherein Z is defined as the same as claim 1, R$^{18}$ is straight chain alkyl having 1 to 6 carbon atoms, branched alkyl having 3 to 8 carbon atoms, cycloalkyl having 3 to 12 carbon atoms, cycloalkylalkylene having 4 to 7 carbon atoms, cycloalkyl having 3 to 12 carbon atoms substituted by 1 to 3 R$^7$ (wherein R$^7$ is defined as the same as above), cycloalkylalkylene having 4 to 7 carbon atoms substituted by 1 to 3 R$^7$ (wherein R$^7$ is defined as the same as above), phenyl, or substituted phenyl (wherein a substituent is the same as above), and R$^{19}$ represents fluorine or chlorine; or

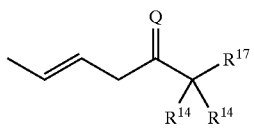

(C)

wherein Q is the same as above:
(1) =O;
(2) —OR$^3$
    —R$^2$
(3) —R$^2$
    —R$^2$ R$^2$ is hydrogen, straight chain alkyl having 1 to 4 carbon atoms, branched alkyl having 3 or 4 carbon atoms, or trifluoromethyl in the definition of claim 1, R$^3$ is the same as above, and two R$^2$ groups may be the same or different, R$^{14}$ is the same as above, two R$^{14}$ may be the same or different, R$^{17}$ is the same as above:
(1) —Z—R$^{18}$; or
(2) —Z—O—R$^{18}$ wherein Z is defined as the same as above, R$^{18}$ is straight chain alkyl having 1 to 6 carbon atoms, branched alkyl having 3 to 8 carbon atoms, cycloalkyl having 3 to 12 carbon atoms, cycloalkylalkylene having 4 to 7 carbon atoms, cycloalkyl having 3 to 12 carbon atoms substituted by 1 to 3 R$^7$ (wherein R$^7$ is defined as the same as above), cycloalkylalkylene having 4 to 7 carbon atoms substituted by 1 to 3 R$^7$ (wherein R$^7$ is defined as the same as above), phenyl, or substituted phenyl (wherein a substituent is the same as above), E is hydrogen or —OR$^3$, and A is:

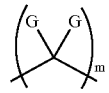

wherein m represents an integer of 0 to 3, G represents hydrogen, fluorine, chlorine, bromine, iodine, trifluoromethyl, or straight chain alkyl having 1 to 4 carbon atoms, all G groups may be the same or different; or

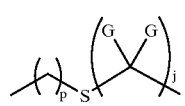

wherein j represents an integer of 1 or 2, p is 0 or 1, G represents hydrogen, fluorine, chlorine, bromine, iodine, trifluoromethyl, or straight chain alkyl having 1 to 4 carbon atoms, and all G groups may be the same or different; and the formula (1) represents a d-, l- or dl-isomer.

3. A 5,6,7-trinor-4,8-inter-m-phenylene PGI$_2$ derivative represented by the following formula (I):

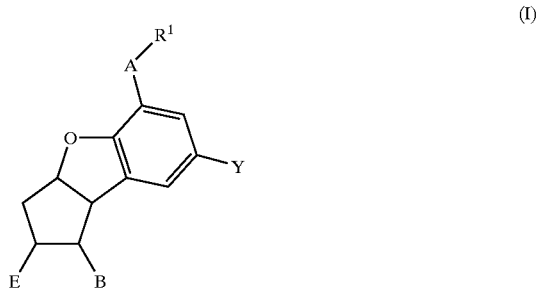

(I)

wherein R$^1$ represents:
(D) —CH$_2$—R$^{13}$
    wherein R$^{13}$ is:

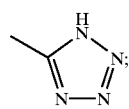

(1)

Y is hydrogen or fluorine, and B is:

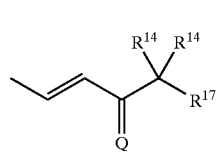

(A)

wherein Q is:
(1) =O; or
(2) —OR$^3$
    —H

R$^3$ is hydrogen, tetrahydropyranyl, tetrahydrofuranyl, or tert-butyldimethylsilyl and R$^{14}$ is hydrogen, fluorine, or alkyl having 1 to 4 carbon atoms, two $R^{14}$ may be the same or different, and $R^{17}$ is:
(1) —Z—$R^{18}$; or
(2) —Z—O—$R^{18}$ wherein Z is a valance bond or straight chain or branched alkylene represented by $C_tH_{2t}$, wherein t represents an integer of 1 to 6, $R^{18}$ is straight chain alkyl having 1 to 4 carbon atoms, branched alkyl having 3 to 6 carbon atoms, cycloalkyl having 3 to 9 carbon atoms, cycloalkylalkylene having 4 to 7 carbon atoms, cycloalkyl having 3 to 9 carbon atoms substituted by 1 to 3 $R^7$ (wherein $R^7$ is hydrogen or alkyl having 1 to 4 carbon atoms), cycloalkylalkylene having 4 to 7 carbon atoms substituted by 1 to 3 $R^7$ (wherein $R^7$ is defined as the same as above), or phenyl; or

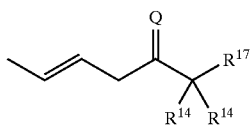

(C)

wherein Q is the same as above:
(1) =O; or
(2) —$OR^3$
—$R^2$ $R^2$ is hydrogen, or straight chain alkyl having 1 to 4 carbon atoms, $R^3$ is hydrogen, tetrahydropyranyl, tetrahydrofuranyl, or tert-butyldimethylsilyl, $R^{14}$ is hydrogen, fluorine, or alkyl having 1 to 4 carbon atoms, two $R^{14}$ may be the same or different, and $R^{17}$ is the following:
(1) —Z—$R^{18}$; or
(2) —Z—O—$R^{18}$ wherein Z is defined as the same as above, $R^{18}$ is straight chain alkyl having 1 to 4 carbon atoms, branched alkyl having 3 to 6 carbon atoms, cycloalkyl having 3 to 9 carbon atoms, cycloalkylalkylene having 4 to 7 carbon atoms, cycloalkyl having 3 to 9 carbon atoms substituted by 1 to 3 $R^7$ (wherein $R^7$ is defined as the same as above), cycloalkylalkylene having 4 to 7 carbon atoms substituted by 1 to 3 $R^7$ (wherein $R^7$ is defined as the same as above), or phenyl, E is hydrogen or —$OR^3$ wherein $R^3$ is hydrogen, tetrahydropyranyl, tetrahydrofuranyl, or tert-butyldimethylsilyl, and A is:

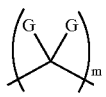

wherein m represents an integer of 0 to 2, G represents hydrogen, fluorine, or straight chain alkyl having 1 to 4 carbon atoms, all G groups may be the same or different; or

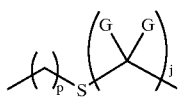

wherein j is 1 or 2 and p is 0 or 1, G represents hydrogen, fluorine, or straight chain alkyl having 1 to 4 carbon atoms, and all G groups may be the same or different; and the formula (I) represents a d-, l- or dl-isomer.

4. A 5,6,7-tenor-4,8-inter-m-phenylene $PGI_2$ derivative represented by the following formula (I):

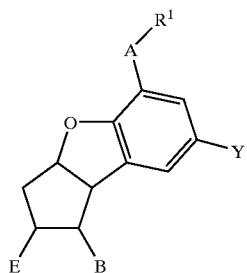

(I)

wherein $R^1$ represents, (D) —$CH_2$—$R^{13}$
wherein $R^{13}$ is:

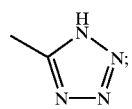

(1)

Y is hydrogen or fluorine, and B is:

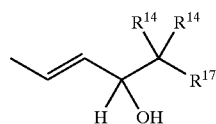

(A)

wherein $R^{14}$ is hydrogen, fluorine, or alkyl having 1 to 4 carbon atoms, two $R^{14}$ may be the same or different, and $R^{17}$ is:
(1) —Z—$R^{18}$
(2) —Z—O—$R^{18}$ wherein Z is a valance bond or straight chain or branched alkylene represented by $C_tH_{2t}$, wherein t represents an integer of 1 to 6, $R^{18}$ is cycloalkyl having 5 to 7, or phenyl;

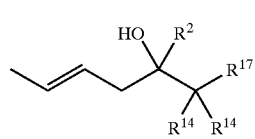

(C)

wherein $R^2$ is hydrogen or methyl, $R^{14}$ is defined as the same as above, two $R^{14}$ may be the same or different, $R^{17}$ is the following:
(1) —Z—$R^{18}$; or
(2) —Z—O—$R^{18}$ wherein Z is defined as the same as above, $R^{18}$ is straight chain alkyl having 1 to 4 carbon atoms, cycloalkyl having 5 to 7 carbon atoms, or phenyl;

E represents hydrogen or —OH; and A is:

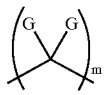

wherein m is an integer of 0 to 2, G represents hydrogen or fluorine, all G groups may be the same or different; or

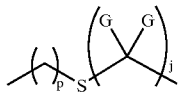

wherein j is 1 or 2 and p is 0 or 1, G represents hydrogen or fluorine, and all G groups may be the same or different; and the formula (I) represents a d-, l- or dl-isomer.

5. A pharmaceutical composition comprising a 5,6,7-trinor-4,8-inter-m-phenylene $PGI_2$ derivative according to claim 1 as an active ingredient.

6. A medicine comprising a 5,6,7-trinor-4,8-inter-m-phenylene $PGI_2$ derivative according to claim 1 as an active ingredient.

7. An anti Helicobacter agent composition comprising a 5,6,7-trinor-4,8-inter-m-phenylene $PGI_2$ derivative according to claim 1 as an active ingredient.

8. A platelet function potentiating agent comprising a 5,6,7-trinor-4,8-inter-m-phenylene $PGI_2$ derivative according to claim 1 as an active ingredient.

9. A cervical ripening agent comprising a 5,6,7-trinor-4,8-inter-m-phenylene $PGI_2$ derivative according to claim 1 as an active ingredient.

* * * * *

UNITED STATES PATENT AND TRADEMARK OFFICE
CERTIFICATE OF CORRECTION

PATENT NO.    : 6,555,559 B1
DATED         : April 29, 2003
INVENTOR(S)   : Wakita et al.

It is certified that error appears in the above-identified patent and that said Letters Patent is hereby corrected as shown below:

Column 2,
Line 20, please change "fatal" to -- fetal --.

Column 42,
Line 18, please delete "($M^+$)".

Column 47,
Line 66, please delete ",d".

Column 50,
Line 16, please delete "$M^+$)".

Column 52,
Line 2, please change "83.7" to -- 837 --.

Column 58,
Line 32, please delete "+d".

Column 92,
Line 42, please change "phase" to -- layer --.

Column 98,
Line 63, please change "J=8.24" to -- J=8.24Hz --.

Column 113,
Line 18, please change "cyclomethane" to -- dichloromethane --.

Signed and Sealed this

Third Day of February, 2004

JON W. DUDAS
*Acting Director of the United States Patent and Trademark Office*